United States Patent
Wang et al.

(10) Patent No.: US 11,525,164 B2
(45) Date of Patent: Dec. 13, 2022

(54) SPATIAL METAGENOMIC CHARACTERIZATION OF MICROBIAL BIOGEOGRAPHY

(71) Applicant: The Trustees of Columbia University in the City of New York, New York, NY (US)

(72) Inventors: Harris H. Wang, New York, NY (US); Ravi Sheth, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 408 days.

(21) Appl. No.: 16/366,962

(22) Filed: Mar. 27, 2019

(65) Prior Publication Data

US 2019/0300968 A1 Oct. 3, 2019

Related U.S. Application Data

(60) Provisional application No. 62/648,716, filed on Mar. 27, 2018.

(51) Int. Cl.
  *C12Q 1/6886* (2018.01)
  *C12Q 1/686* (2018.01)
  *C12Q 1/6806* (2018.01)

(52) U.S. Cl.
  CPC ........... *C12Q 1/6886* (2013.01); *C12Q 1/686* (2013.01); *C12Q 1/6806* (2013.01); *C12Q 2600/16* (2013.01)

(58) Field of Classification Search
  CPC .............................. C12Q 1/689; C12Q 1/6806
  See application file for complete search history.

(56) References Cited

U.S. PATENT DOCUMENTS

| | | |
|---|---|---|
| 2009/0098555 A1 | 4/2009 | Roth et al. |
| 2010/0285975 A1 | 11/2010 | Mathies et al. |
| 2012/0149584 A1 | 6/2012 | Olle et al. |
| 2012/0165215 A1 | 6/2012 | Andersen et al. |
| 2015/0259728 A1 | 9/2015 | Cutliffe et al. |

FOREIGN PATENT DOCUMENTS

| WO | 2012048341 | 4/2012 |
|---|---|---|

OTHER PUBLICATIONS

Sepp, R. et al., Rapid techniques for DNA extraction from routinely processed archival tissue for use in PCR, J. Clin. Pathol., vol. 47, pp. 318-323 (Year: 1994).*
Xu et al., Virtual microfluidics for digital quantification and single-cell sequencing, Nature Meth., vol. 13, pp. 759-762 plus online methods pp. 1-2 (Year: 2016).*
Welch et al., Biogeography of a human oral microbiome at the micron scale. PNAS 2015, 113(6): E791-800.
Macosko et al., Highly Parallel Genome-wide Expression profiling of Individual Cells Using Nanoliter Droplets. Cell 2015; 161(5): pp. 1202-1214.
Chung et al., Clarity for mapping the nervous system. Nature Methods, 2013; 10(6): pp. 508-513.
Geva-Zatorsky N et al, In vivo imaging and tracking of host-microbiota interactions via metabolic labeling of gut anaerobic bacteria, Nature Medicine, vol. 21/Issue 9, pp. 1091-1100, 2015.
Zhang et al., Spatial heterogeneity and co-occurrence patterns of human mucosal-associated intestinal microbiota, ISME J. vol. 8/Issue 4, pp. 881-893, 2014.
Nava et al., Spatial organization of intestinal microbiota in the mouse ascending colon, ISME J. vol. 5/Issue 4, pp. 327-638, 2011.
Gill et al., Metagenomic analysis of the human distal gut microbiome, Science, vol. 312/Issue 5778, pp. 1355-1359, 2006.
Valm et al., Systems-level analysis of microbial community organization through combinatorial labeling and spectral Imaging, PNAS, vol. 108/ Issue 10, pp. 4152-4157, 2011.
Wang, H., Functional metagenomic reprogramming of the human microbiome through mobilome eng, NIH Grant #:1DP50D009172-01. Award Notice Date: Sep. 20, 2011; Project Start Date: Sep. 20, 2011.
Alm, E., High-resolution analysis of diversity and variation in the human microbiome, NIH Gran #: 5R21AI084032-02. Award Notice Date: Jun. 6, 2011; Project Start Date: Jun. 15, 2010.

* cited by examiner

*Primary Examiner* — Teresa E Strzelecka
(74) *Attorney, Agent, or Firm* — Kelly A. Barton; Casimir Jones, S.C.

(57) ABSTRACT

The present disclosure provides for a method of determining microbial identities and/or abundances in a biological sample. The method may comprise: (a) immobilizing the biological sample in a matrix; (b) fracturing/breaking the matrix (that comprises the biological sample) into clusters; and (c) determining identities and/or abundances of microbes in the clusters.

42 Claims, 56 Drawing Sheets
(50 of 56 Drawing Sheet(s) Filed in Color)

Specification includes a Sequence Listing.

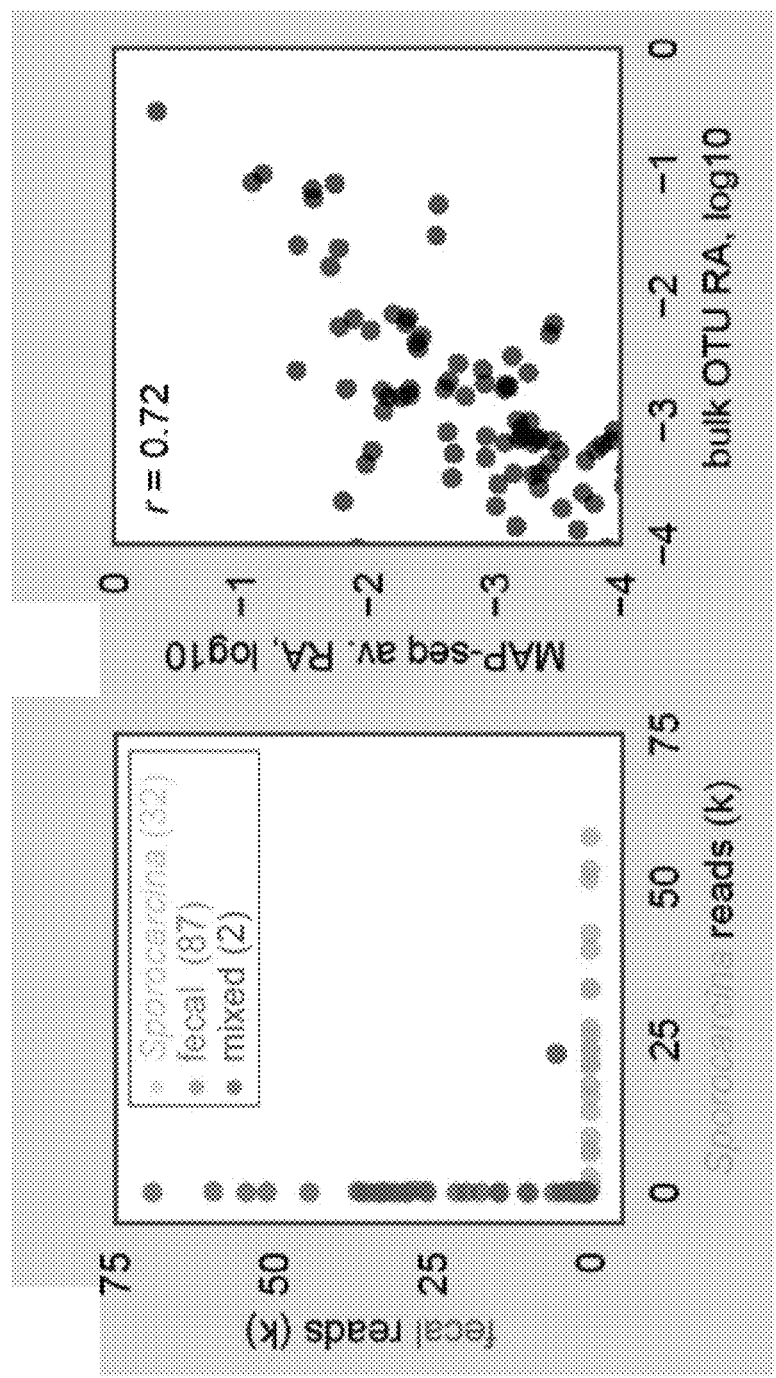

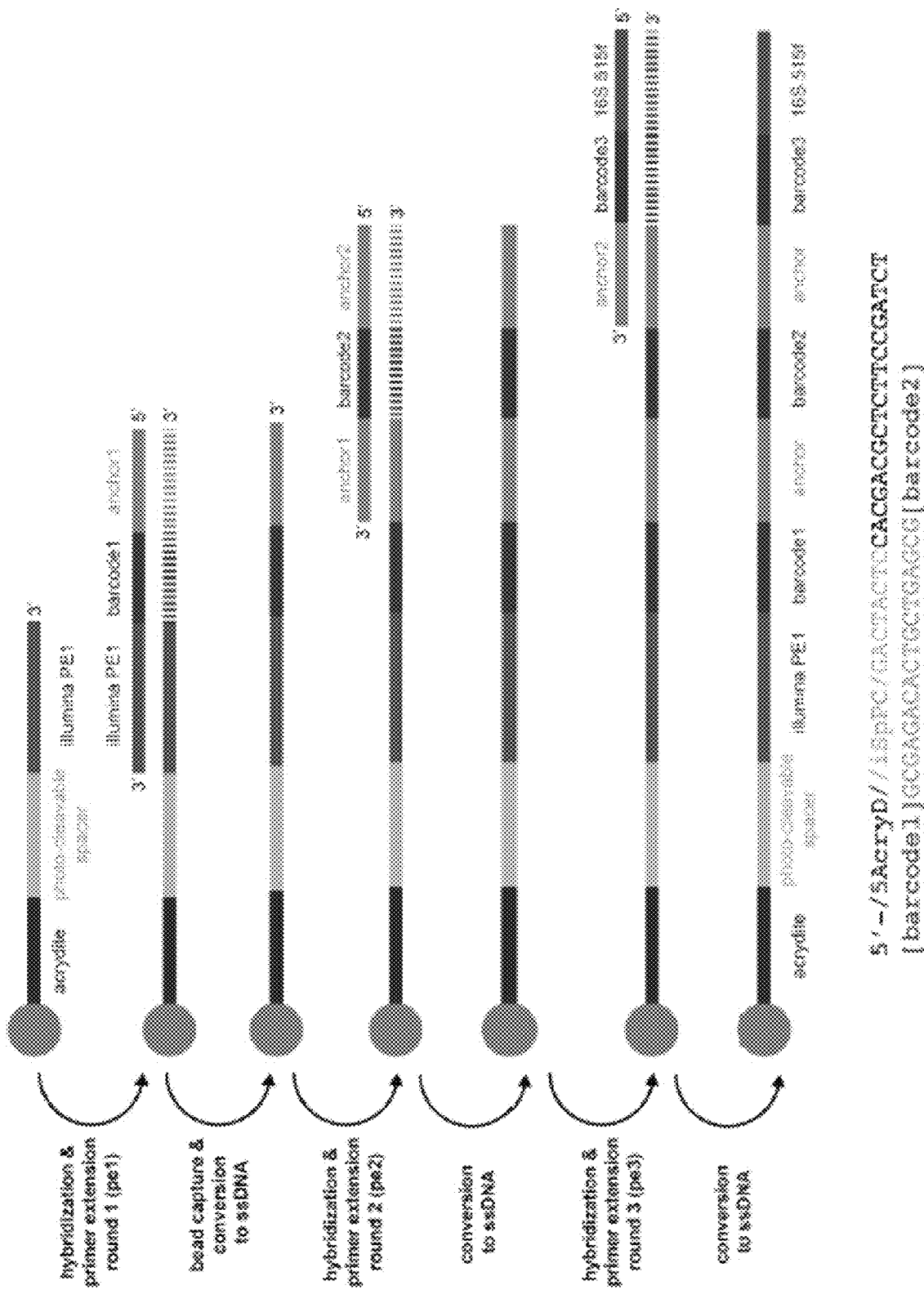

SPATIAL METAGENOMIC CHARACTERIZATION OF MICROBIAL BIOGEOGRAPHY

CROSS REFERENCE TO RELATED APPLICATION

This application claims priority to U.S. Provisional Application No. 62/648,716 filed on Mar. 27, 2018, which is incorporated herein by reference in its entirety.

GOVERNMENT LICENSE RIGHTS

This invention was made with government support under OD009172 and AI132403 awarded by the National Institutes of Health. The government has certain rights in the invention.

SEQUENCE LISTING

This application contains a Sequence Listing which is being submitted electronically in ASCII format and is hereby incorporated by reference in its entirety. Said ASCII copy, created on Jul. 13, 2022, is named 38837-202_SEQUENCE-LISTING_ST25.txt and is 122,158 bytes in size.

FIELD OF THE INVENTION

The present invention provides for a method to determine the micron-scale spatial co-localization of genomic material within a 3-dimensional sample by microdroplet encapsulation and high-throughput sequencing of fractionations of microclusters from the sample.

BACKGROUND OF THE INVENTION

The local spatial organization of the gut microbiome influences a variety of ecological properties, including colonization (see Lee, S. M. et al. Bacterial colonization factors control specificity and stability of the gut microbiota. Nature 1-6 (2013). doi:10.1038/nature12447; Pereira, F. C. & Berry, D. Microbial nutrient niches in the gut. Environ Microbiol 19, 1366-1378 (2017); Donaldson, G. P. et al. Gut microbiota utilize immunoglobulin A for mucosal colonization. Science 360, 795-800 (2018); Whitaker, W. R., Shepherd, E. S. & Sonnenburg, J. L. Tunable Expression Tools Enable Single-Cell Strain Distinction in the Gut Microbiome. Cell 169, 538-546.e12 (2017)), metabolism (see Nagara, Y., Takada, T., Nagata, Y., Kado, S. & Kushiro, A. Microscale spatial analysis provides evidence for adhesive monopolization of dietary nutrients by specific intestinal bacteria. PLoS ONE 12, e0175497 (2017)), host-microbe and inter-microbial interactions (see Wexler, A. G. et al. Human symbionts inject and neutralize antibacterial toxins to persist in the gut. Proc. Natl. Acad. Sci. U.S.A. 201525637-6 (2016). doi:10.1073/pnas.1525637113) and community stability (see Reichenbach, T., Mobilia, M. & Frey, E. Mobility promotes and jeopardizes biodiversity in rock—paper—scissors games. Nature 448, 1046-1049 (2007); Coyte, K. Z., Schluter, J. & Foster, K. R. The ecology of the microbiome: Networks, competition, and stability. Science 350, 663-666 (2015)). However, current microbiome profiling approaches such as metagenomic sequencing require homogenization of the input material and thus the physical destruction of any underlying spatial information. While imaging techniques could reveal useful spatial information, they rely on hybridization by short DNA probes of limited spectral diversity, yielding data with low taxonomic resolution and often requiring extensive empirical optimization (see Valm, A. M., Welch, J. L. M. & Borisy, G. G. CLASI-FISH: Principles of combinatorial labeling and spectral imaging. Systematic and Applied Microbiology 35, 496-502 (2012); Amann, R. & Fuchs, B. M. Single-cell identification in microbial communities by improved fluorescence in situ hybridization techniques. Nature Reviews Microbiology 6, 339-348 (2008)). Bacteria are also densely packed in communities, limiting identification and analysis of individual cells (see Mark Welch, J. L., Hasegawa, Y., McNulty, N. P., Gordon, J. I. & Borisy, G. G. Spatial organization of a model 15-member human gut microbiota established in gnotobiotic mice. Proc. Natl. Acad. Sci. U.S.A. 21, 201711596-E9114 (2017)). Imaging approaches can profile simple synthetic communities composed of a small number of cultivable species (see Geva-Zatorsky, N. et al. (2015); Whitaker, W. R., Shepherd, E. S. & Sonnenburg, J. L. (2017), but imaging techniques are challenging to scale to complex and diverse natural microbiomes. A direct and unbiased method for high-taxonomic resolution and micron-scale dissection of natural microbial biogeography is critically needed to mechanistically elucidate the role of the gut microbiome in health and disease.

In macroecology, plot sampling is used to study the spatial organization of large ecosystems, which are otherwise impractical to fully characterize. By surveying many smaller plots from a larger region, one can delineate local distributions of species and statistically infer fundamental properties of global community organization and function. The methods of the present invention provide a multiplexed sequencing technique that analyzes microbial cells in their native geographical context to statistically reconstruct the local spatial organization of the microbiome. Microbial colocalization can be shown in a variety of biological samples, including, soil, gut and biofilm. The methods of the present invention can determine which microbes are spatially associated with which other microbes and can comprise the following steps: (1) taking an intact sample and preserving its spatial structure via in-situ perfusion and polymerization of a chemical matrix, (2) processing that matrix by chemical or enzymatic steps, (3) fractioning the matrix into smaller microparticles, (4) capture each microparticle in emulsion droplets with unique molecular barcodes, (5) PCR amplification of said genetic material from microparticles in each droplet, (6) breaking up the droplets and pooling amplified material for next-generation sequencing measurements.

SUMMARY

The present disclosure provides for a method of determining the compositions/identities and/or abundances of organisms (e.g., microbes such as microbial identities and/or abundances) in a biological sample. The method may comprise: (a) immobilizing the biological sample in a matrix; (b) fracturing/breaking the matrix (that comprises the biological sample) into clusters; and (c) determining identities and/or abundances of microbes in the clusters.

The clusters (each cluster of the clusters) may comprise co-localized cells.

In step (c), the identities and/or abundances of organisms (e.g., microbes) may be determined by sequencing DNAs (e.g., genomic DNAs) and/or RNAs.

In step (c), the identities and/or abundances of organisms (e.g., microbes) may be determined by analyzing proteins, polypeptides, carbohydrates, and/or metabolites.

The matrix may be a gel matrix.

In step (a), the biological sample may be immobilized via perfusion and polymerization of the matrix.

The matrix may comprise a polymer, such as an acrylamide polymer.

The matrix may comprise a plurality of 16S ribosomal RNA (16S rRNA) (gene) amplification primers. The plurality of 16S rRNA amplification primers may be covalently linked to the matrix. The plurality of 16S rRNA (gene) amplification primers may be linked to the matrix through photocleavable linkers, such as acrydite linkers.

The method may further comprise step (d) processing the matrix by chemical or enzymatic means after step (a) or step (b). For example, step (d) may comprise lysing cells. The method may further comprise step (e) passing the clusters through a filter for size selection. After step (e), the clusters may have a median diameter ranging from about 1 μm to about 100 μm, from about 10 μm to about 50 μm, from about 1 μm to about 20 μm, from about 1 μm to about 50 μm, from about 10 μm to about 40 μm, from about 10 μm to about 80 μm, about 1 μm, about 5 μm, about 10 μm, about 20 μm, about 30 μm, about 40 μm, about 50 μm, about 60 μm, about 70 μm, about 80 μm, about 90 μm, about 100 μm, about 120 μm, about 150 μm, about 170 μm, about 200 μm, about 300 μm, about 400 μm, about 500 μm, about 600 μm, about 700 μm, about 80 μm, or about 900 μm.

The clusters may be microparticles.

In step (b), the matrix may be fractured through cryo-fracturing such as cryo-bead beating.

In step (c), identities and/or abundances of organisms (e.g., microbes) may be determined through droplet-based encapsulation.

The droplet-based encapsulation may be through co-encapsulating the clusters with beads in droplets (e.g., emulsion droplets), wherein each droplet comprises (consists essentially of, or consists of) a cluster and a bead, each bead comprising a unique molecular barcode.

The beads may comprise a plurality of 16S rRNA (gene) amplification primers. The plurality of 16S rRNA (gene) amplification primers linked to each bead may comprise a unique (and/or identical) molecular barcode.

The plurality of 16S rRNA (gene) amplification primers may be covalently linked to the beads.

The plurality of 16S rRNA (gene) amplification primers may be linked to the beads through photocleavable linkers, such as acrydite linkers.

The beads may comprise a polymer, such as an acrylamide polymer.

The droplet-based encapsulation may be through capturing the clusters in emulsion droplets comprising molecular barcodes, each emulsion droplet comprising identical molecular barcodes.

The (emulsion) droplets may have a diameter ranging from about 35 μm to about 45 μm, from about 1 μm to about 100 μm, from about 10 μm to about 50 μm, from about 1 μm to about 20 μm, from about 1 μm to about 50 μm, from about 10 μm to about 40 μm, or from about 10 μm to about 80 μm.

The method may further comprise step (f) cleaving the plurality of 16S rRNA (gene) amplification primers from the matrix and/or the beads.

The method may further comprise step (g) degrading the matrix. The matrix may be degraded through exposure to reducing conditions.

The method may further comprise step (h) polymerase chain reaction (PCR) amplification.

The sequencing/analysis may be deep sequencing or any sequencing or other techniques discussed herein or understood by a skilled artisan.

The biological sample may be obtained from a mammal. The biological sample may be obtained from a nervous system, a pulmonary system, a peripheral vascular system, a cardiovascular system, and/or a gastrointestinal system of a mammal. The biological sample may be obtained from the brain, a lung, a bronchus, an alveolus, an artery, a vein, a heart, an esophagus, a stomach, a small intestine, a large intestine, or combinations thereof.

The biological sample may be obtained from a tumor or may be a tumor sample.

The biological sample may be a soil sample, a gut sample, and/or a biofilm sample.

The biological sample may be an environmental sample.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4a-4h: Quality control of the MaP-seq technique by cluster mixing experiment. a) Schematic of the cluster mixing experiment; clusters containing either *E. coli* or homogenized fecal bacteria are prepared, mixed, and processed through the MaP-seq pipeline. b) Example of resulting distribution of read counts per identified unique barcode for the mixing experiment. A conservative threshold cutoff for considering real clusters is set as the total number reads divided by 2,500 (i.e., the number of clusters that were utilized as input during microfluidic encapsulation, and assuming an equal read distribution for each cluster). The calculated read cutoff (1,440 reads) is indicated by the red line, which results in 399 clusters for downstream analysis. The Y-axis is set to a maximum of 500 clusters for visualization purposes. c) Resulting raw data for the mixing experiment displayed as a cluster map; columns indicate the 399 clusters passing the read cutoff and rows indicate prevalent and abundant OTUs (OTUs present>2% relative abundance in >1% of all clusters). The *E. coli* OTU is the first row, while other rows represent fecal bacterial OTUs. The plot is arranged as in FIG. 2a, RA denotes relative abundance. d) An alternative visualization of FIG. 1b, plotting the fraction of reads in each cluster mapping to the spike-in *E. coli* OTU; most clusters show either entirely spike-in mapping reads or no spike-in mapping reads as expected. A small number of clusters show low levels of residual contamination; for this reason, a conservative relative abundance cutoff is used throughout downstream analysis (>2% relative abundance) to classify an OTU as present within a given cluster. e) Detection sensitivity of MaP-seq; the relative abundance of OTUs is compared to the proportion of clusters an OTU is detected in (with >2% relative abundance cutoff). Higher abundance OTUs display higher detection sensitivity as expected. f) Detection of significant pairwise associations in the cluster mixing experiment. The two communities contain defined spatial associations; the fecal bacteria are expected to be positively associated with each other, whereas the fecal bacteria should be negatively associated with *E. coli*. Association analysis was conducted in the same manner as FIG. 1d; the fecal bacteria are found to be strongly associated and negatively associated with *E. coli* as expected. The associations are much stronger than observed in the murine gut (i.e. note that the color map scale spans a larger range this plot). g-h) To confirm technical reproducibility across different experiments and particles sizes, the cluster mixing experiment was repeated but with particles of ~20 μm median size. Fecal bacteria constituted one community and *Sporocarcina pasteurii*, an environmental taxa constituted a second community. g) is analyzed as in FIGS. 1b and h) as in FIG. 1c. This revealed low mixing rates (1.65% mixed), negligible contamination (<0.003% of reads) and good correlation to bulk 16S sequencing (Pearson correlation r=0.72), confirming technical reproducibility of the technique across different experiments and particle sizes.

FIGS. 12a-12b: Barcoded bead synthesis schematic. a) Beads are synthesized via a three-step split-and-pool synthesis approach, resulting in 96 (see Cordero, 0. X. & Datta, M. S. Microbial interactions and community assembly at microscales. Current Opinion in Microbiology 31, 227-234 (2016)) or 884,736 possible unique barcodes. The three sets of primers are denoted primer extension sets 1-3 (i.e. pe1, pe2, and pe3). b) Extension strategy utilized for bead synthesis. A primer is linked to the gel bead via an acrydite linker and also contains a photocleavable linker group. Barcoded primers are hybridized to this linked primer and serve as an extension template for adding barcodes to the bead-linked primers. After each round, the extension template primer is stripped, and the next round of extension is performed. The sequence of the final primer product is indicated at the bottom.

DETAILED DESCRIPTION

Figure 1A:
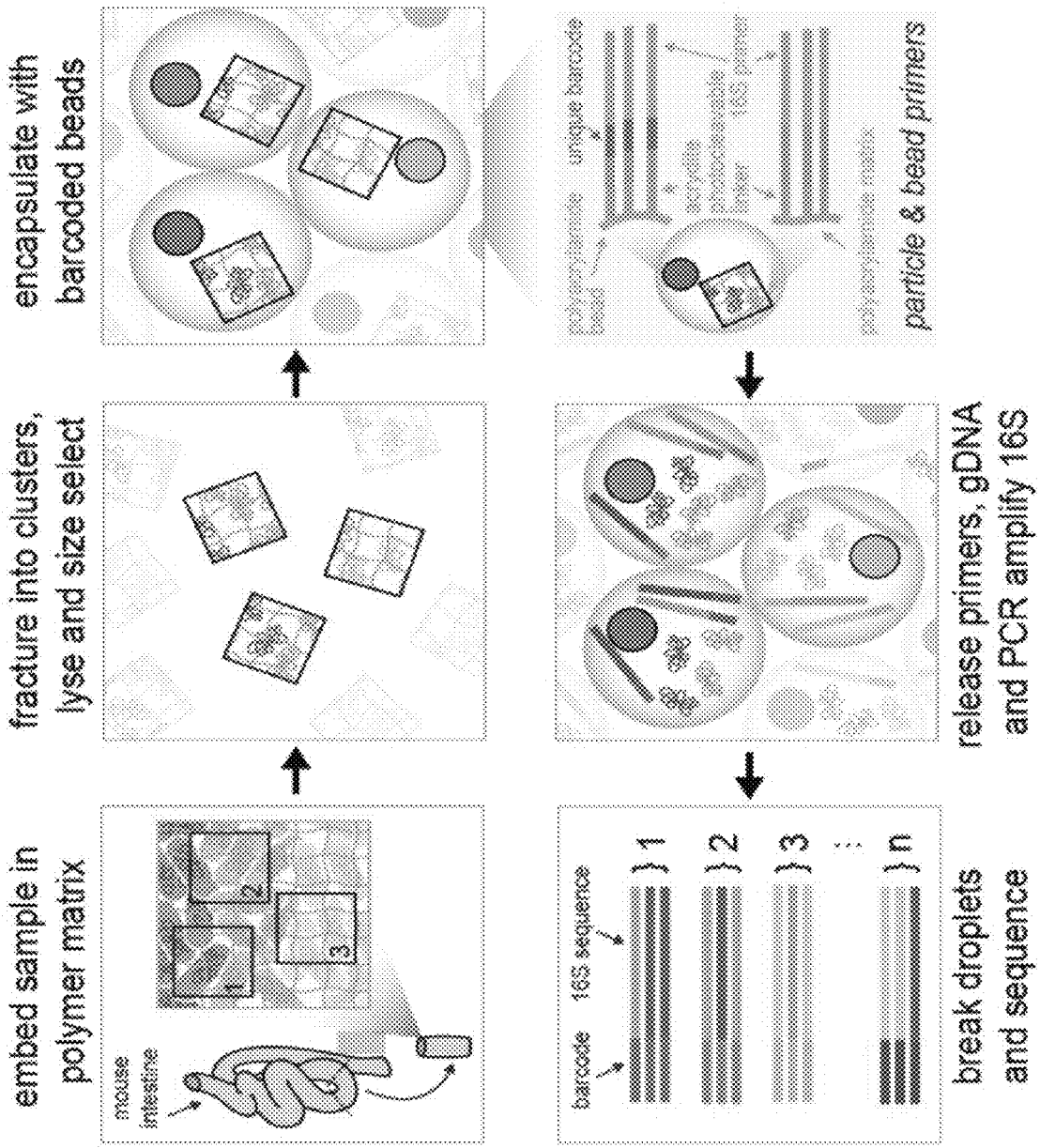
FIGS. 1a-1c: Metagenomic Plot-sampling by sequencing (MaP-seq) and quality control. a) Schematic of the MaP-seq technique for micron-scale plot-sampling of microbiome samples. b) MaP-seq profiling of a mixture of clusters prepared from homogenized fecal bacteria or *E. coli*. The number of reads (k, thousands of reads) for each barcode (of 399 total) belonging to either the *E. coli* OTU or fecal OTUs is displayed as a scatter plot; blue dots: *E. coli* cluster, red dots: fecal cluster, purple dots: mixed cluster. c) Correlation between OTU relative abundance (RA) measurements obtained by standard bulk 16S sequencing of the same homogenized fecal community compared to MaP-seq OTU RA measurements averaged across individual homogenized fecal clusters (162 total, clusters with <10% *E. coli* reads); all RA are plotted on log 10 scale, only OTUs with greater than 0.01% RA are displayed, r indicates Pearson correlation.

The methods and systems of the present disclosure provide a Metagenomic Plot-sampling by sequencing (MaP-seq), a multiplexed sequencing technique that analyzes microbial cells in their native geographical context to statistically reconstruct the local spatial organization of the microbiome (FIG. 1a). To perform MaP-seq, an input sample is first physically fixed by immobilizing the microbiota via perfusion and in situ polymerization of an acrylamide polymer matrix that also contains a covalently linked reverse 16S rRNA amplification primer. The embedded sample is then fractured via cryo-bead beating, subjected to cell lysis, and passed through nylon mesh filters for size selection to yield cell clusters or particles of desired and tunable physical sizes (i.e., by utilizing different mesh filter sizes). Resulting clusters contain genomic DNA immobilized in their original arrangement, preserving local spatial information. Next, a microfluidic device is used to co-encapsulate these clusters with gel beads, each containing uniquely barcoded forward 16S rRNA amplification primers. Primers are photocleaved from the beads and clusters, genomic DNA is released from clusters by triggered degradation of the polymer matrix within droplets, and PCR amplification of the 16S V4 region is performed. Droplets are then broken apart, and the resulting library is subjected to deep sequencing. Sequencing reads are filtered and grouped by their unique barcodes, which yield the identity and abundance of bacterial operational taxonomic units (OTUs) within individual cell clusters.

The present disclosure provides for a method of determining the compositions/identities and/or abundances of organisms (e.g., microbes such as microbial identities and/or abundances) in a biological sample. The method may comprise: (a) immobilizing the biological sample in a matrix; (b) fracturing/breaking the matrix (that comprises the biological sample) into clusters; and (c) determining identities and/or abundances of microbes in the clusters.

The clusters (each cluster of the clusters) may comprise co-localized cells.

In step (c), the identities and/or abundances of organisms (e.g., microbes) may be determined by sequencing DNAs (e.g., genomic DNAs) and/or RNAs.

In step (c), the identities and/or abundances of organisms (e.g., microbes) may be determined by analyzing proteins, polypeptides, carbohydrates, and/or metabolites.

The matrix may be a gel matrix.

In step (a), the biological sample may be immobilized via perfusion and polymerization of the matrix.

The matrix may comprise a polymer, such as an acrylamide polymer.

The matrix may comprise a plurality of 16S ribosomal RNA (16S rRNA) (gene) amplification primers. The plurality of 16S rRNA amplification primers may be covalently linked to the matrix. The plurality of 16S rRNA (gene) amplification primers may be linked to the matrix through photocleavable linkers, such as acrydite linkers.

The method may further comprise step (d) processing the matrix by chemical or enzymatic means after step (a) or step (b). For example, step (d) may comprise lysing cells. The method may further comprise step (e) passing the clusters through a filter for size selection. After step (e), the clusters may have a median diameter ranging from about 1 μm to about 100 μm, from about 10 μm to about 50 μm, from about 1 μm to about 20 μm, from about 1 μm to about 50 μm, from about 10 μm to about 40 μm, from about 10 μm to about 80 μm, about 1 μm, about 5 μm, about 10 μm, about 20 μm, about 30 μm, about 40 μm, about 50 μm, about 60 μm, about 70 μm, about 80 μm, about 90 μm, about 100 μm, about 120 μm, about 150 μm, about 170 μm, about 200 μm, about 300

µm, about 400 µm, about 500 µm, about 600 µm, about 700 µm, about 80 µm, or about 900 µm.

The clusters may be microparticles.

In step (b), the matrix may be fractured through cryo-fracturing such as cryo-bead beating.

In step (c), identities and/or abundances of organisms (e.g., microbes) may be determined through droplet-based encapsulation.

The droplet-based encapsulation may be through co-encapsulating the clusters with beads in droplets (e.g., emulsion droplets), wherein each droplet comprises (consists essentially of, or consists of) a cluster and a bead, each bead comprising a unique molecular barcode.

The beads may comprise a plurality of 16S rRNA (gene) amplification primers. The plurality of 16S rRNA (gene) amplification primers linked to each bead may comprise a unique (and/or identical) molecular barcode.

The plurality of 16S rRNA (gene) amplification primers may be covalently linked to the beads.

The plurality of 16S rRNA (gene) amplification primers may be linked to the beads through photocleavable linkers, such as acrydite linkers.

The beads may comprise a polymer, such as an acrylamide polymer.

The droplet-based encapsulation may be through capturing the clusters in emulsion droplets comprising molecular barcodes, each emulsion droplet comprising identical molecular barcodes.

The (emulsion) droplets may have a diameter ranging from about 35 µm to about 45 µm, from about 1 µm to about 100 µm, from about 10 µm to about 50 µm, from about 1 µm to about 20 µm, from about 1 µm to about 50 µm, from about 10 µm to about 40 µm, or from about 10 µm to about 80 µm.

The method may further comprise step (f) cleaving the plurality of 16S rRNA (gene) amplification primers from the matrix and/or the beads.

The method may further comprise step (g) degrading the matrix. The matrix may be degraded through exposure to reducing conditions.

The method may further comprise step (h) polymerase chain reaction (PCR) amplification.

The sequencing/analysis may be deep sequencing, or any sequencing or other techniques discussed herein or understood by a skilled artisan.

The biological sample may be obtained from a mammal. The biological sample may be obtained from a nervous system, a pulmonary system, a peripheral vascular system, a cardiovascular system, and/or a gastrointestinal system of a mammal. The biological sample may be obtained from the brain, a lung, a bronchus, an alveolus, an artery, a vein, a heart, an esophagus, a stomach, a small intestine, a large intestine, or combinations thereof.

The biological sample may be obtained from a tumor or may be a tumor sample.

The biological sample may be a soil sample, a gut sample, and/or a biofilm sample.

The biological sample may be an environmental sample.

The present nucleic acids (e.g., primers such as 16S rRNA amplification primers) may or may not comprise barcode elements (e.g., a unique molecular barcode for each bead). Barcode elements may be used as identifiers for a cluster and may indicate the presence of one or more specific sequences in a cluster (e.g., DNA or RNA). Members of a set of barcode elements have a sufficiently unique nucleic acid sequence such that each barcode element is readily distinguishable from the other barcode elements of the set. Barcode elements may be of any length of nucleotides, e.g., 1, 2, 3, 4, 5, 6, 7, 8, 9, 10, 11, 12, 13, 14, 15, 16, 17, 18, 19, 20, 21, 22, 23, 25, 26, 27, 28, 29, 30 or more nucleotides in length. Detecting barcode elements and determining the nucleic acid sequence of a barcode element or plurality of barcode elements are used to determine the presence of an associated DNA or RNA element. Barcode elements can be detected by any method known in the art, including sequencing or microarray methods.

In one embodiment, barcoded primers are constructed via a split-and-pool primer extension strategy with 1, 2, 3, 4, 5, 6, 7, 8, 9, 10 or more barcode extension rounds. Klein, A. M. et al. Droplet Barcoding for Single-Cell Transcriptomics Applied to Embryonic Stem Cells. Cell 161, 1187-1201 (2015). Bose, S. et al. Scalable microfluidics for single-cell RNA printing and sequencing. Genome Biology 1-16 (2015). doi:10.1186/s13059-015-0684-3.

Microbial identities and/or abundances, or specific changes in microbiome or microbiota discussed herein can be detected using various methods, including, without limitation, quantitative PCR or high-throughput sequencing methods which detect over- and under-represented genes in the total bacterial population (e.g., 454-sequencing for community analysis; screening of microbial 16S ribosomal RNAs (16S rRNA), etc.), or transcriptomic or proteomic studies that identify lost or gained microbial transcripts or proteins within total bacterial populations. See, e.g., U.S. Patent Publication No. 2010/0074872; Eckburg et al., Science, 2005, 308:1635-8; Costello et al., Science, 2009, 326:1694-7; Orrice et al., Science, 2009, 324:1190-2; Li et al., Nature, 2010, 464: 59-65; Bjursell et al., Journal of Biological Chemistry, 2006, 281:36269-36279; Mahowald et al., PNAS, 2009, 14:5859-5864; Wikoff et al., PNAS, 2009, 10:3698-3703.

The composition/identities and abundance of the established microbiota can be studied by sequencing the 16S ribosomal RNA (or 16S rRNA) gene of a sample. 16S rRNA is a component of the 30S small subunit of prokaryotic ribosomes.

In additional embodiments, the determining step involves screening bacterial 16S rRNA genes using PCR.

The DNA library may be a genomic DNA or metagenomic library. A metagenomic library is a collection of the genomic DNAs of a mixture of organisms, such as a mixture of microbes.

The present method may or may not comprise a step of processing the matrix by chemical or enzymatic means after or before any suitable step, including, but not limited to, cell lysis, addition of a detergent or surfactant, addition of protease, addition of RNase, alcohol precipitation (e.g., ethanol precipitation, or isopropanol precipitation), salt precipitation, organic extraction (e.g., phenol-chloroform extraction), solid phase extraction, silica gel membrane extraction, CsCl gradient purification.

Photocleavable linkers may be cleaved by UV light. Photocleavable linkers may be a photocleavable oligonucleotide. Photocleavable linkers may be o-nitrobenzyl derivatives (Zhao et al. 2012: o-nitrobenzyl alcohol derivatives). U.S. Patent Publication No. 20080227742.

Sequencing

DNA may be amplified via polymerase chain reaction (PCR) before being sequenced.

The present method may comprise a step of analyzing DNA or RNA by sequencing or by microarray analysis. It should be appreciated that any suitable means of determining DNA sequence may be used in the present method.

The DNA may be sequenced using vector-based primers; or a specific gene is sought by using specific primers. PCR and sequencing techniques are well known in the art; reagents and equipment are readily available commercially.

Non-limiting examples of sequencing methods include Sanger sequencing or chain termination sequencing, Maxam-Gilbert sequencing, capillary array DNA sequencing, thermal cycle sequencing (Sears et al., Biotechniques, 13:626-633 (1992)), solid-phase sequencing (Zimmerman et al., Methods Mol. Cell Biol., 3:39-42 (1992)), sequencing with mass spectrometry such as matrix-assisted laser desorption/ionization time-of-flight mass spectrometry (MALDI-TOF/MS; Fu et al., Nat. Biotechnol., 16:381-384 (1998)), and sequencing by hybridization (Chee et al., Science, 274:610-614 (1996); Drmanac et al., Science, 260: 1649-1652 (1993); Drmanac et al., Nat. Biotechnol., 16:54-58 (1998)), NGS (next-generation sequencing) (Chen et al., Genome Res. 18:1143-1149 (2008); Srivatsan et al. PloS Genet. 4:e1000139 (2008)), Polony sequencing (Porreca et al., Curr. Protoc. Mol. Biol. Chp. 7; 7.8 (2006), ion semiconductor sequencing (Elliott et al., J. Biomol Tech. 1:24-30 (2010), DNA nanoball sequencing (Kaji et al., Chem Soc Rev 39:948-56 (2010), single-molecule real-time sequencing (Flusberg et al., Nat. Methods 6:461-5 (2010), sequencing by synthesis (e.g., Illumina/Solexa sequencing), sequencing by ligation, sequencing by hybridization, nanopore DNA sequencing (Wanunu, Phys Life Rev 9:125-58 (2012), massively Parallel Signature Sequencing (MPSS); pyro sequencing, SOLiD sequencing (McKeman et al. 2009 Genome Res 19:1527-1541; Shearer et al. 2010 Proc Natl Acad Sci USA 107:21104-21109); shortgun sequencing; Heliscope single molecule sequencing; single molecule real time (SMRT) sequencing. U.S. Patent Publication No. 20140329705.

High-throughput sequencing, next-generation sequencing (NGS), and/or deep-sequencing technologies include, but are not limited to, Illumina/Solex sequencing technology (Bentley et al. 2008 Nature 456:53-59), Roche/454 (Margulies et al. 2005 Nature 437:376-380), Pacbio (Flusberg et al. 2010 Nature methods 7:461-465; Korlach et al. 2010 Methods in enzymology 472:431-455; Schadt et al. 2010 Nature reviews. Genetics 11:647-657; Schadt et al. 2010 Human molecular genetics 19:R227-240; Eid et al. 2009 Science 323:133-138; Imelfort and Edwards, 2009 Briefings in bioinformatics 10:609-618), Ion Torrent (Rothberg et al. 2011 Nature 475:348-352)) and more. For example, Polony technology utilizes a single step to generate billions of "distinct clones" for sequencing. As another example, ion-sensitive field-effect transistor (ISFET) sequencing technology provides a non-optically based sequencing technique. U.S. Patent Publication No. 20140329712.

Several methods of DNA analysis are encompassed in the present disclosure. As used herein "deep sequencing" indicates that the depth of the process is many times larger than the length of the sequence under study. Deep sequencing is encompassed in next generation sequencing methods which include but are not limited to single molecule realtime sequencing (Pacific Bio), Ion semiconductor (Ion torrent sequencing), Pyrosequencing (454), Sequencing by synthesis (lilumina), Sequencing by ligations (SOLID sequencing) and Chain termination (Sanger sequencing).

Sequencing reads may be first subjected to quality control to identify overrepresented sequences and low-quality ends. The start and/or end of a read may or may not be trimmed. Sequences mapping to the genome may be removed and excluded from further analysis. As used herein, the term "read" refers to the sequence of a DNA fragment obtained after sequencing. In certain embodiments, the reads are paired-end reads, where the DNA fragment is sequenced from both ends of the molecule.

The level of the DNA or RNA (e.g., mRNA) molecules may be determined/detected using routine methods known to those of ordinary skill in the art. The level of the nucleic acid molecule may be determined/detected by nucleic acid hybridization using a nucleic acid probe, or by nucleic acid amplification using one or more nucleic acid primers.

Nucleic acid hybridization can be performed using Southern blots, Northern blots, nucleic acid microarrays, etc.

Nucleic acid microarray technology, which is also known as DNA chip technology, gene chip technology, and solid-phase nucleic acid array technology, may be based on, but not limited to, obtaining an array of identified nucleic acid probes on a fixed substrate, labeling target molecules with reporter molecules (e.g., radioactive, chemiluminescent, or fluorescent tags such as fluorescein, Cye3-dUTP, or Cye5-dUTP, etc.), hybridizing target nucleic acids to the probes, and evaluating target-probe hybridization. Jackson et al. (1996) Nature Biotechnology, 14: 1685-1691. Chee et al. (1995) Science, 274: 610-613.

The sensitivity of the assays may be enhanced through use of a nucleic acid amplification system that multiplies the target nucleic acid being detected.

Nucleic acid amplification assays include, but are not limited to, the polymerase chain reaction (PCR), reverse transcription polymerase chain reaction (RT-PCR), real-time RT-PCR, quantitative RT-PCR, etc.

Measuring or detecting the amount or level of mRNA in a sample can be performed in any manner known to one skilled in the art and such techniques for measuring or detecting the level of an mRNA are well known and can be readily employed. A variety of methods for detecting mRNAs have been described and may include, Northern blotting, microarrays, real-time PCR, RT-PCR, targeted RT-PCR, in situ hybridization, deep-sequencing, single-molecule direct RNA sequencing (RNAseq), bioluminescent methods, bioluminescent protein reassembly, BRET (bioluminescence resonance energy transfer)-based methods, fluorescence correlation spectroscopy and surface-enhanced Raman spectroscopy (Cissell, K. A. and Deo, S. K. (2009) Anal. Bioanal. Chem., 394:1109-1116).

The methods of the present invention may include the step of reverse transcribing RNA when assaying the level or amount of an mRNA.

Sequencing reads (e.g., the quality-corrected reads) may be mapped onto the genome of the microbe using any alignment algorithms known in the art. Non-limiting examples of such mapping algorithms include Bowtie; Bowtie2 (Langmead et al. 2009; Langmead et al., Fast gapped-read alignment with Bowtie 2. Nature methods 9(4), 357-9 (2012); Burrows-Wheeler Aligner (BWA, see, Li et al: Fast and accurate long-read alignment with Burrows-Wheeler transform. Bioinformatics, 26(5), 589-95 (2010)); SOAP2 (Li et al., SOAP2: an improved ultrafast tool for short read alignment. Bioinformatics, 25(15), 1966-7 (2009)); GATK; SMRA; PINDEL; SNAP (Zaharia et al., Faster and More Accurate Sequence Alignment with SNAP, arXiv:1111.5572 (2011)]; TMAP1-4; SMALT; and Masai (Siragusa et al., Fast and sensitive read mapping with approximate seeds and multiple backtracking. CoRR abs/1208.4238 (2012)). A recent overview of the alignment algorithms can be found in Li et al., A survey of sequence alignment algorithms for next-generation sequencing. Briefings in Bioinformatics 2010, 11(5), 473-483. U.S. Patent Publication Nos. 20140214334, 20140108323 and 20140315726.

Mathematical algorithms that can be used for alignment also include, the algorithm of Myers and Miller (1988) CABIOS 4:11-17; the local alignment algorithm of Smith et al. (1981) Adv. Appl. Math. 2:482; the global alignment algorithm of Needleman and Wunsch (1970) J. Mol. Biol. 48:443-453; the search-for-local alignment method of Pearson and Lipman (1988) Proc. Natl. Acad. Sci. 85:2444-2448; the algorithm of Karlin and Altschul (1990) Proc. Natl. Acad. Sci. USA 872264, modified as in Karlin and Altschul (1993) Proc. Natl. Acad. Sci. USA 90:5873-5877. Computer implementations of these mathematical algorithms can be utilized for comparison of sequences to determine optimum alignment. Such implementations include, but are not limited to: CLUSTAL in the PC/Gene program (available from Intelligenetics, Mountain View, Calif); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) Gene 73:237-244 (1988); Higgins et al. (1989) CABIOS 5:151-153; Corpet et al. (1988) Nucleic Acids Res. 16:10881-90; Huang et al. (1992) CABIOS 8:155-65; and Pearson et al. (1994) Meth. Mol. Biol. 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) J. Mol. Biol. 215:403 are based on the algorithm of Karlin and Altschul (1990) supra. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. In another embodiment, GSNAP (Thomas D. Wu, Serban Nacu "Fast and SNP-tolerant detection of complex variants and splicing in short reads. Bioinformatics. 2010 Apr. 1; 26(7):873-81. 2010) can also be used.

Algorithms and parameters for alignment can be adjusted depending on the type of bacteria selected, the type of target sequence being characterized, etc.

Mapped reads may be post-processed by removing PCR duplicates (multiple, identical reads), etc.

Organisms

The organism may be a eukaryotic organism, including human and non-human eukaryotic organisms. The organism may be a multicellular eukaryotic organism. The organism may be an arthropod such as an insect. The organism also may be a plant or a fungus. The organism may be prokaryotic.

In one embodiment, the cell is a mammalian cell, such as a human cell. Human cells may include human embryonic kidney cells (e.g., HEK293T cells), human dermal fibroblasts, human cancer cells, etc.

In another embodiment, the cell is a yeast cell. The organism may be a yeast. In yet another embodiment, the cell is a bacterial cell. The organism may be bacteria.

Molecular Biology

In accordance with the present invention, there may be numerous tools and techniques within the skill of the art, such as those commonly used in molecular immunology, cellular immunology, pharmacology, and microbiology. See, e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

As used herein, the term "isolated" and the like means that the referenced material is free of components found in the natural environment in which the material is normally found. In particular, isolated biological material is free of cellular components. In the case of nucleic acid molecules, an isolated nucleic acid includes a PCR product, an isolated mRNA, a cDNA, an isolated genomic DNA, or a restriction fragment. In another embodiment, an isolated nucleic acid is preferably excised from the chromosome in which it may be found. Isolated nucleic acid molecules can be inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated material may be, but need not be, purified.

The term "purified" and the like as used herein refers to material that has been isolated under conditions that reduce or eliminate unrelated materials, i.e., contaminants. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

The terms "expression profile" or "gene expression profile" refers to any description or measurement of one or more of the genes that are expressed by a cell, tissue, or organism under or in response to a particular condition. Expression profiles can identify genes that are up-regulated, down-regulated, or unaffected under particular conditions. Gene expression can be detected at the nucleic acid level or at the protein level. The expression profiling at the nucleic acid level can be accomplished using any available technology to measure gene transcript levels. For example, the method could employ in situ hybridization, Northern hybridization or hybridization to a nucleic acid microarray, such as an oligonucleotide microarray, or a cDNA microarray. Alternatively, the method could employ reverse transcriptase-polymerase chain reaction (RT-PCR) such as fluorescent dye-based quantitative real time PCR (TaqMan® PCR). In the Examples section provided below, nucleic acid expression profiles were obtained using Affymetrix GeneChip® oligonucleotide microarrays. The expression profiling at the protein level can be accomplished using any available technology to measure protein levels, e.g., using peptide-specific capture agent arrays.

The terms "gene signature" and "signature genes" will be used interchangeably herein and mean the particular transcripts that have been found to be differentially expressed in some prostate cancer patients.

The terms "gene", "gene transcript", and "transcript" are used interchangeably in the application. The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. "Transcript" or "gene transcript" is a sequence of RNA produced by transcription of a particular gene. Thus, the expression of the gene can be measured via the transcript.

The term "genomic DNA" as used herein means all DNA from a subject including coding and non-coding DNA, and DNA contained in introns and exons.

The term "nucleic acid hybridization" refers to anti-parallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid).

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include, but are not limited to, plasmids, phages, and viruses.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA which codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct" or "gene construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

"Nucleic acid" refers to deoxyribonucleotides or ribonucleotides and polymers thereof in either single- or double-stranded form. The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, and carbamates) and with charged linkages (e.g., phosphorothioates, and phosphorodithioates). Polynucleotides may contain one or more additional covalently linked moieties, such as, for example, proteins (e.g., nucleases, toxins, antibodies, signal peptides, and poly-L-lysine), intercalators (e.g., acridine, and psoralen), chelators (e.g., metals, radioactive metals, iron, and oxidative metals), and alkylators. The polynucleotides may be derivatized by formation of a methyl or ethyl phosphotriester or an alkyl phosphoramidate linkage. Modifications of the ribose-phosphate backbone may be done to facilitate the addition of labels, or to increase the stability and half-life of such molecules in physiological environments. Nucleic acid analogs can find use in the methods of the invention as well as mixtures of naturally occurring nucleic acids and analogs. Furthermore, the polynucleotides herein may also be modified with a label capable of providing a detectable signal, either directly or indirectly. Exemplary labels include radioisotopes, fluorescent molecules, and biotin.

The term "polypeptide" as used herein means a compound of two or more amino acids linked by a peptide bond. "Polypeptide" is used herein interchangeably with the term "protein."

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Tissue Fixation/Immobilization of Sample

In one embodiment, a tissue section is fixed and embedded in a gel matrix by in situ perfusion and acrylamide polymerization. Other methods of tissue fixation include using methyl methacrylate and glycol methacrylate, also referred to as Technovit® (emsdiasum.com/microscopy/technical/datasheet/14654 immunohistochemistry.aspx, retrieved, Mar. 26, 2019; see also, Hasegawa et al. Preservation of three-dimensional spatial structure in the gut microbiome, biorxiv.org/content/biorxiv/early/2017/08/11/175224.full.pdf, retrieved, Mar. 26, 2019). Tissues can also be fixed using a combination of sodium acrylate, a monomer used to produce superabsorbent materials, along with the comonomer acrylamide and the crosslinker N—N'-methylenebisacrylamide such as that used with expansion microscopy. Chen et al. Expansion Microscopy Science 347 (6221):543-548 (2015). Other techniques for tissue fixation, include nanoporous hydrogel-fixation, also referred to as CLARITY. Chung et al. Structural and molecular interrogation of intact biological systems. Nature 497:332-337 (2013).

Metagenomic Plot Sampling by Sequencing (MaP-Seq)

MaP-seq was applied to the mouse colonic microbiome. The methods and systems of the present invention could be applied to any structural, anatomic system, including, but not limited to the brain (central nervous system), the pulmonary system (the lungs, bronchi and alveoli), the genitouringary tract, including, but not limited to the kidneys, ureters, bladder, urethra, ovaries, testicles, prostate, penis and vagina, the peripheral vascular and cardiovascular systems, including, but not limited to the arteries (coronary, pulmonary, aorta, femoral, carotid, basilar), veins (pulmonary, vena cava, femoral), heart (left ventricle, right ventricle, left atrium, right atrium), the gastrointestinal system such as the esophagus, stomach (including, but not limited to the fundus and pyloric valve), the liver, gall balder, small intestines (ileum and jejunum), large intestines (colon), the eye and the skin. The methods and systems of the present invention could be applied to any mammalian or non-mammalian species, including, but not limited to, rats, mice, canines, felines, cows, sheep, horses, goats, birds, humans (cadaver material), reptiles and fish.

The methods and systems of the present invention could also be applied to any three-dimensional structure such as a solid tumor of any organ, including, but not limited to, bladder, bone, colon, esophagus, salivary glands, kidney, lung, Central Nervous System, Neuroendocrine System, ovaries, prostate, testicles, soft tissue and skin.

The methods and systems of the present invention could also be applied to biofilms.

Figure 2A:
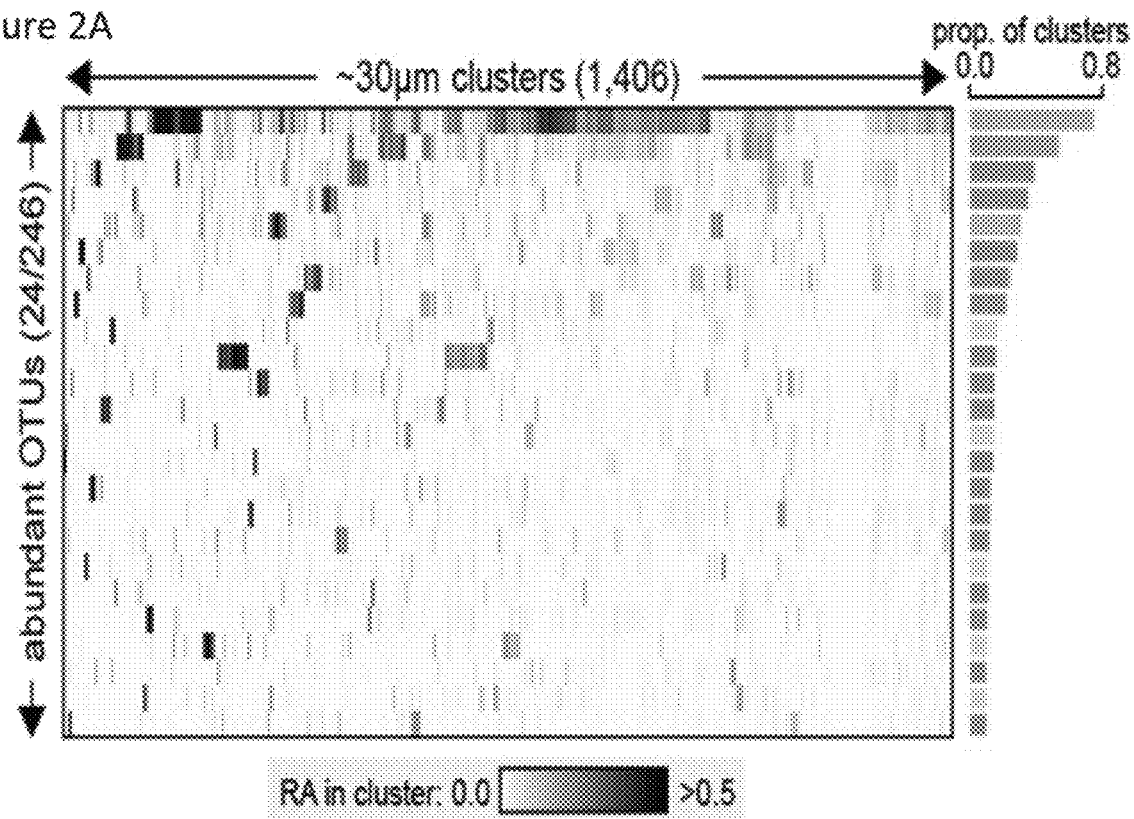
FIGS. 2a-2d: Spatial organization of the mouse distal colon microbiota. a) MaP-seq profiling of ~30 μm median diameter distal colon clusters. Raw relative abundance (RA) data from MaP-seq is displayed as a heatmap; columns represent individual clusters (of 1,406), and rows represent abundant and prevalent OTUs (>2% RA in >10% of all clusters; 24 of 246 detected OTUs) aggregated from two technical replicate datasets of the same sample. Shading denotes the RA of individual OTUs in each cluster (linear scale); OTUs are sorted by decreasing prevalence (proportion of clusters OTU is >2% RA), and clusters are clustered by Euclidean distance. The prevalence of each OTU across clusters is displayed to the right as a bar plot, and each bar is colored by the OTUs assigned taxonomy at the family level (legend in d). b) Correlation between OTU RA measurements obtained by standard bulk 16S sequencing of the same sample compared to OTU prevalence across clusters as calculated in a); n.d. indicates not detected>2% RA in any clusters, only OTUs greater than 0.01% RA as measured by bulk 16S sequencing are displayed. c) Histogram of the number of OTUs per cluster (OTUs>2% RA), shown for homogenized fecal clusters which serve as a mixed control (red outline, 162 total) and distal colon clusters (grey, 1,406 total) of the same size. Dotted lines indicate median value for each group. d) For each abundant and prevalent OTU pair (OTUi,j) spatial associations were calculated, shading indicates log 2 odds ratio, x denotes statistically significant association (Fisher's exact test, p<0.05, FDR=0.05); colored boxes represent OTU taxonomy at the family level.
Figure 2B:
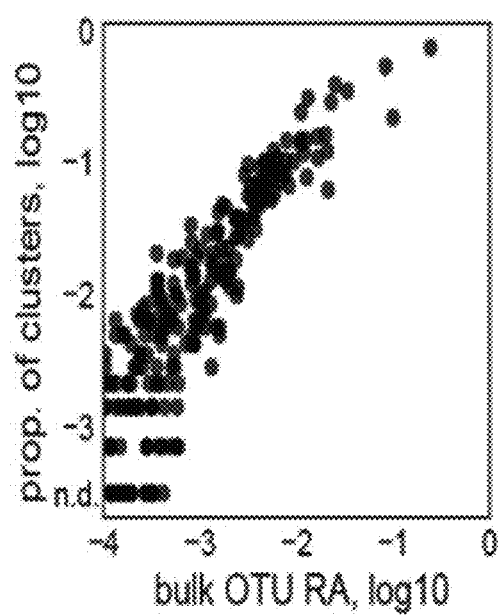
Figure 2C:
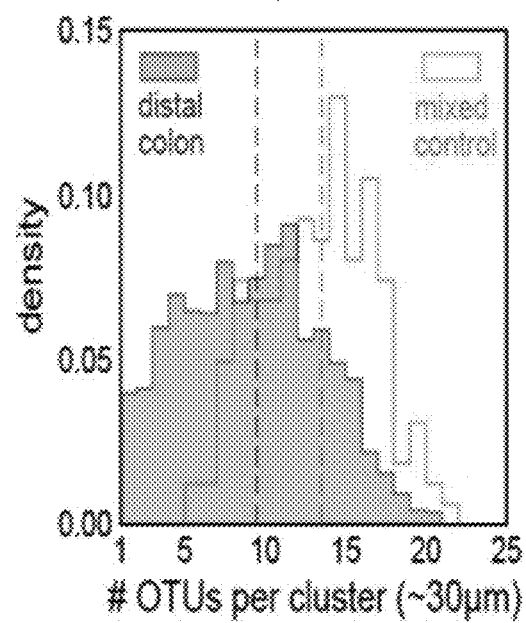
Figure 3A:
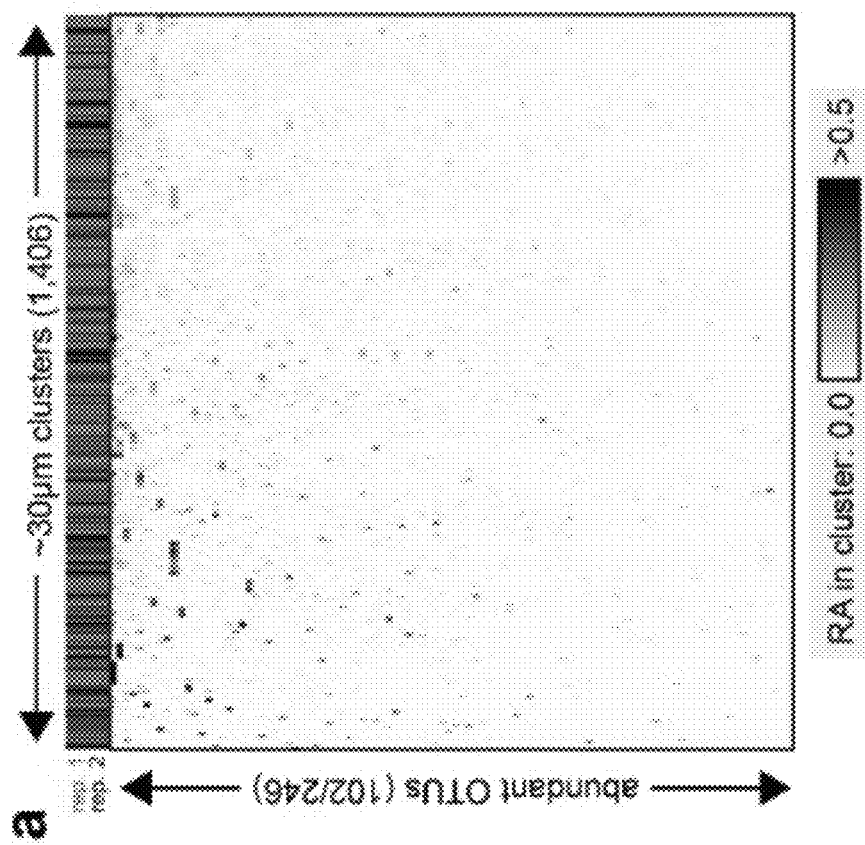
FIGS. 3a-3e: Spatial association detection and technical reproducibility. a) Expanded view of FIG. 2a; abundant and prevalent OTUs (>2% abundance in >1% of clusters) are displayed; the cluster map is organized as in FIG. 2a, RA denotes relative abundance. The column indicators on top indicate the technical replicate each cluster originated from (red, replicate 1; black, replicate 2). b) A volcano plot visualization of data from FIG. 2d; red dotted line indicates threshold for statistically significant associations (Fisher's exact test, p<0.05). c) Correlation between association detection utilizing raw or subsampled reads. Reads were subsampled for all clusters to the minimum read cutoff (717 reads) and association detection was performed as before. The resulting odds ratios of pairwise associations were highly correlated to those calculated from the raw reads (Pearson r=0.96). These results suggest that variable read counts for each cluster do not significantly alter detected associations (i.e. due to use of a 2% abundance threshold). d) Dependence of association detection on cluster sampling depth. The full dataset was subsampled, and the same association detection was performed. The number of significant associations detected is plotted; the line indicates the mean and error band indicates the standard deviation of ten iterations of subsampling. The number of significant associations detected linearly increases with the number of clusters sampled, implying even deeper cluster data collection could enable characterization of weaker associations between less abundant taxa. e) Technical reproducibility of association detection between the two technical replicate datasets of the same sample. Association detection was performed on each technical replicate, and the calculated odds ratio of association is plotted for all pairwise associations. For associations detected as significant in at least one of the two replicates, the sign of association is the same between both replicates for the majority of cases (64/74 associations). For associations detected as significant in both replicates (15 associations) the sign is the same in all cases. These results indicate good correspondence of detected microscopic spatial associations between technical replicates.

We generated and characterized cell clusters (~30 µm median diameter) from a segment of the distal colon (including both epithelium and digesta) of a mouse fed a plant-polysaccharide diet, yielding 1,406 clusters passing strict quality filtering across two technical replicates (FIG. 2a, FIG. 3a (Methods). Other cell cluster sizes are encompassed by the methods and systems of the invention, including, ~10 µm, ~20 µm, ~25 µm, ~35 µm, ~40 µm, ~50 µm, ~60 µm, ~70 µm, ~80 µm, ~90 µm or ~100 µm. Additional sizes range from ~100 µm to ~500 µm. 236 total OTUs were identified with their prevalence across clusters highly correlating to bulk abundance obtained by standard 16S sequencing, implying that more abundant taxa are also physically dispersed over more space (FIG. 2b, Pearson correlation r=0.90). The spatial distribution of taxa across clusters appeared mixed (median 9 OTUs per cluster), but some clusters contained only a few OTUs indicating spatial aggregation or clumping in a fraction of the community (FIG. 2c). Moreover, this observed distribution of OTUs per cluster was significantly lower than clusters of the same size generated from homogenized fecal bacteria, which serve as a control for a well-mixed community (Mann-Whitney U test, $p<10^{-26}$). These results suggest that at the scale of tens of microns, individual taxa in the gut microbiome are neither fully mixed nor highly structured, but rather are heterogeneously distributed in mixed patches.

Figure 2D:
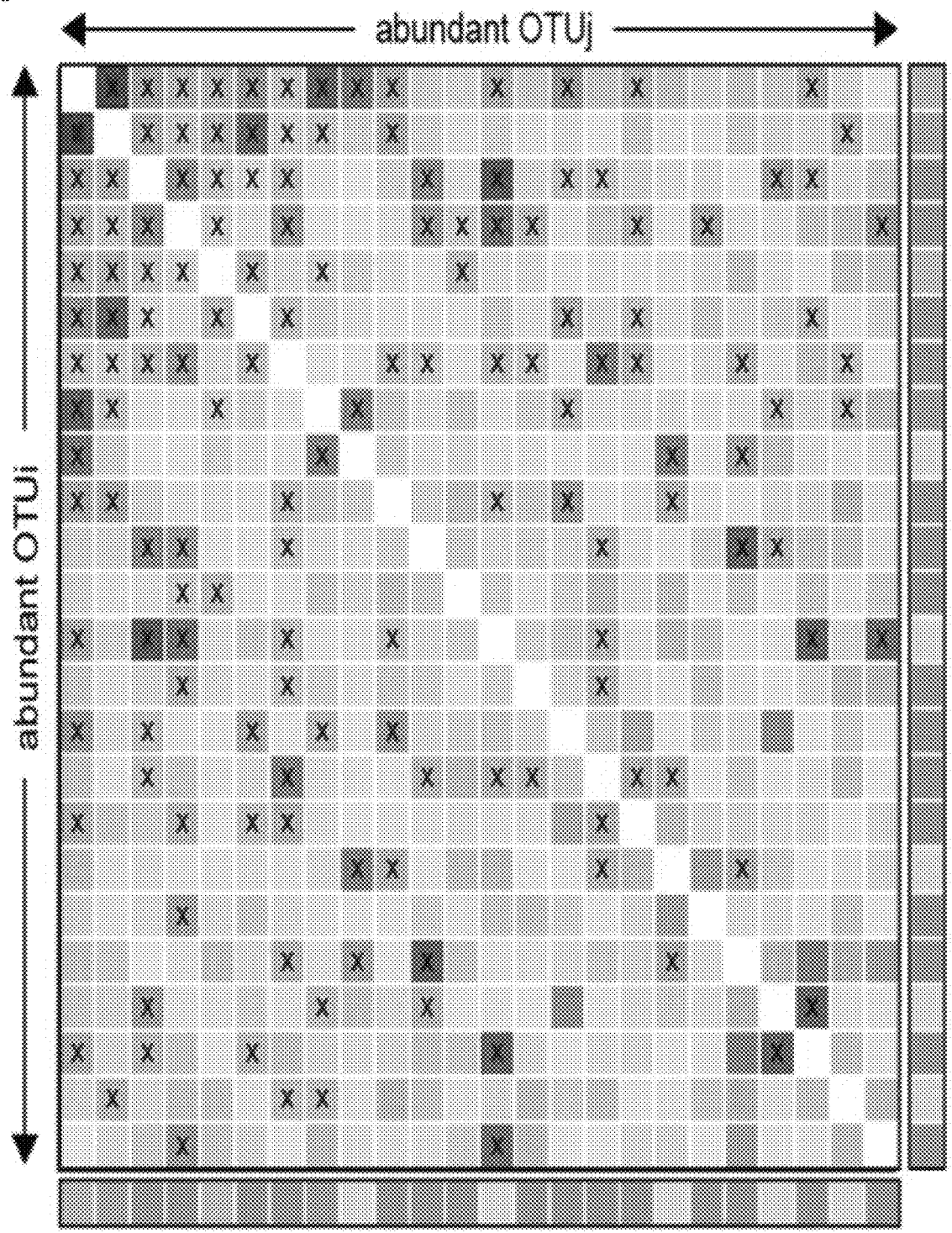
Figure 3B:
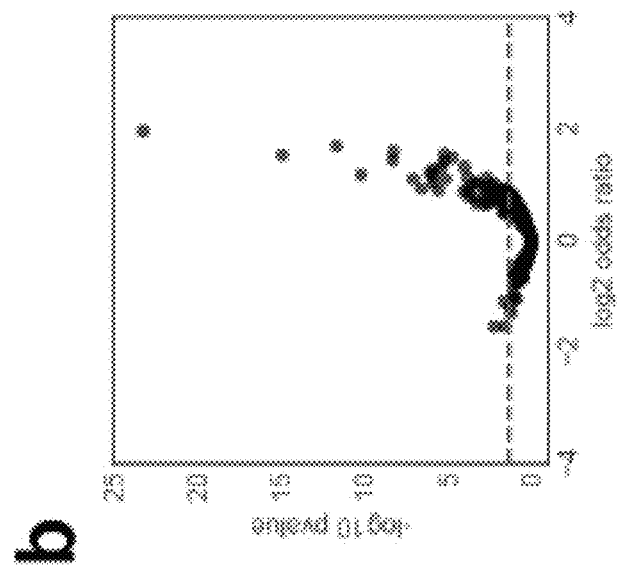
Figure 3C:
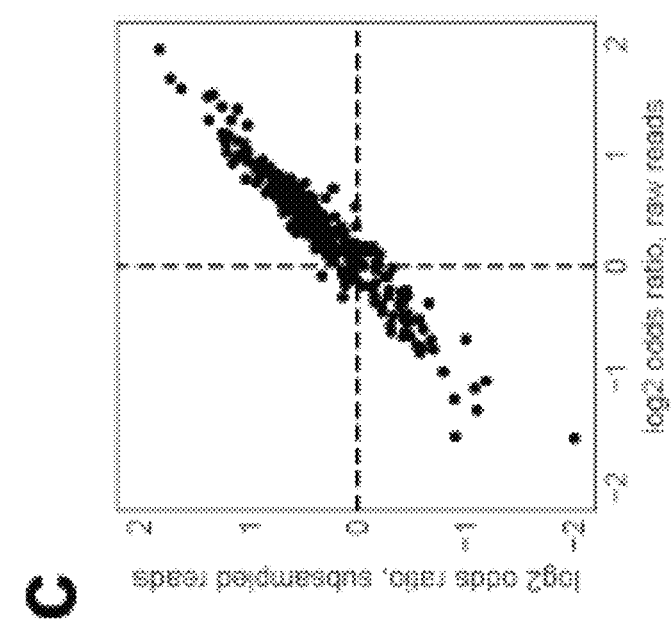
Figure 4B:
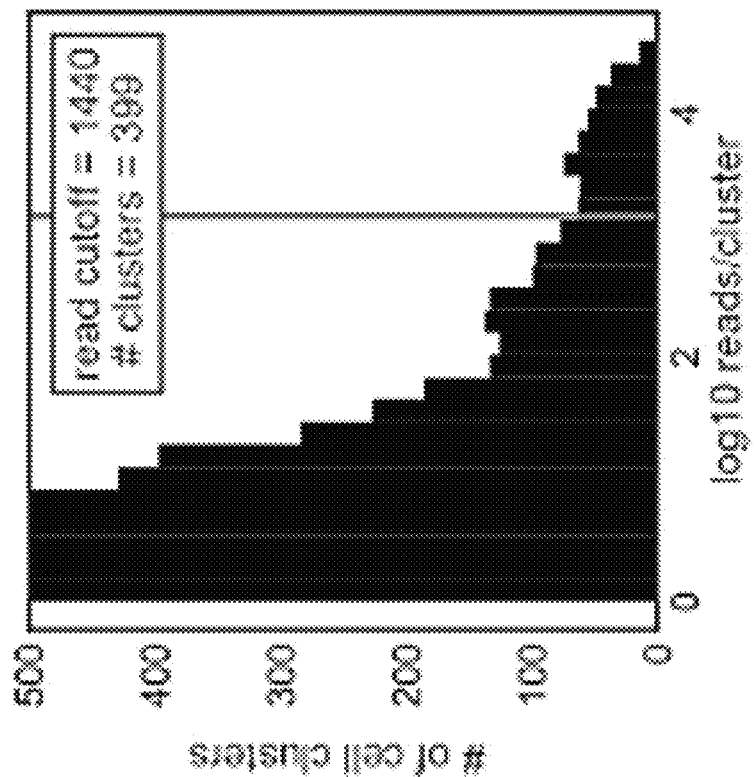
Figure 4A:
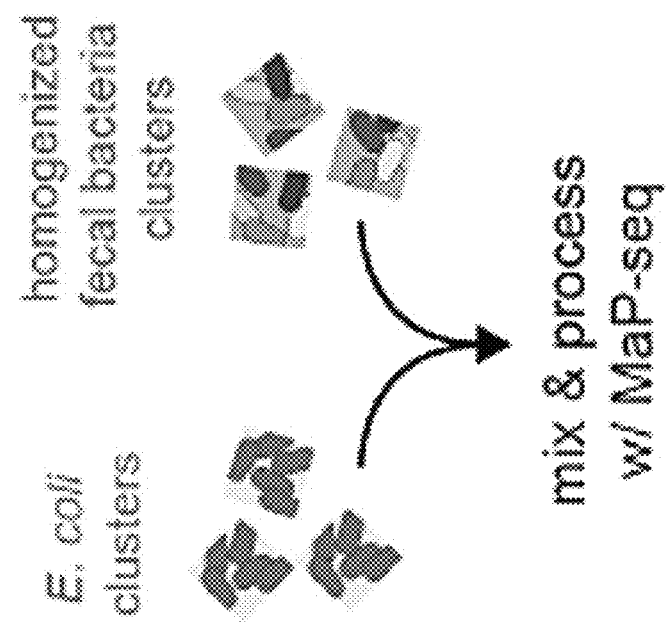
Figure 4C:
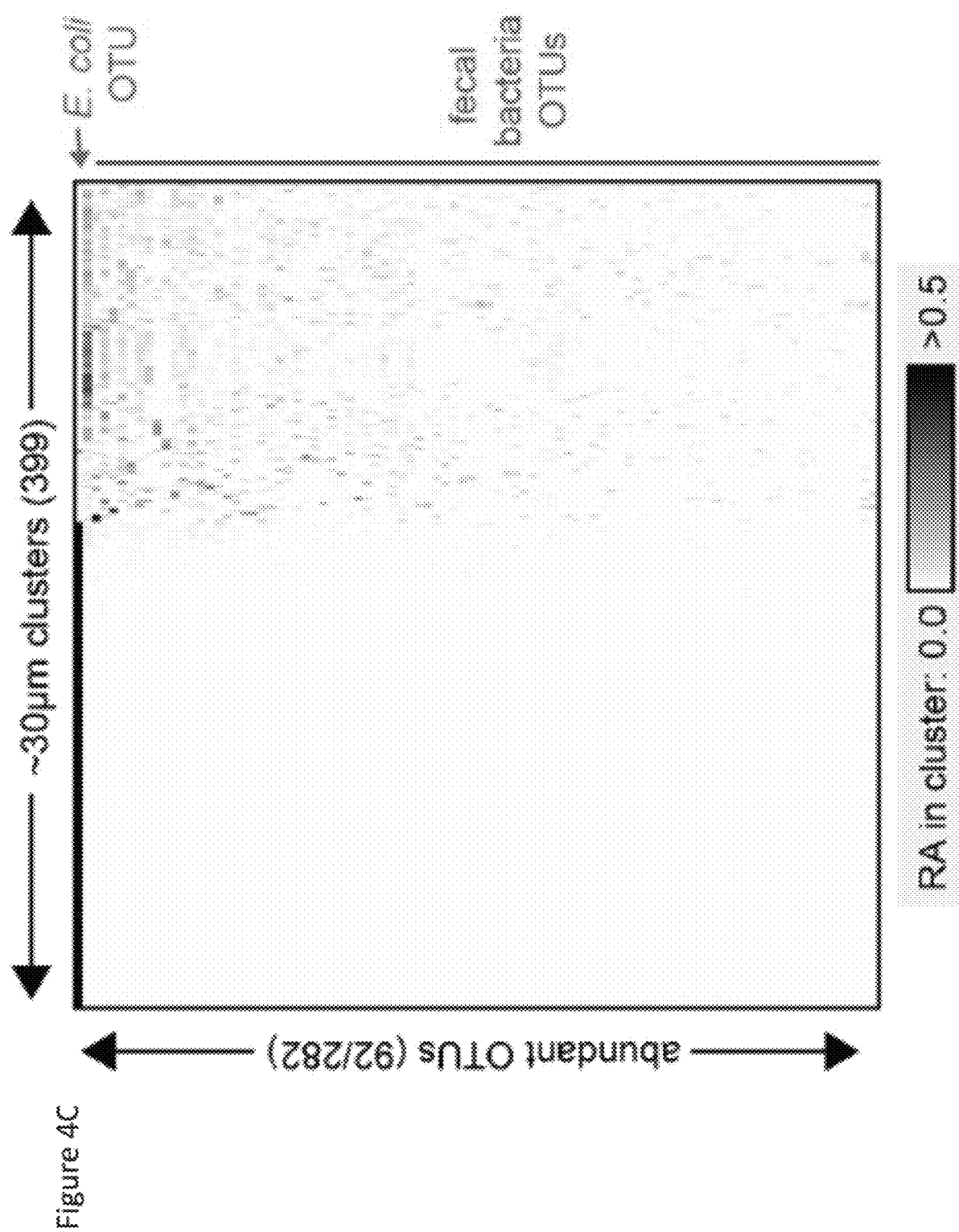
Figure 4E:
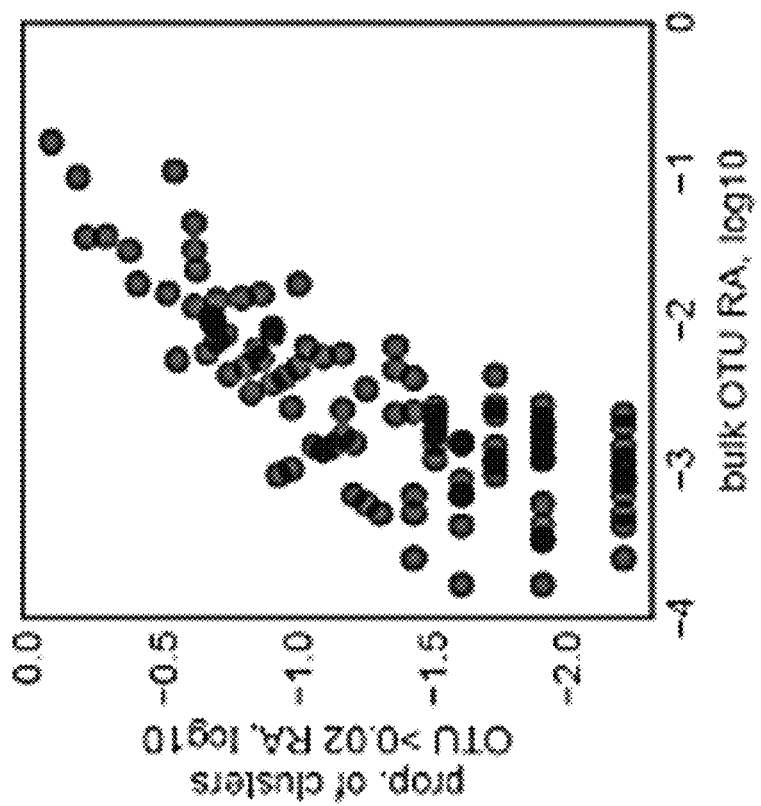

We next explored whether these observed spatial distributions reflect specific associations between individual bacterial taxa that may result from processes such as positive or negative interspecies interactions (e.g., cooperative metabolism (see Rakoff-Nahoum, S., Coyne, M. J. & Comstock, L. E. An Ecological Network of Polysaccharide Utilization among Human Intestinal Symbionts. Current Biology 24, 40-49 (2014)); contact-dependent killing (see Wexler, A. G. et al. (2016))) or local habitat filtering (see Nagara, Y., Takada, T., Nagata, Y., Kado, S. & Kushiro, A. (2017). Across abundant and prevalent OTUs (>2% abundance in >10% of clusters, n=24), we assessed whether their pairwise co-occurrences were detected more or less frequently than expected in comparison to a null model of independent, random assortment of OTUs (Methods, Fisher's exact test, $p<0.05$, FDR=0.05). Application of this strategy to the cluster mixing control experiment confirmed our ability to accurately detect positive and negative spatial associations that are expected (FIG. 4f). Out of 276 possible pairwise combinations of taxa in the murine colon, we detected 75 statistically significant associations between diverse taxa, the majority of which were positive (72/75) but relatively weak in magnitude (FIG. 2d, FIG. 3b-c). The strongest co-occurrence was a positive association between abundant Bacteroidaceae and Porphyromonadaceae taxa from the Bacteroidales order (odds ratio 3.9, $p<10^{-23}$). In addition, a small number of negative associations were observed, which could reflect antagonistic processes such as production of inhibitory factors or competitive exclusion.

Figure 3D:
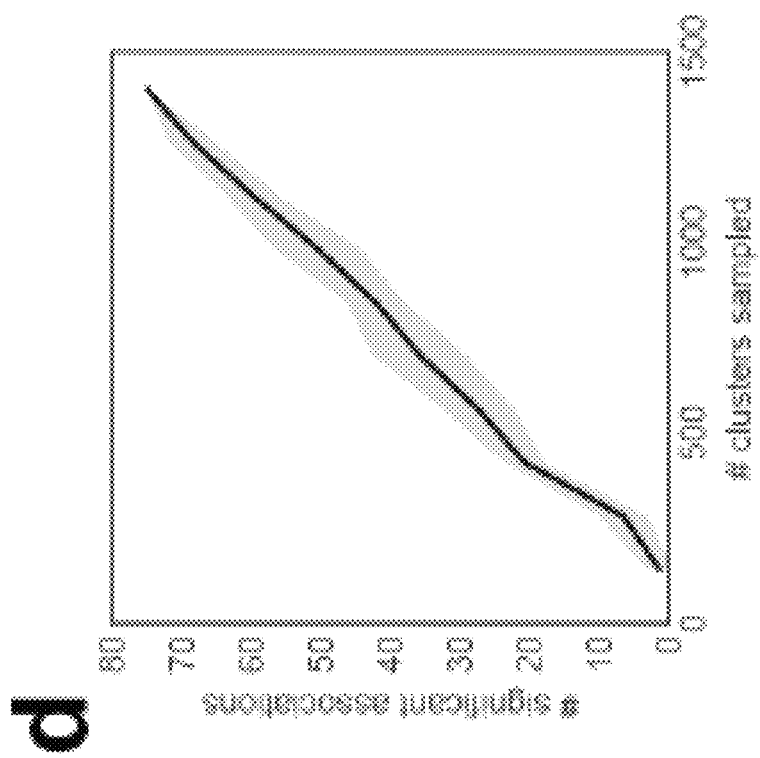
Figure 3E:
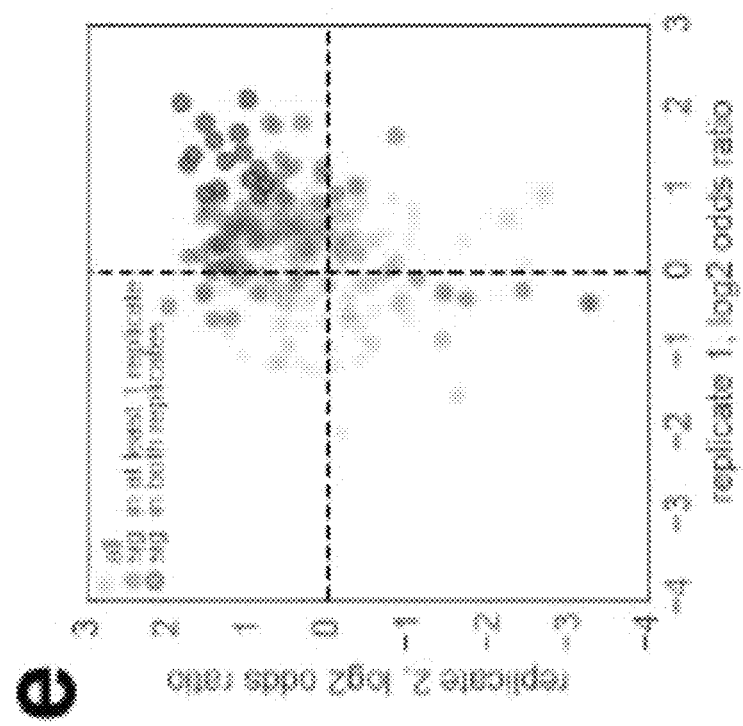

The number of detected associations increased as more of the dataset is sampled, implying that detection of weaker relationships between less abundant taxa can be improved by analyzing more clusters FIG. 3d). Nonetheless, the detected associations showed good correspondence between technical replicates FIG. 3e). Importantly, despite high inter-host microbiome variability, the nature of the associations (i.e., sign, magnitude, and number) and some strong associations could be recapitulated in MaP-seq profiling of a second co-housed mouse, such as the co-occurrence of Bacteroidales taxa. This characterization implies that individual taxa in the colon are organized in distinct and reproducible spatial relationships.

To further investigate how the spatial organization of the microbiota is influenced by their environmental context, we applied spatial metagenomics along the gastrointestinal (GI) tract. The mammalian GI tract is composed of distinct anatomical regions with different pH levels, oxygen concentrations, host-derived antimicrobials and transit times that together influence the local microbial assemblage (see Donaldson, G. P., Lee, S. M. & Mazmanian, S. K. Gut biogeography of the bacterial microbiota. 1-13 (2015). doi: 10.1038/nrmicro3552). We first performed an adapted 16S community profiling approach along the murine GI tract that could also infer absolute OTU abundances (see Ji, B. W. et al. Quantifying spatiotemporal dynamics and noise in absolute microbiota abundances using replicate sampling. biorxiv.org doi:10.1101/310649 (2018)) FIG. 5a (Methods). This new mouse cohort (2 co-housed mice) shared only ~20% of OTUs with the previous group, illustrating the significant inter-animal microbiome heterogeneity inherent to such studies. This further highlights challenges for other spatial profiling techniques such as 16S FISH imaging where probes must be designed in advance, in comparison to MaP-seq, which can be applied to measure diverse bacteria without advance specification. Analysis of microbiota in absolute abundance across the intestine revealed increased bacterial density (~16 fold higher) and species richness in the large intestine compared to the small intestine, with the cecum harboring the highest bacterial density and number of OTUs. We chose three separate GI regions that exhibited distinct microbiota assemblages for characterization by MaP-seq: the ileum (si6), cecum (cec) and distal colon (co2). Given the high degree of species mixing previously observed at ~30 µm, we used smaller sized clusters (~20 µm median diameter) to capture higher-resolution spatial associations. Ranges of clusters can include, 1, 5, 10, 20, 30, 40, 50, 60, 70, 80, 90, 100, 200, 400, 600, 800, 1000 µm.

Figure 5A:
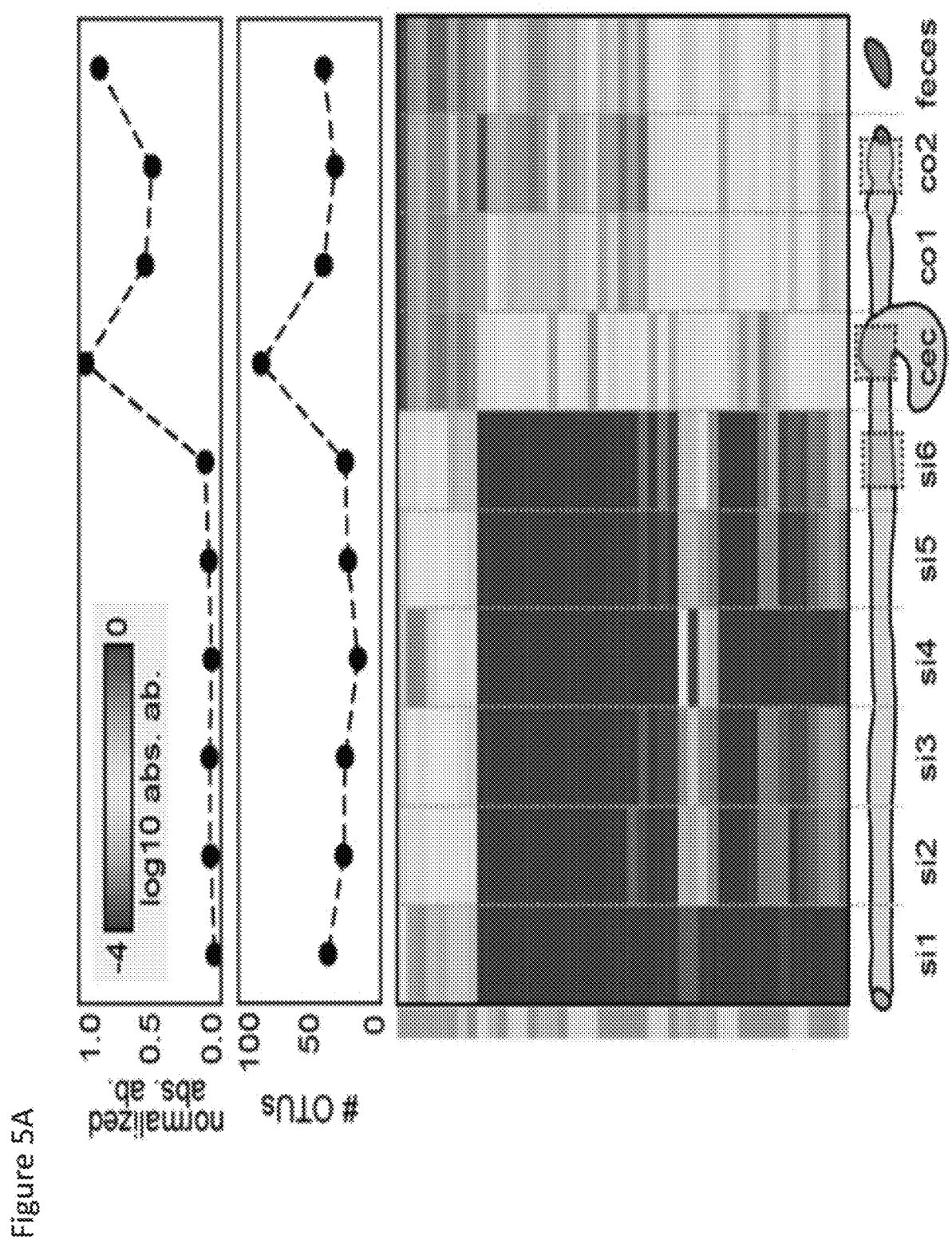
FIGS. 5a-5d: Survey of spatial organization across the mouse gastrointestinal tract. a) Top: absolute abundance within gut intestinal compartments calculated from spike-in sequencing (arbitrary units, normalized to the maximum value) and number of OTUs (i.e. alpha diversity, number of OTUs>0.1% relative abundance). Bottom: absolute abundance of abundant OTUs (>1% of maximum OTU absolute abundance in any sample) is shown below as a heatmap (log 10 scale); OTUs are clustered by Bray-Curtis dissimilarity. b) Histogram of the number of OTUs per cluster (OTUs>2% RA). The number of clusters aggregated from two technical replicates is indicated (si6 n=386, cec n=405, co2 n=259), and dotted line indicates median value. c) tSNE visualization of clusters utilizing Bray-Curtis dissimilarity of OTU relative abundances (subsampled to 314 reads across all clusters, number of clusters indicated above). On the left, each cluster is colored by site of origin; on the right each cluster is colored by the relative abundance of the six most abundant families within each cluster (linear scale). d) Pairwise spatial associations for abundant and prevalent OTUs visualized as a circular graph; the number of clusters utilized is subsampled to the lowest number across the three samples (259 clusters). Nodes indicate OTUs, sizing is proportional to the prevalence of OTUs across clusters and color represents OTU taxonomy at the family level, dotted edges denote all possible associations and shaded edges denote statistically significant associations (p<0.05, FDR=0.05).

The distribution of OTUs per cluster was compared with the spatial organization of taxa in the three regions FIG. 5a. ~20 µm clusters displayed lower numbers of OTUs per cluster than ~30 µm clusters (median 3-4 OTUs per cluster). The ileum possessed significantly fewer OTUs per cluster than the cecum or distal colon (Mann-Whitney U test, $p<10^{-18}$ and $p<10^{-14}$ respectively). By comparison, the cecum and colon displayed similar OTU distributions, while the cecum harbored more clusters with a large number of OTUs.

Figure 5B:
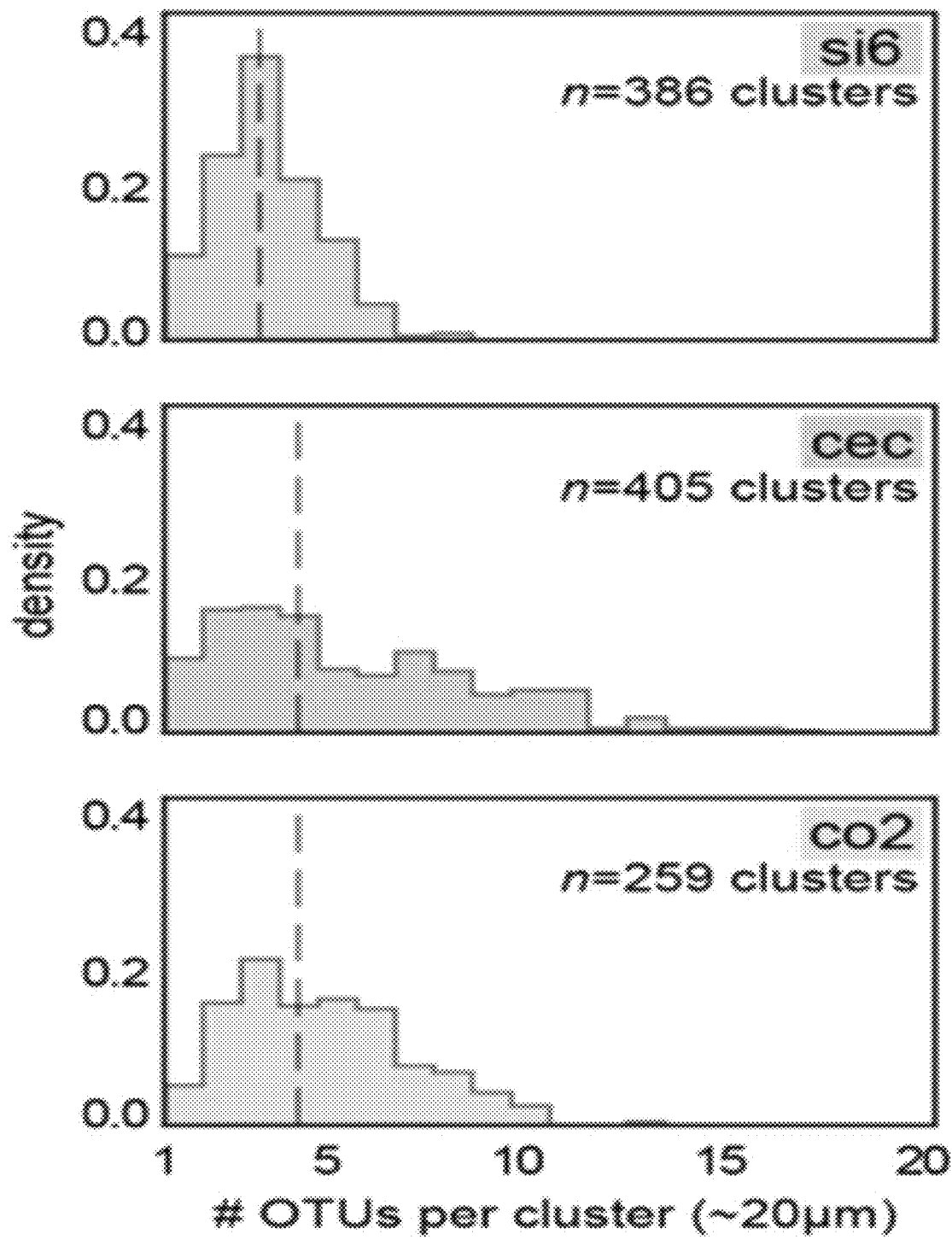
Figure 5C:
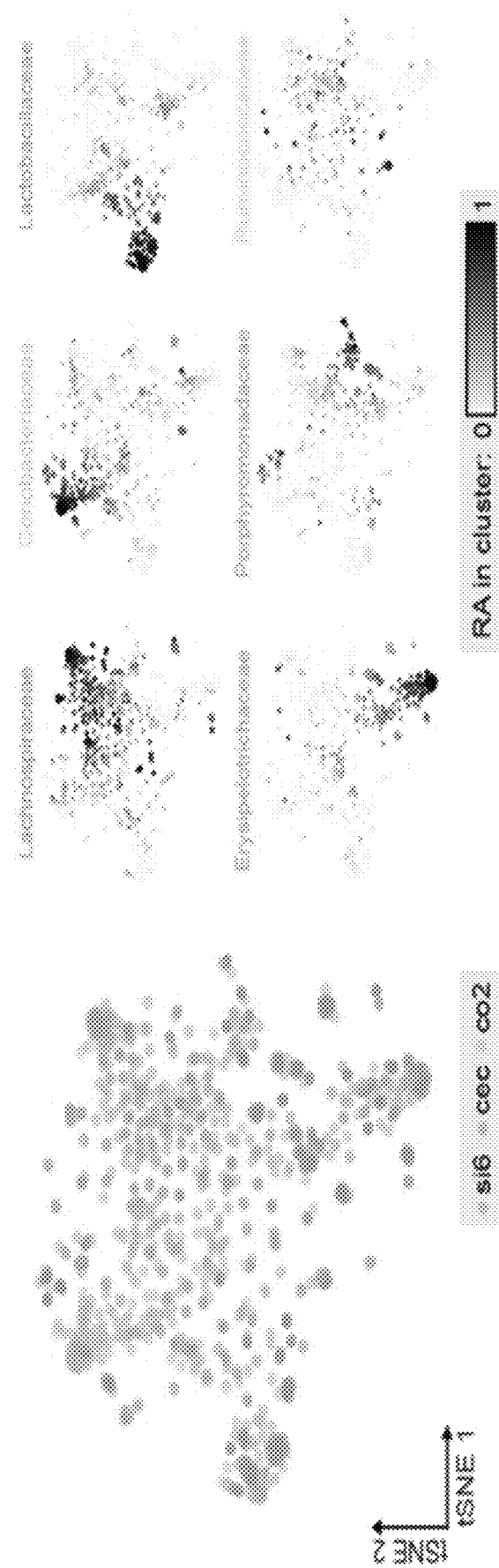

To understand how the local spatial organization of the microbiome may vary within and across different gut compartments, we visualized the cell clusters data across the three gut regions using t-distributed Stochastic Neighbor Embedding (tSNE, utilizing Bray-Curtis distance of OTU relative abundance within clusters), as well as the abundance of prevalent bacterial families in cell clusters across the resulting manifold FIG. 5c (Methods, FIG. 3c). While some cell clusters from the ileum, cecum and distal colon separately projected into distinct groups, other clusters from each site projected more broadly across the manifold. Interestingly, a subset of cell clusters from the cecum projected into a dense group and are compositionally dominated by Lachnospiraceae, which were generally not present in clusters from the ileum or distal colon. When cell clusters from a second co-housed mouse were added to the tSNE analysis, they were distributed in a similar manner to clusters from the first mouse across the manifold and displayed a similar cecum-specific Lachnospiraceae group.

Figure 5D:
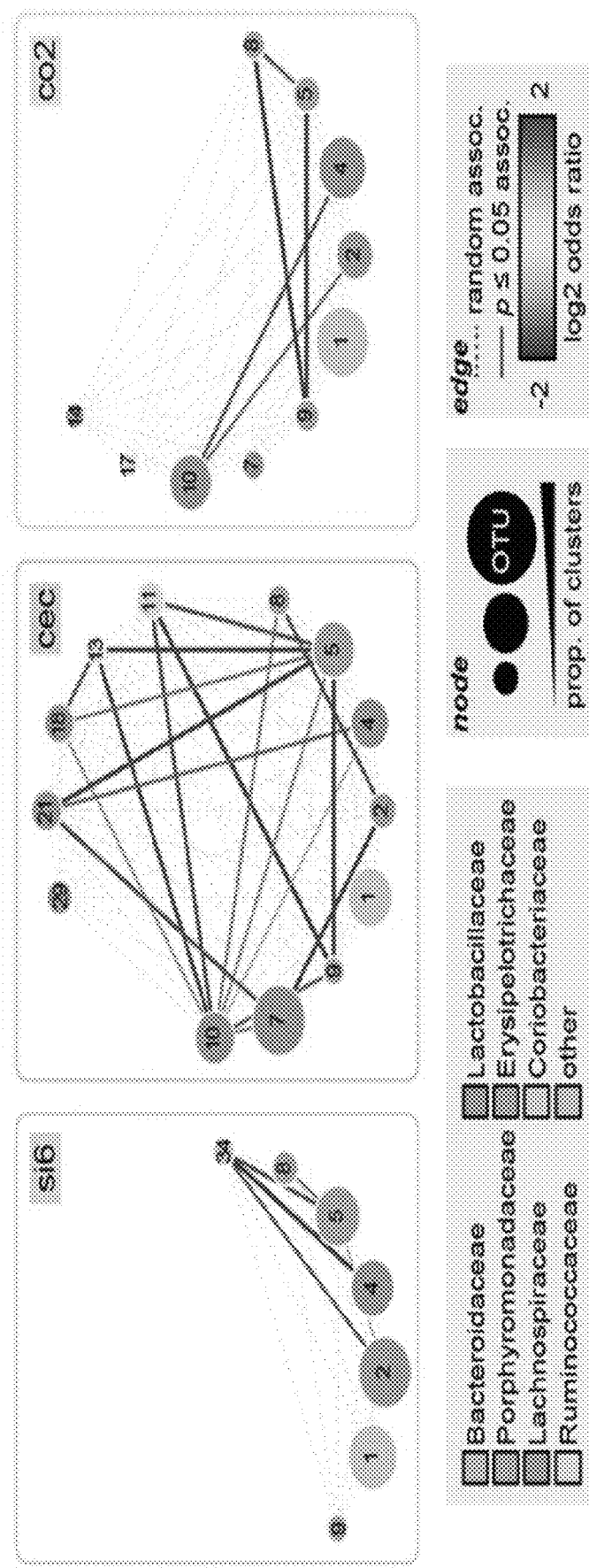
Figure 6A:
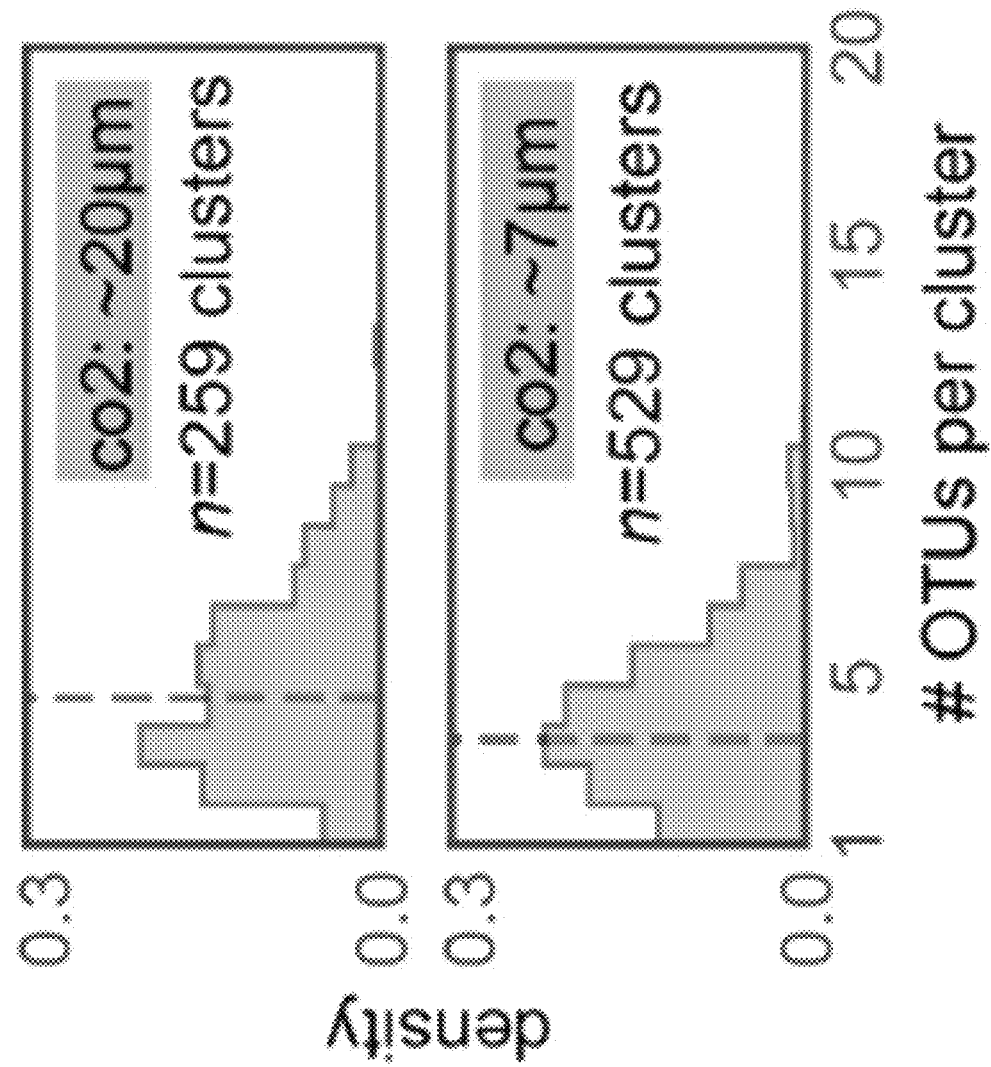
FIGS. 6a-6b: MaP-seq profiling of colonic samples at a smaller size scale. a) Colonic clusters of ~7 μm diameter were profiled in parallel. A histogram is shown with the number of OTUs per cluster compared to the ~20 μm clusters profiled in FIG. 3b. The smaller size-scale contains a significantly lower number of OTUs per cluster as expected (Mann-Whitney U test, p<10$^{-6}$). The number of clusters aggregated across two technical replicates is indicated, and the dotted line indicates the median value. b) Pairwise spatial associations for prevalent and abundant OTUs visualized as a force directed graph. Nodes indicate OTUs, and sizes are proportional to prevalence of OTUs across clusters and coloring represent taxonomy at the family level. Edges represent statistically significant associations (Fisher's exact test, p<0.05, FDR=0.05). ~20 μm colonic clusters display same data as shown in FIG. 3d. The full dataset for each sample is utilized in calculation of pairwise associations. Robust positive co-associations are recapitulated between the Bacteroidales taxa between at both of the size scales.
Figure 6B:
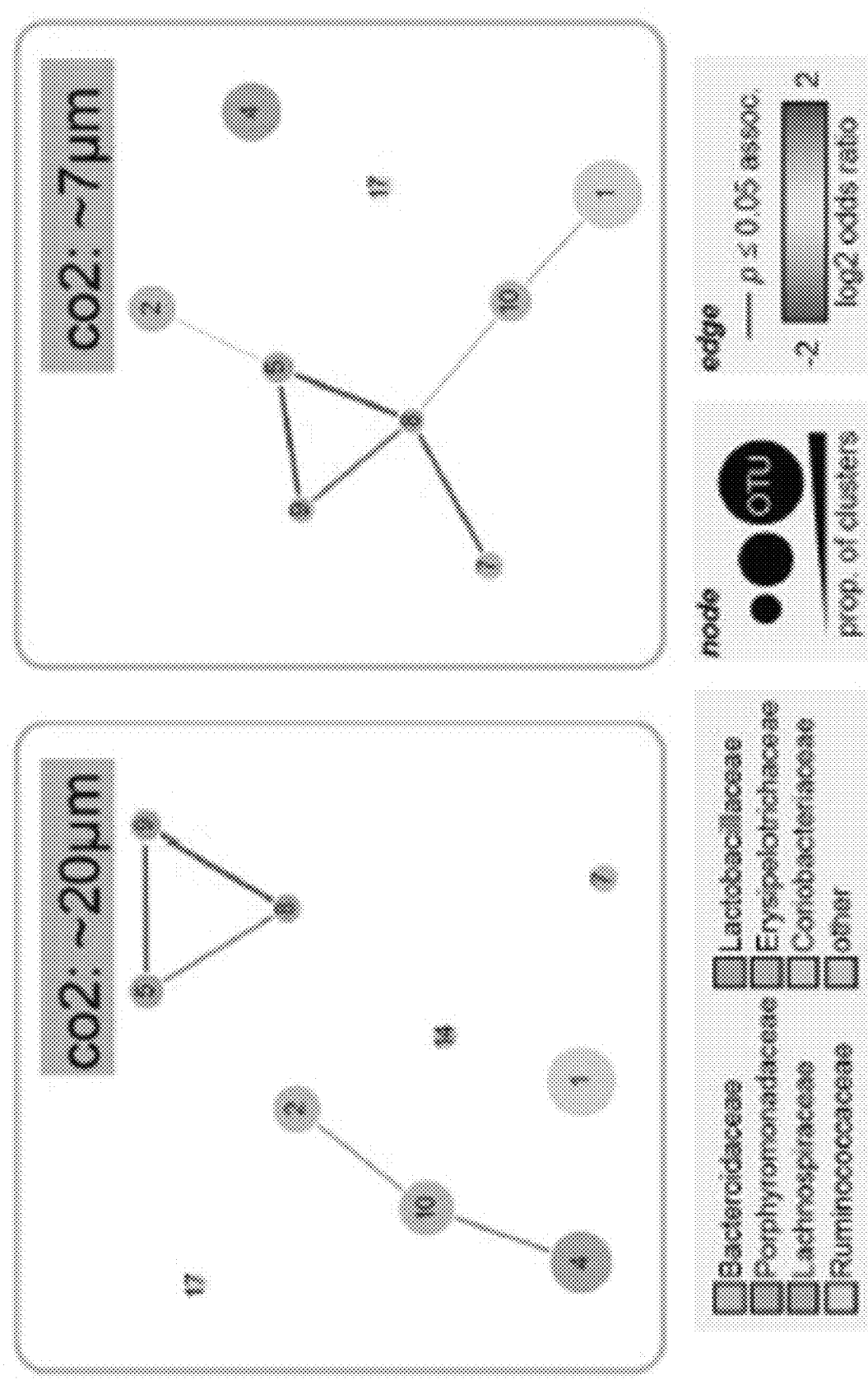

Next, we explored whether these different spatial distributions reflect distinct spatial co-associations between taxa at each GI site (FIG. 5d). The ileum harbored a network of positive and negative associations between the few taxa present. On the other hand, the cecum exhibited a dense network of positively co-associated taxa, primarily between abundant Lachnospiraceae, Ruminococcaceae, and Porphyromonadaceae. Similar to the cecum, the distal colon displayed only positive associations, including strong groupings between three abundant Porphyromonadaceae (OTUs 5, 8, 9). Profiling the colon at an even smaller size-scale (~7 µm) confirmed strong positive associations between these three taxa FIG. 6, indicating that this spatial clustering occurs robustly at short, local length-scales.

Figure 7A:
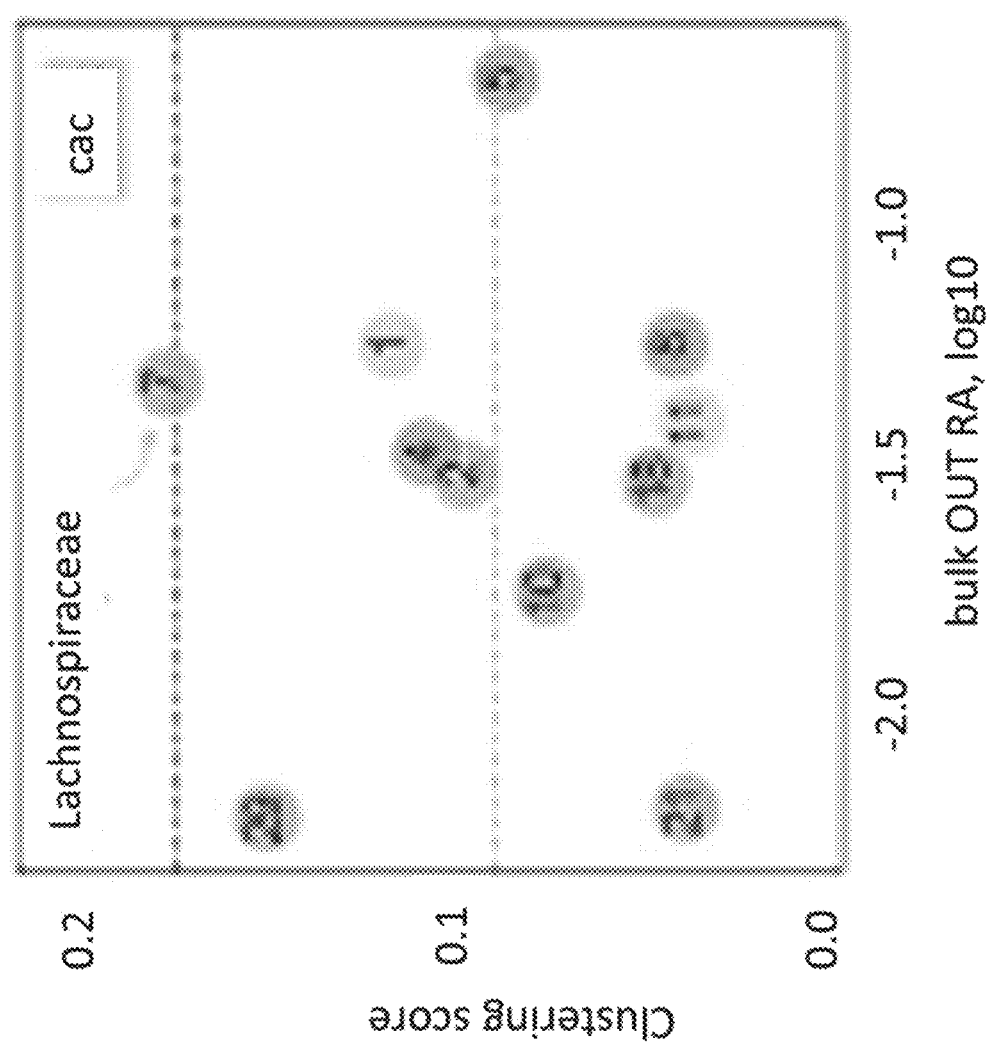
FIGS. 7a-7h: Analysis of taxa with altered spatial structuring in the cecum. a) OTU clustering or self-aggregation in the murine cecum; for prevalent OTUs (>2% RA in >10% all clusters) the proportion of times an OTU is observed as the majority of the cluster (>50% relative abundance) is plotted. Grey dotted line indicates the average clustering value, and black dotted line indicates two times the average clustering value. b) FISH imaging of a cecum section from the same sample profiled by MaP-seq; green is Erec482 probe targeting Lachnospiraceae, blue is Lab148 probe targeting Lactobacillaceae, and magenta is Ato291 probe targeting Coriobacteriales. c-f) Four representative regions showing Erec482 targeted Lachnospiraceae displaying self-aggregating clusters. The source of each of the four regions is indicated by a yellow outline in b). g-h) Two representative regions showing areas with no Lachnospiraceae self-aggregation. The source of the two regions is indicated by a red outline in b).
Figure 7B:
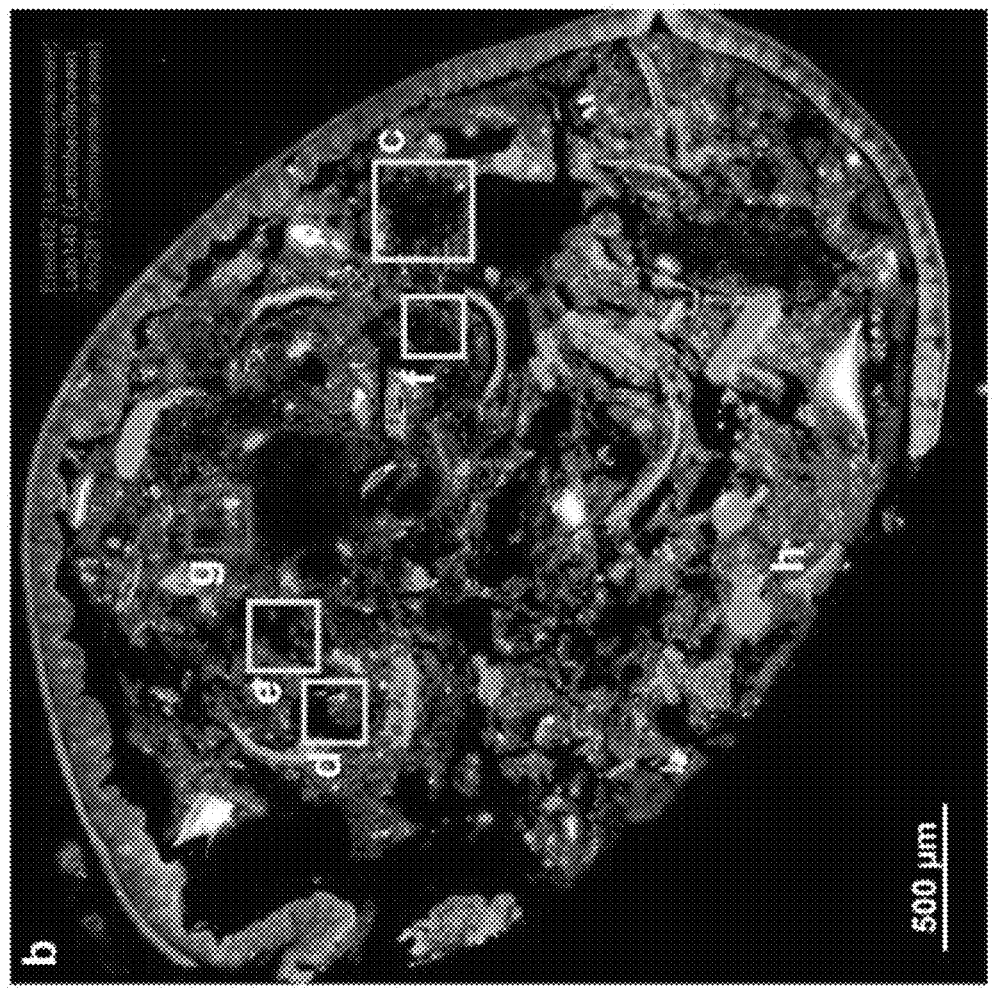
Figure 7D:
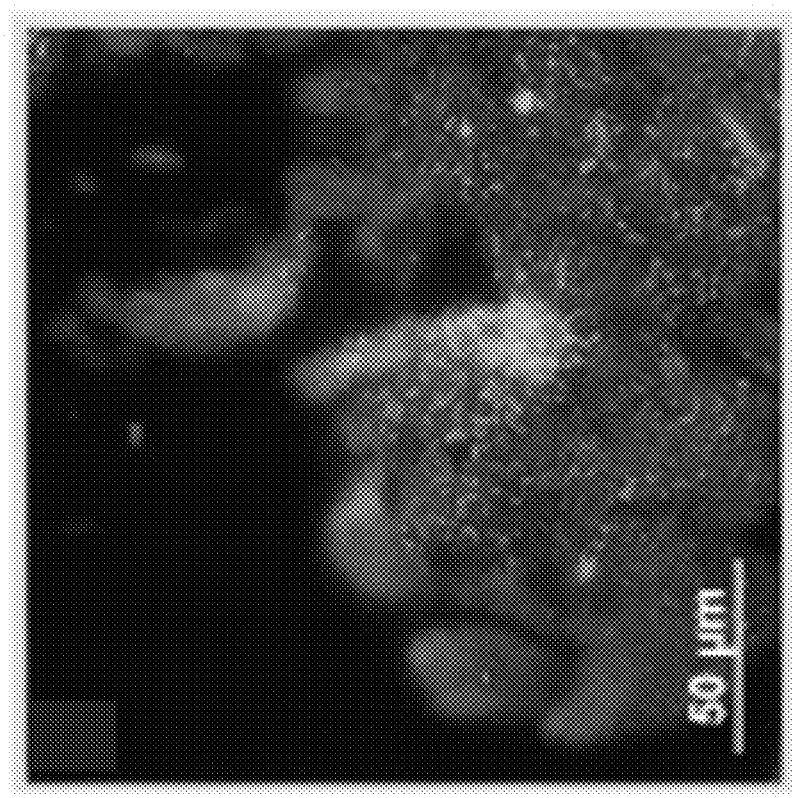
Figure 7C:
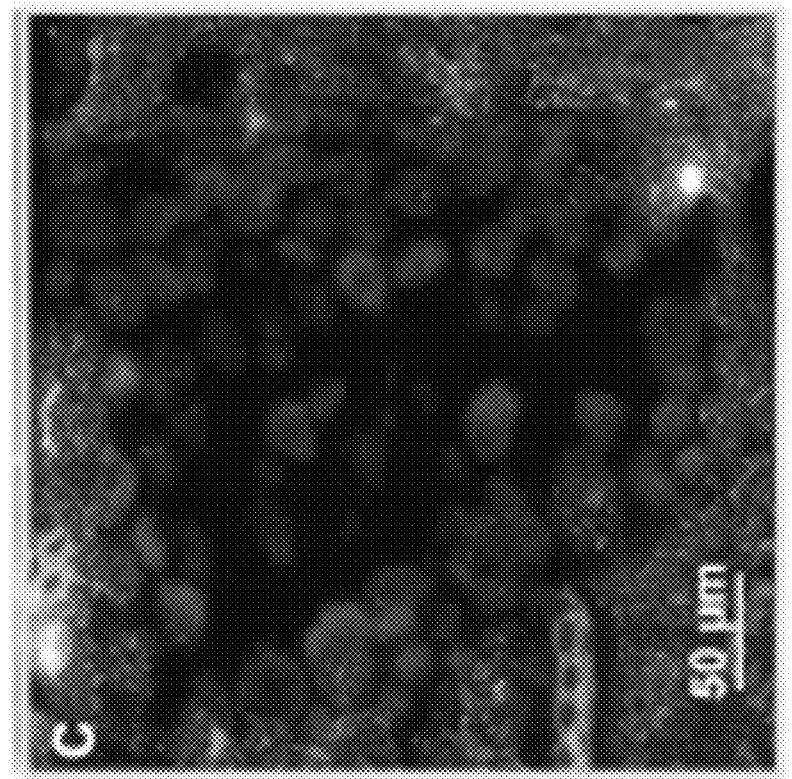
Figure 7E:
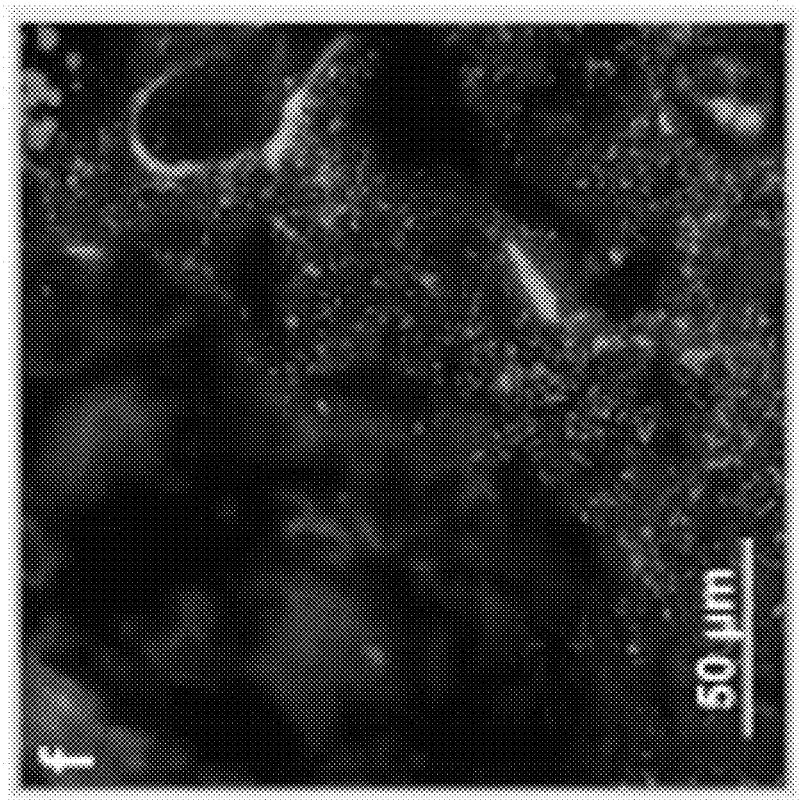
Figure 7F:
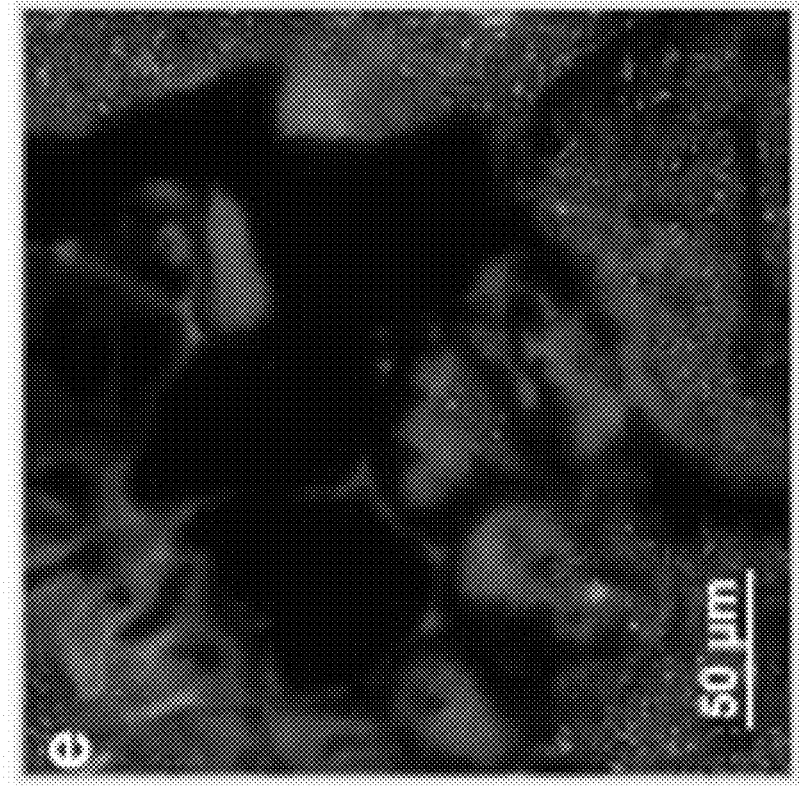
Figure 7H:
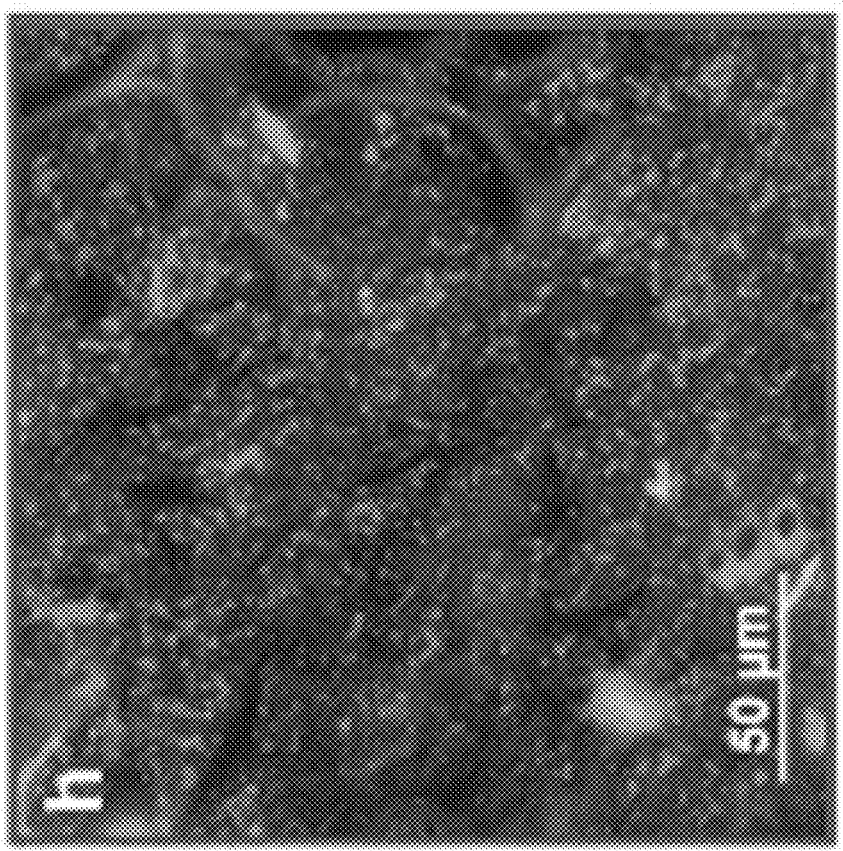
Figure 7G:
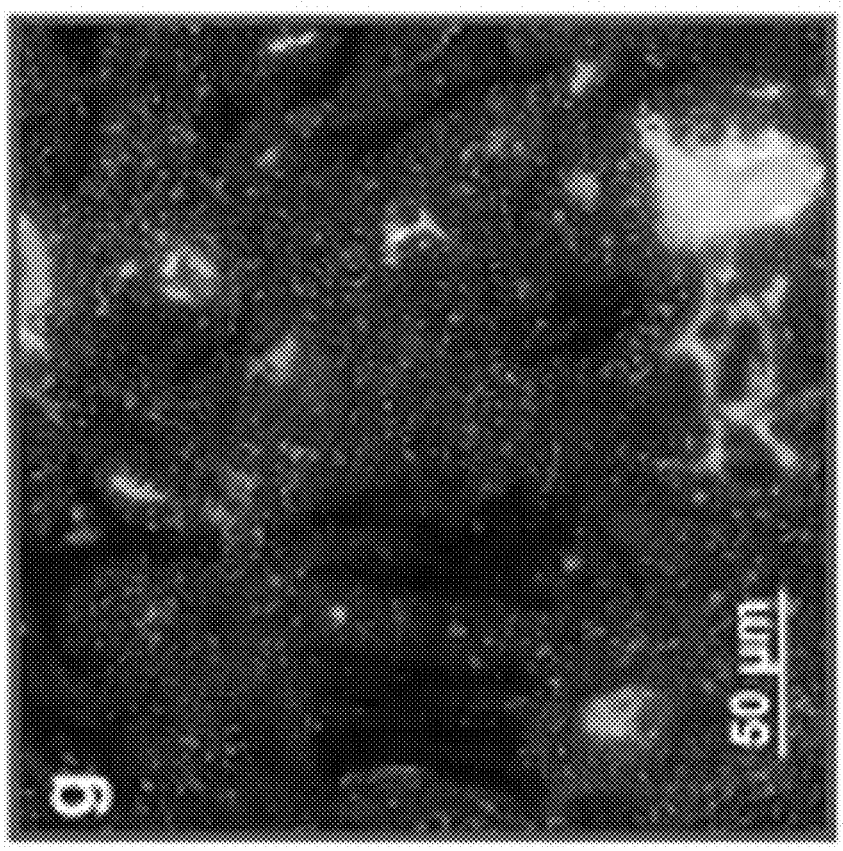
Figure 8A:
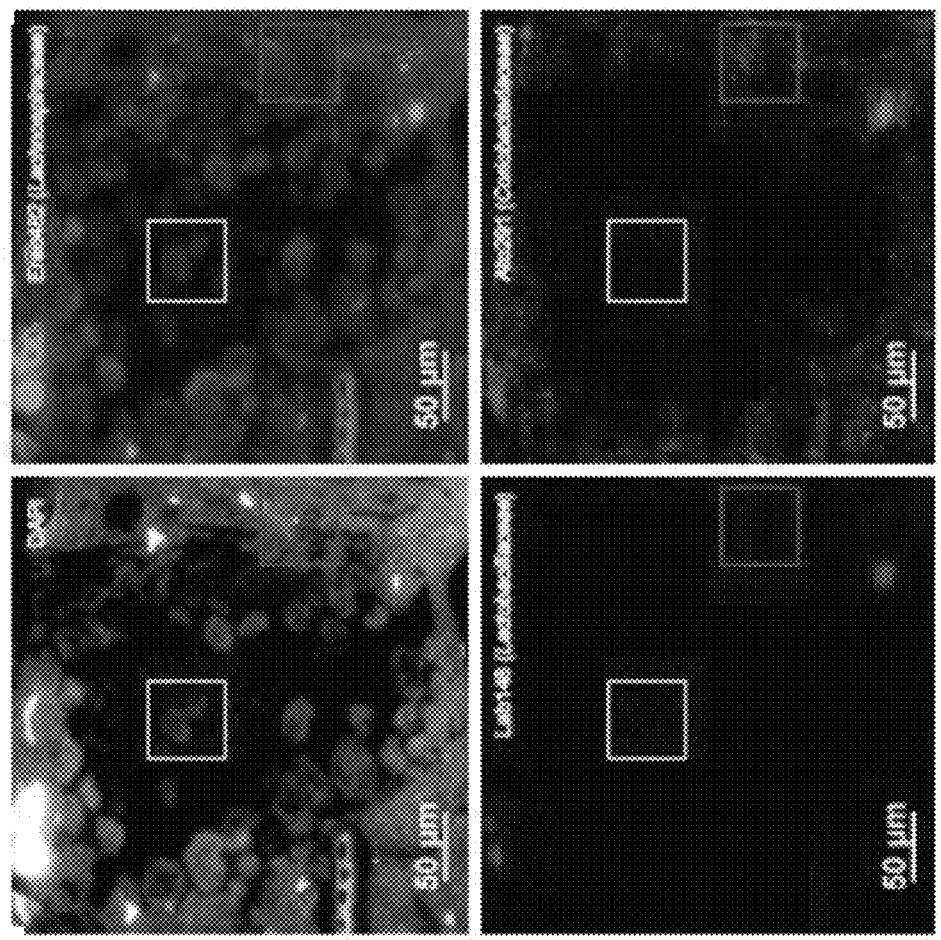
FIGS. 8a-8h: Erec482-stained bacterial aggregations appear to exclude other bacteria and additional imaging controls. a) The same region shown in FIG. 512c is displayed, but the four channels are displayed independently. b) To investigate if other bacteria not targeted by the utilized FISH probes (Lab148 and Ato291 probes) may be present in the apparent Erec482 targeted Lachnospiraceae clusters, DAPI counterstaining (targeted to cell gDNA) was also investigated. A bacterial aggregation is displayed from the image in a); the region is indicated by a yellow outline. Apparent Erec482 aggregations display a single bacterial morphology under DAPI staining, and the DAPI staining co-localizes with Erec482 probe fluorescence. These results imply that the apparent Erec482 Lachnospiraceae clusters exclude other bacteria in the cecum. c) A representative region not displaying Erec482 targeted Lachnospiraceae clusters; a variety of cell morphologies are observable with DAPI staining and Erec482, Lab148 and Ato291 stained bacteria are present. The region displayed is indicated by a red outline in a). d-f) To validate the Erec482-stained structures, we performed two-color FISH utilizing the Erec482 probe (this time with a Cy3 fluorophore) and a Eub338 probe targeted to all bacteria. d) shows the Eub338 probe, e) shows the Erec482 probe, demonstrating that similar aggregations as observed previously (i.e. see inset zoom of specific structures, yellow outline) are co-stained in both channels, indicating they are bacteria. f) shows a different section not stained with a Cy3 probe but with same exposure settings, indicating that the Erec482 staining is specific and not due to autofluorescence. g-h) Additional controls showing Eub338 and Non338 (scrambled control probe) FISH with same exposure settings. g) shows Eub338 probe, h) shows Non338 probe. Lumenal bacteria are bound by the Eub338 and not Non338 probe validating the FISH staining conditions.
Figure 8B:
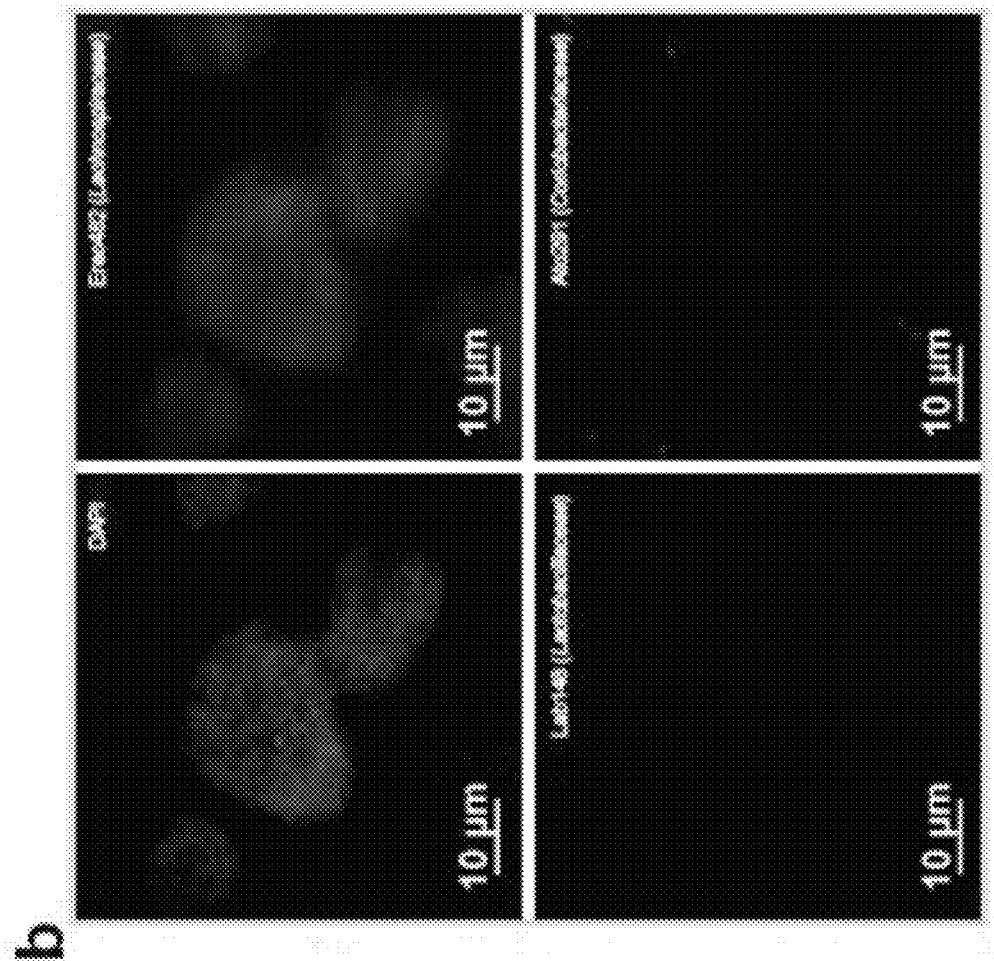
Figure 8C:
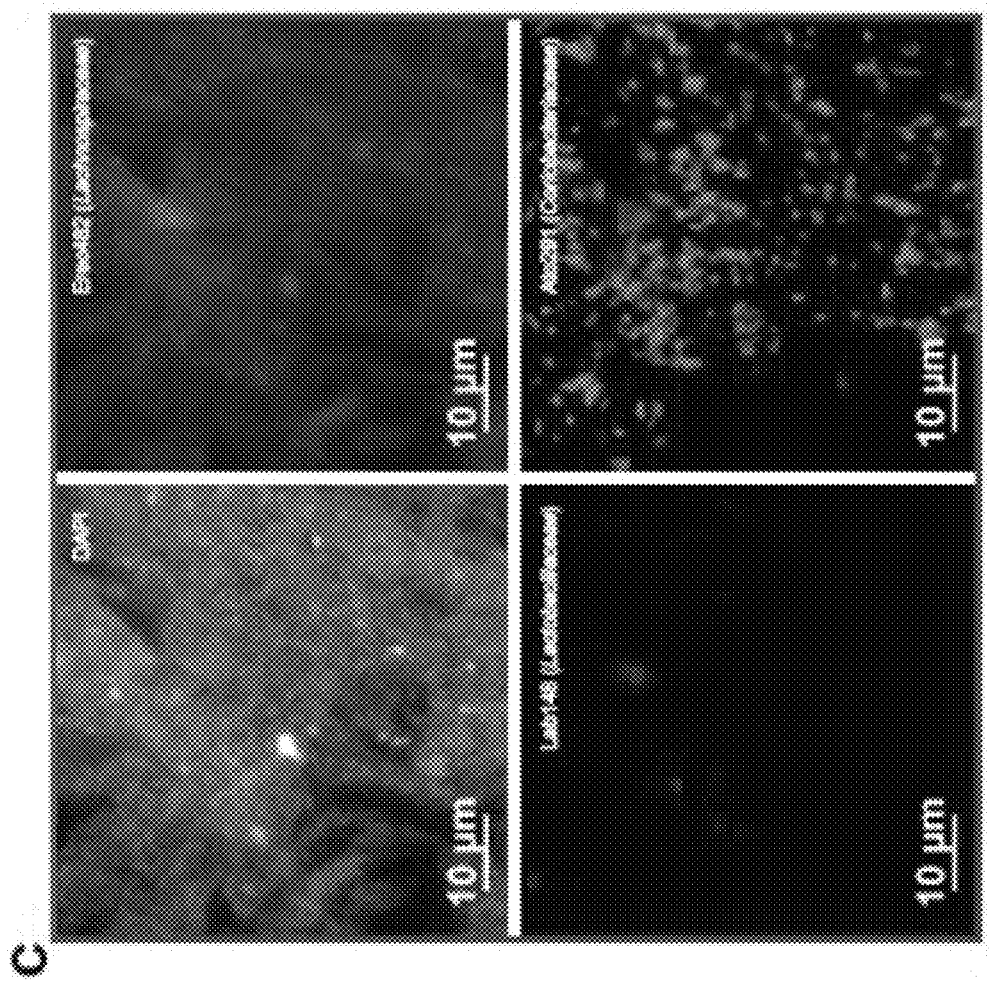
Figure 8D:
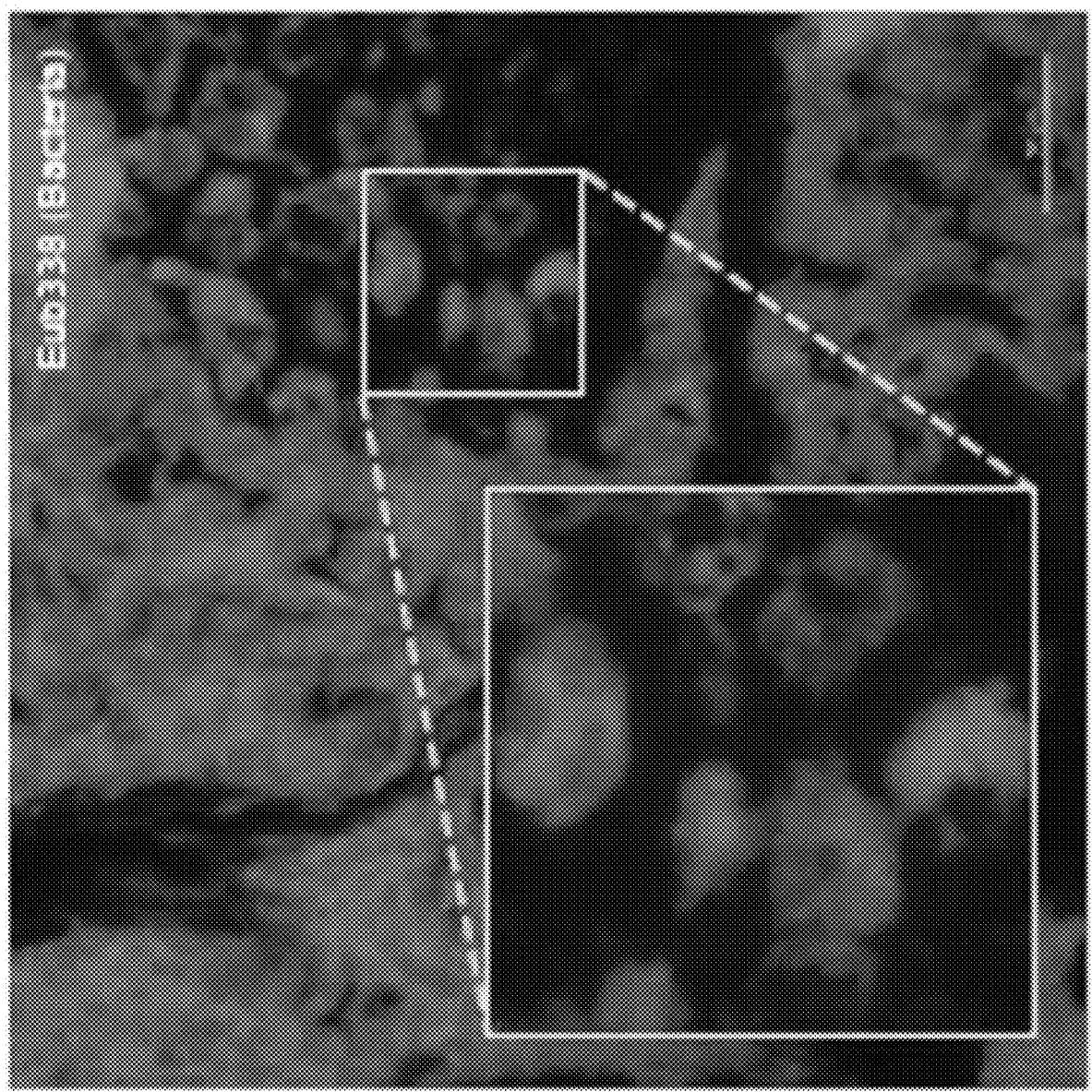
Figure 8E:
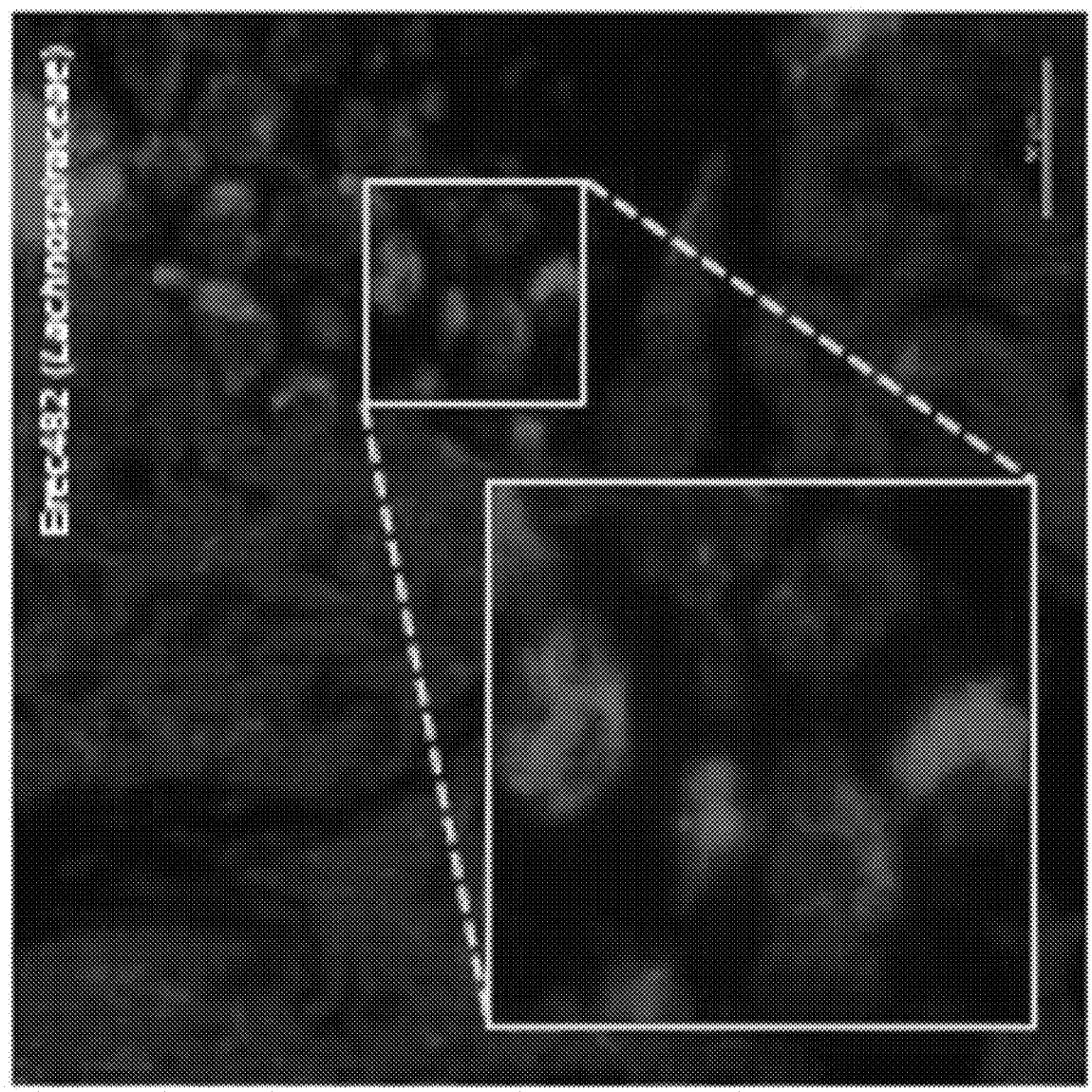
Figure 8F:
Figure 8G:
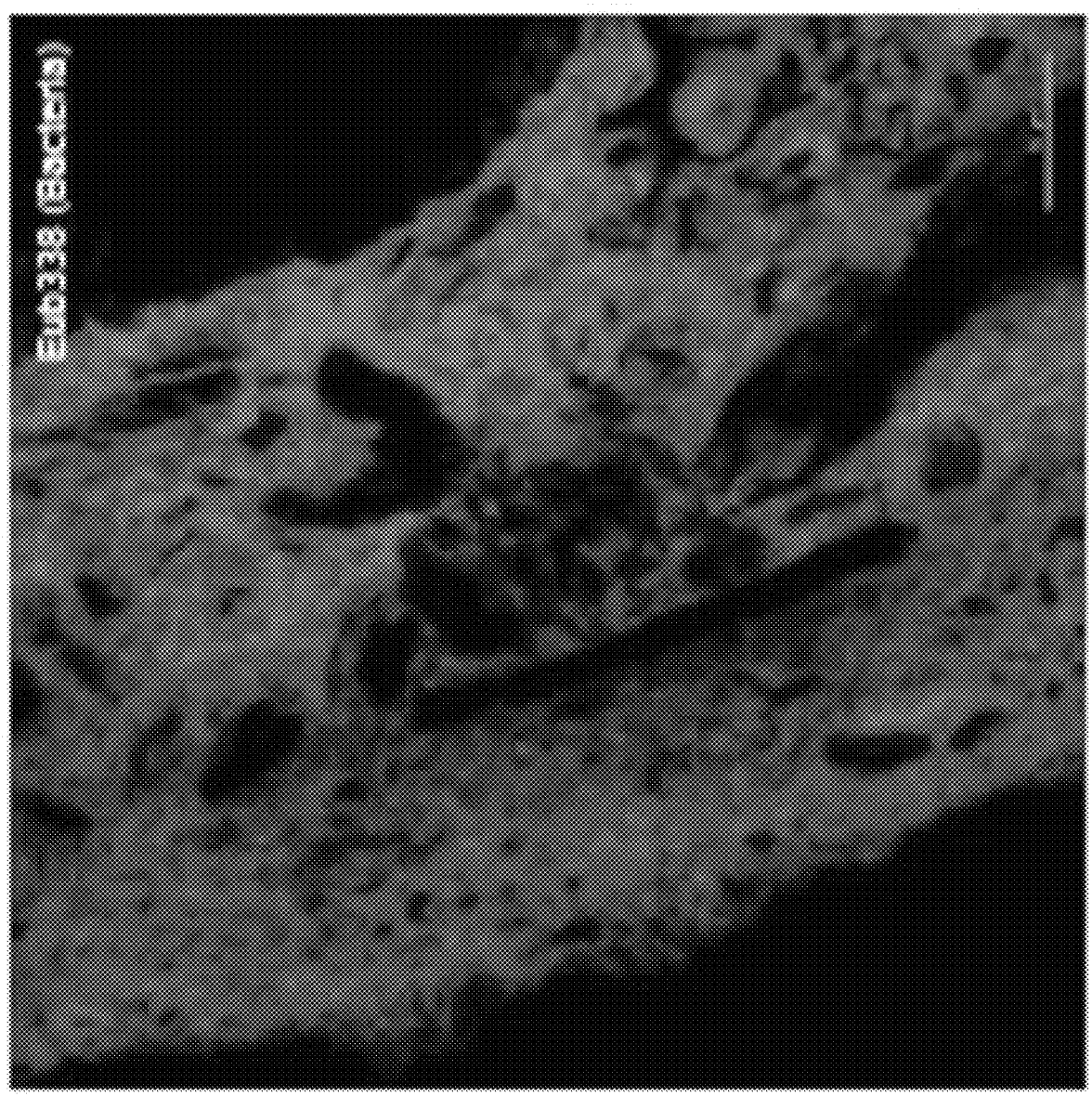
Figure 8H:
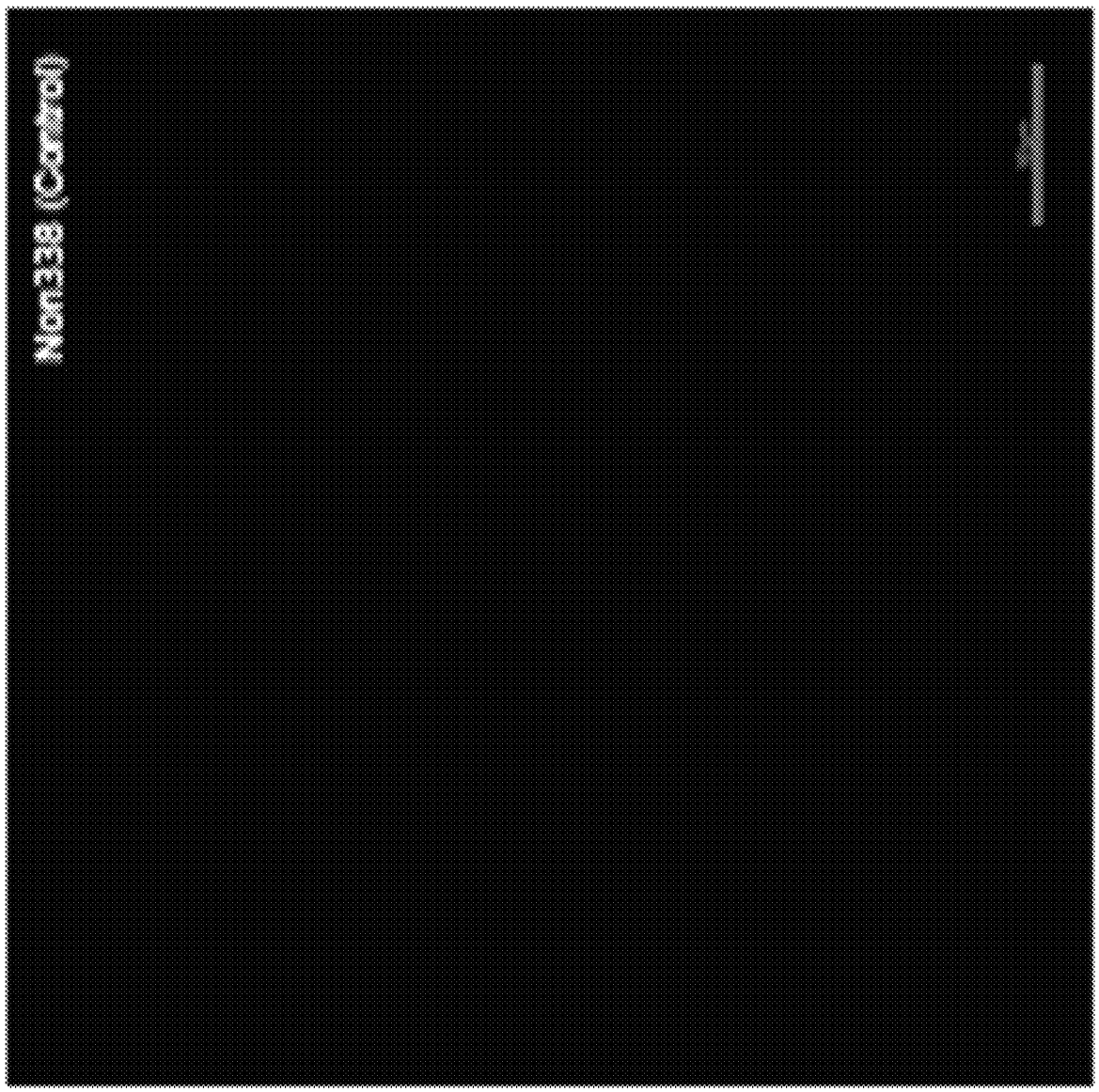

We further investigated whether MaP-seq could identify individual taxa with unique or altered spatial patterns. While the cecum harbored the densest community and the highest degree of species mixing of the three sites FIG. 5a-b, we hypothesized that specific taxa may self-aggregate to a higher degree than others, for example by uniquely utilizing a specific metabolite (see Nagara, Y., Takada, T., Nagata, Y., Kado, S. & Kushiro, A. (2017). Assessing the aggregation of abundant taxa revealed a Lachnospiraceae (OTU 7; putatively of the genus Dorea, 60% confidence by RDP) that clustered two-fold greater than the average clustering metric value of all taxa (FIG. 7a). To validate this finding with an orthogonal approach, we performed 16S FISH on GI sections from the same murine sample using previously validated probes that targeted Lachnospiraceae (Erec482) as well as two other abundant taxa for which FISH probes were available but were predicted not to cluster at a similar degree (Coriobacteriaceae: Ato291, Lactobacillaceae: Lab148; Methods). Strikingly, imaging confirmed that while Lachnospiraceae were distributed across the cecum, they also formed large clustered aggregates that appeared to exclude other bacteria FIGS. 7-8. Importantly, this result highlights that individual taxa in the gut can organize in unique and spatially varying micron-scale structures that can be revealed by using MaP-seq.

Having established the local spatial organization across the GI tract of mice fed a standard plant-polysaccharide diet, we next sought to understand the extent to which diet might influence spatial structuring. Diet is known to play a major role in shaping the variation of gut microbiota across individuals (see Carmody, R. N. et al. Diet Dominates Host Genotype in Shaping the Murine Gut Microbiota. Cell Host & Microbe 17, 72-84 (2015); Sonnenburg, E. D. et al. Diet-induced extinctions in the gut microbiota compound over generations. Nature 529, 212-215 (2016)). While diet shifts can rapidly alter microbiota composition within days (see David, L. A. et al. Diet rapidly and reproducibly alters the human gut microbiome. Nature 505, 559-563 (2014)), the detailed ecological mechanisms underlying these community-scale changes are not well understood. We thus took co-housed mice and split them into two cohorts where one was maintained on the plant-polysaccharide based diet (LF, same as in the previous cohorts) and one was switched to a high fat, high sugar diet (HF, commonly utilized in dietary-induced obesity studies) to assess microbiota changes associated with these two diets representing distinct macronutrient profiles. After 10 days on the two diets, a considerable loss of species richness in the cecum and colon was observed in HF-fed mice compared to LF-fed mice FIG. 9.

To determine if a dietary shift could alter the spatial organization of the microbiota, which could contribute to the observed loss of species diversity, we performed MaP-seq on distal colon samples from mice fed the LF or HF diet. We found that the distribution of unique OTUs per ~20 μm cluster was similar between both diets FIG. 9b (top). This implies that species distributions at the local ~20 μm scale is governed by factors that are either common to or not affected by the two diets, for example spatial autocorrelation of bacterial growth. However, assessing diversity at the higher taxonomic family-rank revealed significantly higher diversity in HF clusters (Mann-Whitney U test, $p<10^{-22}$, FIG. 9b, bottom, indicating that while both LF and HF clusters contained similar numbers of OTUs, taxa within individual HF clusters were more phylogenetically diverse. Furthermore, positive co-associations were more frequently observed between diverse taxa in HF diet than in LF diet, which in contrast had co-associations mostly between Porphyromonadaceae or Lachnospiraceae.

Figure 9A:
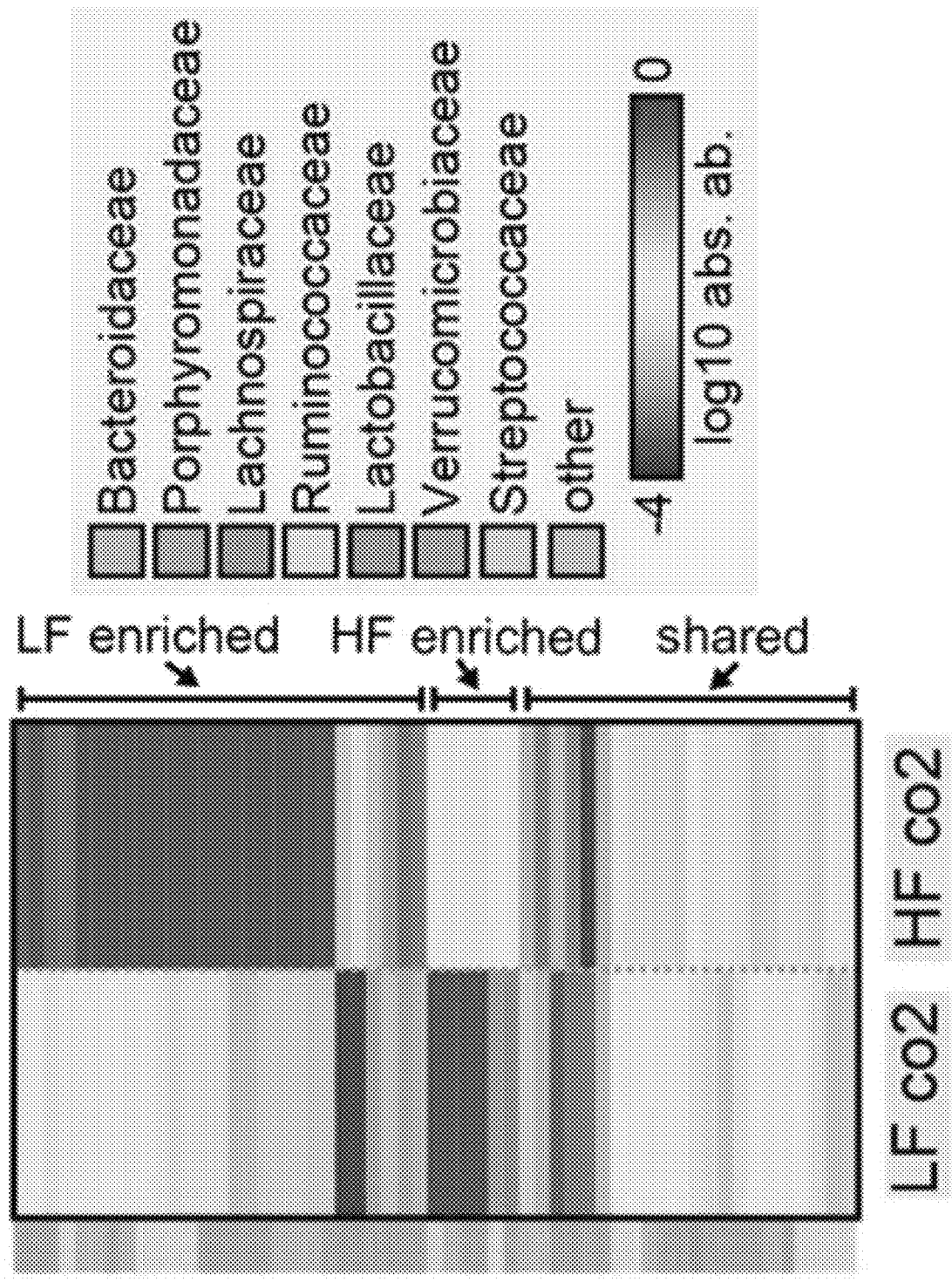
FIGS. 9a-9d: Spatial organization in the colon after dietary perturbation. a) Absolute abundance of dominant OTUs (>1% of maximum OTU absolute abundance in any sample) in the distal colon of co-housed mice fed a low fat, plant-polysaccharide diet (LF) or high fat diet (HF) for 10 days is shown as a heatmap (log 10 scale). Labels on right indicate LF enriched, HF enriched and shared OTUs. b) Top: histogram of the number of OTUs per cluster (OTUs>2% RA). Bottom: histogram of the number of distinct families per cluster (families>2% RA). For both plots, green indicates LF clusters and orange indicates HF clusters, dotted line indicates median value, and the number of clusters aggregated from two technical replicates is indicated (LF co2 n=495, HF co2 n=938). c) Histogram of net relatedness index (NRI) calculated for each cluster containing at least two OTUs, green indicates LF clusters and orange indicates HF clusters. d) tSNE visualization of clusters utilizing Bray-Curtis dissimilarity of OTU relative abundances (sub-sampled to 121 reads across all clusters). Left, cluster colored by site of origin; LF (green), HF (orange), number of clusters indicated above. In addition a biological replicate from an adjacent colonic segment of the same LF mouse is shown (LF(rep), dark green, n=359 clusters). Red arrows indicate examples of cluster configurations observed in both diet conditions. Right, each cluster is colored by the relative abundance of the eight most abundant families within each cluster (linear scale).
Figure 9B:
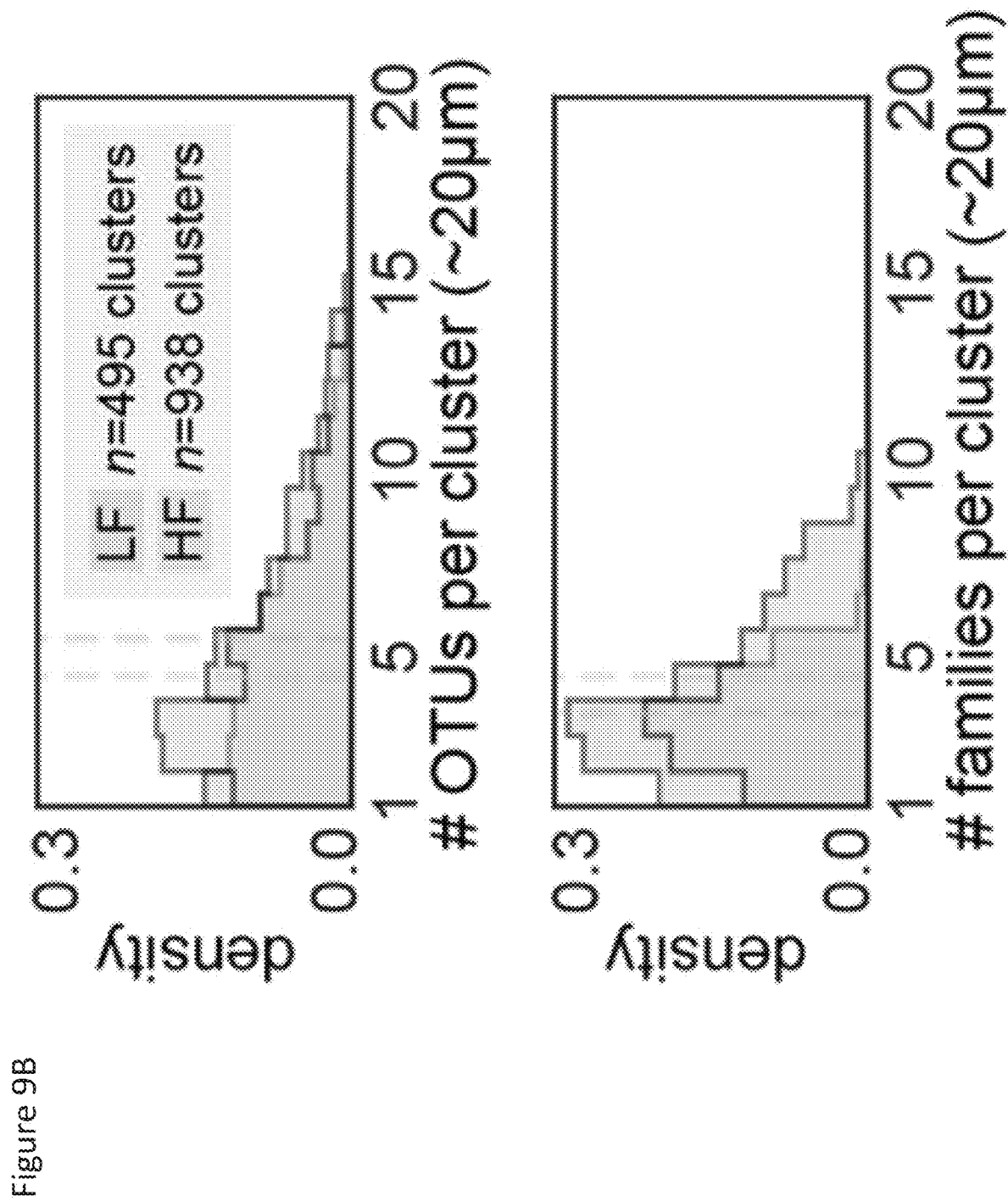
Figure 9C:
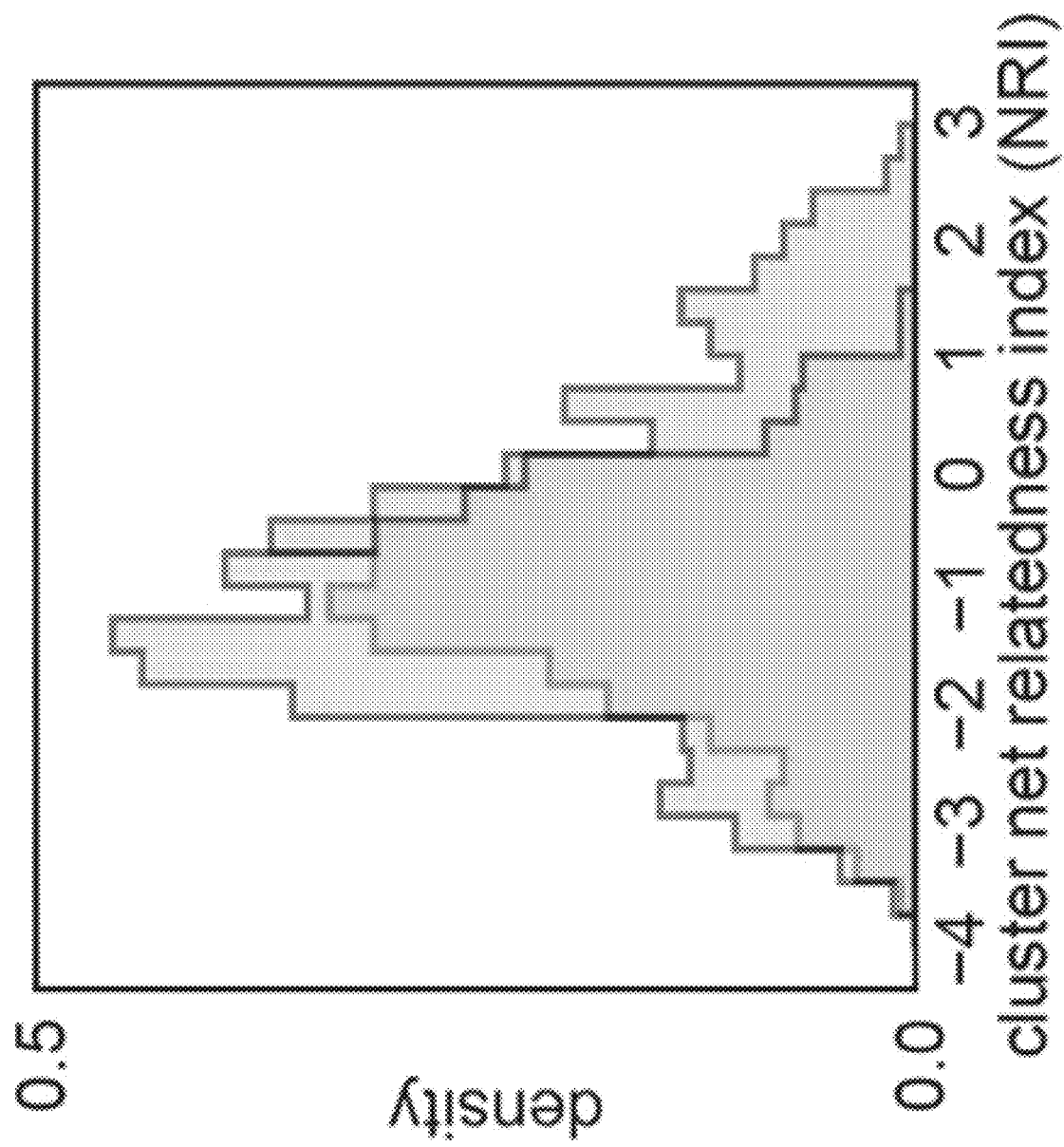
Figure 9D:
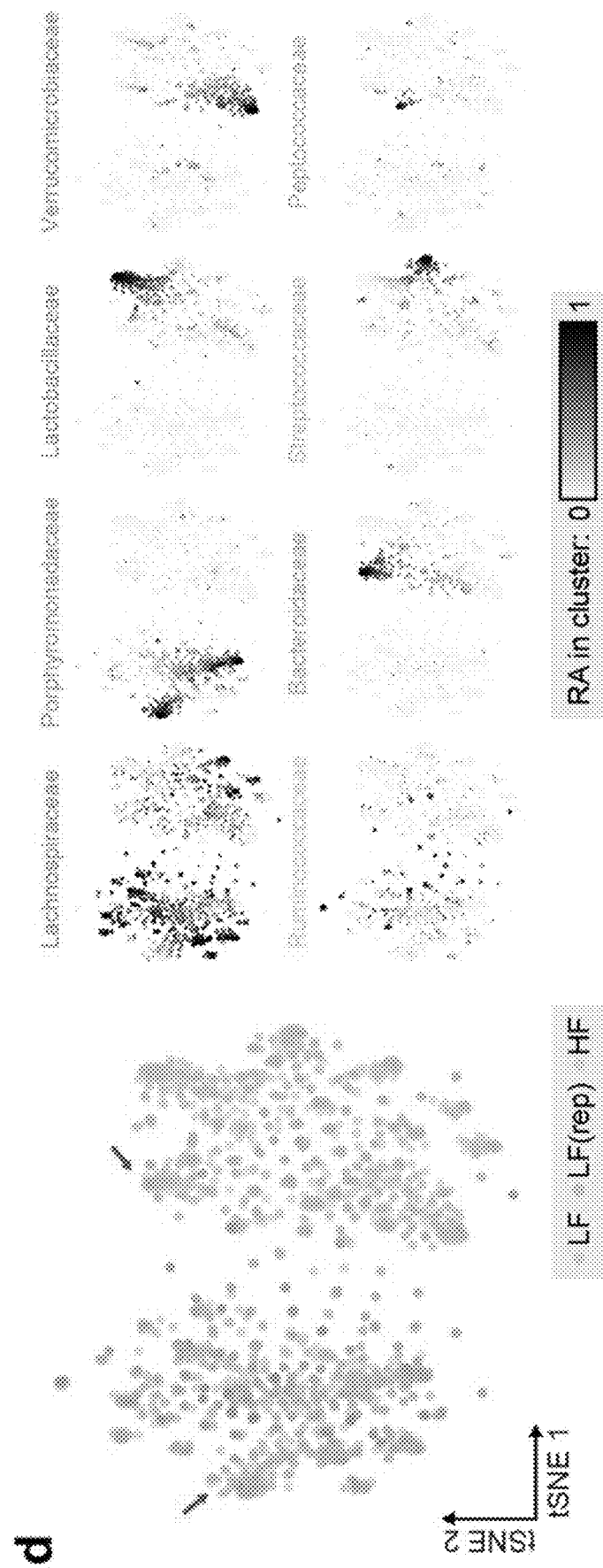
Figure 10A:
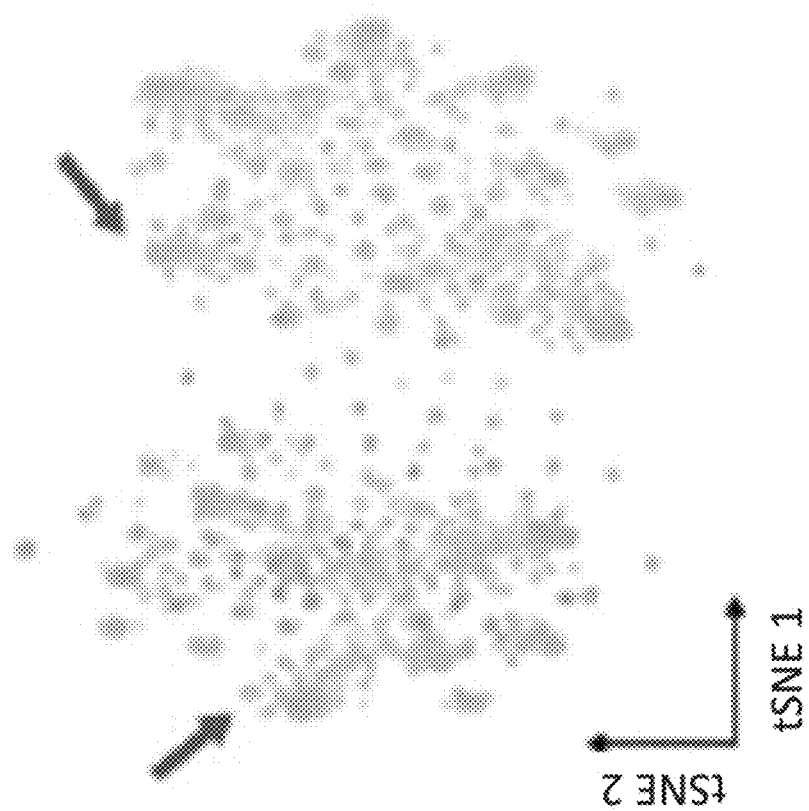
FIGS. 10a-10d: Additional information for tSNE analysis of dietary perturbation clusters. a) Same figure as FIG. 4d for reference. b) Clusters from each source (LF, LF(rep), HF) plotted separately on the same tSNE manifold for visualization purposes. c) Clusters are shaded by the number of OTUs per cluster (OTUs>2% RA in the subsampled dataset utilized for tSNE analysis). d) Clusters are shaded by the log 10 relative abundance of individual OTUs within each cluster. Red arrows on Bacteroidaceae OTU 6 and Porphyromondaceae OTU 5 plots indicate the same regions in FIG. 4d where clusters dominated by each of these taxa respectively are observed in both diets. The 24 OTUs with the highest average relative abundance across all clusters are displayed.
Figure 10B:
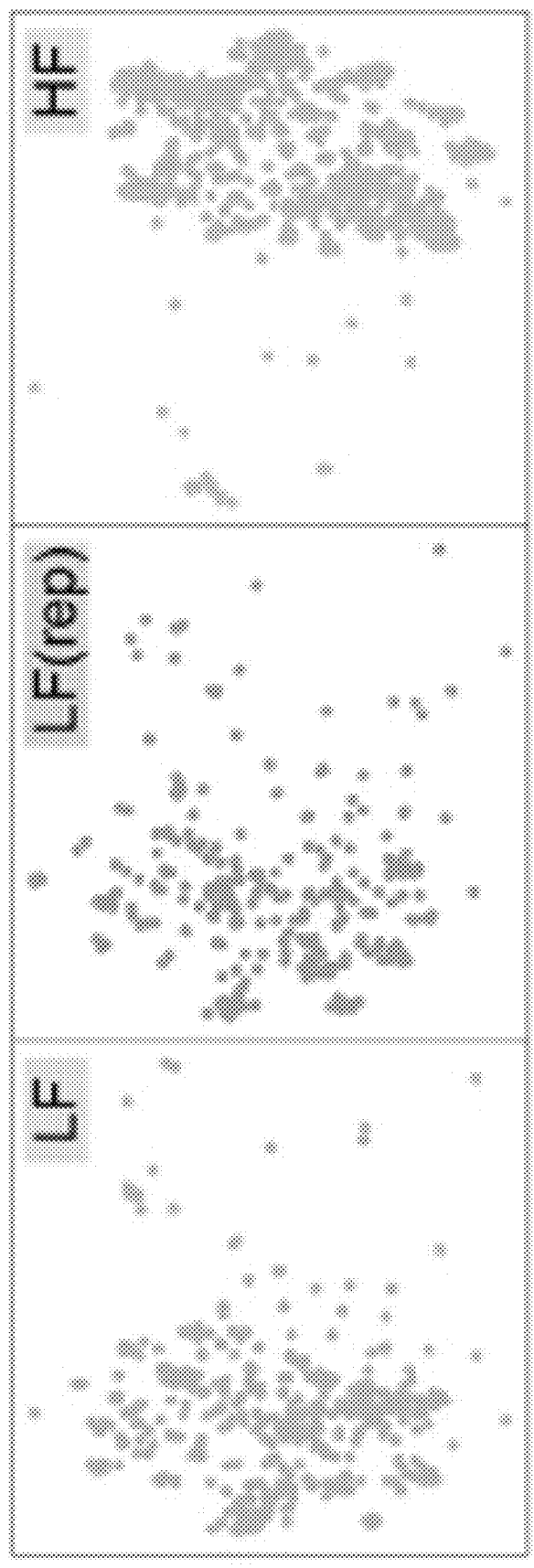
Figure 10C:
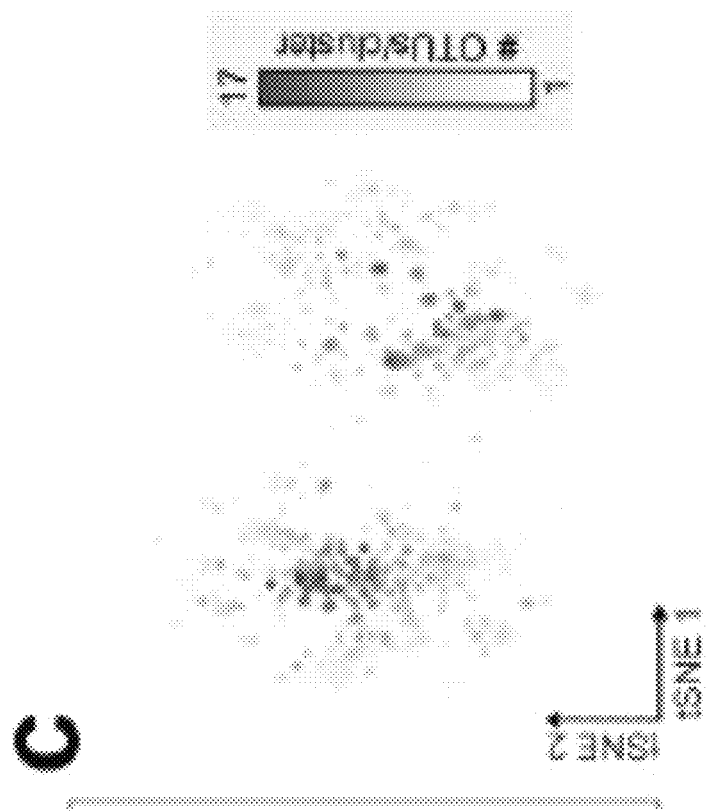
Figure 10D:
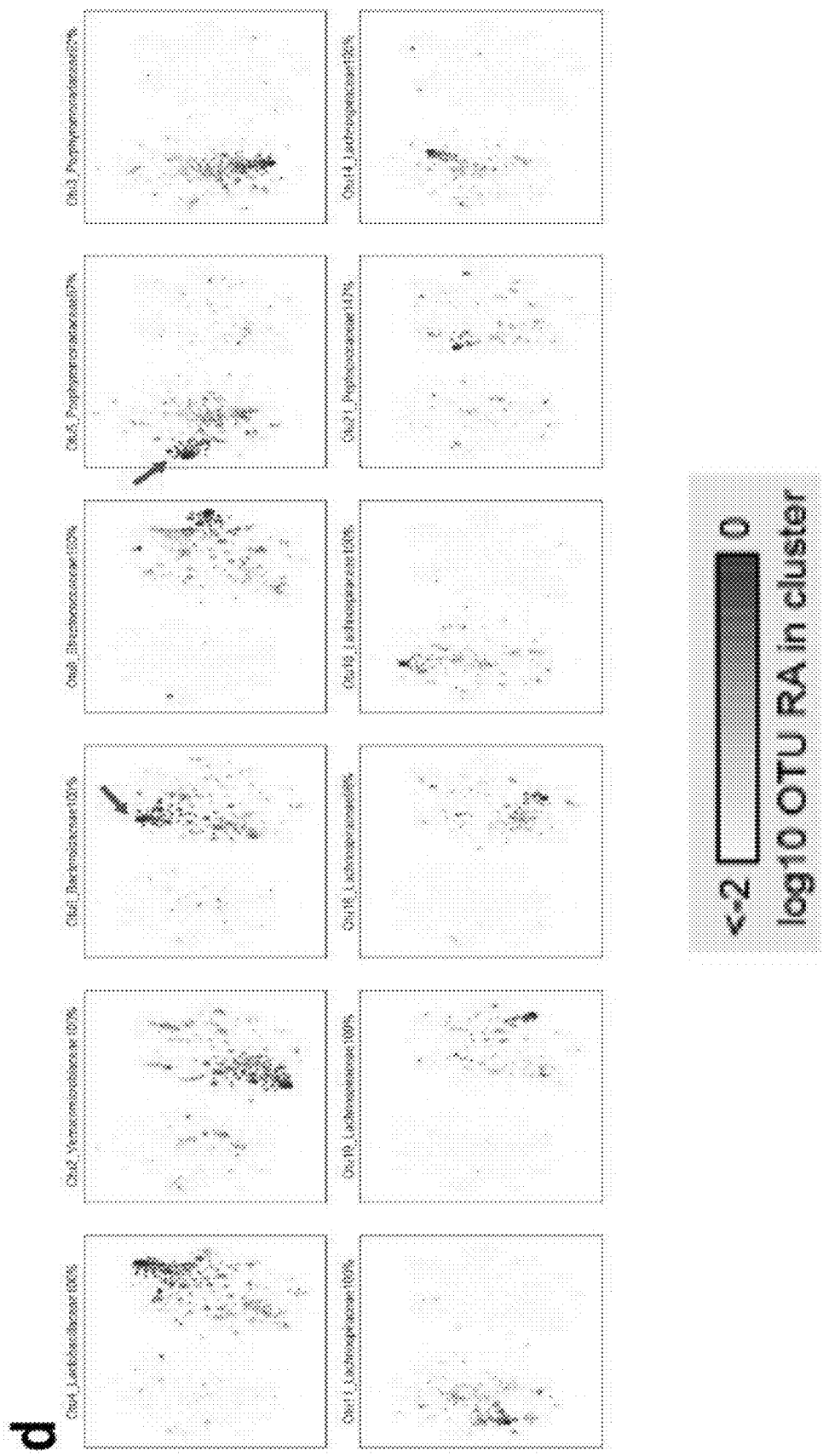
Figure 10D:
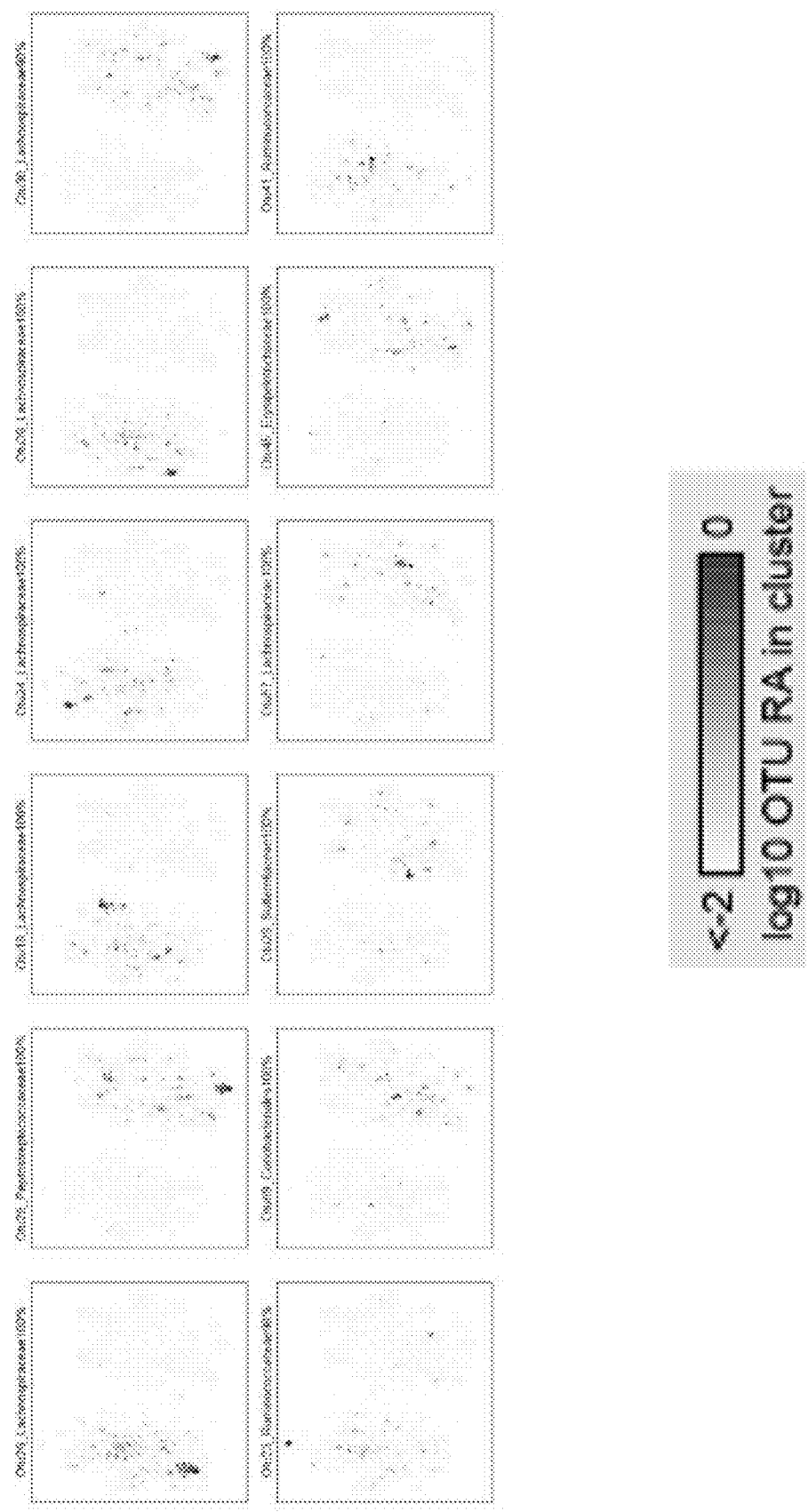
Figure 11A:
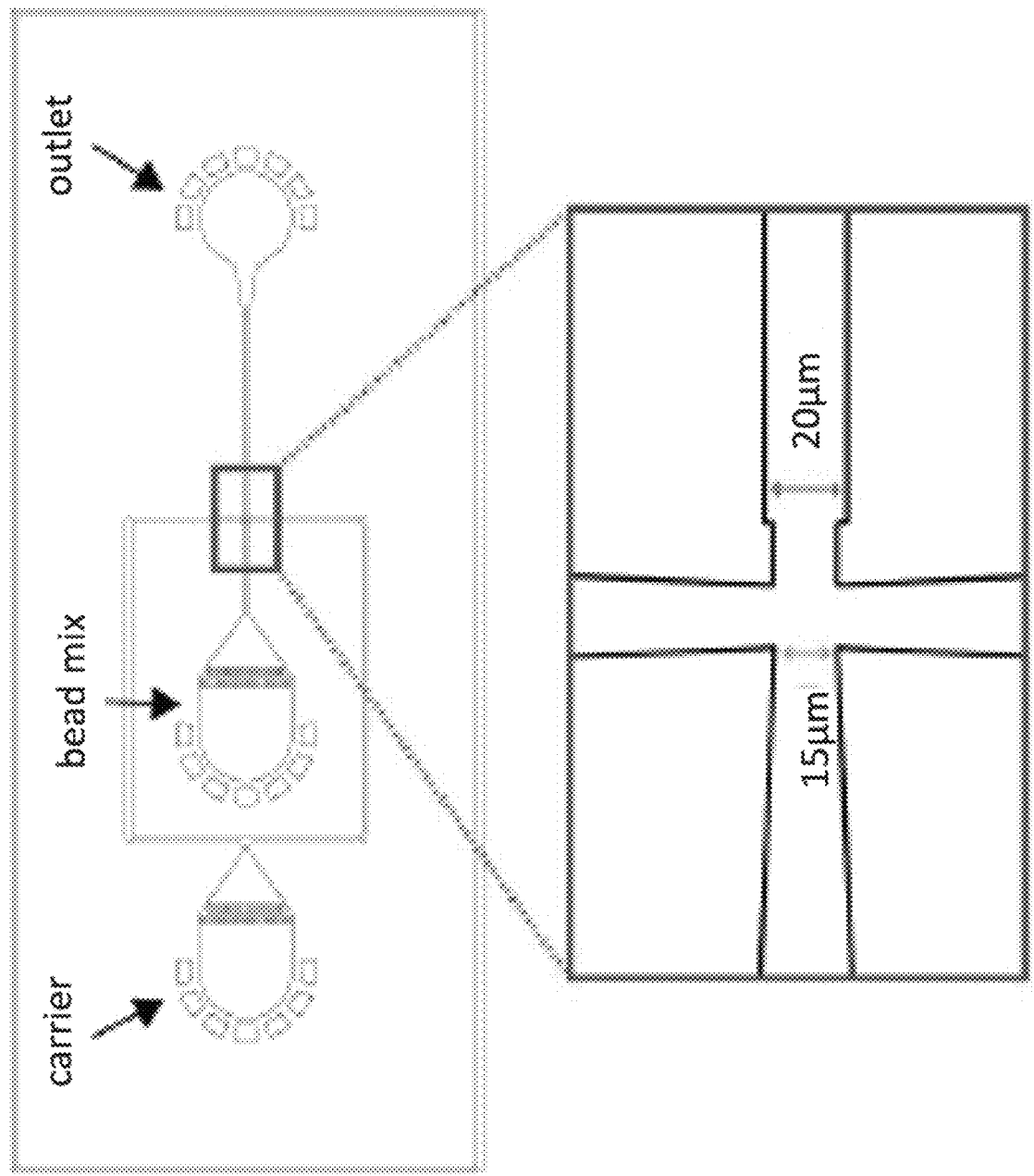
FIGS. 11a-11d: Barcoded bead quality control. a) Schematic of the microfluidic droplet generation device utilized to fabricate barcoded beads. b) Image of resulting barcoded gel beads visualized by phase contrast and hybridized with a FISH probe targeted to the terminal 16S 515f primer region present in fully extended primer product (bead_515f_cy5, see Table 4). c) Quantification of cleanup of primer synthesis intermediates by ExoI cleanup; the mean fluorescence intensity of beads was quantified (using Nikon Elements AR) when hybridized by a FISH probe targeted to the 515f site present on fully extended primer product (bead_515f_cy5) or a FISH probe targeted to the pe1 primer extension site (bead_pe1_cy5, see Table 4) present in all synthesis intermediates. Before cleanup the amount of pe1 sites on beads are higher than 515f sites, while after cleanup the amount of pe1 and 515f sites on beads are roughly equal, implying removal of un-extended primer intermediates (which contain pe1 sites, but not the terminal 515f site). d) Photorelease of amplification primer from beads; beads were subjected to no UV exposure or UV exposure for 10 minutes and supernatant was collected and analyzed via Agilent Bioanalyzer dsDNA HS assay; peaks at ~40 s and ~110 s are gel migration markers. A short primer product is observed to be released in a UV exposure dependent fashion.
Figure 11B:
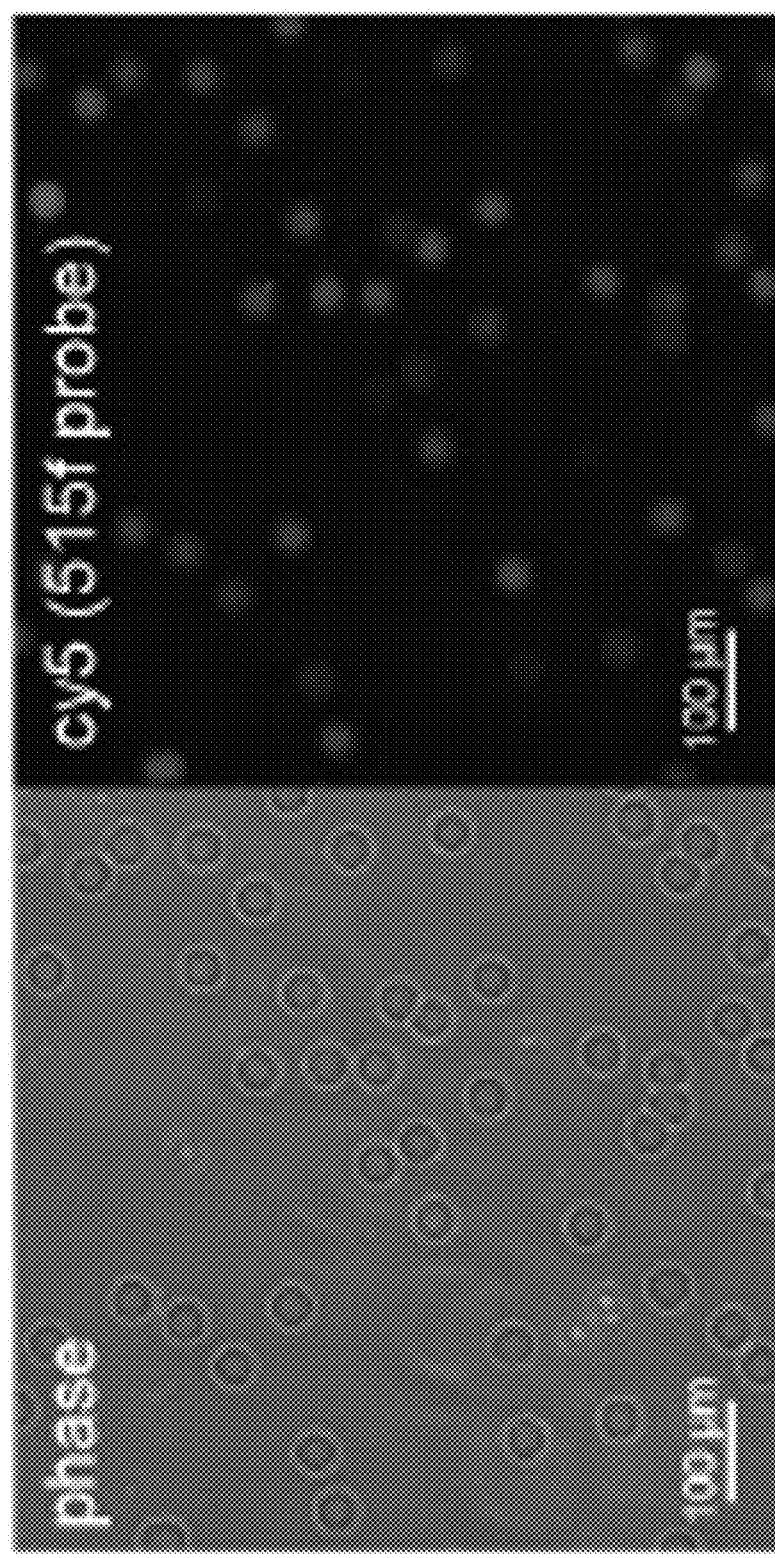
Figure 11C:
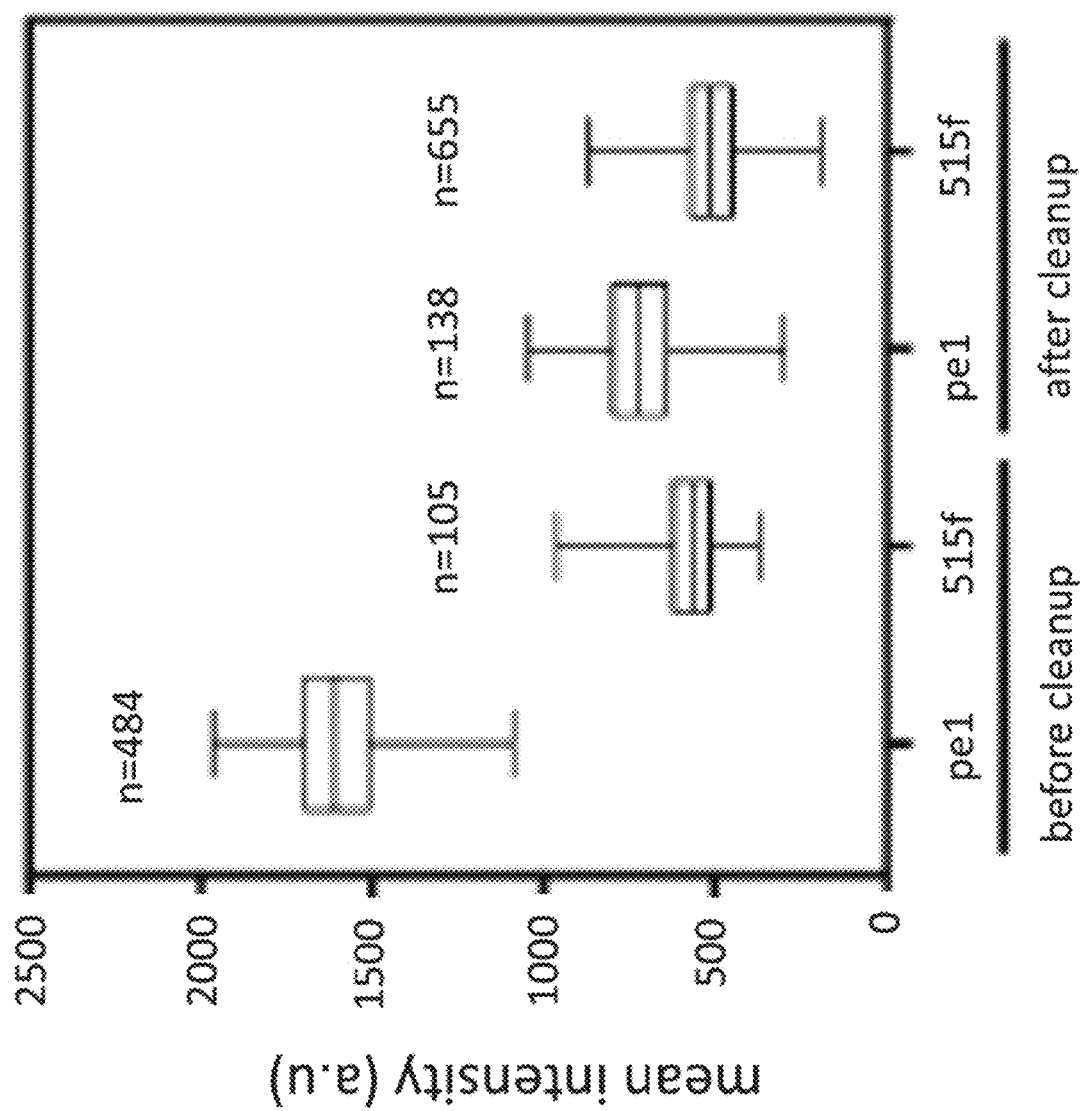
Figure 11D:
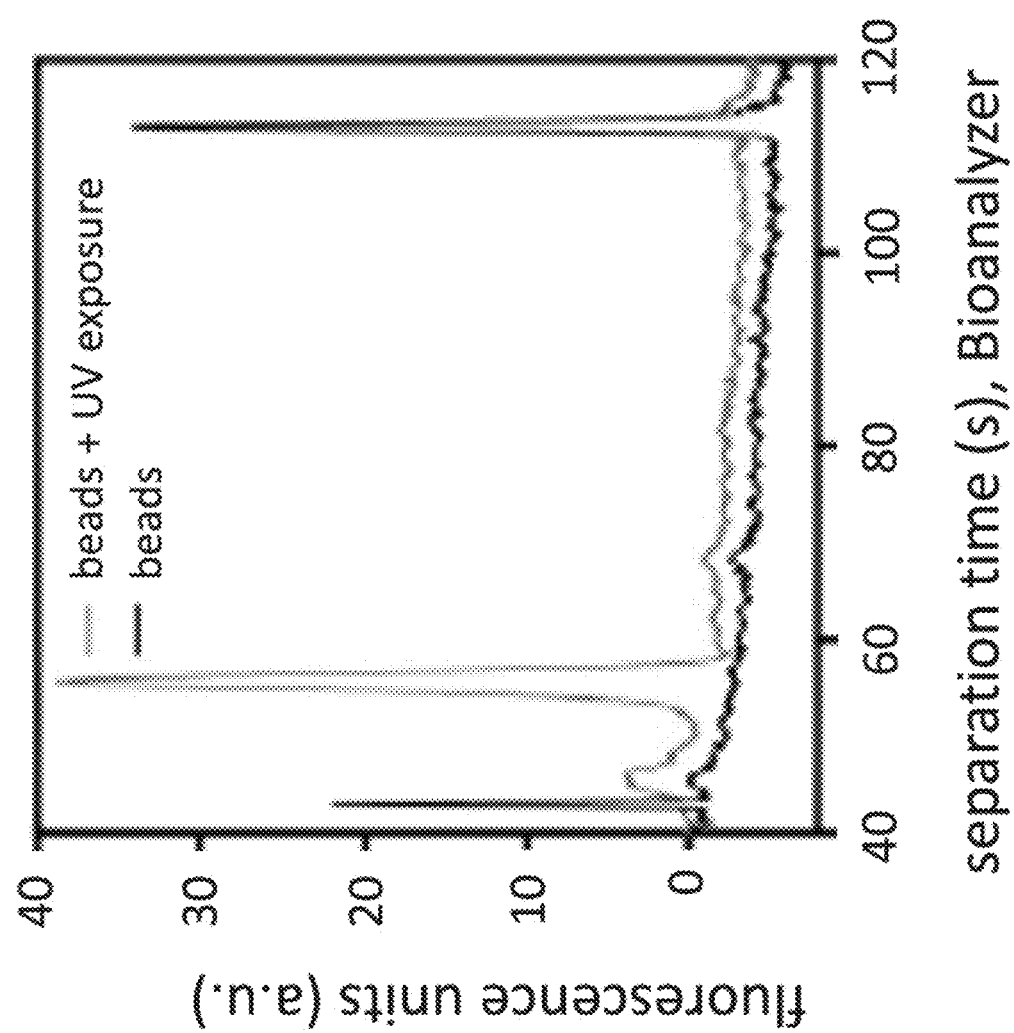

Next, to compare the taxa spatial organization across the two diets, we visualized clusters using tSNE as before FIG. 9d, FIG. 10. Cell clusters from the two diets each formed highly distinct groups with minimal overlap, indicating that the spatial organization in the distal colon was significantly altered by the dietary shift. Despite this overall separation, we observed examples of cluster configurations that were shared between the two diets. For example, HF clusters were observed in a predominantly LF region marked by high abundance of a Porphyromondaceae taxa (OTU 5), and LF clusters were observed in a predominantly HF region marked by high abundance of a Bacteroidaceae taxa (OTU 6) FIG. 10d.

The following are examples of the present invention and are not to be construed as limiting.

EXAMPLES

Example 1 Spatial Metagenomic Characterization of Microbial Biogeography in the Gut Spatial structuring promotes biodiversity and is important to the maintenance of natural ecological systems[1,2]. Many microbial communities, including the mammalian gut microbiome, display intricate spatial organization[3-9]. Mapping spatial distributions of bacterial species enables the detailed delineation of fundamental ecological processes and interactions that underlie community-wide behaviors[10-12]. However, current approaches have a limited capacity to measure the spatial organization of natural microbiomes with hundreds of species[13-17]. Here, we describe spatial metagenomics, a framework to dissect the organization of a microbiome at micron-scale spatial resolution and metagenomic depth through nucleic acid "plot sampling". Intact microbiome samples are immobilized within a gel matrix and subjected to cryo-fracturing to generate clusters of co-localized cells, and the identities and abundances of taxa present in these clusters are determined via droplet-based encapsulation and deep sequencing. Analysis of thousands of microbiome clusters from the mouse intestine across three distinct regions revealed heterogeneous microbial distributions with positive and negative co-associations between specific taxa. While the murine intestinal microbiome mostly exhibited regionally distinct spatial organizations, robust associations between Bacteroidales taxa were observed across gut compartments. Analysis of a dietary perturbation revealed phylogenetically clustered regions suggesting local habitat filtering that may be important to maintenance of diversity observed on plant-polysaccharide diets, and enabled identification of spatial niches that may be shared across distinct diets. Spatial metagenomics constitutes a powerful new culture-independent technique to mechanistically study microbial biogeography in complex habitats.

To perform MaP-seq, an input sample is first physically fixed by immobilizing the microbiota via perfusion and in situ polymerization of an acrylamide polymer matrix that also contains a covalently linked reverse 16S rRNA amplification primer. The embedded sample is then fractured via cryo-bead beating, subjected to cell lysis, and passed through nylon mesh filters for size selection to yield cell clusters or particles of desired and tunable physical sizes (i.e. by utilizing different mesh filter sizes). Resulting clusters contain genomic DNA immobilized in their original arrangement, preserving local spatial information. Next, a microfluidic device is used to co-encapsulate these clusters with gel beads, each containing uniquely barcoded forward 16S rRNA amplification primers. Primers are photocleaved from the beads and clusters, genomic DNA is released from clusters by triggered degradation of the polymer matrix within droplets, and PCR amplification of the 16S V4 region is performed. Droplets are then broken apart, and the resulting library is subjected to deep sequencing. Sequencing reads are filtered and grouped by their unique barcodes, which yield the identity and abundance of bacterial operational taxonomic units (OTUs) within individual cell clusters.

Figure 1B:
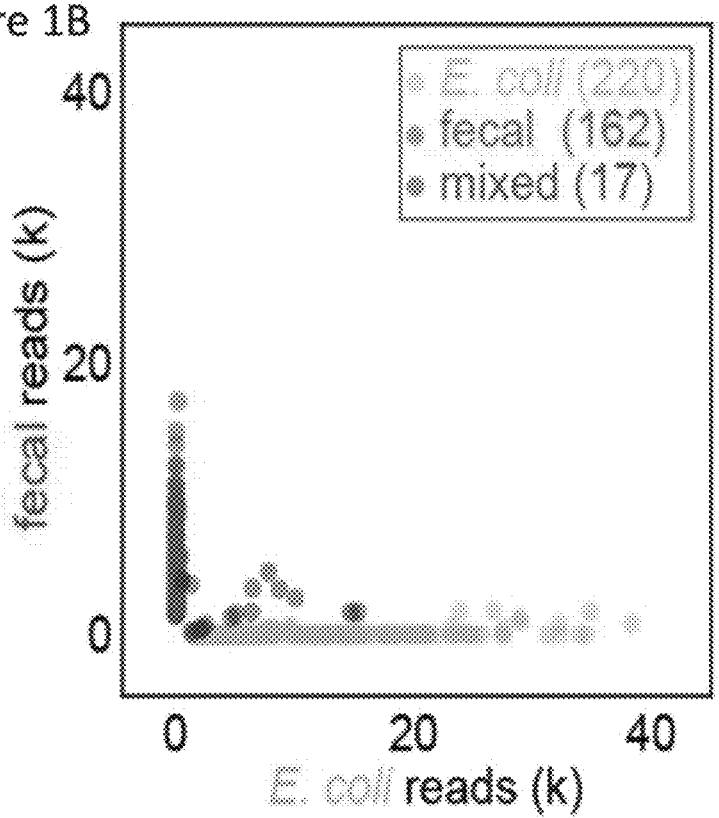
Figure 1C:
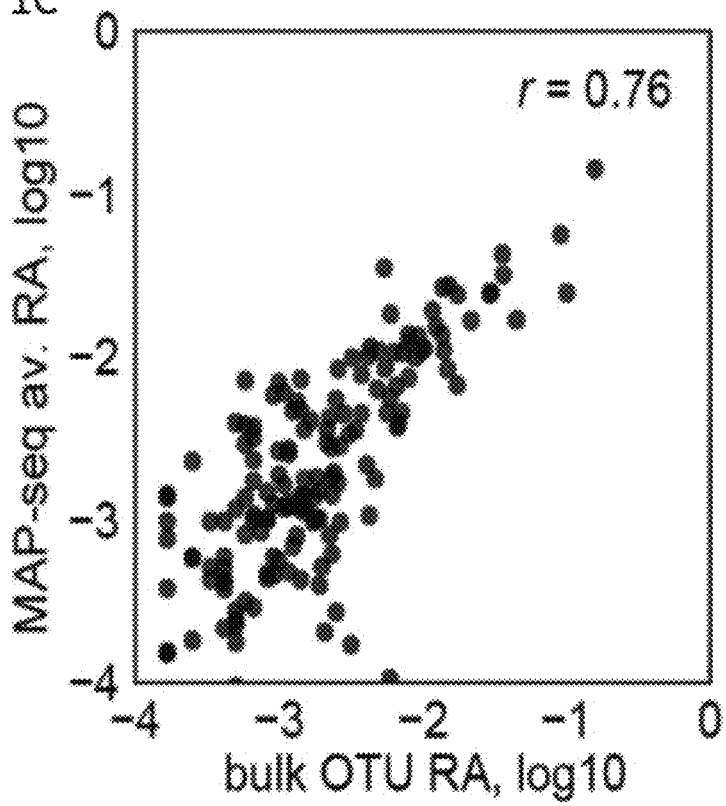

To rigorously test the feasibility of this spatial metagenomics approach, we first generated separate cluster communities from either homogenized mouse fecal bacteria or *E. coli* (Methods) and profiled them with MaP-seq. The resulting data revealed that the majority of detected barcodes mapped uniquely to their respective initial communities with minimal mixing (FIG. 1b, 4.3% mixed) and negligible contamination introduced during sample processing (<0.2% of reads). In addition, the average abundance of taxa across individual fecal clusters obtained by enzymatic lysis and droplet PCR displayed good correlation with standard mechanical cell lysis and bulk 16S PCR measurements (FIG. 1c, Pearson correlation $r=0.76$). A replicate community mixing experiment with new particles of a smaller size confirmed technical performance of the approach. Together, these results indicate that MaP-seq accurately measures bacterial identity and abundance within individual spatially constrained cell clusters.

To explore the utility of spatial metagenomics to map the natural biogeography of microbiota in complex communities, we applied MaP-seq to the mouse colonic microbiome. We generated and characterized cell clusters (~30 μm median diameter) from a segment of the distal colon (including both epithelium and digesta) of a mouse fed a plant-polysaccharide diet, yielding 1,406 clusters passing strict quality filtering across two technical replicates (FIG. 2a, Methods). 236 total OTUs were identified with their prevalence across clusters highly correlating to bulk abundance obtained by standard 16S sequencing, implying that more abundant taxa are also physically dispersed over more space (FIG. 2b, Pearson correlation r=0.90). The spatial distribution of taxa across clusters appeared mixed (median 9 OTUs per cluster), but some clusters contained only a few OTUs indicating spatial aggregation or clumping in a fraction of the community (FIG. 2c). Moreover, this observed distribution of OTUs per cluster was significantly lower than clusters of the same size generated from homogenized fecal bacteria, which serve as a control for a well-mixed community (Mann-Whitney U test, p<10-26). These results suggest that at the scale of tens of microns, individual taxa in the gut microbiome are neither fully mixed nor highly structured, but rather are heterogeneously distributed in mixed patches. Peristaltic mixing across the gut likely acts to decrease strong spatial segregation between taxa, but nevertheless the weak but significant spatial structuring observed could play an important role in the maintenance of high microbial diversity observed in the healthy gut[1,22].

We next explored whether these observed spatial distributions reflect specific associations between individual taxa that may result from processes such as positive or negative interspecies interactions (e.g., cooperative metabolism[24], contact-dependent killing[20]) or local habitat filtering[11]. Across abundant and prevalent OTUs (>2% abundance in >10% of clusters, n=24), we assessed whether their pairwise co-occurrences were detected more or less frequently than expected in comparison to a null model of independent, random assortment of OTUs (Methods, Fisher's exact test, p<0.05, FDR=0.05). Application of this strategy to the cluster mixing control experiment confirmed our ability to accurately detect positive and negative spatial associations that are expected. Out of 276 possible pairwise combinations of taxa in the murine colon, we detected 75 statistically significant associations between diverse taxa, the majority of which were positive (72/75) but relatively weak in magnitude (FIG. 2d). The strongest co-occurrence was a positive association between abundant Bacteroidaceae and Porphyromonadaceae taxa from the Bacteroidales order (odds ratio 3.9, p<10-23). In addition, a small number of negative associations were observed, which could reflect antagonistic processes such as production of inhibitory factors or competitive exclusion.

The number of detected associations increased as more of the dataset is sampled, implying that detection of weaker relationships between less abundant taxa can be improved by analyzing more clusters. Nonetheless, the detected associations showed good correspondence between technical replicates. Importantly, despite high inter-host microbiome variability, the nature of the associations (i.e., sign, magnitude, and number) and some strong associations could be recapitulated in MaP-seq profiling of a second co-housed mouse, such as the co-occurrence of Bacteroidales taxa. This characterization implies that individual taxa in the colon are organized in distinct and reproducible spatial relationships.

To further investigate how the spatial organization of the microbiota is influenced by their environmental context, we applied spatial metagenomics along the gastrointestinal (GI) tract. The mammalian GI tract is composed of distinct anatomical regions with different pH levels, oxygen concentrations, host-derived antimicrobials and transit times that together influence the local microbiota assemblage[9]. We first performed an adapted 16S community profiling approach along the murine GI tract that could also infer absolute OTU abundances25 (FIG. 3a). This new mouse cohort (2 co-housed mice) shared only ~20% of OTUs with the previous group, illustrating the significant inter-animal microbiome heterogeneity inherent to such studies. This further highlights challenges for other spatial profiling techniques such as 16S FISH imaging where probes must be designed in advance, in comparison to MaP-seq, which can be applied to measure diverse bacteria without advance specification. Analysis of microbiota in absolute abundance across the intestine revealed increased bacterial density (~16 fold higher) and species richness in the large intestine compared to the small intestine, with the cecum harboring the highest bacterial density and number of OTUs. We chose three separate GI regions that exhibited distinct microbiota assemblages for characterization by MaP seq: the ileum (si6), cecum (cec) and distal colon (co2). Given the high degree of species mixing previously observed at ~30 we used smaller sized clusters (~20 μm median diameter) to capture higher-resolution spatial associations.

We first assessed the distribution of OTUs per cluster to compare the spatial organization of taxa in the three regions (FIG. 3b). ~20 μm clusters displayed lower numbers of OTUs per cluster than ~30 μm clusters (median 3-4 OTUs per cluster). The ileum possessed significantly fewer OTUs per cluster than the cecum or distal colon (Mann-Whitney U test, p<10-18 and p<10-14 respectively). In comparison, the cecum and colon displayed similar OTU distributions, while the cecum harbored more clusters with a large number of OTUs. This suggests that GI regions with more diverse microbiota also exhibit higher spatial diversity at microscopic scales.

To understand how the local spatial organization of the microbiome may vary within and across different gut compartments, we visualized the cell clusters data across the three gut regions using t-distributed Stochastic Neighbor Embedding (tSNE, utilizing Bray-Curtis distance of OTU relative abundance within clusters), as well as the abundance of prevalent bacterial families in cell clusters across the resulting manifold (Methods, FIG. 3c). While some cell clusters from the ileum, cecum and distal colon separately projected into distinct groups, other clusters from each site projected more broadly across the manifold. Interestingly, a subset of cell clusters from the cecum projected into a dense group and are compositionally dominated by Lachnospiraceae, which were generally not present in clusters from the ileum or distal colon. When cell clusters from a second co-housed mouse were added to the tSNE analysis, they were distributed in a similar manner to clusters from the first mouse across the manifold and displayed a similar cecum-specific Lachnospiraceae group, further strengthening these results. Our observations suggest that the spatial distribution of some taxa at different GI regions may have distinct local organizations from one another while other taxa may have similar local organization along the GI tract.

Next, we explored whether these different spatial distributions reflect distinct spatial co-associations between taxa at each GI site (FIG. 3d). The ileum harbored a network of positive and negative associations between the few taxa present. On the other hand, the cecum exhibited a dense network of positively co-associated taxa, primarily between abundant Lachnospiraceae, Ruminococcaceae, and Porphyromonadaceae. Similar to the cecum, the distal colon displayed only positive associations, including strong groupings between three abundant Porphyromonadaceae (OTUs 5, 8, 9). Profiling the colon at an even smaller size-scale (~7 μm) confirmed strong positive associations between these three taxa, indicating that this spatial clustering occurs robustly at short, local length scales. Species from these abundant Bacteroidales taxa often contain diverse carbohydrate-active enzymes[26] and are known to engage in cooperative metabolic cross-feeding[24,27], which could promote these spatial co-associations.

While the spatial association networks revealed by MaP-seq differed across the three GI regions, some common co-associations (or lack of associations) were observed. For example, a positive association between Lachnospiraceae (OTU 10) and Lactobacillaceae (OTU 4) was found in both the cecum and colon; on the other hand, Coriobacteriaceae (OTU 1), an abundant taxon at all sites, lacked co-associations with other taxa and was thus randomly assorted at all sites. Together, the differing spatial architectures observed across GI sites suggest that regional environmental factors can variably shape some local spatial structuring of the microbiota, while conserved spatial patterns across sites are more likely the result of robust ecological interactions not affected by environmental variations.

We further investigated whether MaP-seq could identify individual taxa with unique or altered spatial patterns. While the cecum harbored the densest community and the highest degree of species mixing of the three sites (FIG. 3a-b), we hypothesized that specific taxa may self-aggregate to a higher degree than others, for example by uniquely utilizing a specific metabolite[11]. Assessing the aggregation of abundant taxa revealed a Lachnospiraceae (OTU 7; putatively of the genus *Dorea*, 60% confidence by RDP) that clustered two-fold greater than the average clustering metric value of all taxa. To validate this finding with an orthogonal approach, we performed 16S FISH on GI sections from the same murine sample using previously validated probes that targeted Lachnospiraceae (Erec482) as well as two other abundant taxa for which FISH probes were available but were predicted not to cluster at a similar degree (Coriobacteriaceae: Ato291, Lactobacillaceae: Lab148; Methods). Strikingly, imaging confirmed that while Lachnospiraceae were distributed across the cecum, they also formed large clustered aggregates that appeared to exclude other bacteria. Importantly, this result highlights that individual taxa in the gut can organize in unique and spatially varying micron scale structures that can be revealed by MaP-seq.

Having established the local spatial organization across the GI tract of mice fed a standard plant polysaccharide diet, we next sought to understand the extent to which diet might influence spatial structuring. Diet is known to play a major role in shaping the variation of gut microbiota across individuals[28,29]. While diet shifts can rapidly alter microbiota composition within days[30], the detailed ecological mechanisms underlying these community-scale changes are not well understood. We thus took co-housed mice and split them into two cohorts where one was maintained on the plant polysaccharide based diet (LF, same as in the previous cohorts) and one was switched to a high fat, high sugar diet (HF, commonly utilized in dietary-induced obesity studies) to assess microbiota changes associated with these two diets representing distinct macronutrient profiles. After 10 days on the two diets, a considerable loss of species richness in the cecum and colon was observed in HF-fed mice compared to LF-fed mice (FIG. 4a).

To determine if a dietary shift could alter the spatial organization of the microbiota, which could contribute to the observed loss of species diversity, we performed MaP-seq on distal colon samples from mice fed the LF or HF diet. We found that the distribution of unique OTUs per ~20 μm cluster was similar between both diets (FIG. 4b, top). This implies that species distributions at the local ~20 μm scale is governed by factors that are either common to or not affected by the two diets, for example 202 spatial autocorrelation of bacterial growth. However, assessing diversity at the higher taxonomic family-rank revealed significantly higher diversity in HF clusters (Mann-Whitney U test, $p<10-22$, FIG. 4b, bottom), indicating that while both LF and HF clusters contained similar numbers of OTUs, taxa within individual HF clusters were more phylogenetically diverse. Furthermore, positive co-associations were more frequently observed between diverse taxa in HF diet than in LF diet, which in contrast had co-associations mostly between Porphyromonadaceae or Lachnospiraceae. Interestingly, our observation of increased bacterial mixing at higher taxonomic levels has also been documented in mice fed with a plant polysaccharide deficient diet (compared to a LF plant-polysaccharide rich diet) using confocal imaging with 16S FISH probes of limited phylum-level specificity6, which further highlights the utility of examining spatial organization at a higher taxonomic resolution that is achievable by MaP-seq.

Understanding the phylogenetic distribution of an ecosystem can provide important insights into ecological processes underlying community assembly[31,32]. To better quantify possible changes in phylogenetic diversity between the two diets, we calculated the net relatedness index (NRI) of clusters, a standardized effect size of the mean phylogenetic distance of taxa present within clusters against a null model of random sampling from the local species pool (Methods) 31. For each microbiota cluster, a positive NRI value indicates phylogenetic clustering of its taxa, whereas a negative NRI indicates phylogenetic over-dispersion. While most clusters had NRI values near 0, suggesting random phylogenetic distributions, both LF and HF diets showed a subset of clusters with high negative NRI values suggesting a high degree of phylogenetic over-dispersion. Interestingly, NRI values in LF clusters were overall significantly higher compared to HF values (Mann-Whitney U test, $p<10-18$), driven by a subset of LF clusters with positive NRIs not observed in HF clusters (FIG. 4c). The phylogenetic clustering observed in this subset of LF clusters suggests that ecological habitat filtering due to factors associated with the LF diet (e.g. complex plant polysaccharides) may be important in shaping in the formation of these clusters at length-scale of ~20 μm (assuming that more phylogenetically similar taxa also have more similar phenotypes). A possible explanation for the loss of species diversity when transitioning from a LF to a HF diet could thus be the loss of this LF-specific local niche, which stably hosts these closely related taxa. Indeed, the same taxa (predominantly Lachnospiraceae OTUs) that are abundantly found in LF clusters with high NRI values are those that are almost completely lost on HF diet.

Figure 4D:
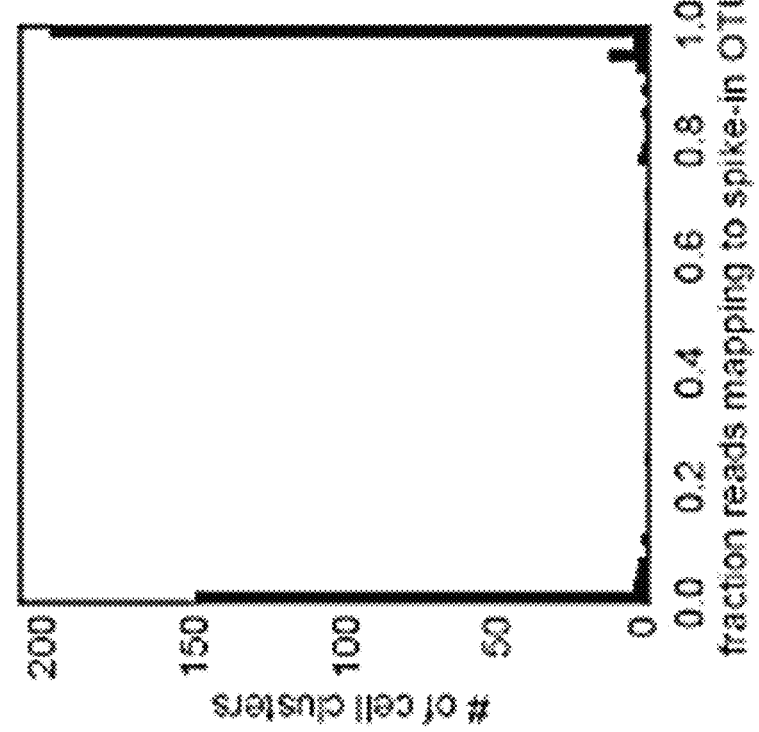
Figure 4F:
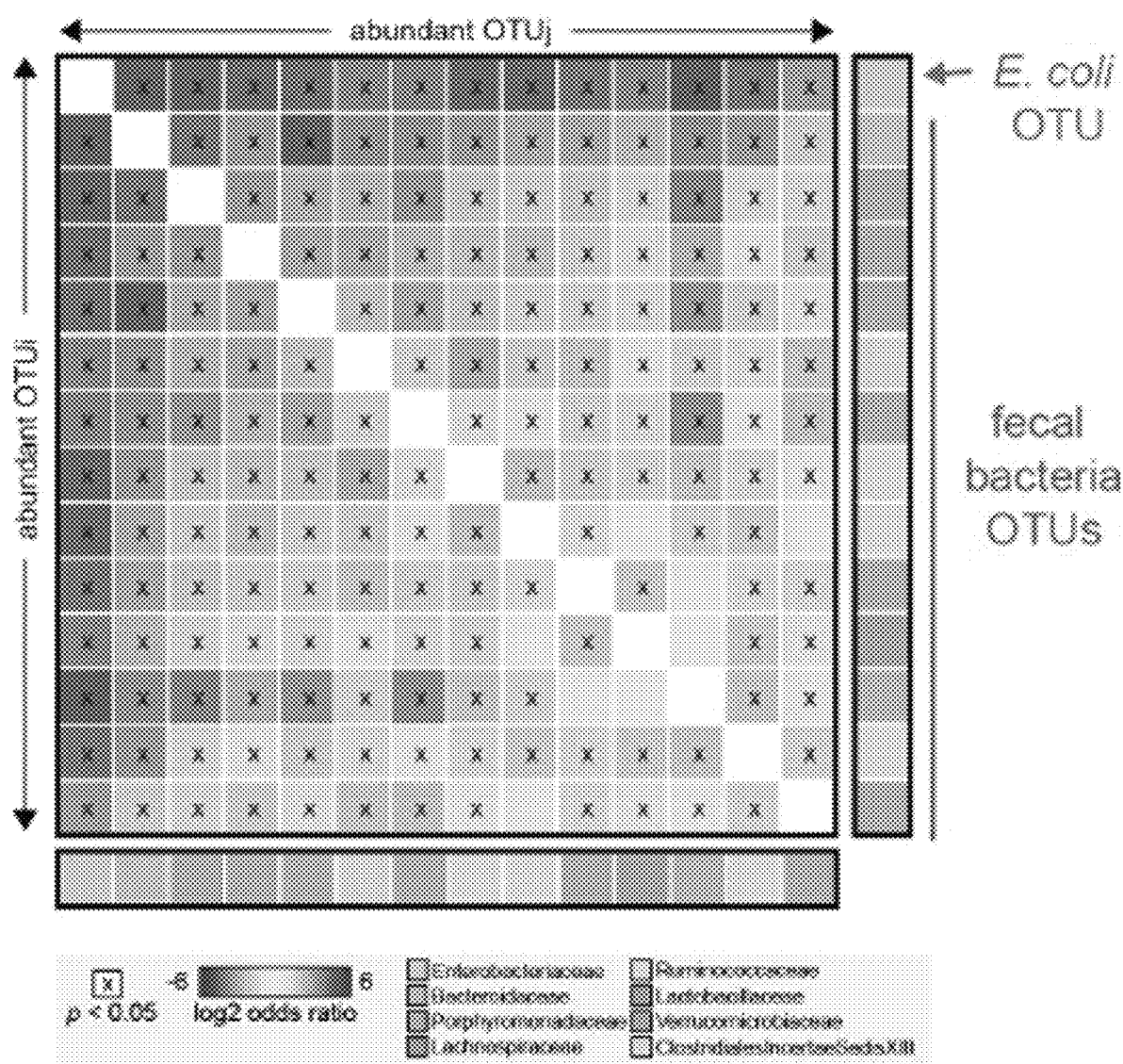

Next, to compare the taxa spatial organization across the two diets, we visualized clusters using tSNE as before (FIG. 4d). Cell clusters from the two diets each formed highly distinct groups with minimal overlap, indicating that the spatial organization in the distal colon was significantly altered by the dietary shift. Despite this overall separation, we observed examples of cluster configurations that were shared between the two diets. For example, HF clusters were observed in a predominantly LF region marked by high abundance of a Porphyromondaceae taxa (OTU 5), and LF clusters were observed in a predominantly HF region marked by high abundance of a Bacteroidaceae taxa (OTU 6). These shared cluster regions could represent spatial niches that may be independent of the diet (e.g. mucus layers secreted by the host). Taken together, MaP-seq profiling of a diet perturbation enabled mechanistic analysis of ecological processes underlying community shifts and loss of diversity.

Spatial metagenomics enables the high-throughput characterization of microbial biogeography through microscopic plot sampling of co-localized nucleic acids at tunable length scales. This general approach could be applied to interrogate a variety of perturbations in the gut (e.g., diet, antibiotics, fecal microbiota transplantation), other mammalian associated microbiota (e.g. skin, genital), or diverse environmental ecosystems, such as soils or biofilms. Importantly, MaP-seq enables in-depth analysis of these processes at previously inaccessible and ecologically meaningful local length scales within individual microbiomes. Improvements to further increase the throughput of the approach could better delineate weaker or rarer co-associations and help investigate structuring across many different characteristic length scales within microbiomes. A variety of established spatial ecology tools and emerging computational and analytical approaches could be applied to this new type of high-dimensional microbiome dataset. Extensions of this general framework to spatially profile other biological molecules such as RNA, proteins and metabolites will enable mapping of complex cellular systems across mechanistically important and functionally distinct axes. Plot sampling of biological structures at microscopic scales opens up new directions of research that employ spatial ecology tools to study these complex systems.

Materials and reagents. All primers and FISH probes were ordered from Integrated DNA Technologies. Primers containing any modifications were HPLC purified by the manufacturer. Photocleavable primers were protected from unnecessary light exposure throughout.

Animal procedures. All mouse procedures were approved by the Columbia University Medical Center Institutional Animal Care and Use Committee (protocol AC-AAAR1513) and complied with all relevant regulations. 6-8 week-old female C57BL6/J mice were obtained from Taconic (colonic analysis, FIG. 2) or Jackson (analysis across GI tract, FIG. 3; dietary perturbation, FIG. 4) and fed a plant-polysaccharide based diet (LabDiet 5053). Dietary perturbation was performed by splitting four co-housed mice into two cages; one cage received the same plant-polysaccharide based diet and one cage received high fat diet (Teklad TD.06414).

Microfluidic device fabrication. Devices were fabricated utilizing standard SU-8 soft lithography. Silanized SU-8 silicon wafer molds were fabricated by FlowJEM with a feature height of ~40 µm. PDMS (Dow Corning Sylgard 184) was mixed for 5 minutes at a ratio of 10:1 base to curing agent, degassed under house vacuum for 30 minutes, and poured over the wafer. The PDMS mixture was cured at 80° C. for 1 hour, allowed to cool to room temperature and removed from the wafer. Individual devices were cut from the PDMS slab and ports were punched utilizing a 1 mm biopsy punch (World Precision Instruments 504646). FIG. 11. Uniquely barcoded bead design and construction. We designed custom barcoded hydrogel beads containing one of 884,736 unique barcoded primers per bead and a partial sequencing adapter and 16S V4 primer 515f (see Parada, A. E., Needham, D. M. & Fuhrman, J. A. Every base matters: assessing small subunit rRNA primers for marine microbiomes with mock communities, time series and global field samples. Environ Microbiol 18, 1403-1414 (2016); Walters, W. et al. Improved Bacterial 16S rRNA Gene (V4 and V4-5) and Fungal Internal Transcribed Spacer Marker Gene Primers for Microbial Community Surveys. mSystems 1, e00009-15-10 (2015)). Theoretically, around 17,500 clusters can be captured per sample with a 1% multiple barcoding rate (see Klein, A. M. et al. Droplet Barcoding for Single-Cell Transcriptomics Applied to Embryonic Stem Cells. Cell 161, 1187-1201 (2015)). Barcoded primer sequences were constructed via a split-and-pool primer extension strategy (see Klein, A. M. et al. (2015); Bose, S. et al. Scalable microfluidics for single-cell RNA printing and sequencing. Genome 672 Biology 1-16 (2015). doi:10.1186/s13059-015-0684-3) with three barcode extension rounds. Each barcode position contained 96 possible sequences, and each set of barcodes was selected such that each had at least 3 bp hamming distance from the other barcodes in each set (allowing for 1 bp error correction). The first barcode position was 7-9 bp in length (allowing for dephasing of reads to improve sequencing quality) while the second and third positions were 8 bp in length.

Figure 12A:
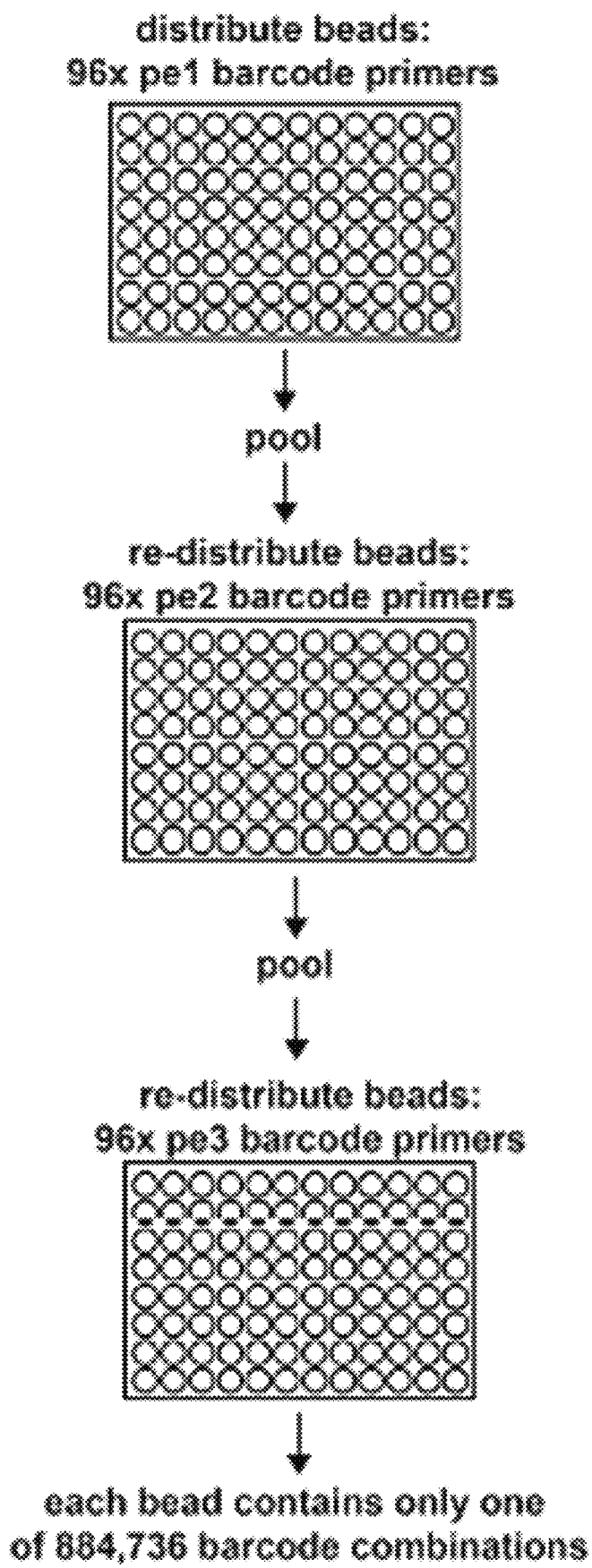
Figure 13A:
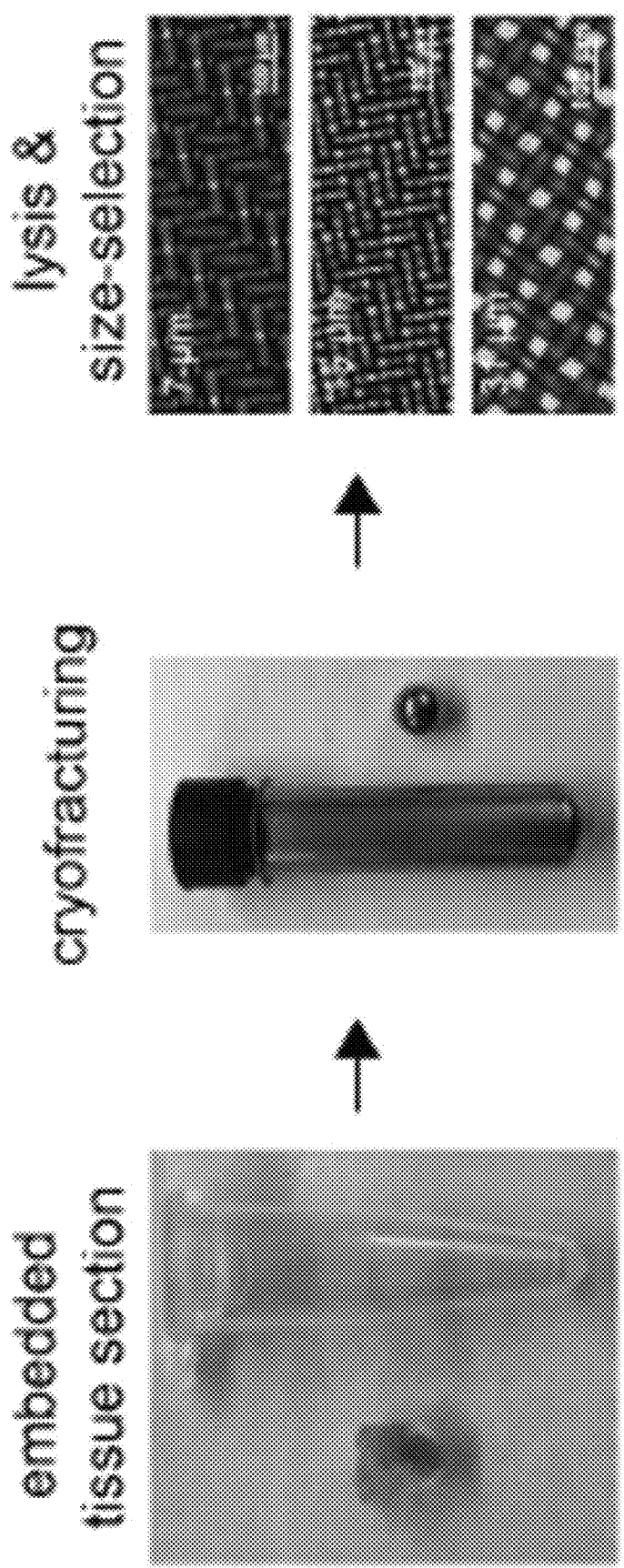
FIGS. 13a-13e: Cluster generation and quality control. a) Schematic of cluster generation process. A tissue section is fixed and embedded in a gel matrix by in situ acrylamide perfusion and polymerization. Shown is a murine intestinal section within a set gel as an example (excess gel is untrimmed at this step); a PCR tube placed to the right for scale. The gel-embedded sample is then subjected to cryofracturing, lysis preparation steps, and finally size-selection by passing clusters through nylon mesh filters of various sizes. b) Microscopy of four resulting clusters generated from murine colonic samples (size-selected for "large" clusters) visualized with phase-contrast or stained with SYBR Green I targeting genomic DNA; individual cells fixed in their original spatial orientation can be observed as punctate dots within the clusters. c) Resulting size distributions of clusters after size-selection to three size scales (small, medium and large); size-selected clusters were stained with SYBR Green I and imaged, clusters were identified by a fluorescence threshold, and the equivalent diameter of identified clusters was calculated using Nikon Elements AR. d) Photorelease of reverse amplification primer from clusters; clusters were subjected to no UV exposure or UV exposure for 10 minutes and supernatant was collected and analyzed via Agilent Bioanalyzer dsDNA HS assay; peaks at ~40 s and ~110 s are gel migration markers. A short primer product is observed to be released in a UV exposure dependent fashion. e) Degradation of cluster polyacrylamide gel matrices by exposure to reducing conditions; clusters were incubated in PCR encapsulation mix with and without 1 mM DTT (i.e., final concentration of DTT in droplets) for 2 hours; without DTT clusters remain stable and retain their structure; with DTT reducing conditions, the gel matrix degrades resulting in dispersion of individual cells observable as stained puncta.
Figure 13B:
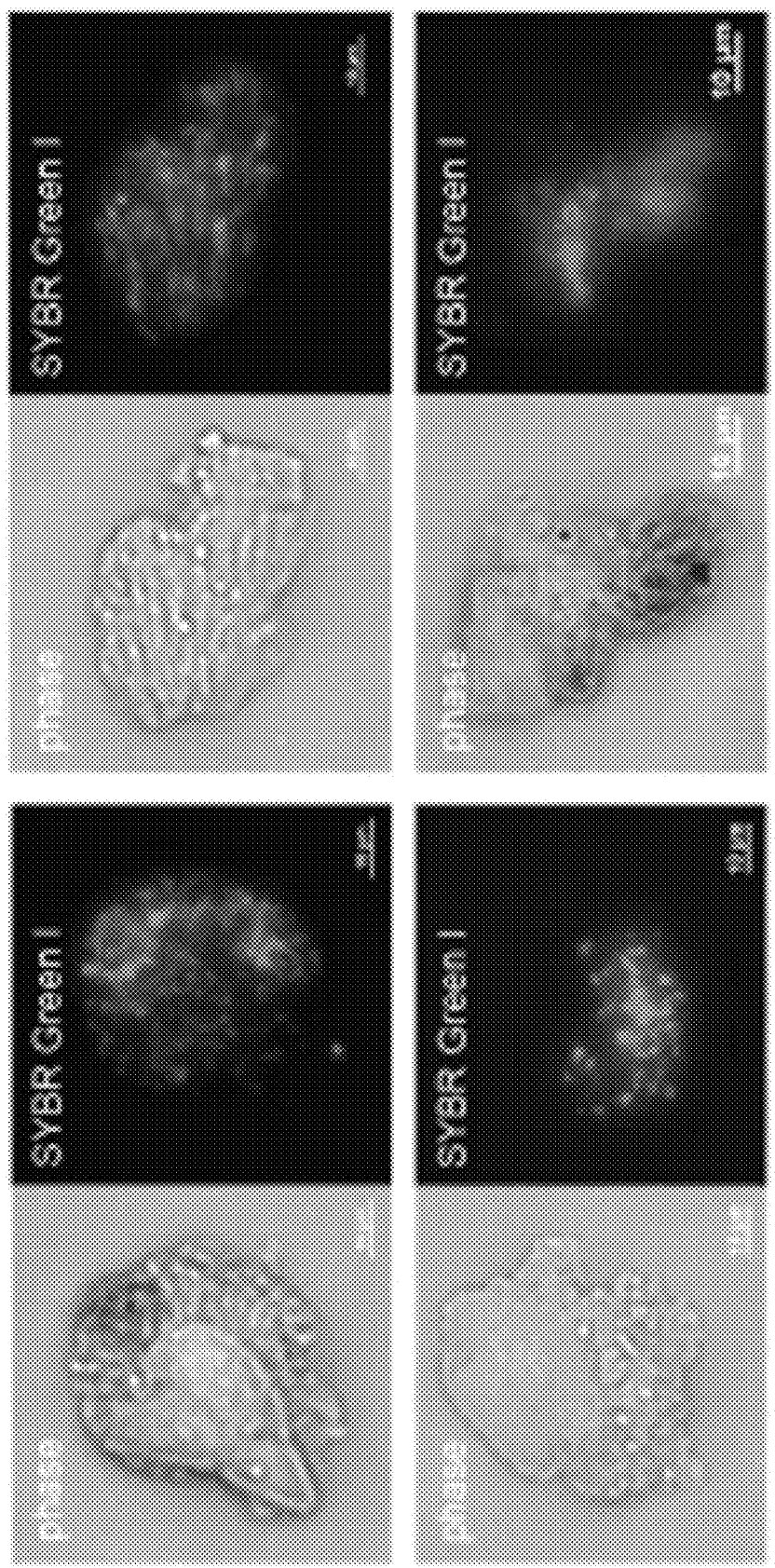
Figure 13C:
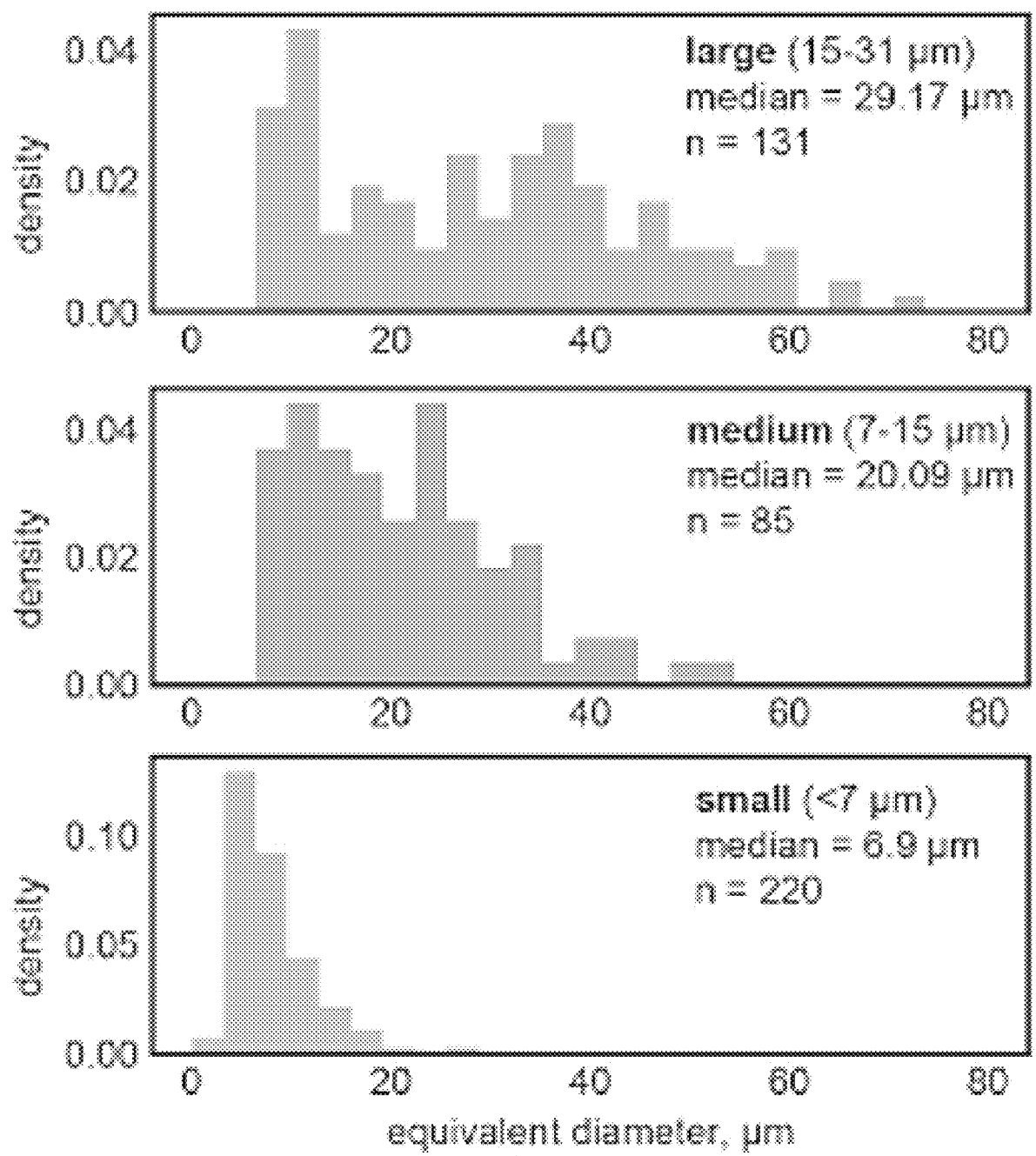
Figure 13D:
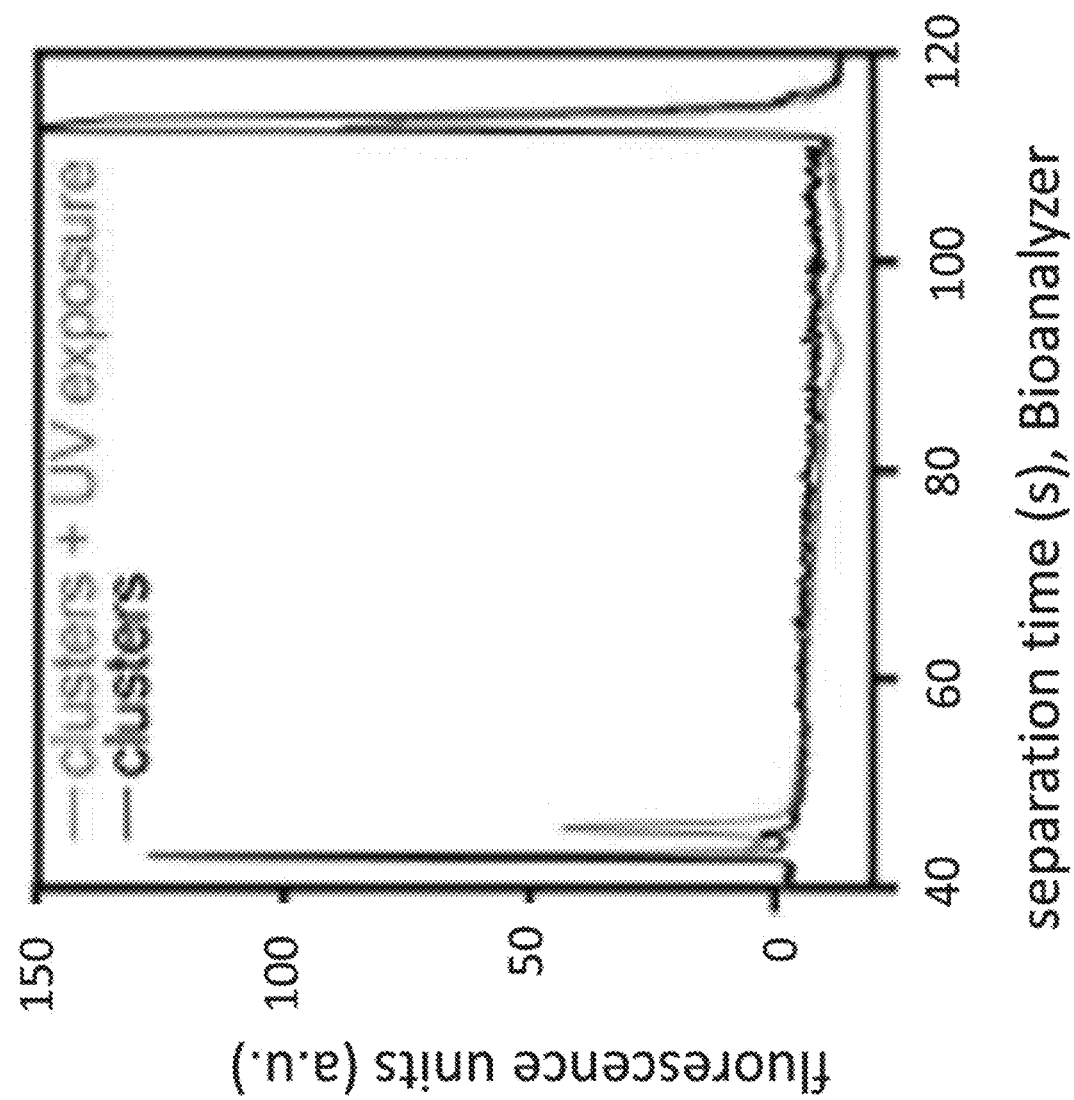
Figure 13E:
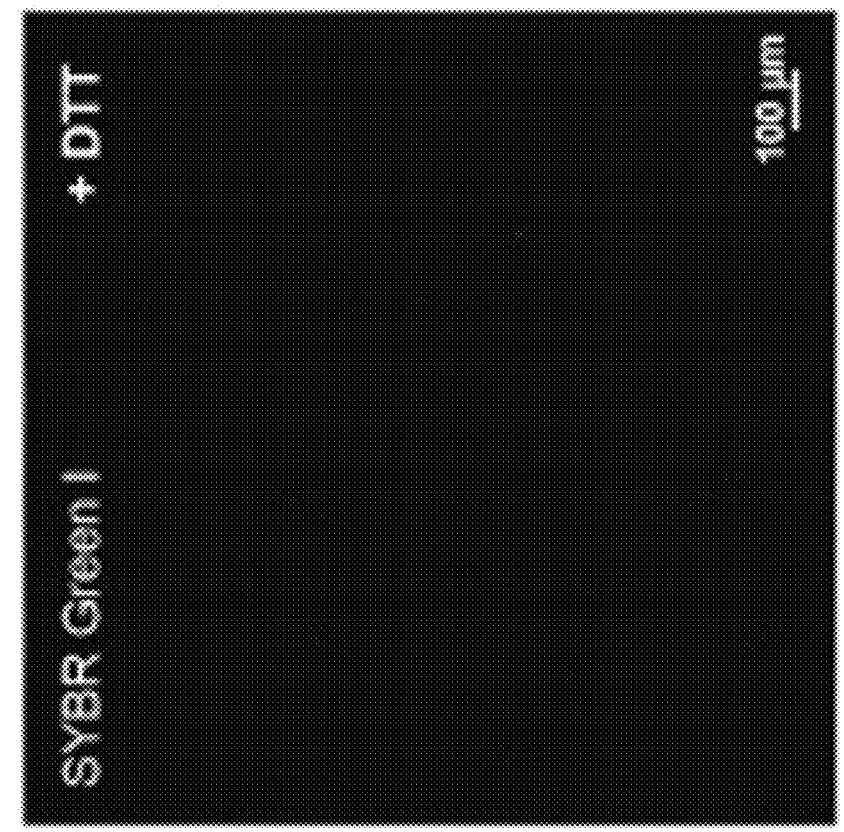
Figure 13E:
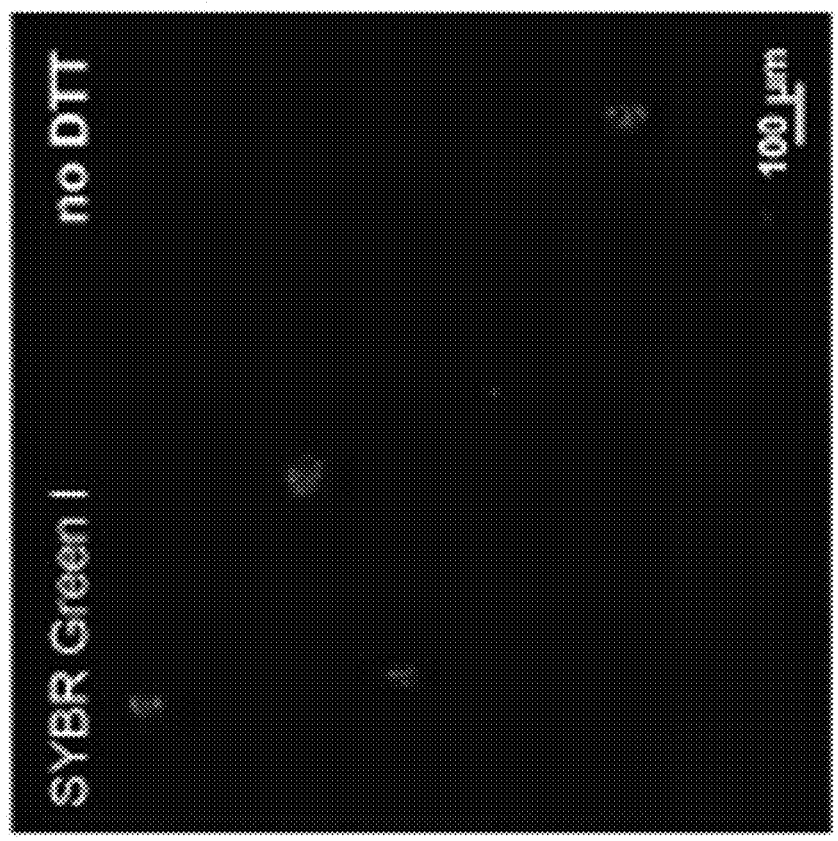

Construction of the barcoded beads followed procedures from Zilionis et al. (see Zilionis, R. et al. Single-cell barcoding and sequencing using droplet microfluidics. Nat Protoc 12, 44-73 (2017)) with minor modification for our barcoding scheme. Briefly, acrylamide beads (6% w/w acrylamide, 0.18% w/w N,N'-methylenebisacrylamide [Sigma-Aldrich 146072], 20 µM acry_pcp_pe1 [see Table 1]) were generated using a custom microfluidic droplet device. Resulting beads were ~20-25 µm in diameter. Batches of ~20 million beads were then subjected to three rounds of primer extension using the three sets of 96 barcode sequences (pe1, pe2, and pe3 primer extension sets, see Table 2). For each round, beads and primers were distributed into wells of a 96 well PCR microplate and primers were annealed to the beads by incubation. A Bst polymerase reaction master mix (NEB M0537L) was then distributed to each well and incubated to allow for extension. Finally, the reaction was quenched with EDTA and pooled for cleanup steps. The beads were then subjected to denaturing of the extension primers by sodium hydroxide and washing, and the extension protocol was repeated. These procedures were automated on a Biomek 4000 liquid handling robot where possible. After the final extension step, a primer targeted to the terminal 515f primer sequence (515f RC, see Table 1) was annealed, and an ExoI enzymatic cleanup (NEB M0293L) was utilized to remove extension intermediates. Resulting barcoded beads were subjected to a final denaturing and washing step and stored at 4° C. in TET (10 mM Tris HCl [pH 8.0], 1 mM EDTA, 0.1% Tween-20). FIG. 12.

TABLE 1

| Primer name | Primer sequence |
|---|---|
| acry_pc_pe1 | /5Acryd//iSpPC/GACTACTCCACGACG CTCTTCCGATCT (SEQ ID NO: 1) |

TABLE 1-continued

| Primer name | Primer sequence |
|---|---|
| acry_pc_pe2_816r | /5Acryd//iSpPC/ATTAGGTCGACGTGTGC<br>TCTTCCGATCTGGACTACNVGGGTWTCTAAT<br>(SEQ ID NO: 2) |
| 515f_RC | TTACCGCGGCKGCTGRCAC<br>(SEQ ID NO: 3) |

TABLE 2

| Primer name | Primer sequence | Barcode sequence |
|---|---|---|
| pe1_1 | CGCTCAGCAGTGTCTCGCACCTAGTAGATCGGA<br>AGAGCGTCGTG<br>(SEQ ID NO: 4) | ACTAGGT<br>(SEQ ID NO: 292) |
| pe1_2 | CGCTCAGCAGTGTCTCGCTAGAGCTAGATCGGA<br>AGAGCGTCGTG<br>(SEQ ID NO: 5) | AGCTCTA<br>(SEQ ID NO: 293) |
| pe1_3 | CGCTCAGCAGTGTCTCGCACTCTCTAGATCGGA<br>AGAGCGTCGTG<br>(SEQ ID NO: 6) | AGAGAGT<br>(SEQ ID NO: 294) |
| pe1_4 | CGCTCAGCAGTGTCTCGCGGAACACAGATCGG<br>AAGAGCGTCGTG<br>(SEQ ID NO: 7) | GTGTTCC<br>(SEQ ID NO: 295) |
| pe1_5 | CGCTCAGCAGTGTCTCGCCAGCTAAAGATCGGA<br>AGAGCGTCGTG<br>(SEQ ID NO: 8) | TTAGCTG<br>(SEQ ID NO: 296) |
| pe1_6 | CGCTCAGCAGTGTCTCGCGTATGGTAGATCGGA<br>AGAGCGTCGTG<br>(SEQ ID NO: 9) | ACCATAC<br>(SEQ ID NO: 297) |
| pe1_7 | CGCTCAGCAGTGTCTCGCAACGGTAAGATCGG<br>AAGAGCGTCGTG<br>(SEQ ID NO: 10) | TACCGTT<br>(SEQ ID NO: 298) |
| pe1_8 | CGCTCAGCAGTGTCTCGCAGTTGGCAGATCGGA<br>AGAGCGTCGTG<br>(SEQ ID NO: 11) | GCCAACT<br>(SEQ ID NO: 299) |
| pe1_9 | CGCTCAGCAGTGTCTCGCAGACTTCAGATCGGA<br>AGAGCGTCGTG<br>(SEQ ID NO: 12) | GAAGTCT<br>(SEQ ID NO: 300) |
| pe1_10 | CGCTCAGCAGTGTCTCGCGTGCTTAAGATCGGA<br>AGAGCGTCGTG<br>(SEQ ID NO: 13) | TAAGCAC<br>(SEQ ID NO: 301) |
| pe1_11 | CGCTCAGCAGTGTCTCGCCCACTAGAGATCGGA<br>AGAGCGTCGTG<br>(SEQ ID NO: 14) | CTAGTGG<br>(SEQ ID NO: 302) |
| pe1_12 | CGCTCAGCAGTGTCTCGCGCGCTATAGATCGGA<br>AGAGCGTCGTG<br>(SEQ ID NO: 15) | ATAGCGC<br>(SEQ ID NO: 303) |
| pe1_13 | CGCTCAGCAGTGTCTCGCTGACACTAGATCGGA<br>AGAGCGTCGTG<br>(SEQ ID NO: 16) | AGTGTCA<br>(SEQ ID NO: 304) |
| pe1_14 | CGCTCAGCAGTGTCTCGCGAGGAACAGATCGG<br>AAGAGCGTCGTG<br>(SEQ ID NO: 17) | GTTCCTC<br>(SEQ ID NO: 305) |
| pe1_15 | CGCTCAGCAGTGTCTCGCTTGACCAAGATCGGA<br>AGAGCGTCGTG<br>(SEQ ID NO: 18) | TGGTCAA<br>(SEQ ID NO: 306) |
| pe1_16 | CGCTCAGCAGTGTCTCGCGGTAGCAAGATCGG<br>AAGAGCGTCGTG<br>(SEQ ID NO: 19) | TGCTACC<br>(SEQ ID NO: 307) |

TABLE 2-continued

| Primer name | Primer sequence | Barcode sequence |
|---|---|---|
| pe1_17 | CGCTCAGCAGTGTCTCGCCGTTGAGAGATCGGA<br>AGAGCGTCGTG<br>(SEQ ID NO: 20) | CTCAACG<br>(SEQ ID NO: 308) |
| pe1_18 | CGCTCAGCAGTGTCTCGCACAACTGAGATCGGA<br>AGAGCGTCGTG<br>(SEQ ID NO: 21) | CAGTTGT<br>(SEQ ID NO: 309) |
| pe1_19 | CGCTCAGCAGTGTCTCGCTCAGTCAAGATCGGA<br>AGAGCGTCGTG<br>(SEQ ID NO: 22) | TGACTGA<br>(SEQ ID NO: 310) |
| pe1_20 | CGCTCAGCAGTGTCTCGCCGTACATAGATCGGA<br>AGAGCGTCGTG<br>(SEQ ID NO: 23) | ATGTACG<br>(SEQ ID NO: 311) |
| pe1_21 | CGCTCAGCAGTGTCTCGCTGAGTGCAGATCGGA<br>AGAGCGTCGTG<br>(SEQ ID NO: 24) | GCACTCA<br>(SEQ ID NO: 312) |
| pe1_22 | CGCTCAGCAGTGTCTCGCCCTGTTAAGATCGGA<br>AGAGCGTCGTG<br>(SEQ ID NO: 25) | TAACAGG<br>(SEQ ID NO: 313) |
| pe1_23 | CGCTCAGCAGTGTCTCGCACCTCTAAGATCGGA<br>AGAGCGTCGTG<br>(SEQ ID NO: 26) | TAGAGGT<br>(SEQ ID NO: 314) |
| pe1_24 | CGCTCAGCAGTGTCTCGCATTCCACAGATCGGA<br>AGAGCGTCGTG<br>(SEQ ID NO: 27) | GTGGAAT<br>(SEQ ID NO: 315) |
| pe1_25 | CGCTCAGCAGTGTCTCGCTCGTATGAGATCGGA<br>AGAGCGTCGTG<br>(SEQ ID NO: 28) | CATACGA<br>(SEQ ID NO: 316) |
| pe1_26 | CGCTCAGCAGTGTCTCGCAGGTTGTAGATCGGA<br>AGAGCGTCGTG<br>(SEQ ID NO: 29) | ACAACCT<br>(SEQ ID NO: 317) |
| pe1_27 | CGCTCAGCAGTGTCTCGCCGTAGTCAGATCGGA<br>AGAGCGTCGTG<br>(SEQ ID NO: 30) | GACTACG<br>(SEQ ID NO: 318) |
| pe1_28 | CGCTCAGCAGTGTCTCGCCTTCTCGAGATCGGA<br>AGAGCGTCGTG<br>(SEQ ID NO: 31) | CGAGAAG<br>(SEQ ID NO: 319) |
| pe1_29 | CGCTCAGCAGTGTCTCGCAGGTAAGAGATCGG<br>AAGAGCGTCGTG<br>(SEQ ID NO: 32) | CTTACCT<br>(SEQ ID NO: 320) |
| pe1_30 | CGCTCAGCAGTGTCTCGCGATCTCAAGATCGGA<br>AGAGCGTCGTG<br>(SEQ ID NO: 33) | TGAGATC<br>(SEQ ID NO: 321) |
| pe1_31 | CGCTCAGCAGTGTCTCGCATCGAACAGATCGGA<br>AGAGCGTCGTG<br>(SEQ ID NO: 34) | GTTCGAT<br>(SEQ ID NO: 322) |
| pe1_32 | CGCTCAGCAGTGTCTCGCCACGCATAGATCGGA<br>AGAGCGTCGTG<br>(SEQ ID NO: 35) | ATGCGTG<br>(SEQ ID NO: 323) |
| pe1_33 | CGCTCAGCAGTGTCTCGCAACTCAGGAGATCGG<br>AAGAGCGTCGTG<br>(SEQ ID NO: 36) | CCTGAGTT<br>(SEQ ID NO: 324) |
| pe1_34 | CGCTCAGCAGTGTCTCGCTGCCACAAAGATCGG<br>AAGAGCGTCGTG<br>(SEQ ID NO: 37) | TTGTGGCA<br>(SEQ ID NO: 325) |
| pe1_35 | CGCTCAGCAGTGTCTCGCATGGCGATAGATCGG<br>AAGAGCGTCGTG<br>(SEQ ID NO: 38) | ATCGCCAT<br>(SEQ ID NO: 326) |

TABLE 2-continued

| Primer name | Primer sequence | Barcode sequence |
|---|---|---|
| pe1_36 | CGCTCAGCAGTGTCTCGCAATCAGCGAGATCGG AAGAGCGTCGTG (SEQ ID NO: 39) | CGCTGATT (SEQ ID NO: 327) |
| pe1_37 | CGCTCAGCAGTGTCTCGCGGTTGTACAGATCGG AAGAGCGTCGTG (SEQ ID NO: 40) | GTACAACC (SEQ ID NO: 328) |
| pe1_38 | CGCTCAGCAGTGTCTCGCCTCGACTTAGATCGG AAGAGCGTCGTG (SEQ ID NO: 41) | AAGTCGAG (SEQ ID NO: 329) |
| pe1_39 | CGCTCAGCAGTGTCTCGCTAGGAAGCAGATCGG AAGAGCGTCGTG (SEQ ID NO: 42) | GCTTCCTA (SEQ ID NO: 330) |
| pe1_40 | CGCTCAGCAGTGTCTCGCGTGCATGTAGATCGG AAGAGCGTCGTG (SEQ ID NO: 43) | ACATGCAC (SEQ ID NO: 331) |
| pe1_41 | CGCTCAGCAGTGTCTCGCTCAATCGGAGATCGG AAGAGCGTCGTG (SEQ ID NO: 44) | CCGATTGA (SEQ ID NO: 332) |
| pe1_42 | CGCTCAGCAGTGTCTCGCTCAAGCTCAGATCGG AAGAGCGTCGTG (SEQ ID NO: 45) | GAGCTTGA (SEQ ID NO: 333) |
| pe1_43 | CGCTCAGCAGTGTCTCGCAGTGTCACAGATCGG AAGAGCGTCGTG (SEQ ID NO: 46) | GTGACACT (SEQ ID NO: 334) |
| pe1_44 | CGCTCAGCAGTGTCTCGCTGTGTTCCAGATCGG AAGAGCGTCGTG (SEQ ID NO: 47) | GGAACACA (SEQ ID NO: 335) |
| pe1_45 | CGCTCAGCAGTGTCTCGCTCCGAATCAGATCGG AAGAGCGTCGTG (SEQ ID NO: 48) | GATTCGGA (SEQ ID NO: 336) |
| pe1_46 | CGCTCAGCAGTGTCTCGCGGAGTACAAGATCGG AAGAGCGTCGTG (SEQ ID NO: 49) | TGTACTCC (SEQ ID NO: 337) |
| pe1_47 | CGCTCAGCAGTGTCTCGCAGGACAGAAGATCGG AAGAGCGTCGTG (SEQ ID NO: 50) | TCTGTCCT (SEQ ID NO: 338) |
| pe1_48 | CGCTCAGCAGTGTCTCGCGCACAGTTAGATCGG AAGAGCGTCGTG (SEQ ID NO: 51) | AACTGTGC (SEQ ID NO: 339) |
| pe1_49 | CGCTCAGCAGTGTCTCGCCGACAACAAGATCGG AAGAGCGTCGTG (SEQ ID NO: 52) | TGTTGTCG (SEQ ID NO: 340) |
| pe1_50 | CGCTCAGCAGTGTCTCGCAGCACGTAAGATCGG AAGAGCGTCGTG (SEQ ID NO: 53) | TACGTGCT (SEQ ID NO: 341) |
| pe1_51 | CGCTCAGCAGTGTCTCGCCCAACAGTAGATCGG AAGAGCGTCGTG (SEQ ID NO: 54) | ACTGTTGG (SEQ ID NO: 342) |
| pe1_52 | CGCTCAGCAGTGTCTCGCTCAGGACAAGATCGG AAGAGCGTCGTG (SEQ ID NO: 55) | TGTCCTGA (SEQ ID NO: 343) |
| pe1_53 | CGCTCAGCAGTGTCTCGCCTATCCTGAGATCGG AAGAGCGTCGTG (SEQ ID NO: 56) | CAGGATAG (SEQ ID NO: 344) |
| pe1_54 | CGCTCAGCAGTGTCTCGCTGTCTGTCAGATCGG AAGAGCGTCGTG (SEQ ID NO: 57) | GACAGACA (SEQ ID NO: 345) |
| pe1_55 | CGCTCAGCAGTGTCTCGCCCTAGTCTAGATCGG AAGAGCGTCGTG (SEQ ID NO: 58) | AGACTAGG (SEQ ID NO: 346) |
| pe1_56 | CGCTCAGCAGTGTCTCGCGTAATGGCAGATCGG AAGAGCGTCGTG (SEQ ID NO: 59) | GCCATTAC (SEQ ID NO: 347) |
| pe1_57 | CGCTCAGCAGTGTCTCGCTAGTGGCTAGATCGG AAGAGCGTCGTG (SEQ ID NO: 60) | AGCCACTA (SEQ ID NO: 348) |
| pe1_58 | CGCTCAGCAGTGTCTCGCGAATCTGCAGATCGG AAGAGCGTCGTG (SEQ ID NO: 61) | GCAGATTC (SEQ ID NO: 349) |
| pe1_59 | CGCTCAGCAGTGTCTCGCTTCGATGCAGATCGG AAGAGCGTCGTG (SEQ ID NO: 62) | GCATCGAA (SEQ ID NO: 350) |
| pe1_60 | CGCTCAGCAGTGTCTCGCGCTTGGTTAGATCGG AAGAGCGTCGTG (SEQ ID NO: 63) | AACCAAGC (SEQ ID NO: 351) |
| pe1_61 | CGCTCAGCAGTGTCTCGCAGCTGATCAGATCGG AAGAGCGTCGTG (SEQ ID NO: 64) | GATCAGCT (SEQ ID NO: 352) |
| pe1_62 | CGCTCAGCAGTGTCTCGCATAAGCGGAGATCGG AAGAGCGTCGTG (SEQ ID NO: 65) | CCGCTTAT (SEQ ID NO: 353) |
| pe1_63 | CGCTCAGCAGTGTCTCGCACTTCGGAAGATCGG AAGAGCGTCGTG (SEQ ID NO: 66) | TCCGAAGT (SEQ ID NO: 354) |
| pe1_64 | CGCTCAGCAGTGTCTCGCCTAGTCGAAGATCGG AAGAGCGTCGTG (SEQ ID NO: 67) | TCGACTAG (SEQ ID NO: 355) |
| pe1_65 | CGCTCAGCAGTGTCTCGCCGTTCTTGCAGATCG GAAGAGCGTCGTG (SEQ ID NO: 68) | GCAAGAACG (SEQ ID NO: 356) |
| pe1_66 | CGCTCAGCAGTGTCTCGCTGTAGACTCAGATCG GAAGAGCGTCGTG (SEQ ID NO: 69) | GAGTCTACA (SEQ ID NO: 357) |
| pe1_67 | CGCTCAGCAGTGTCTCGCGAAGGCCTAAGATCG GAAGAGCGTCGTG (SEQ ID NO: 70) | TAGGCCTTC (SEQ ID NO: 358) |
| pe1_68 | CGCTCAGCAGTGTCTCGCTTCGTAAGGAGATCG GAAGAGCGTCGTG (SEQ ID NO: 71) | CCTTACGAA (SEQ ID NO: 359) |
| pe1_69 | CGCTCAGCAGTGTCTCGCTGATCACCTAGATCG GAAGAGCGTCGTG (SEQ ID NO: 72) | AGGTGATCA (SEQ ID NO: 360) |
| pe1_70 | CGCTCAGCAGTGTCTCGCTAGCTAACGAGATCG GAAGAGCGTCGTG (SEQ ID NO: 73) | CGTTAGCTA (SEQ ID NO: 361) |
| pe1_71 | CGCTCAGCAGTGTCTCGCCGTAGAAGGAGATCG GAAGAGCGTCGTG (SEQ ID NO: 74) | CCTTCTACG (SEQ ID NO: 362) |
| pe1_72 | CGCTCAGCAGTGTCTCGCTCTCTCGAAGATCG GAAGAGCGTCGTG (SEQ ID NO: 75) | TTCGAGAGA (SEQ ID NO: 363) |
| pe1_73 | CGCTCAGCAGTGTCTCGCTCTAGTTCCAGATCG GAAGAGCGTCGTG (SEQ ID NO: 76) | GGAACTAGA (SEQ ID NO: 364) |

TABLE 2-continued

| Primer name | Primer sequence | Barcode sequence |
|---|---|---|
| pe1_74 | CGCTCAGCAGTGTCTCGCCCGAAGAGAAGATCG GAAGAGCGTCGTG (SEQ ID NO: 77) | TCTCTTCGG (SEQ ID NO: 365) |
| pe1_75 | CGCTCAGCAGTGTCTCGCAGGTGACATAGATCG GAAGAGCGTCGTG (SEQ ID NO: 78) | ATGTCACCT (SEQ ID NO: 366) |
| pe1_76 | CGCTCAGCAGTGTCTCGCCTGAGAACGAGATCG GAAGAGCGTCGTG (SEQ ID NO: 79) | CGTTCTCAG (SEQ ID NO: 367) |
| pe1_77 | CGCTCAGCAGTGTCTCGCCCAGCTGAAAGATCG GAAGAGCGTCGTG (SEQ ID NO: 80) | TTCAGCTGG (SEQ ID NO: 368) |
| pe1_78 | CGCTCAGCAGTGTCTCGCCGTTCGACAAGATCG GAAGAGCGTCGTG (SEQ ID NO: 81) | TGTCGAACG (SEQ ID NO: 369) |
| pe1_79 | CGCTCAGCAGTGTCTCGCTCTTAGACCAGATCG GAAGAGCGTCGTG (SEQ ID NO: 82) | GGTCTAAGA (SEQ ID NO: 370) |
| pe1_80 | CGCTCAGCAGTGTCTCGCCACGAGCAAAGATCG GAAGAGCGTCGTG (SEQ ID NO: 83) | TTGCTCGTG (SEQ ID NO: 371) |
| pe1_81 | CGCTCAGCAGTGTCTCGCCTGCCGAATAGATCG GAAGAGCGTCGTG (SEQ ID NO: 84) | ATTCGGCAG (SEQ ID NO: 372) |
| pe1_82 | CGCTCAGCAGTGTCTCGCGGGCTCATAAGATCG GAAGAGCGTCGTG (SEQ ID NO: 85) | TATGAGCCC (SEQ ID NO: 373) |
| pe1_83 | CGCTCAGCAGTGTCTCGCCACCGTACTAGATCG GAAGAGCGTCGTG (SEQ ID NO: 86) | AGTACGGTG (SEQ ID NO: 374) |
| pe1_84 | CGCTCAGCAGTGTCTCGCGTGTCTCGAAGATCG GAAGAGCGTCGTG (SEQ ID NO: 87) | TCGAGACAC (SEQ ID NO: 375) |
| pe1_85 | CGCTCAGCAGTGTCTCGCTTACTGCGAAGATCG GAAGAGCGTCGTG (SEQ ID NO: 88) | TCGCAGTAA (SEQ ID NO: 376) |
| pe1_86 | CGCTCAGCAGTGTCTCGCTCCATACGAAGATCG GAAGAGCGTCGTG (SEQ ID NO: 89) | TCGTATGGA (SEQ ID NO: 377) |
| pe1_87 | CGCTCAGCAGTGTCTCGCGATCCAGGTAGATCG GAAGAGCGTCGTG (SEQ ID NO: 90) | ACCTGGATC (SEQ ID NO: 378) |
| pe1_88 | CGCTCAGCAGTGTCTCGCAGTTGCGAAGATCG GAAGAGCGTCGTG (SEQ ID NO: 91) | TTCGCAACT (SEQ ID NO: 379) |
| pe1_89 | CGCTCAGCAGTGTCTCGCAGGTTGAGAAGATCG GAAGAGCGTCGTG (SEQ ID NO: 92) | TCTCAACCT (SEQ ID NO: 380) |
| pe1_90 | CGCTCAGCAGTGTCTCGCGTTGCGCTTAGATCG GAAGAGCGTCGTG (SEQ ID NO: 93) | AAGCGCAAC (SEQ ID NO: 381) |
| pe1_91 | CGCTCAGCAGTGTCTCGCCTCGAGAGAAGATCG GAAGAGCGTCGTG (SEQ ID NO: 94) | TCTCTCGAG (SEQ ID NO: 382) |
| pe1_92 | CGCTCAGCAGTGTCTCGCTGTTCCTAGAGATCG GAAGAGCGTCGTG (SEQ ID NO: 95) | CTAGGAACA (SEQ ID NO: 383) |
| pe1_93 | CGCTCAGCAGTGTCTCGCCTCACACTGAGATCG GAAGAGCGTCGTG (SEQ ID NO: 96) | CAGTGTGAG (SEQ ID NO: 384) |
| pe1_94 | CGCTCAGCAGTGTCTCGCACCACATGTAGATCG GAAGAGCGTCGTG (SEQ ID NO: 97) | ACATGTGGT (SEQ ID NO: 385) |
| pe1_95 | CGCTCAGCAGTGTCTCGCAGCTTAACCAGATCG GAAGAGCGTCGTG (SEQ ID NO: 98) | GGTTAAGCT (SEQ ID NO: 386) |
| pe1_96 | CGCTCAGCAGTGTCTCGCCACCTATGCAGATCG GAAGAGCGTCGTG (SEQ ID NO: 99) | GCATAGGTG (SEQ ID NO: 387) |
| pe2_1 | CGACGAGGCTGGAGTGACACTGGTACCGCTCAG CAGTGTCTCGC (SEQ ID NO: 100) | GTACCAGT (SEQ ID NO: 388) |
| pe2_2 | CGACGAGGCTGGAGTGACGGTACTGTCGCTCAG CAGTGTCTCGC (SEQ ID NO: 101) | ACAGTACC (SEQ ID NO: 389) |
| pe2_3 | CGACGAGGCTGGAGTGACTCTGTGTGCGCTCAG CAGTGTCTCGC (SEQ ID NO: 102) | CACACAGA (SEQ ID NO: 390) |
| pe2_4 | CGACGAGGCTGGAGTGACTATGGCTCCGCTCAG CAGTGTCTCGC (SEQ ID NO: 103) | GAGCCATA (SEQ ID NO: 391) |
| pe2_5 | CGACGAGGCTGGAGTGACGTTGTCAGCGCTCAG CAGTGTCTCGC (SEQ ID NO: 104) | CTGACAAC (SEQ ID NO: 392) |
| pe2_6 | CGACGAGGCTGGAGTGACATGCCAGTCGCTCAG CAGTGTCTCGC (SEQ ID NO: 105) | ACTGGCAT (SEQ ID NO: 393) |
| pe2_7 | CGACGAGGCTGGAGTGACCGCTACTACGCTCAG CAGTGTCTCGC (SEQ ID NO: 106) | TAGTAGCG (SEQ ID NO: 394) |
| pe2_8 | CGACGAGGCTGGAGTGACCATACACGCGCTCA GCAGTGTCTCGC (SEQ ID NO: 107) | CGTGTATG (SEQ ID NO: 395) |
| pe2_9 | CGACGAGGCTGGAGTGACTCGAGGATCGCTCA GCAGTGTCTCGC (SEQ ID NO: 108) | ATCCTCGA (SEQ ID NO: 396) |
| pe2_10 | CGACGAGGCTGGAGTGACGGTTCGATCGCTCAG CAGTGTCTCGC (SEQ ID NO: 109) | ATCGAACC (SEQ ID NO: 397) |
| pe2_11 | CGACGAGGCTGGAGTGACACGGAACACGCTCA GCAGTGTCTCGC (SEQ ID NO: 110) | TGTTCCGT (SEQ ID NO: 398) |
| pe2_12 | CGACGAGGCTGGAGTGACCGTTGCATCGCTCAG CAGTGTCTCGC (SEQ ID NO: 111) | ATGCAACG (SEQ ID NO: 399) |
| pe2_13 | CGACGAGGCTGGAGTGACATACGTCCCGCTCAG CAGTGTCTCGC (SEQ ID NO: 112) | GGACGTAT (SEQ ID NO: 400) |
| pe2_14 | CGACGAGGCTGGAGTGACGATCTGGACGCTCA GCAGTGTCTCGC (SEQ ID NO: 113) | TCCAGATC (SEQ ID NO: 401) |
| pe2_15 | CGACGAGGCTGGAGTGACTCTCGAAGCGCTCAG CAGTGTCTCGC (SEQ ID NO: 114) | CTTCGAGA (SEQ ID NO: 402) |

TABLE 2-continued

| Primer name | Primer sequence | Barcode sequence |
|---|---|---|
| pe2_16 | CGACGAGGCTGGAGTGACCTGTGCTACGCTCAGCAGTGTCTCGC (SEQ ID NO: 115) | TAGCACAG (SEQ ID NO: 403) |
| pe2_17 | CGACGAGGCTGGAGTGACAGGTGGAACGCTCAGCAGTGTCTCGC (SEQ ID NO: 116) | TTCCACCT (SEQ ID NO: 404) |
| pe2_18 | CGACGAGGCTGGAGTGACTAGCAACGCGCTCAGCAGTGTCTCGC (SEQ ID NO: 117) | CGTTGCTA (SEQ ID NO: 405) |
| pe2_19 | CGACGAGGCTGGAGTGACGGTCATTCCGCTCAGCAGTGTCTCGC (SEQ ID NO: 118) | GAATGACC (SEQ ID NO: 406) |
| pe2_20 | CGACGAGGCTGGAGTGACAGATACGCCGCTCAGCAGTGTCTCGC (SEQ ID NO: 119) | GCGTATCT (SEQ ID NO: 407) |
| pe2_21 | CGACGAGGCTGGAGTGACGAACTGCTCGCTCAGCAGTGTCTCGC (SEQ ID NO: 120) | AGCAGTTC (SEQ ID NO: 408) |
| pe2_22 | CGACGAGGCTGGAGTGACAGTGCACACGCTCAGCAGTGTCTCGC (SEQ ID NO: 121) | TGTGCACT (SEQ ID NO: 409) |
| pe2_23 | CGACGAGGCTGGAGTGACCCGATCATCGCTCAGCAGTGTCTCGC (SEQ ID NO: 122) | ATGATCGG (SEQ ID NO: 410) |
| pe2_24 | CGACGAGGCTGGAGTGACACAAGGACGCTCAGCAGTGTCTCGC (SEQ ID NO: 123) | GTCCTTGT (SEQ ID NO: 411) |
| pe2_25 | CGACGAGGCTGGAGTGACATTCGGTCCGCTCAGCAGTGTCTCGC (SEQ ID NO: 124) | GACCGAAT (SEQ ID NO: 412) |
| pe2_26 | CGACGAGGCTGGAGTGACTTGTGACGCGCTCAGCAGTGTCTCGC (SEQ ID NO: 125) | CGTCACAA (SEQ ID NO: 413) |
| pe2_27 | CGACGAGGCTGGAGTGACGAAGTCTGCGCTCAGCAGTGTCTCGC (SEQ ID NO: 126) | CAGACTTC (SEQ ID NO: 414) |
| pe2_28 | CGACGAGGCTGGAGTGACTGGACGAACGCTCAGCAGTGTCTCGC (SEQ ID NO: 127) | TTCGTCCA (SEQ ID NO: 415) |
| pe2_29 | CGACGAGGCTGGAGTGACGAGTTCCTCGCTCAGCAGTGTCTCGC (SEQ ID NO: 128) | AGGAACTC (SEQ ID NO: 416) |
| pe2_30 | CGACGAGGCTGGAGTGACGATAGGAGCGCTCAGCAGTGTCTCGC (SEQ ID NO: 129) | CTCCTATC (SEQ ID NO: 417) |
| pe2_31 | CGACGAGGCTGGAGTGACAGCTTGGACGCTCAGCAGTGTCTCGC (SEQ ID NO: 130) | TCCAAGCT (SEQ ID NO: 418) |
| pe2_32 | CGACGAGGCTGGAGTGACCCACATCCTCGCTCAGCAGTGTCTCGC (SEQ ID NO: 131) | AGGATGTG (SEQ ID NO: 419) |
| pe2_33 | CGACGAGGCTGGAGTGACAGTCCTGACGCTCAGCAGTGTCTCGC (SEQ ID NO: 132) | TCAGGACT (SEQ ID NO: 420) |
| pe2_34 | CGACGAGGCTGGAGTGACCTTGTAGCCGCTCAGCAGTGTCTCGC (SEQ ID NO: 133) | GCTACAAG (SEQ ID NO: 421) |
| pe2_35 | CGACGAGGCTGGAGTGACCAGGAGTACGCTCAGCAGTGTCTCGC (SEQ ID NO: 134) | TACTCCTG (SEQ ID NO: 422) |
| pe2_36 | CGACGAGGCTGGAGTGACCACAAGGACGCTCAGCAGTGTCTCGC (SEQ ID NO: 135) | TCCTTGTG (SEQ ID NO: 423) |
| pe2_37 | CGACGAGGCTGGAGTGACTTCCTCTGCGCTCAGCAGTGTCTCGC (SEQ ID NO: 136) | CAGAGGAA (SEQ ID NO: 424) |
| pe2_38 | CGACGAGGCTGGAGTGACCCATTGCTCGCTCAGCAGTGTCTCGC (SEQ ID NO: 137) | AGCAATGG (SEQ ID NO: 425) |
| pe2_39 | CGACGAGGCTGGAGTGACGCACATAGCGCTCAGCAGTGTCTCGC (SEQ ID NO: 138) | CTATGTGC (SEQ ID NO: 426) |
| pe2_40 | CGACGAGGCTGGAGTGACCACTGTACCGCTCAGCAGTGTCTCGC (SEQ ID NO: 139) | GTACAGTG (SEQ ID NO: 427) |
| pe2_41 | CGACGAGGCTGGAGTGACGTGATCTCCGCTCAGCAGTGTCTCGC (SEQ ID NO: 140) | GAGATCAC (SEQ ID NO: 428) |
| pe2_42 | CGACGAGGCTGGAGTGACAATGCCGTCGCTCAGCAGTGTCTCGC (SEQ ID NO: 141) | ACGGCATT (SEQ ID NO: 429) |
| pe2_43 | CGACGAGGCTGGAGTGACTCCTTGTCCGCTCAGCAGTGTCTCGC (SEQ ID NO: 142) | GACAAGGA (SEQ ID NO: 430) |
| pe2_44 | CGACGAGGCTGGAGTGACAGTAGGCACGCTCAGCAGTGTCTCGC (SEQ ID NO: 143) | TGCCTACT (SEQ ID NO: 431) |
| pe2_45 | CGACGAGGCTGGAGTGACAGCCTCTTCGCTCAGCAGTGTCTCGC (SEQ ID NO: 144) | AAGAGGCT (SEQ ID NO: 432) |
| pe2_46 | CGACGAGGCTGGAGTGACCGATTACGCGCTCAGCAGTGTCTCGC (SEQ ID NO: 145) | CGTAATCG (SEQ ID NO: 433) |
| pe2_47 | CGACGAGGCTGGAGTGACCCAGGAATCGCTCAGCAGTGTCTCGC (SEQ ID NO: 146) | ATTCCTGG (SEQ ID NO: 434) |
| pe2_48 | CGACGAGGCTGGAGTGACGAGTCAGTCGCTCAGCAGTGTCTCGC (SEQ ID NO: 147) | ACTGACTC (SEQ ID NO: 435) |
| pe2_49 | CGACGAGGCTGGAGTGACTGAGAGGACGCTCAGCAGTGTCTCGC (SEQ ID NO: 148) | TCCTCTCA (SEQ ID NO: 436) |
| pe2_50 | CGACGAGGCTGGAGTGACACGACTCACGCTCAGCAGTGTCTCGC (SEQ ID NO: 149) | TGAGTCGT (SEQ ID NO: 437) |
| pe2_51 | CGACGAGGCTGGAGTGACTAGCTCAGCGCTCAGCAGTGTCTCGC (SEQ ID NO: 150) | CTGAGCTA (SEQ ID NO: 438) |
| pe2_52 | CGACGAGGCTGGAGTGACTAACCGGTCGCTCAGCAGTGTCTCGC (SEQ ID NO: 151) | ACCGGTTA (SEQ ID NO: 439) |
| pe2_53 | CGACGAGGCTGGAGTGACGTACTGAGCGCTCAGCAGTGTCTCGC (SEQ ID NO: 152) | CTCAGTAC (SEQ ID NO: 440) |

TABLE 2-continued

| Primer name | Primer sequence | Barcode sequence |
|---|---|---|
| pe2_54 | CGACGAGGCTGGAGTGACAACCACTCCGCTCAGCAGTGTCTCGC (SEQ ID NO: 153) | GAGTGGTT (SEQ ID NO: 441) |
| pe2_55 | CGACGAGGCTGGAGTGACCAGTTACCCGCTCAGCAGTGTCTCGC (SEQ ID NO: 154) | GGTAACTG (SEQ ID NO: 442) |
| pe2_56 | CGACGAGGCTGGAGTGACGATGGATGCGCTCAGCAGTGTCTCGC (SEQ ID NO: 155) | CATCCATC (SEQ ID NO: 443) |
| pe2_57 | CGACGAGGCTGGAGTGACCTACCTCTCGCTCAGCAGTGTCTCGC (SEQ ID NO: 156) | AGAGGTAG (SEQ ID NO: 444) |
| pe2_58 | CGACGAGGCTGGAGTGACGTCAAGAGCGCTCAGCAGTGTCTCGC (SEQ ID NO: 157) | CTCTTGAC (SEQ ID NO: 445) |
| pe2_59 | CGACGAGGCTGGAGTGACGATCTACGCGCTCAGCAGTGTCTCGC (SEQ ID NO: 158) | CGTAGATC (SEQ ID NO: 446) |
| pe2_60 | CGACGAGGCTGGAGTGACACATTCCGCGCTCAGCAGTGTCTCGC (SEQ ID NO: 159) | CGGAATGT (SEQ ID NO: 447) |
| pe2_61 | CGACGAGGCTGGAGTGACCTGAATCCCGCTCAGCAGTGTCTCGC (SEQ ID NO: 160) | GGATTCAG (SEQ ID NO: 448) |
| pe2_62 | CGACGAGGCTGGAGTGACTGGCCATACGCTCAGCAGTGTCTCGC (SEQ ID NO: 161) | TATGGCCA (SEQ ID NO: 449) |
| pe2_63 | CGACGAGGCTGGAGTGACGTCTTGCTCGCTCAGCAGTGTCTCGC (SEQ ID NO: 162) | AGCAAGAC (SEQ ID NO: 450) |
| pe2_64 | CGACGAGGCTGGAGTGACACGTGTTGCGCTCAGCAGTGTCTCGC (SEQ ID NO: 163) | CAACACGT (SEQ ID NO: 451) |
| pe2_65 | CGACGAGGCTGGAGTGACGAAGCGTTCGCTCAGCAGTGTCTCGC (SEQ ID NO: 164) | AACGCTTC (SEQ ID NO: 452) |
| pe2_66 | CGACGAGGCTGGAGTGACTAACGCCACGCTCAGCAGTGTCTCGC (SEQ ID NO: 165) | TGGCGTTA (SEQ ID NO: 453) |
| pe2_67 | CGACGAGGCTGGAGTGACAGGCTGTACGCTCAGCAGTGTCTCGC (SEQ ID NO: 166) | TACAGCCT (SEQ ID NO: 454) |
| pe2_68 | CGACGAGGCTGGAGTGACCTACAGTGCGCTCAGCAGTGTCTCGC (SEQ ID NO: 167) | CACTGTAG (SEQ ID NO: 455) |
| pe2_69 | CGACGAGGCTGGAGTGACTTCAGAGCCGCTCAGCAGTGTCTCGC (SEQ ID NO: 168) | GCTCTGAA (SEQ ID NO: 456) |
| pe2_70 | CGACGAGGCTGGAGTGACTGCCTACACGCTCAGCAGTGTCTCGC (SEQ ID NO: 169) | TGTAGGCA (SEQ ID NO: 457) |
| pe2_71 | CGACGAGGCTGGAGTGACCGGATTGACGCTCAGCAGTGTCTCGC (SEQ ID NO: 170) | TCAATCCG (SEQ ID NO: 458) |
| pe2_72 | CGACGAGGCTGGAGTGACGGAGGATTCGCTCAGCAGTGTCTCGC (SEQ ID NO: 171) | AATCCTCC (SEQ ID NO: 459) |
| pe2_73 | CGACGAGGCTGGAGTGACCATTAGCCCGCTCAGCAGTGTCTCGC (SEQ ID NO: 172) | GGCTAATG (SEQ ID NO: 460) |
| pe2_74 | CGACGAGGCTGGAGTGACTTGGTCACCGCTCAGCAGTGTCTCGC (SEQ ID NO: 173) | GTGACCAA (SEQ ID NO: 461) |
| pe2_75 | CGACGAGGCTGGAGTGACCAAGCAAGCGCTCAGCAGTGTCTCGC (SEQ ID NO: 174) | CTTGCTTG (SEQ ID NO: 462) |
| pe2_76 | CGACGAGGCTGGAGTGACCAACATCCCGCTCAGCAGTGTCTCGC (SEQ ID NO: 175) | GGATGTTG (SEQ ID NO: 463) |
| pe2_77 | CGACGAGGCTGGAGTGACGACGACAACGCTCAGCAGTGTCTCGC (SEQ ID NO: 176) | TTGTCGTC (SEQ ID NO: 464) |
| pe2_78 | CGACGAGGCTGGAGTGACATCGAGTCCGCTCAGCAGTGTCTCGC (SEQ ID NO: 177) | GACTCGAT (SEQ ID NO: 465) |
| pe2_79 | CGACGAGGCTGGAGTGACTATGCGAGCGCTCAGCAGTGTCTCGC (SEQ ID NO: 178) | CTCGCATA (SEQ ID NO: 466) |
| pe2_80 | CGACGAGGCTGGAGTGACTAGCTTCCCGCTCAGCAGTGTCTCGC (SEQ ID NO: 179) | GGAAGCTA (SEQ ID NO: 467) |
| pe2_81 | CGACGAGGCTGGAGTGACACCAACGTCGCTCAGCAGTGTCTCGC (SEQ ID NO: 180) | ACGTTGGT (SEQ ID NO: 468) |
| pe2_82 | CGACGAGGCTGGAGTGACACGCGATACGCTCAGCAGTGTCTCGC (SEQ ID NO: 181) | TATCGCGT (SEQ ID NO: 469) |
| pe2_83 | CGACGAGGCTGGAGTGACGTCAGCTACGCTCAGCAGTGTCTCGC (SEQ ID NO: 182) | TAGCTGAC (SEQ ID NO: 470) |
| pe2_84 | CGACGAGGCTGGAGTGACCACCAGATCGCTCAGCAGTGTCTCGC (SEQ ID NO: 183) | ATCTGGTG (SEQ ID NO: 471) |
| pe2_85 | CGACGAGGCTGGAGTGACCAACCTTGCGCTCAGCAGTGTCTCGC (SEQ ID NO: 184) | CAAGGTTG (SEQ ID NO: 472) |
| pe2_86 | CGACGAGGCTGGAGTGACTTGCCTTGCGCTCAGCAGTGTCTCGC (SEQ ID NO: 185) | CAAGGCAA (SEQ ID NO: 473) |
| pe2_87 | CGACGAGGCTGGAGTGACAGTCTGCTCGCTCAGCAGTGTCTCGC (SEQ ID NO: 186) | AGCAGACT (SEQ ID NO: 474) |
| pe2_88 | CGACGAGGCTGGAGTGACGTCCTTCACGCTCAGCAGTGTCTCGC (SEQ ID NO: 187) | TGAAGGAC (SEQ ID NO: 475) |
| pe2_89 | CGACGAGGCTGGAGTGACCGGTCTATCGCTCAGCAGTGTCTCGC (SEQ ID NO: 188) | ATAGACCG (SEQ ID NO: 476) |
| pe2_90 | CGACGAGGCTGGAGTGACTCTGCCTTCGCTCAGCAGTGTCTCGC (SEQ ID NO: 189) | AAGGCAGA (SEQ ID NO: 477) |
| pe2_91 | CGACGAGGCTGGAGTGACCAAGTTGGCGCTCAGCAGTGTCTCGC (SEQ ID NO: 190) | CCAACTTG (SEQ ID NO: 478) |

TABLE 2-continued

| Primer name | Primer sequence | Barcode sequence |
|---|---|---|
| pe2_92 | CGACGAGGCTGGAGTGACATCTACGGCGCTCAGCAGTGTCTCGC (SEQ ID NO: 191) | CCGTAGAT (SEQ ID NO: 479) |
| pe2_93 | CGACGAGGCTGGAGTGACCACTTCTGCGCTCAGCAGTGTCTCGC (SEQ ID NO: 192) | CAGAAGTG (SEQ ID NO: 480) |
| pe2_94 | CGACGAGGCTGGAGTGACCACACAACCGCTCAGCAGTGTCTCGC (SEQ ID NO: 193) | GTTGTGTG (SEQ ID NO: 481) |
| pe2_95 | CGACGAGGCTGGAGTGACGCCTAATGCGCTCAGCAGTGTCTCGC (SEQ ID NO: 194) | CATTAGGC (SEQ ID NO: 482) |
| pe2_96 | CGACGAGGCTGGAGTGACGTTCGCATCGCTCAGCAGTGTCTCGC (SEQ ID NO: 195) | ATGCGAAC (SEQ ID NO: 483) |
| pe3_1 | TTACCGCGGCKGCTGRCACACGAGTCTAGCGACGAGGCTGGAGTGAC (SEQ ID NO: 196) | CTAGACTC (SEQ ID NO: 484) |
| pe3_2 | TTACCGCGGCKGCTGRCACACGCCTCTATCGACGAGGCTGGAGTGAC (SEQ ID NO: 197) | ATAGAGGC (SEQ ID NO: 485) |
| pe3_3 | TTACCGCGGCKGCTGRCACACGCCATTCTCGACGAGGCTGGAGTGAC (SEQ ID NO: 198) | AGAATGGC (SEQ ID NO: 486) |
| pe3_4 | TTACCGCGGCKGCTGRCACACTACGGTTGCGACGAGGCTGGAGTGAC (SEQ ID NO: 199) | CAACCGTA (SEQ ID NO: 487) |
| pe3_5 | TTACCGCGGCKGCTGRCACACTCTACCCGACGAGGCTGGAGTGAC (SEQ ID NO: 200) | GGTAGAGT (SEQ ID NO: 488) |
| pe3_6 | TTACCGCGGCKGCTGRCACACTAGGTCCACGACGAGGCTGGAGTGAC (SEQ ID NO: 201) | TGGACCTA (SEQ ID NO: 489) |
| pe3_7 | TTACCGCGGCKGCTGRCACACTCCTGAGTCGACGAGGCTGGAGTGAC (SEQ ID NO: 202) | ACTCAGGA (SEQ ID NO: 490) |
| pe3_8 | TTACCGCGGCKGCTGRCACACGTGGATAGCGACGAGGCTGGAGTGAC (SEQ ID NO: 203) | CTATCCAC (SEQ ID NO: 491) |
| pe3_9 | TTACCGCGGCKGCTGRCACACGCGCTATTCGACGAGGCTGGAGTGAC (SEQ ID NO: 204) | AATAGCGC (SEQ ID NO: 492) |
| pe3_10 | TTACCGCGGCKGCTGRCACACGGAAGGAACGACGAGGCTGGAGTGAC (SEQ ID NO: 205) | TTCCTTCC (SEQ ID NO: 493) |
| pe3_11 | TTACCGCGGCKGCTGRCACACGGACTCAACGACGAGGCTGGAGTGAC (SEQ ID NO: 206) | TTGAGTCC (SEQ ID NO: 494) |
| pe3_12 | TTACCGCGGCKGCTGRCACACAACACTCGCGACGAGGCTGGAGTGAC (SEQ ID NO: 207) | CGAGTGTT (SEQ ID NO: 495) |
| pe3_13 | TTACCGCGGCKGCTGRCACACCCGGAATTCGACGAGGCTGGAGTGAC (SEQ ID NO: 208) | AATTCCGG (SEQ ID NO: 496) |
| pe3_14 | TTACCGCGGCKGCTGRCACACAACTTGCCCGACGAGGCTGGAGTGAC (SEQ ID NO: 209) | GGCAAGTT (SEQ ID NO: 497) |
| pe3_15 | TTACCGCGGCKGCTGRCACACTTGACAGGCGACGAGGCTGGAGTGAC (SEQ ID NO: 210) | CCTGTCAA (SEQ ID NO: 498) |
| pe3_16 | TTACCGCGGCKGCTGRCACACTCTTAGCGCGACGAGGCTGGAGTGAC (SEQ ID NO: 211) | CGCTAAGA (SEQ ID NO: 499) |
| pe3_17 | TTACCGCGGCKGCTGRCACACCTGTTGCACGACGAGGCTGGAGTGAC (SEQ ID NO: 212) | TGCAACAG (SEQ ID NO: 500) |
| pe3_18 | TTACCGCGGCKGCTGRCACACAGAACACGCGACGAGGCTGGAGTGAC (SEQ ID NO: 213) | CGTGTTCT (SEQ ID NO: 501) |
| pe3_19 | TTACCGCGGCKGCTGRCACACCCTTGATGCGACGAGGCTGGAGTGAC (SEQ ID NO: 214) | CATCAAGG (SEQ ID NO: 502) |
| pe3_20 | TTACCGCGGCKGCTGRCACACAGCGATCTCGACGAGGCTGGAGTGAC (SEQ ID NO: 215) | AGATCGCT (SEQ ID NO: 503) |
| pe3_21 | TTACCGCGGCKGCTGRCACACGCTCAGAACGACGAGGCTGGAGTGAC (SEQ ID NO: 216) | TTCTGAGC (SEQ ID NO: 504) |
| pe3_22 | TTACCGCGGCKGCTGRCACACATTGCGTGCGACGAGGCTGGAGTGAC (SEQ ID NO: 217) | CACGCAAT (SEQ ID NO: 505) |
| pe3_23 | TTACCGCGGCKGCTGRCACACCATCCGTTCGACGAGGCTGGAGTGAC (SEQ ID NO: 218) | AACGGATG (SEQ ID NO: 506) |
| pe3_24 | TTACCGCGGCKGCTGRCACACTCTCTGGTCGACGAGGCTGGAGTGAC (SEQ ID NO: 219) | ACCAGAGA (SEQ ID NO: 507) |
| pe3_25 | TTACCGCGGCKGCTGRCACACAACGAGCACGACGAGGCTGGAGTGAC (SEQ ID NO: 220) | TGCTCGTT (SEQ ID NO: 508) |
| pe3_26 | TTACCGCGGCKGCTGRCACACACGTTCACCGACGAGGCTGGAGTGAC (SEQ ID NO: 221) | GTGAACGT (SEQ ID NO: 509) |
| pe3_27 | TTACCGCGGCKGCTGRCACACATCAGCACCGACGAGGCTGGAGTGAC (SEQ ID NO: 222) | GTGCTGAT (SEQ ID NO: 510) |
| pe3_28 | TTACCGCGGCKGCTGRCACACGATAGCGACGACGAGGCTGGAGTGAC (SEQ ID NO: 223) | TCGCTATC (SEQ ID NO: 511) |
| pe3_29 | TTACCGCGGCKGCTGRCACACAGAGCTTGCGACGAGGCTGGAGTGAC (SEQ ID NO: 224) | CAAGCTCT (SEQ ID NO: 512) |
| pe3_30 | TTACCGCGGCKGCTGRCACACTGATCGTCCGACGAGGCTGGAGTGAC (SEQ ID NO: 225) | GACGATCA (SEQ ID NO: 513) |
| pe3_31 | TTACCGCGGCKGCTGRCACACACGATACGCGACGAGGCTGGAGTGAC (SEQ ID NO: 226) | CGTATCGT (SEQ ID NO: 514) |
| pe3_32 | TTACCGCGGCKGCTGRCACACCTAACTGGCGACGAGGCTGGAGTGAC (SEQ ID NO: 227) | CCAGTTAG (SEQ ID NO: 515) |
| pe3_33 | TTACCGCGGCKGCTGRCACACTCGCGTAACGACGAGGCTGGAGTGAC (SEQ ID NO: 228) | TTACGCGA (SEQ ID NO: 516) |

TABLE 2-continued

| Primer name | Primer sequence | Barcode sequence |
|---|---|---|
| pe3_34 | TTACCGCGGCKGCTGRCACACCGGTTCTTCGAC GAGGCTGGAGTGAC (SEQ ID NO: 229) | AAGAACCG (SEQ ID NO: 517) |
| pe3_35 | TTACCGCGGCKGCTGRCACACTTGGTTCGCGAC GAGGCTGGAGTGAC (SEQ ID NO: 230) | CGAACCAA (SEQ ID NO: 518) |
| pe3_36 | TTACCGCGGCKGCTGRCACACGAAGTAGCCGAC GAGGCTGGAGTGAC (SEQ ID NO: 231) | GCTACTTC (SEQ ID NO: 519) |
| pe3_37 | TTACCGCGGCKGCTGRCACACGGCTAGAACGAC GAGGCTGGAGTGAC (SEQ ID NO: 232) | TTCTAGCC (SEQ ID NO: 520) |
| pe3_38 | TTACCGCGGCKGCTGRCACACCATCGTGACGAC GAGGCTGGAGTGAC (SEQ ID NO: 233) | TCACGATG (SEQ ID NO: 521) |
| pe3_39 | TTACCGCGGCKGCTGRCACACTCACCAACCGAC GAGGCTGGAGTGAC (SEQ ID NO: 234) | GTTGGTGA (SEQ ID NO: 522) |
| pe3_40 | TTACCGCGGCKGCTGRCACACCTTCAAGGCGAC GAGGCTGGAGTGAC (SEQ ID NO: 235) | CCTTGAAG (SEQ ID NO: 523) |
| pe3_41 | TTACCGCGGCKGCTGRCACACAGTAGCTCCGAC GAGGCTGGAGTGAC (SEQ ID NO: 236) | GAGCTACT (SEQ ID NO: 524) |
| pe3_42 | TTACCGCGGCKGCTGRCACACGCCACATTCGAC GAGGCTGGAGTGAC (SEQ ID NO: 237) | AATGTGGC (SEQ ID NO: 525) |
| pe3_43 | TTACCGCGGCKGCTGRCACACTTCACGGACGAC GAGGCTGGAGTGAC (SEQ ID NO: 238) | TCCGTGAA (SEQ ID NO: 526) |
| pe3_44 | TTACCGCGGCKGCTGRCACACTGACGTTGCGAC GAGGCTGGAGTGAC (SEQ ID NO: 239) | CAACGTCA (SEQ ID NO: 527) |
| pe3_45 | TTACCGCGGCKGCTGRCACACTCATCTGGCGAC GAGGCTGGAGTGAC (SEQ ID NO: 240) | CCAGATGA (SEQ ID NO: 528) |
| pe3_46 | TTACCGCGGCKGCTGRCACACCGTTCATCCGAC GAGGCTGGAGTGAC (SEQ ID NO: 241) | GATGAACG (SEQ ID NO: 529) |
| pe3_47 | TTACCGCGGCKGCTGRCACACAACCGTCACGAC GAGGCTGGAGTGAC (SEQ ID NO: 242) | TGACGGTT (SEQ ID NO: 530) |
| pe3_48 | TTACCGCGGCKGCTGRCACACTGCTAAGCCGAC GAGGCTGGAGTGAC (SEQ ID NO: 243) | GCTTAGCA (SEQ ID NO: 531) |
| pe3_49 | TTACCGCGGCKGCTGRCACACCAGGTAGACGAC GAGGCTGGAGTGAC (SEQ ID NO: 244) | TCTACCTG (SEQ ID NO: 532) |
| pe3_50 | TTACCGCGGCKGCTGRCACACAAGAACCGCGAC GAGGCTGGAGTGAC (SEQ ID NO: 245) | CGGTTCTT (SEQ ID NO: 533) |
| pe3_51 | TTACCGCGGCKGCTGRCACACAGGAGACTCGAC GAGGCTGGAGTGAC (SEQ ID NO: 246) | AGTCTCCT (SEQ ID NO: 534) |
| pe3_52 | TTACCGCGGCKGCTGRCACACAGTGAAGGCGAC GAGGCTGGAGTGAC (SEQ ID NO: 247) | CCTTCACT (SEQ ID NO: 535) |
| pe3_53 | TTACCGCGGCKGCTGRCACACTCTTCAGCCGAC GAGGCTGGAGTGAC (SEQ ID NO: 248) | GCTGAAGA (SEQ ID NO: 536) |
| pe3_54 | TTACCGCGGCKGCTGRCACACAACGGAGTCGAC GAGGCTGGAGTGAC (SEQ ID NO: 249) | ACTCCGTT (SEQ ID NO: 537) |
| pe3_55 | TTACCGCGGCKGCTGRCACACGAAGAGACCGA CGAGGCTGGAGTGAC (SEQ ID NO: 250) | GTCTCTTC (SEQ ID NO: 538) |
| pe3_56 | TTACCGCGGCKGCTGRCACACATTGGTGGCGAC GAGGCTGGAGTGAC (SEQ ID NO: 251) | CCACCAAT (SEQ ID NO: 539) |
| pe3_57 | TTACCGCGGCKGCTGRCACACCTGTCAAGCGAC GAGGCTGGAGTGAC (SEQ ID NO: 252) | CTTGACAG (SEQ ID NO: 540) |
| pe3_58 | TTACCGCGGCKGCTGRCACACAGGCATCACGAC GAGGCTGGAGTGAC (SEQ ID NO: 253) | TGATGCCT (SEQ ID NO: 541) |
| pe3_59 | TTACCGCGGCKGCTGRCACACAAGAGGTCCGAC GAGGCTGGAGTGAC (SEQ ID NO: 254) | GACCTCTT (SEQ ID NO: 542) |
| pe3_60 | TTACCGCGGCKGCTGRCACACTGCATTCGCGAC GAGGCTGGAGTGAC (SEQ ID NO: 255) | CGAATGCA (SEQ ID NO: 543) |
| pe3_61 | TTACCGCGGCKGCTGRCACACTTGGACGTCGAC GAGGCTGGAGTGAC (SEQ ID NO: 256) | ACGTCCAA (SEQ ID NO: 544) |
| pe3_62 | TTACCGCGGCKGCTGRCACACTTGCTGGACGAC GAGGCTGGAGTGAC (SEQ ID NO: 257) | TCCAGCAA (SEQ ID NO: 545) |
| pe3_63 | TTACCGCGGCKGCTGRCACACTGGAGATGCGAC GAGGCTGGAGTGAC (SEQ ID NO: 258) | CATCTCCA (SEQ ID NO: 546) |
| pe3_64 | TTACCGCGGCKGCTGRCACACTACGTACCCGAC GAGGCTGGAGTGAC (SEQ ID NO: 259) | GGTACGTA (SEQ ID NO: 547) |
| pe3_65 | TTACCGCGGCKGCTGRCACACTGACACCTCGAC GAGGCTGGAGTGAC (SEQ ID NO: 260) | AGGTGTCA (SEQ ID NO: 548) |
| pe3_66 | TTACCGCGGCKGCTGRCACACGTCCATTGCGAC GAGGCTGGAGTGAC (SEQ ID NO: 261) | CAATGGAC (SEQ ID NO: 549) |
| pe3_67 | TTACCGCGGCKGCTGRCACACCAGAGAAGCGA CGAGGCTGGAGTGAC (SEQ ID NO: 262) | CTTCTCTG (SEQ ID NO: 550) |
| pe3_68 | TTACCGCGGCKGCTGRCACACTGCTTCAGCGAC GAGGCTGGAGTGAC (SEQ ID NO: 263) | CTGAAGCA (SEQ ID NO: 551) |
| pe3_69 | TTACCGCGGCKGCTGRCACACTACACTGCCGAC GAGGCTGGAGTGAC (SEQ ID NO: 264) | GCAGTGTA (SEQ ID NO: 552) |
| pe3_70 | TTACCGCGGCKGCTGRCACACGGACGTATCGAC GAGGCTGGAGTGAC (SEQ ID NO: 265) | ATACGTCC (SEQ ID NO: 553) |
| pe3_71 | TTACCGCGGCKGCTGRCACACCTCGCATACGAC GAGGCTGGAGTGAC (SEQ ID NO: 266) | TATGCGAG (SEQ ID NO: 554) |

TABLE 2-continued

| Primer name | Primer sequence | Barcode sequence |
|---|---|---|
| pe3_72 | TTACCGCGGCKGCTGRCACACGCATCCTACGAC GAGGCTGGAGTGAC (SEQ ID NO: 267) | TAGGATGC (SEQ ID NO: 555) |
| pe3_73 | TTACCGCGGCKGCTGRCACACAGGCTTACCGAC GAGGCTGGAGTGAC (SEQ ID NO: 268) | GTAAGCCT (SEQ ID NO: 556) |
| pe3_74 | TTACCGCGGCKGCTGRCACACGTAAGTCGCGAC GAGGCTGGAGTGAC (SEQ ID NO: 269) | CGACTTAC (SEQ ID NO: 557) |
| pe3_75 | TTACCGCGGCKGCTGRCACACTTCTGGAGCGAC GAGGCTGGAGTGAC (SEQ ID NO: 270) | CTCCAGAA (SEQ ID NO: 558) |
| pe3_76 | TTACCGCGGCKGCTGRCACACGACACACACGAC GAGGCTGGAGTGAC (SEQ ID NO: 271) | TGTGTGTC (SEQ ID NO: 559) |
| pe3_77 | TTACCGCGGCKGCTGRCACACACCAGACACGAC GAGGCTGGAGTGAC (SEQ ID NO: 272) | TGTCTGGT (SEQ ID NO: 560) |
| pe3_78 | TTACCGCGGCKGCTGRCACACTGCAGCTTCGAC GAGGCTGGAGTGAC (SEQ ID NO: 273) | AAGCTGCA (SEQ ID NO: 561) |
| pe3_79 | TTACCGCGGCKGCTGRCACACGCAACTTCCGAC GAGGCTGGAGTGAC (SEQ ID NO: 274) | GAAGTTGC (SEQ ID NO: 562) |
| pe3_80 | TTACCGCGGCKGCTGRCACACACTCGCTTCGAC GAGGCTGGAGTGAC (SEQ ID NO: 275) | AAGCGAGT (SEQ ID NO: 563) |
| pe3_81 | TTACCGCGGCKGCTGRCACACTGAACTCCCGAC GAGGCTGGAGTGAC (SEQ ID NO: 276) | GGAGTTCA (SEQ ID NO: 564) |
| pe3_82 | TTACCGCGGCKGCTGRCACACGTGTAAGCCGAC GAGGCTGGAGTGAC (SEQ ID NO: 277) | GCTTACAC (SEQ ID NO: 565) |
| pe3_83 | TTACCGCGGCKGCTGRCACACATGCACCTCGAC GAGGCTGGAGTGAC (SEQ ID NO: 278) | AGGTGCAT (SEQ ID NO: 566) |
| pe3_84 | TTACCGCGGCKGCTGRCACACTCCGTCAACGAC GAGGCTGGAGTGAC (SEQ ID NO: 279) | TTGACGGA (SEQ ID NO: 567) |
| pe3_85 | TTACCGCGGCKGCTGRCACACGTCGGTATCGAC GAGGCTGGAGTGAC (SEQ ID NO: 280) | ATACCGAC (SEQ ID NO: 568) |
| pe3_86 | TTACCGCGGCKGCTGRCACACACAGATCCCGAC GAGGCTGGAGTGAC (SEQ ID NO: 281) | GGATCTGT (SEQ ID NO: 569) |
| pe3_87 | TTACCGCGGCKGCTGRCACACTCGGATCTCGAC GAGGCTGGAGTGAC (SEQ ID NO: 282) | AGATCCGA (SEQ ID NO: 570) |
| pe3_88 | TTACCGCGGCKGCTGRCACACAGAGTCGTCGAC GAGGCTGGAGTGAC (SEQ ID NO: 283) | ACGACTCT (SEQ ID NO: 571) |
| pe3_89 | TTACCGCGGCKGCTGRCACACGAATAGCGCGAC GAGGCTGGAGTGAC (SEQ ID NO: 284) | CGCTATTC (SEQ ID NO: 572) |
| pe3_90 | TTACCGCGGCKGCTGRCACACGGATTGGTCGAC GAGGCTGGAGTGAC (SEQ ID NO: 285) | ACCAATCC (SEQ ID NO: 573) |

TABLE 2-continued

| Primer name | Primer sequence | Barcode sequence |
|---|---|---|
| pe3_91 | TTACCGCGGCKGCTGRCACACGCCATAGACGAC GAGGCTGGAGTGAC (SEQ ID NO: 286) | TCTATGGC (SEQ ID NO: 574) |
| pe3_92 | TTACCGCGGCKGCTGRCACACTGTCAGAGCGAC GAGGCTGGAGTGAC (SEQ ID NO: 287) | CTCTGACA (SEQ ID NO: 575) |
| pe3_93 | TTACCGCGGCKGCTGRCACACCCTACGAACGAC GAGGCTGGAGTGAC (SEQ ID NO: 288) | TTCGTAGG (SEQ ID NO: 576) |
| pe3_94 | TTACCGCGGCKGCTGRCACACGTTACGTCCGAC GAGGCTGGAGTGAC (SEQ ID NO: 289) | GACGTAAC (SEQ ID NO: 577) |
| pe3_95 | TTACCGCGGCKGCTGRCACACCGAGATACCGAC GAGGCTGGAGTGAC (SEQ ID NO: 290) | GTATCTCG (SEQ ID NO: 578) |
| pe3_96 | TTACCGCGGCKGCTGRCACACGCATTGACCGAC GAGGCTGGAGTGAC (SEQ ID NO: 291) | GTCAATGC (SEQ ID NO: 579) |

TABLE 3

| Primer name | Primer sequence | Barcode sequence |
|---|---|---|
| p7_1 | CAAGCAGAAGACGGCATACGAGATTCGATGAGGTGA CTGGAGTTCAGACGTGTGCTCTTCCGATCT (SEQ ID NO: 580) | CTCATCGA (SEQ ID NO: 612) |
| p7_2 | CAAGCAGAAGACGGCATACGAGATAACGATCCGTGA CTGGAGTTCAGACGTGTGCTCTTCCGATCT (SEQ ID NO: 581) | GGATCGTT (SEQ ID NO: 613) |
| p7_3 | CAAGCAGAAGACGGCATACGAGATTAACGTGGGTGA CTGGAGTTCAGACGTGTGCTCTTCCGATCT (SEQ ID NO: 582) | CCACGTTA (SEQ ID NO: 614) |
| p7_4 | CAAGCAGAAGACGGCATACGAGATATGGAGGAGTGA CTGGAGTTCAGACGTGTGCTCTTCCGATCT (SEQ ID NO: 583) | TCCTCCAT (SEQ ID NO: 615) |
| p7_5 | CAAGCAGAAGACGGCATACGAGATGCGAAGATGTGA CTGGAGTTCAGACGTGTGCTCTTCCGATCT (SEQ ID NO: 584) | ATCTTCGC (SEQ ID NO: 616) |
| p7_6 | CAAGCAGAAGACGGCATACGAGATACTTCGCTGTGA CTGGAGTTCAGACGTGTGCTCTTCCGATCT (SEQ ID NO: 585) | AGCGAAGT (SEQ ID NO: 617) |
| p7_7 | CAAGCAGAAGACGGCATACGAGATTGCGTAAGGTGA CTGGAGTTCAGACGTGTGCTCTTCCGATCT (SEQ ID NO: 586) | CTTACGCA (SEQ ID NO: 618) |
| p7_8 | CAAGCAGAAGACGGCATACGAGATGGTCAAGTGTGA CTGGAGTTCAGACGTGTGCTCTTCCGATCT (SEQ ID NO: 587) | ACTTGACC (SEQ ID NO: 619) |
| p7_9 | CAAGCAGAAGACGGCATACGAGATAGGCTTACGTGA CTGGAGTTCAGACGTGTGCTCTTCCGATCT (SEQ ID NO: 588) | GTAAGCCT (SEQ ID NO: 620) |
| p7_10 | CAAGCAGAAGACGGCATACGAGATGATTCTCGGTGA CTGGAGTTCAGACGTGTGCTCTTCCGATCT (SEQ ID NO: 589) | CGAGAATC (SEQ ID NO: 621) |
| p7_11 | CAAGCAGAAGACGGCATACGAGATGTCTCCTAGTGA CTGGAGTTCAGACGTGTGCTCTTCCGATCT (SEQ ID NO: 590) | TAGGAGAC (SEQ ID NO: 622) |

TABLE 3-continued

| Primer name | Primer sequence | Barcode sequence |
|---|---|---|
| p7_12 | CAAGCAGAAGACGGCATACGAGATGACGGTATGTGA CTGGAGTTCAGACGTGTGCTCTTCCGATCT (SEQ ID NO: 591) | ATACCGTC (SEQ ID NO: 623) |
| p7_13 | CAAGCAGAAGACGGCATACGAGATCATGGTGTGTGA CTGGAGTTCAGACGTGTGCTCTTCCGATCT (SEQ ID NO: 592) | ACACCATG (SEQ ID NO: 624) |
| p7_14 | CAAGCAGAAGACGGCATACGAGATTGTCTACCGTGA CTGGAGTTCAGACGTGTGCTCTTCCGATCT (SEQ ID NO: 593) | GGTAGACA (SEQ ID NO: 625) |
| p7_15 | CAAGCAGAAGACGGCATACGAGATACCATGCAGTGA CTGGAGTTCAGACGTGTGCTCTTCCGATCT (SEQ ID NO: 594) | TGCATGGT (SEQ ID NO: 626) |
| p7_16 | CAAGCAGAAGACGGCATACGAGATCATTCCTGGTGA CTGGAGTTCAGACGTGTGCTCTTCCGATCT (SEQ ID NO: 595) | CAGGAATG (SEQ ID NO: 627) |
| p7_17 | CAAGCAGAAGACGGCATACGAGATAGGACTAGGTGA CTGGAGTTCAGACGTGTGCTCTTCCGATCT (SEQ ID NO: 596) | CTAGTCCT (SEQ ID NO: 628) |
| p7_18 | CAAGCAGAAGACGGCATACGAGATGCTTGTTGGTGA CTGGAGTTCAGACGTGTGCTCTTCCGATCT (SEQ ID NO: 597) | CAACAAGC (SEQ ID NO: 629) |
| p7_19 | CAAGCAGAAGACGGCATACGAGATAGTCACACGTGA CTGGAGTTCAGACGTGTGCTCTTCCGATCT (SEQ ID NO: 598) | GTGTGACT (SEQ ID NO: 630) |
| p7_20 | CAAGCAGAAGACGGCATACGAGATCCAGTTGTGTGA CTGGAGTTCAGACGTGTGCTCTTCCGATCT (SEQ ID NO: 599) | ACAACTGG (SEQ ID NO: 631) |
| p7_21 | CAAGCAGAAGACGGCATACGAGATCTCCATTCGTG ACTGGAGTTCAGACGTGTGCTCTTCCGATCT (SEQ ID NO: 600) | GAATGGAG (SEQ ID NO: 632) |
| p7_22 | CAAGCAGAAGACGGCATACGAGATTTGCCAACGTGA CTGGAGTTCAGACGTGTGCTCTTCCGATCT (SEQ ID NO: 601) | GTTGGCAA (SEQ ID NO: 633) |
| p7_23 | CAAGCAGAAGACGGCATACGAGATGAGCACATGTGA CTGGAGTTCAGACGTGTGCTCTTCCGATCT (SEQ ID NO: 602) | ATGTGCTC (SEQ ID NO: 634) |
| p7_24 | CAAGCAGAAGACGGCATACGAGATATGTGGTGGTGA CTGGAGTTCAGACGTGTGCTCTTCCGATCT (SEQ ID NO: 603) | CACCACAT (SEQ ID NO: 635) |
| p5_1 | AATGATACGGCGACCACCGAGATCTACACTAGATC GCACACTCTTTCCCTACACGACGCTCTTCCGATCT (SEQ ID NO: 604) | TAGATCGC (SEQ ID NO: 636) |
| p5_2 | AATGATACGGCGACCACCGAGATCTACACCTCTCT ATACACTCTTTCCCTACACGACGCTCTTCCGATCT (SEQ ID NO: 605) | CTCTCTAT (SEQ ID NO: 637) |
| p5_3 | AATGATACGGCGACCACCGAGATCTACACTATCCTC TACACTCTTTCCCTACACGACGCTCTTCCGATCT (SEQ ID NO: 606) | TATCCTCT (SEQ ID NO: 638) |
| p5_4 | AATGATACGGCGACCACCGAGATCTACACAGAGTAG AACACTCTTTCCCTACACGACGCTCTTCCGATCT (SEQ ID NO: 607) | AGAGTAGA (SEQ ID NO: 639) |
| p5_5 | AATGATACGGCGACCACCGAGATCTACACGTAAGGA GACACTCTTTCCCTACACGACGCTCTTCCGATCT (SEQ ID NO: 608) | GTAAGGAG (SEQ ID NO: 640) |
| p5_6 | AATGATACGGCGACCACCGAGATCTACACACTGCAT AACACTCTTTCCCTACACGACGCTCTTCCGATCT (SEQ ID NO: 609) | ACTGCATA (SEQ ID NO: 641) |
| p5_7 | AATGATACGGCGACCACCGAGATCTACACAAGGAGT AACACTCTTTCCCTACACGACGCTCTTCCGATCT (SEQ ID NO: 610) | AAGGAGTA (SEQ ID NO: 642) |
| p5_8 | AATGATACGGCGACCACCGAGATCTACACCTAAGCC TACACTCTTTCCCTACACGACGCTCTTCCGATCT (SEQ ID NO: 611) | CTAAGCCT (SEQ ID NO: 643) |

TABLE 4

| Primer name | Primer sequence |
|---|---|
| bead_pe1_cy5 | /5Cy5/AGATCGGAAGAGCGTCGTG (SEQ ID NO: 644) |
| bead_515f_cy5 | /5Cy5/TTACCGCGGCKGCTGRCAC (SEQ ID NO: 645) |
| erec482_a488 | /5Alex488N/GCTTCTTAGTCAGGTACCG (SEQ ID NO: 646) |
| lab158_cy3 | /5Cy3/GGTATTAGCAYCTGTTTCCA (SEQ ID NO: 647) |
| ato291_cy5 | /5Cy5/GGTCGGTCTCTCAACCC (SEQ ID NO: 648) |
| erec482_cy3 | /5Cy3/GCTTCTTAGTCAGGTACCG (SEQ ID NO: 649) |
| eub338_cy5 | /5Cy5/GCTGCCTCCCGTAGGAGT (SEQ ID NO: 650) |
| non338_cy5 | /5Cy5/ACTCCTACGGGAGGCAGC (SEQ ID NO: 651) |

TABLE 5

| Dataset | Cluster size (microns) | Reads, cutoff, TR1 | Clusters, TR1 | Reads cutoff, TR2 | Clusters, TR2 | Number clusters discarded | Final number of clusters |
|---|---|---|---|---|---|---|---|
| Community mixing, *E. coli* + homogenized fecal material | 30 | 1440 | 399 | N/A | N/A | N/A | 399 |
| Community mixing, *S. pasteurii* + homogenized fecal material | 20 | 566 | 88 | N/A | N/A | N/A | 88 |

TABLE 5-continued

| Dataset | Cluster size (microns) | Reads, cutoff, TR1 | Clusters, TR1 | Reads cutoff, TR2 | Clusters, TR2 | Number clusters discarded | Final number of clusters |
|---|---|---|---|---|---|---|---|
| Mouse distal colon | 30 | 992 | 715 | 717 | 754 | 63 | 1406 |
| Mouse distal colon (co-housed mouse) | 30 | 920 | 730 | 651 | 624 | 126 | 1228 |
| Mouse ileum (si6) | 20 | 432 | 379 | 510 | 114 | 107 | 386 |
| Mouse cecum (cec) | 20 | 405 | 235 | 314 | 193 | 23 | 405 |
| Mouse distal colon (co2) | 20 | 404 | 164 | 442 | 124 | 29 | 259 |
| Mouse distal colon (co2) | 7 | 540 | 292 | 438 | 237 | 0 | 529 |
| Mouse ileum (si6; co-housed mouse) | 20 | 379 | 157 | 396 | 104 | 0 | 261 |
| Mouse cecum (cec; co-housed mouse) | 20 | 239 | 112 | 256 | 177 | 66 | 223 |
| Mouse distal colon (co2; co-housed mouse) | 7 | 328 | 111 | 286 | 40 | 0 | 151 |
| Mouse distal colon, LF diet | 20 | 121 | 240 | 124 | 255 | 0 | 495 |
| Mouse distal colon, LF diet, adjacent segment | 20 | 184 | 225 | 125 | 192 | 58 | 359 |
| Mouse distal colon, HF diet | 20 | 262 | 503 | 279 | 460 | 25 | 938 |

All mouse samples were collected in technical replicate (TR), a single technical replicate was collected for community mixing experiments. The procedure to remove technical artifacts (i.e. "Number clusters discarded") was not performed on community mixing experiments given that they are composed of highly homogenous communities.

Sample fixation and in situ polymerization. Intact tissue segments (from the colon, cecum or small intestine as noted) were obtained by dissection and immediately fixed in methacarn solution (60% methanol, 30% chloroform, 10% acetic acid) for 24 hours (see Johansson, M. E. V. & Hansson, G. C. Preservation of mucus in histological sections, immunostaining of mucins in fixed tissue, and localization of bacteria with FISH. Methods Mol. Biol. 842, 229-235 (2012)). The fixed tissue was trimmed with a sterile razor into segments no larger than 3 mm in length, and segments containing digesta were selected. Thus, all input samples for MaP-seq analysis contained undisturbed epithelial tissue and lumenal digesta contents. The trimmed sample was then incubated in phosphate buffered saline (PBS) for 5 minutes and was permeabilized in PBS with 0.1% v/v Triton-X 100 for 5 minutes. Next, a matrix embedding solution (see Chung, K. et al. Structural and molecular interrogation of intact biological systems. Nature 497, 332-337 (2013); Chen, F., Tillberg, P. W. & Boyden, E. S. Expansion microscopy. Science 347, 543-548 (2015) containing a reverse sequencing primer with 16S V4 primer 806rB (see Klein, A. M. et al. (2015); Apprill, A., McNally, S., Parsons, R. & Weber, L. Minor revision to V4 region SSU rRNA 806R gene primer greatly increases detection of SAR11 bacterioplankton. Aquat. Microb. Ecol. 75, 129-137 (2015)) and acrydite and photocleavable linker groups was prepared on ice by mixing concentrated stocks of the following components in order: 1×PBS, 10% w/w acrylamide (Sigma-Aldrich A9099), 0.4% w/w N,N'-Bis(acryloyl)cystamine (BAC, Alfa Aesar 44132-03), 5 µM acry_pc_pe2_816r (see Table 1), 0.01% w/w 4-hydroxy-2,2,6,6-tetramethylpiperidin-1-oxyl (Sigma-Aldrich 176141), 0.2% w/w tetramethylethylenediamine (Sigma-Aldrich T7024) and 0.2% w/w ammonium persulfate (Sigma-Aldrich A3678). The BAC crosslinker enables gel degradation upon exposure to reducing conditions. The sample was dabbed dry with a sterile Kimwipe and placed in a PCR tube with excess matrix embedding solution (~50 µL per segment) and incubated on ice for 5 minutes. Excess embedding solution was removed by pipetting and replaced, and the sample was subsequently incubated on ice for >1 hour for perfusion. Excess embedding solution was removed, and samples were placed in a 37° C. incubator in an anaerobic chamber (Coy Laboratory Products) for >3 hours. Gel-embedded samples were removed, excess polymer matrix was trimmed from the sample with a sterile razor, and the sample was washed twice with PBS and once with TET and stored in TET at 4° C. FIG. 13.

Sample fracturing, lysis and size-selection. Samples were placed in a stainless-steel vial (Biospec 2007) along with a 6.35 mm stainless steel bead (Biospec 11709635ss), and were sealed with a silicone rubber plug cap (Biospec 2008). The vial was placed in liquid nitrogen for >2 minutes, vigorously shaken to dislodge the sample from the vial wall, and quickly transferred to a bead beater (Biospec 112011) and subjected to beating for 10 seconds. PBS was added to the vial and vortexed; clusters in PBS were removed and washed twice with PBS via centrifugation at 15K RPM for 1 minute (Eppendorf 5424). Next, embedded cells were lysed (see Spencer, S. J. et al. Massively parallel sequencing of single cells by epicPCR links functional genes with phylogenetic markers. 1-10 (2015). doi:10.1038/ismej.2015.124); clusters were resuspended in 500 µL lysis buffer (10 mM Tris-HCl [pH 8.0], 1 mM ethylenediaminetetraacetic acid [EDTA], 100 mM NaCl) with 75 U/μL lysozyme (Epicentre R1810M) and were incubated at 37° C. for 1 hour. Clusters were then resuspended in 500 μL digestion buffer (30 mM Tris-HCl [pH 8.0], 1 mM EDTA, 0.5% Triton X-100, 800 mM guanidine hydrochloride [Sigma-Aldrich G9284]) with 0.1 μg/μL proteinase K (Epicentre MPRK092), and were incubated at 65° C. for 15 minutes. Finally, clusters were incubated at 95° C. for 5 minutes to inactivate proteinase K and washed three times with TET.

Samples were next subjected to size-selection. Clusters were first passed through a 40 μm cell strainer (Fisher 22-363-547) to remove large particulate matter. Next, nylon mesh filters (Component Supply Company, 7 μm: U-CMN-7-A, 15 μm: U-CMN-15-A, 31 μm: U-CMN-31-A) were cut to size using a ½" hole punch and two filter punches were placed in a holder (EMD Millipore SX0001300) for each size. Clusters were passed through the 31 μm filter, 15 μm filter, and 7 μm filter sequentially using a 3 mL syringe (BD 309657); for each filter, clusters were passed through three times, and retained clusters on filters were washed once with TET. Clusters were washed off the 15 μm filter (large, ~30 μm median diameter) and 7 μm (medium, ~20 μm median diameter) or collected from the pass-through from the final 7 μm filter (small, ~7 μm median diameter). The concentration of clusters was quantified by counting on a hemocytometer (INCYTO DHC-N01) and stored at 4° C. in TET for processing within ~2 days. FIG. 13.

Co-encapsulation of beads and clusters. A microfluidic co-encapsulation strategy was utilized with three syringe pumps (Harvard Apparatus Pump 11 Elite) and observed under a microscope (Nikon Eclipse Ti2). First, 300 μL of HFE-7500 (3M) with 5% w/w surfactant (RAN Biotechnologies 008—FluoroSurfactant) was loaded into a 1 mL low dead volume syringe (Air-Tite Products A1), the syringe was fitted with a needle (BD 305122) and polyethylene tubing (Scientific Commodities Inc., BB31695—PE/2) and primed on a syringe pump. 30 μL of packed barcoded beads were then removed and washed twice with wash buffer (WB, 10 mM Tris HCl [pH 8.0], 0.1 mM EDTA, 0.1% Tween-20) and twice with bead buffer (10 mM Tris HCl [pH 8.0], 0.1% Tween-20, 50 mM KCl, 10 mM fresh DTT [utilized to degrade clusters within droplets]) by addition of buffer and centrifugation at 15K RPM for 1 minute. After the 4 washes, remaining buffer supernatant was removed with a gel-loading tip (Fisher 02-707-139). ~5 μL of packed beads were loaded into polyethylene tubing and primed with a 1 mL syringe (BD 309626) backfilled with 500 μL HFE-7500. The tubing was protected from light with a black tubing sheath (McMaster-Carr 5231K31) and primed on a syringe pump with needle facing upwards.

Next, a cluster stock was vortexed for 1 minute, 2,500 clusters were removed, washed three times in WB, and the remaining buffer was removed as above. A 45 μL encapsulation mix was prepared (25 μL NEBNext Q5 Hot Start HiFi PCR Master Mix [NEB M0543L], 4 μL Nycoprep Universal [Accurate Chemical & Scientific Corp. AN1106865], 5 μL 10% w/v Pluronic F-127 [Sigma-Aldrich P2443], 1.25 μL 20 mg/mL BSA [NEB B90005], 9.75 μL nuclease-free water) and clusters were resuspended in the mix and vortexed for >10 s. A 1 mL low dead volume syringe was backfilled with 500 μL HFE-7500, and the encapsulation mix was added directly into the tip of the syringe. A needle and polyethylene tubing were fitted to the syringe, protected from light with a black tubing sheath, and primed on a syringe pump with needle facing upwards.

Figure 14A:
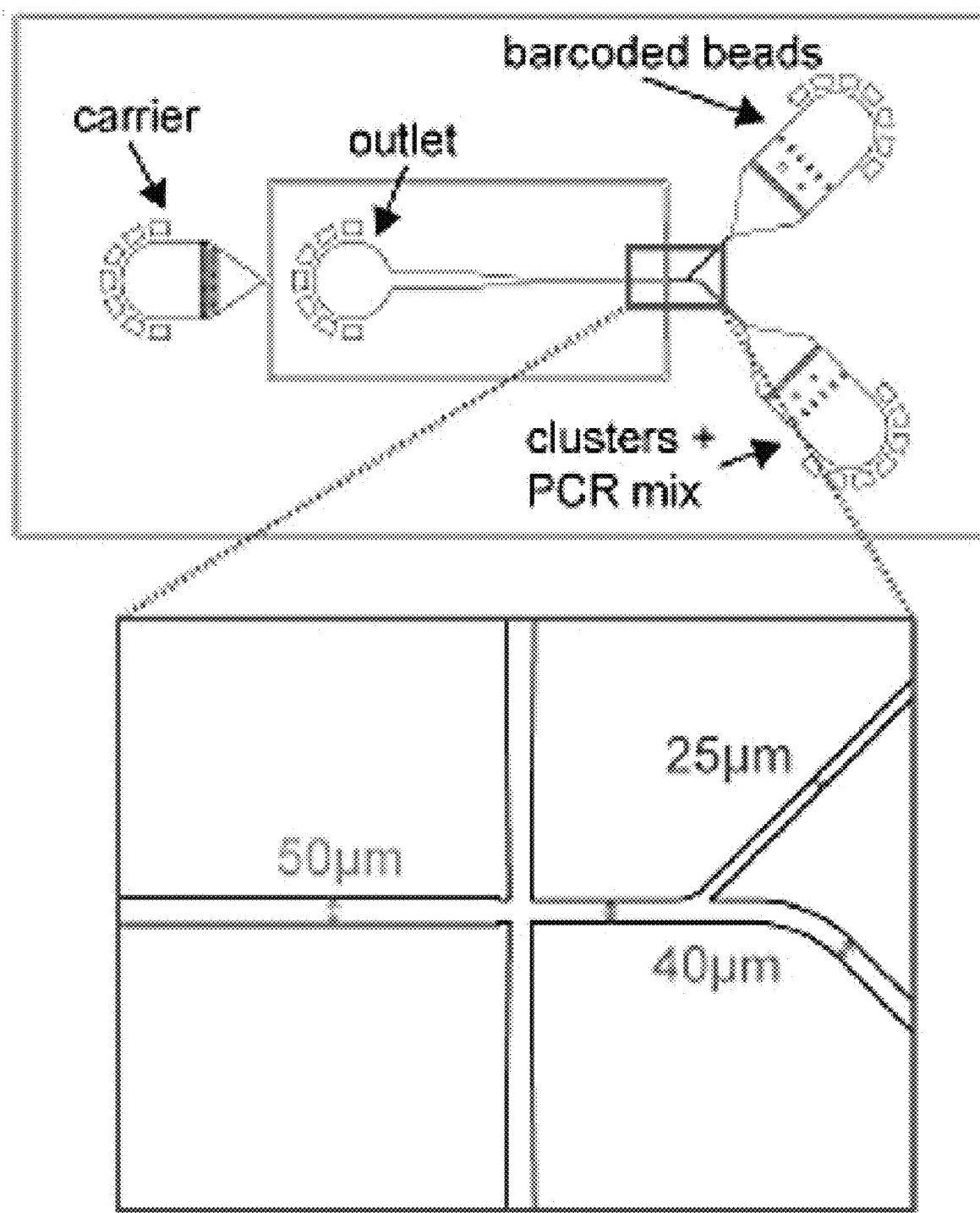
FIGS. 14a-14c: Microfluidic encapsulation of barcoded beads and clusters. a) Schematic of the microfluidic droplet generation device utilized to co-encapsulate barcoded beads and clusters. Beads are packed single file to enable loading that beats Poisson encapsulation statistics expected by random loading. b) Image of the microfluidic device during operation. c) Resulting emulsion after encapsulation; beads can be observed as a faint sphere within droplets; orange arrows indicate three example droplets (of many in the field of view) with a single barcoded bead (but no clusters). One droplet with a single barcoded bead (red arrow) and a single cluster (blue arrow) can be observed in this field of view.
Figure 14B:
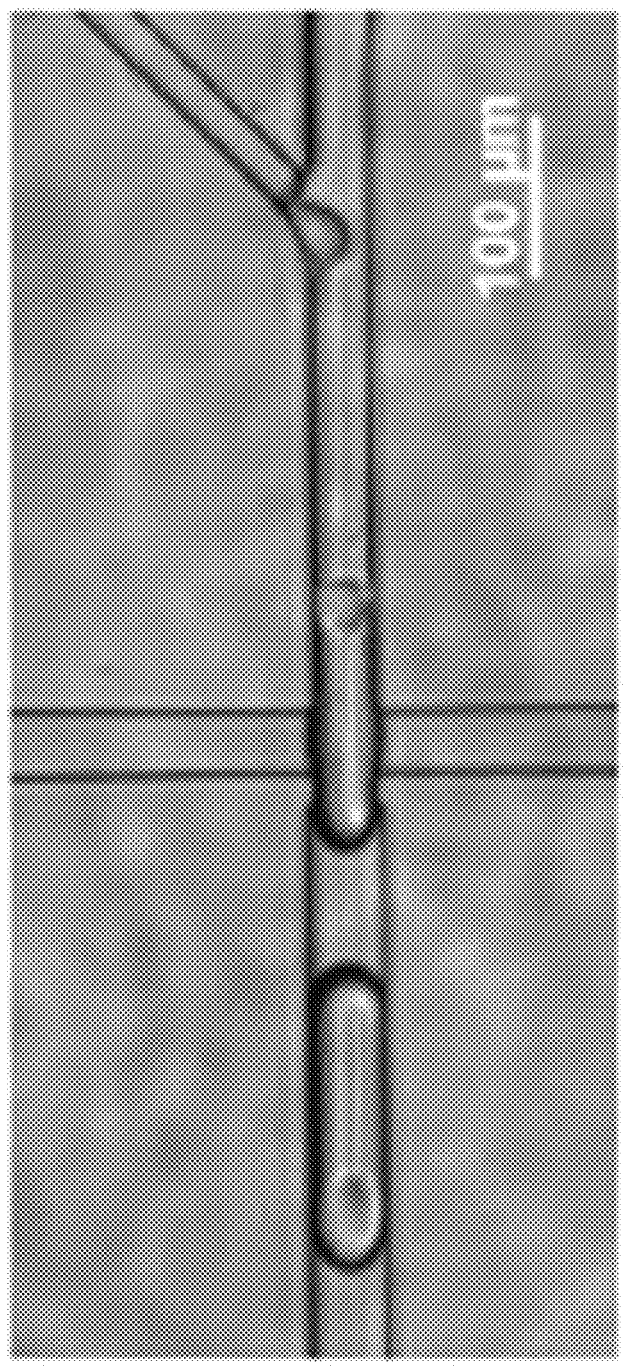
Figure 14C:
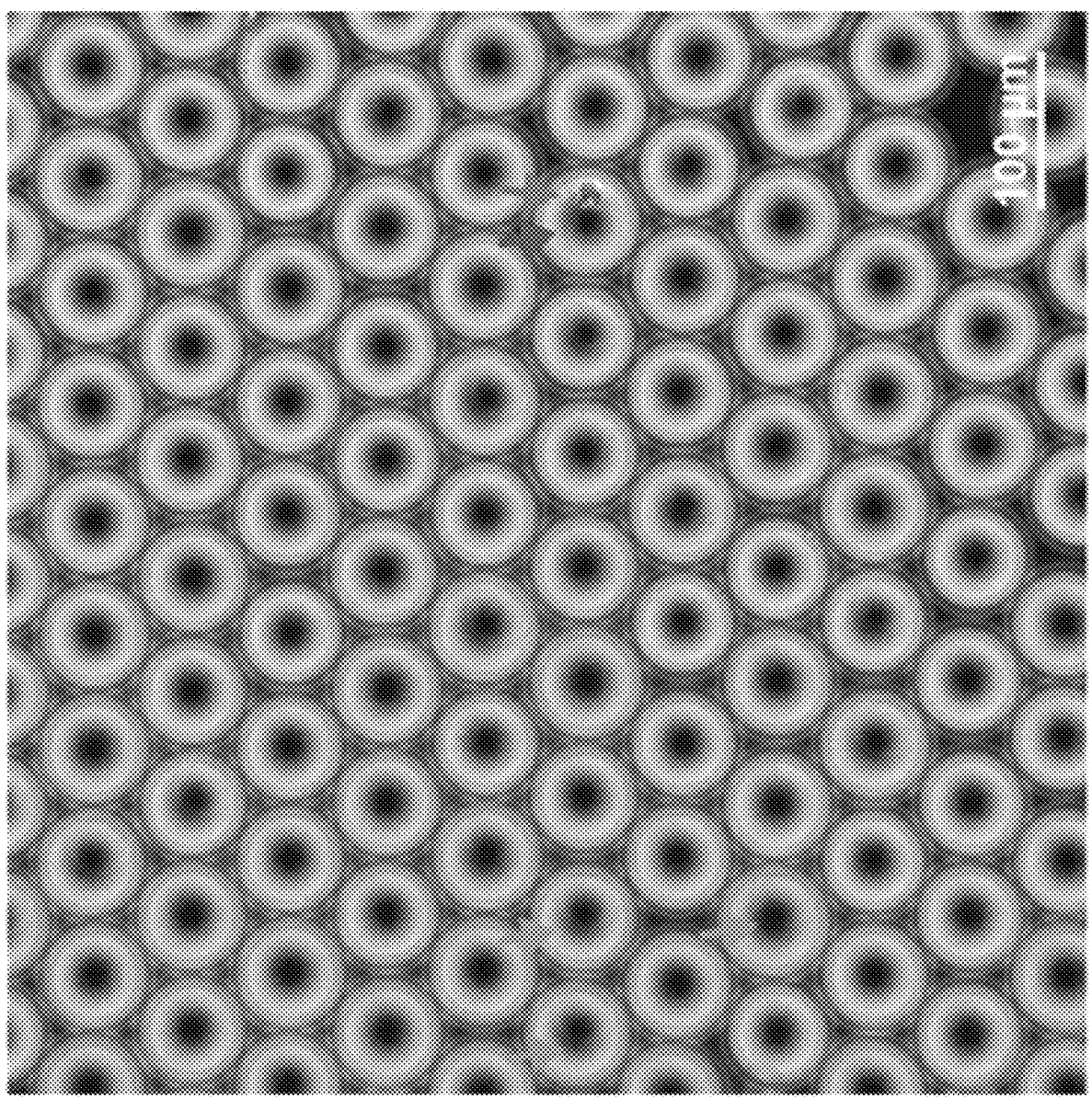

Tubing was connected for the carrier, bead and cluster encapsulation mix channels to a new microfluidic device. Pumps were primed for the carrier, beads and cluster encapsulation mix channels in order and once stable bead packing was observed set to final flow rates of 2 μL/min for carrier, 0.3 μL/min for beads, and 2.7 μL/min for cluster encapsulation mix. Once stable droplet formation was observed, polyethylene tubing was connected to the outlet port and emulsion was collected in a PCR tube (Axygen PCR-02-L-C) prefilled with 10 μL of 30% w/w surfactant in HFE-7500 and 50 μL of mineral oil. Under these conditions, generated droplets were ~35-45 μm in diameter with bead occupancy of ~25-50% (packed bead ordering enables loading beating expected Poisson encapsulation statistics (see Abate, A. R., Chen, C.-H., Agresti, J. J. & Weitz, D. A. Beating Poisson encapsulation statistics using close-packed ordering. Lab Chip 9, 2628-2631 (2009)) and extremely low cluster occupancy of <0.1% (cluster aggregation and channel clogging is a limiting factor at higher concentrations). FIG. 14. Emulsion PCR, library preparation and sequencing. The carrier phase underneath the emulsion was removed and replaced with 30 μL of 30% w/w surfactant in HFE-7500 to ensure droplet stability during PCR cycling. Tubes were placed on ice under a 365 nm UV light (Ted Pella Blak-Ray) and exposed for 10 minutes to release amplification primers. The emulsion was then subjected to PCR cycling (10° C. for 2 h, 98° C. for 30 s; 30 cycles of: 98° C. for 10 s, 55° C. for 20 s, 65° C. for 30 s; 65° C. for 2 m) with heated lid off. Coalesced droplet fraction, if present, was removed by pipetting and the carrier phase and mineral oil were removed. Droplets were broken by addition of 20 μL 1H,1H, 2H,2H-perfluoro-1-octanol (Sigma-Aldrich 370533), and brief centrifugation in a microfuge tube. The aqueous phase was extracted and passed through a 0.45 μm spin column (Corning 8162) and subjected to an ExoI cleanup by adding 50 uL of 1× ExoI buffer with 1 U/uL ExoI (NEB M0293L) and incubating at 37° C. for 30 minutes. The mixture was then subjected to a 1×SPRI bead cleanup (Beckman Coulter A63881) per the manufacturer's protocol with addition of 1× volume beads and elution in 20 μL of 10 mM Tris-HCl (pH 8.0).

The resulting products were then subjected to a second PCR to add sample indexes and Illumina P5 and P7 adapters. 10 μL of cleanup product was used as template for a 50 μL reaction with 1×NEBNext Q5 Hot Start HiFi PCR Master Mix, 0.5 μM of each of the indexing primers (p5_X, p7_X, see Table 3), and 0.1×SYBR Green I (Invitrogen S7567). The PCR (98° C. for 30 s, cycle: 98° C. for 10 s, 68° C. for 20 s, 65° C. for 30 s; 65° C. for 2 m) was run on a real-time PCR machine (Bio-Rad CFX96) to stop reactions during exponential amplification (typically ~10 cycles). Products were assessed on an agarose gel (2% E-gel, Thermo Fisher G501802) to confirm the expected ~490 bp amplicon and were subjected to a 1×SPRI bead cleanup as above. Resulting libraries were quantified via fluorometric quantitation (Thermo Fisher Q32854), pooled, and were subjected to sequencing with an Illumina MiSeq 500 cycle v2 kit (read1: 254 bp, read2: 254 bp) at 12 pM loading concentration with 20% PhiX spike in. Sequence filtering and 16S analysis. For MaP-seq data, a custom python script was utilized to demultiplex reads based on barcode identity and strip primer sequences from reads. Reads were merged and filtered using USEARCH 9.2.64 (see Edgar, R. C. & Flyvbjerg, H. Error filtering, pair assembly and error correction for next-generation sequencing reads. Bioinformatics 31, 3476-3482 (2015) with maximum expected errors of 1. The resulting sequences were then dereplicated, de-novo clustered with a minimum cluster size of 2, and reads were mapped to OTUs at 97% identity (see Edgar, R. C. UPARSE: highly accurate OTU sequences from microbial amplicon reads. Nat. Methods 10, 996-998 (2013). Taxonomy was assigned to OTUs using the RDP classifier (see Wang, Q., Garrity, G. M., Tiedje, J. M. & Cole, J. R. Naive Bayesian classifier for rapid assignment of rRNA sequences into the new bacterial taxonomy. Applied and Environmental Microbiology 73, 5261-5267 (2007). This yielded an OTU table consisting of individual barcodes (i.e., putative clusters) as samples.

Cluster mixing quality control experiment. Two bacterial communities were assembled; the first contained a single strain (e.g. *E. coli* NEB-beta), the second contained homogenized fecal bacteria. *E. coli* is not expected in the mouse gut at high abundances (see Xiao, L. et al. A catalog of the mouse gut metagenome. Nature Biotechnology 33, 1103-1108 (2015). To generate homogenized fecal bacteria, fecal pellets were subjected to bead beating (Biospec 1001) with 0.1 mm glass beads in PBS for 1 minute and passed through a 40 μm cell strainer. The two communities were fixed in methacarn, resuspended in approximately equal volume matrix embedding solution to fixed pellet volume and subjected to cluster generation as per the MaP-seq protocol above. The resulting size-selected clusters were then mixed in equal quantity and subjected to encapsulation and sequencing.

Analysis of MaP-seq data. An overview of all MaP-seq datasets generated in this study can be found in Table 5. The resulting dataset contained a large number of barcodes/clusters with varying numbers of reads. A conservative threshold cutoff for considering real clusters was set as the total number of reads in a sample divided by 2,500 (i.e., the number of clusters that were utilized as input during microfluidic encapsulation, and assuming an equal read distribution for each cluster). Reactions yielding an extremely low number of clusters passing this threshold (i.e., <50) were conservatively excluded as they may represent failed encapsulation or amplification reactions.

Clusters were first pre-processed to remove a small number of clusters displaying highly similar OTU abundance profiles within a single technical replicate that appeared to represent technical artifacts (i.e., clusters encapsulated into droplets containing multiple barcoded beads or beads erroneously containing multiple barcodes) which could confound association detection. The pairwise Pearson correlation of all clusters was calculated, and highly correlated sets of clusters (r>0.95) dominated by a single technical replicate and large in size (>90% belonging to a single technical replicate, clusters constitute>1% of the overall dataset) were removed. These artifacts constituted a low amount of the overall dataset. For analysis of presence or absence of species within a cluster, a 2% relative abundance threshold within clusters was utilized, given observation of a small amount of background read-through across clusters and to ensure that at least 2 reads (and not singletons) were required to denote presence of a species.

To determine pairwise associations, prevalent and abundant OTUs within filtered clusters (>2% relative abundance in >10% of clusters) were identified, and 2 by 2 contingency tables of appearance (>2% relative abundance) were calculated for all pairs of OTUs. Fishers exact test was then used to calculate the probability of pairs occurring more or less together than expected (i.e. a null model of random assortment of the two species, assuming equiprobable occupancy at all sites), and resulting p-values were adjusted via the Benjamini-Hochberg procedure (FDR=0.05).

For t-distributed Stochastic Neighbor Embedding (tSNE) analysis (see Maaten, L. V. D. & Hinton, G. Visualizing Data using t-SNE. Journal of Machine Learning Research 9, 2579-2605 (2008), reads for each cluster were subsampled to the lowest number for all clusters in the dataset (as specified in the text) since raw relative abundance values were analyzed (i.e. not utilizing a 2% relative abundance threshold as in other analyses). Bray-Curtis distance between taxa relative abundances within clusters was calculated, and this resulting distance matrix was utilized as the input for tSNE analysis.

The Net Relatedness Index (NRI) was calculated as previously described (see David, L. A. et al. Diet rapidly and reproducibly alters the human gut microbiome. Nature 505, 559-563 (2014) adapting code from the relatedness_library.py script from Qiime 1.9.1 (see Caporaso, J. G. et al. QIIME allows analysis of high-throughput community sequencing data. Nat. Methods 7, 335-336 (2010)) which implements the same calculation as in phylocom 4.2 (see Webb, C. O., Ackerly, D. D. & Kembel, S. W. Phylocom: software for the analysis of phylogenetic community structure and trait evolution. Bioinformatics 24, 2098-2100 (2008)). Briefly, species presence and absences across clusters were defined using the same 2% relative abundance threshold, and clusters containing only one OTU were omitted from analysis. OTU sequences were aligned and a neighbor-joining tree was constructed using MUSCLE 3.8.31 (see Edgar, R. C. MUSCLE: multiple sequence alignment with high accuracy and high throughput. Nucleic Acids Research 32, 1792-1797 (2004). The NRI was calculated as a standardized effect size for each cluster: $NRI=-1*(MPD_{./012}-MPD_{3,..})/sd(MPD_{3,..})$, where $MPD_{./012}$ denotes the mean phylogenetic distance (MPD), and $MPD_{./012}$ & $sd(MPD_{3,..})$ indicate the mean MPD, and the standard deviation of the MPD over 1000 iterations of a null mode. The null model, calculated for each cluster, was random draws for the number of OTUs present in the sample (i.e. preserving cluster OTU richness) from the sample pool (i.e. any OTU observed at least once in any cluster in the sample) without replacement. The null model therefore preserves the OTU richness of each cluster but randomizes the OTUs present from the set of OTUs occurring in the sample.

Bulk 16S sequencing and spike-in for absolute abundance calculation. The bulk sequencing protocol followed our established spike-in sequencing pipeline (see Ji, B. W. et al. (2018)). Briefly, genomic DNA (gDNA) extraction was performed using a custom liquid handling protocol on a Biomek 4000 robot based on the Qiagen MagAttract PowerMicrobiome DNA/RNA Kit (Qiagen 27500-4-EP) but adapted for lower volumes. Samples were subjected to bead beating for a total of 10 minutes. For samples processed with the spike-in sequencing approach for absolute abundance calculation, the sample added was weighed on an analytical balance, and 10 uL of a frozen spike-in strain concentrate (*Sporocarcina pasteurii*, ATCC 11859, an environmental bacterium not found in the gut microbiome) was added during gDNA preparation. Resulting gDNA was subjected to amplification and sequencing of the 16S V4 region following a dual indexing scheme (see Kozich, J. J., Westcott, S. L., Baxter, N. T., Highlander, S. K. & Schloss, P. D. Development of a Dual-Index Sequencing Strategy and Curation Pipeline for Analyzing Amplicon Sequence Data on the MiSeq Illumina Sequencing Platform. Applied and Environmental Microbiology 79, 5112-5120 (2013)) but utilized updated 515f and 806rB primers as in the MaP-seq technique. A 20 μL PCR amplification was performed (1 μM forward and 1 μM reverse barcoded primers, 1 μL prepared gDNA, 10 µL NEBNext Q5 Hot Start HiFi Master Mix, 0.2× final concentration SYBR Green I). The PCR (98° C. for 30 s; cycle: 98° C. for 20 s, 55° C. for 20 s, 65° C. for 60 s, 65° C. for 5 m) was run on a real-time PCR machine to stop reactions during exponential amplification. Amplicon products were quantified and pooled, the expected 390 bp product was gel-extracted, and paired-end sequencing was performed with an Illumina MiSeq 300 cycle v2 kit (read1: 154 bp, read2: 154 bp, custom sequencing primers spiked into sequencing kit) at 10 pM loading concentration with 20% PhiX spike in. Resulting sequences were processed with USEARCH as above. The absolute bacterial density for a sample (A) was calculated by utilizing the weight of sample added (w) and proportion of reads mapping to spike in strain (p/) in the following formula: $A=(1-p/)/(p/*w)$. The absolute density of individual OTUs was calculated by rescaling the total sample absolute density by the relative abundance of sample OTUs. 16S FISH and imaging. Samples were fixed as with the MaP-seq protocol, embedded within paraffin blocks, 4 µm thick lumenal sections were cut and deparaffinized. 16S FISH was performed as previously described (see Mark Welch, J. L., Rossetti, B. J., Rieken, C. W., Dewhirst, F. E. & Borisy, G. G. Biogeography of a human oral microbiome at the micron scale. Proceedings of the National Academy of Sciences 113, E791-800 (2016); Whitaker, W. R., Shepherd, E. S. & Sonnenburg, J. L. (2017). Briefly, previously validated FISH probes targeting abundant taxa present in the sample were obtained with conjugated fluorophores suitable for multiplex imaging: Erec482_a488 or Erec482_cy3 (see Franks, A. H. et al. Variations of bacterial 710 populations in human feces measured by fluorescent in situ hybridization with group-specific 16S rRNA-targeted oligonucleotide probes. Applied and Environmental Microbiology 64, 3336-3345 (1998) targeting Lachnospiraceae, Lab158_cy3 (see Harmsen, H., Elfferich, P. & Schut, F. A 16S rRNA-targeted probe for detection of lactobacilli and enterococci in faecal samples by fluorescent in situ hybridization. Microbial Ecology in Health and Disease 11, 3-12 (1999)) targeting Lactobacillaceae and Enterococcaceae, Ato291_cy5 (see Harmsen, H. et al. Development of 16S rRNA-based probes for the Coriobacterium group and the Atopobium cluster and their application for enumeration of Coriobacteriaceae in human feces from volunteers of different age groups. Applied and Environmental Microbiology 66, 4523-4527 (2000)) targeting Coriobacteriaceae, Eub338_cy5 (see Amann, R. I. et al. Combination of 16S rRNA-targeted oligonucleotide probes with flow cytometry for analyzing mixed microbial populations. Applied and Environmental Microbiology 56, 1919-1925 (1990)) targeting Bacteria, and Non338_cy5 (see Wallner, G., Amann, R. & Beisker, W. Optimizing fluorescent in situ hybridization with rRNA-targeted oligonucleotide probes for flow cytometric identification of microorganisms. Cytometry 14, 136-143 (1993)) control probe (see Table 4). Sections were incubated with probes at 10 ng/µL in FISH hybridization buffer (0.9 M NaCl, 20 mM Tris-HCl pH 7.5, 0.01% SDS, 10% formamide) at 47° C. for 4 hours. Sections were then incubated in preheated FISH wash buffer (0.9 M NaCl, 20 mM Tris-HCl pH 7.5) for 10 minutes, washed 3× times in PBS, incubated with 10 µg/mL DAPI in PBS for 10 minutes and washed 3× times in PBS. Sections were then mounted in mounting medium (Vector Laboratories H1000).

Images were acquired on a Nikon Eclipse Ti2 epifluorescence microscope with a SOLA-SE2 illuminator and Andor Zyla 4.2 plus camera controlled by Nikon Elements AR software. DAPI, FITC/GFP, RFP and CY5 filter cubes (Nikon 96359, 96362, 96364, 96366 respectively) were utilized. Large area four-color fluorescence scans with three 0.6 µm Z-stacks within the 4 µm section were performed with a Plan Apo λ 40× objective. The extended depth of focus (EDF) module was applied to resulting Z-stacks to obtain a focused image across the stack, and images across the entire section were stitched together.

REFERENCES

1. Reichenbach, T., Mobilia, M. & Frey, E. Mobility promotes and jeopardizes biodiversity in rock—paper—scissors games. Nature 448, 1046-1049 (2007).
2. MacArthur, R. H. & Wilson, E. O. The theory of island biogeography. (1967).
3. Cordero, O. X. & Datta, M. S. Microbial interactions and community assembly at microscales. Current Opinion in Microbiology 31, 227-234 (2016).
4. Swidsinski, A., Loening Baucke, V., Verstraelen, H., Osowska, S. & Doerffel, Y. Biostructure of Fecal Microbiota in Healthy Subjects and Patients With Chronic Idiopathic Diarrhea. Gastroenterology 135, 568-579.e2 (2008).
5. Yasuda, K. et al. Biogeography of the Intestinal Mucosal and Lumenal Microbiome in the Rhesus Macaque. Cell Host & Microbe 17, 385-391 (2015).
6. Earle, K. A. et al. Quantitative Imaging of Gut Microbiota Spatial Organization. Cell Host & Microbe 18, 478-488 (2015).
7. Mark Welch, J. L., Rossetti, B. J., Rieken, C. W., Dewhirst, F. E. & Borisy, G. G. Biogeography of a human oral microbiome at the micron scale. Proceedings of the National Academy of Sciences 113, E791-800 (2016).
8. Mark Welch, J. L., Hasegawa, Y., McNulty, N. P., Gordon, J. I. & Borisy, G. G. Spatial organization of a model 15-member human gut microbiota established in gnotobiotic mice. Proc. Natl. Acad. Sci. U.S.A. 21, 201711596-E9114 (2017).
9. Donaldson, G. P., Lee, S. M. & Mazmanian, S. K. Gut biogeography of the bacterial microbiota. 1-13 (2015). doi:10.1038/nrmicro3552
10. Lee, S. M. et al. Bacterial colonization factors control specificity and stability of the gut microbiota. Nature 1-6 (2013). doi:10.1038/nature12447
11. Nagara, Y., Takada, T., Nagata, Y., Kado, S. & Kushiro, A. Microscale spatial analysis provides evidence for adhesive monopolization of dietary nutrients by specific intestinal bacteria. PLoS ONE 12, e0175497 (2017).
12. Tropini, C., Earle, K. A., Huang, K. C. & Sonnenburg, J. L. The Gut Microbiome: Connecting Spatial Organization to Function. Cell Host & Microbe 21, 433-442 (2017).
13. Nava, G. M., Friedrichsen, H. J. & Stappenbeck, T. S. Spatial organization of intestinal microbiota in the mouse ascending colon. ISME J 5, 627-638 (2010).
14. Pedron, T. et al. A Crypt-Specific Core Microbiota Resides in the Mouse Colon. mBio 3, e00116-12-e00116-12 (2012).
15. Valm, A. M., Welch, J. L. M. & Borisy, G. G. CLASI-FISH: Principles of combinatorial labeling and spectral imaging. Systematic and Applied Microbiology 35, 496-502 (2012).
16. Geva-Zatorsky, N. et al. In vivo imaging and tracking of host-microbiota interactions via metabolic labeling of gut anaerobic bacteria. Nature Medicine 21, 1091-1100 (2015).

17. Whitaker, W. R., Shepherd, E. S. & Sonnenburg, J. L. Tunable Expression Tools Enable Single-Cell Strain Distinction in the Gut Microbiome. *Cell* 169, 538-546.e12 (2017).
18. Pereira, F. C. & Berry, D. Microbial nutrient niches in the gut. *Environ Microbiol* 19, 1366-1378 (2017).
19. Donaldson, G. P. et al. Gut microbiota utilize immunoglobulin A for mucosal colonization. *Science* 360, 795-800 (2018).
20. Wexler, A. G. et al. Human symbionts inject and neutralize antibacterial toxins to persist in the gut. *Proc. Natl. Acad. Sci. U.S.A.* 201525637-6 (2016). doi:10.1073/pnas.1525637113.
21. Kim, H. J., Boedicker, J. Q., Choi, J. W. & Ismagilov, R. F. Defined spatial structure stabilizes a synthetic multi species bacterial community. *Proceedings of the National Academy of Sciences* 105, 18188-18193 (2008).
22. Coyte, K. Z., Schluter, J. & Foster, K. R. The ecology of the microbiome: Networks, competition, and stability. *Science* 350, 663-666 (2015).
23. Amann, R. & Fuchs, B. M. Single-cell identification in microbial communities by improved fluorescence in situ hybridization techniques. *Nature Reviews Microbiology* 6, 339-348 (2008).
24. Rakoff-Nahoum, S., Coyne, M. J. & Comstock, L. E. An Ecological Network of Polysaccharide Utilization among Human Intestinal Symbionts. *Current Biology* 24, 40-49 (2014).
25. Ji, B. W. et al. Quantifying spatiotemporal dynamics and noise in absolute microbiota abundances using replicate sampling. *biorxiv.org* doi:10.1101/310649
26. Ormerod, K. L. et al. Genomic characterization of the uncultured Bacteroidales family S24-7 inhabiting the guts of homeothermic animals. *Microbiome* 1-17 (2016). doi: 10.1186/s40168-016-0181-2
27. Rakoff-Nahoum, S., Foster, K. R. & Comstock, L. E. The evolution of cooperation within the gut microbiota. *Nature* 533, 255-259 (2016).
28. Carmody, R. N. et al. Diet Dominates Host Genotype in Shaping the Murine Gut Microbiota. *Cell Host & Microbe* 17, 72-84 (2015).
29. Sonnenburg, E. D. et al. Diet-induced extinctions in the gut microbiota compound over generations. *Nature* 529, 212-215 (2016).
30. David, L. A. et al. Diet rapidly and reproducibly alters the human gut microbiome. *Nature* 505, 559-563 (2014).
31. Webb, C. O., Ackerly, D. D., McPeek, M. A. & Donoghue, M. J. Phylogenies and Community Ecology. *Annu. Rev. Ecol. Syst.* 33, 475-505 (2002).
32. Cavender-Bares, J., Kozak, K. H., Fine, P. V. A. & Kembel, S. W. The merging of community ecology and phylogenetic biology. *Ecology Letters* 12, 693-715 (2009).
33. Mazutis, L. et al. Single-cell analysis and sorting using droplet-based microfluidics. *Nat Protoc* 8, 870-891 (2013).
34. Parada, A. E., Needham, D. M. & Fuhrman, J. A. Every base matters: assessing small subunit rRNA primers for marine microbiomes with mock communities, time series and global field samples. *Environ Microbiol* 18, 1403-1414 (2016).
35. Walters, W. et al. Improved Bacterial 16S rRNA Gene (V4 and V4-5) and Fungal Internal Transcribed Spacer Marker Gene Primers for Microbial Community Surveys. *mSystems* 1, e00009-15-10 (2015).
36. Klein, A. M. et al. Droplet Barcoding for Single-Cell Transcriptomics Applied to Embryonic Stem Cells. *Cell* 161, 1187-1201 (2015).
37. Bose, S. et al. Scalable microfluidics for single-cell RNA printing and sequencing. *Genome Biology* 1-16 (2015). doi:10.1186/s13059-015-0684-3
38. Zilionis, R. et al. Single-cell barcoding and sequencing using droplet microfluidics. *Nat Protoc* 12, 44-73 (2017).
39. Johansson, M. E. V. & Hansson, G. C. Preservation of mucus in histological sections, immunostaining of mucins in fixed tissue, and localization of bacteria with FISH. *Methods Mol. Biol.* 842, 229-235 (2012).
40. Chung, K. et al. Structural and molecular interrogation of intact biological systems. *Nature* 497, 332-337 (2013).
41. Chen, F., Tillberg, P. W. & Boyden, E. S. Expansion microscopy. *Science* 347, 543-548 (2015).
42. Apprill, A., McNally, S., Parsons, R. & Weber, L. Minor revision to V4 region SSU rRNA 806R gene primer greatly increases detection of SAR11 bacterioplankton. *Aquat. Microb. Ecol.* 75, 129-137 (2015).
43. Spencer, S. J. et al. *Massively parallel sequencing of single cells by epicPCR links functional genes with phylogenetic markers.* 1-10 (2015). doi:10.1038/ismej.2015.124
44. Abate, A. R., Chen, C.-H., Agresti, J. J. & Weitz, D. A. Beating Poisson encapsulation statistics using close-packed ordering. *Lab Chip* 9, 2628-2631 (2009).
45. Edgar, R. C. & Flyvbjerg, H. Error filtering, pair assembly and error correction for next generation sequencing reads. *Bioinformatics* 31, 3476-3482 (2015).
46. Edgar, R. C. UPARSE: highly accurate OTU sequences from microbial amplicon reads. *Nat. Methods* 10, 996-998 (2013).
47. Wang, Q., Garrity, G. M., Tiedje, J. M. & Cole, J. R. Naive Bayesian classifier for rapid assignment of rRNA sequences into the new bacterial taxonomy. *Applied and Environmental Microbiology* 73, 5261-5267 (2007).
48. Xiao, L. et al. A catalog of the mouse gut metagenome. *Nature Biotechnology* 33, 1103-1108 (2015).
49. Maaten, L. V. D. & Hinton, G. Visualizing Data using t-SNE. *Journal of Machine Learning Research* 9, 2579-2605 (2008).
50. Caporaso, J. G. et al. QIIME allows analysis of high-throughput community sequencing data. *Nat. Methods* 7, 335-336 (2010).
51. Webb, C. O., Ackerly, D. D. & Kembel, S. W. Phylocom: software for the analysis of phylogenetic community structure and trait evolution. *Bioinformatics* 24, 2098-2100 (2008).
52. Edgar, R. C. MUSCLE: multiple sequence alignment with high accuracy and high throughput. *Nucleic Acids Research* 32, 1792-1797 (2004).
53. Kozich, J. J., Westcott, S. L., Baxter, N. T., Highlander, S. K. & Schloss, P. D. Development of a Dual-Index Sequencing Strategy and Curation Pipeline for Analyzing Amplicon Sequence Data on the MiSeq Illumina Sequencing Platform. *Applied and Environmental Microbiology* 79, 5112-5120 (2013).
54. Franks, A. H. et al. Variations of bacterial 710 populations in human feces measured by fluorescent in situ hybridization with group-specific 16S rRNA-targeted oligonucleotide probes. *Applied and Environmental Microbiology* 64, 3336-3345 (1998).
55. Harmsen, H., Elfferich, P. & Schut, F. A 16S rRNA-targeted probe for detection of lactobacilli and enterococci in faecal samples by fluorescent in situ hybridization. *Microbial Ecology in Health and Disease* 11, 3-12 (1999).
56. Harmsen, H. et al. Development of 16S rRNA-based probes for the Coriobacterium group and the Atopobium cluster and their application for enumeration of Coriobacteriaceae in human feces from volunteers of different age groups. *Applied and Environmental Microbiology* 66, 4523-4527 (2000).
57. Amann, R. I. et al. Combination of 16S rRNA-targeted oligonucleotide probes with flow cytometry for analyzing mixed microbial populations. *Applied and Environmental Microbiology* 56, 1919-1925 (1990).
58. Wallner, G., Amann, R. & Beisker, W. Optimizing fluorescent in situ hybridization with rRNA-targeted oligonucleotide probes for flow cytometric identification of microorganisms. Cytometry 14, 136-143 (1993).

Example 2 Precision Microbiome Replacement to Enhance Cancer Checkpoint Immunotherapy The human gut contains trillions of microorganisms (microbiota) that form a complex and unique ecosystem within our bodies. It is now clear that these bacteria have systemic effects on the host and can directly interact with many classes of pharmaceutical interventions, altering efficacy and clinical outcomes[1,2]. A prime example of this effect is in cancer immunotherapy, where recent studies suggest that the commensal microbiota modulate the efficacy of therapies involving monoclonal antibodies (mAbs) targeted to the PD-1 receptor, via stimulation of the immune system[2-7]. Importantly, it has been observed that living bacteria in gut are required to elicit this effect[3]. Correspondingly, approaches to alter microbiomes to improve the efficacy of cancer immunotherapy are sorely needed.

Current microbiome manipulation strategies broadly fall under two approaches: chemical perturbation and probiotic supplementation[8]. The abundance of bacterial species within a given microbiome can be altered by administration of chemical compounds (i.e. different diets, prebiotic compounds, antibiotics). Alternatively, new bacterial strains or combinations of strains (probiotics or fecal microbiota transplant) with functionality of interest can be administered. However, the pervasive variability of individual microbiomes limits the efficacy of these techniques. Chemical perturbations will be unsuccessful if a targeted bacterial species is not present, and their effect can be highly variable. Supplemented probiotic strains may not robustly colonize all microbiomes[9]. An alternative to these approaches is to completely replace a microbiome with a new defined microbiome containing specific desired functionality. Here, precision microbiome replacement, a new paradigm in manipulating microbiomes, can be used to enhance cancer immunotherapy.

Specific aims: To develop a precision microbiome replacement therapy to improve the efficacy of cancer immunotherapies, we will (1) generate a comprehensive reference collection of gut bacterial strains, (2) identify strains promoting immunotherapy efficacy using combinatorial in vivo animal model screens, and (3) develop a microbiome transplantation therapy and formulate strains into stable consortia for delivery.

Approach: (1) Generate a comprehensive reference collection of gut bacterial strains. Individual bacterial strains can act as effectors (i.e., stimulating the host immune system) in the context of complex communities[10]. Fecal samples will be collected from geographically and environmentally distinct individuals representing global gut microbial diversity. Samples will then be subjected to culturing and isolation in anaerobic settings, and individual strains will be isolated utilizing colony picking robots. Resulting bacterial strains will be identified and characterized using whole-genome sequencing and unique strains of interest will be subjected to long-term cryogenic storage. This sequencing characterization may be conducted by utilizing robotic liquid handling for library preparation (i.e. Labcyte Echo 550, Agilent Bravo, Formulatrix Mantis; sequence on HiSeq X Ten). This automated approach will allow for generation of a gut bacterial strain collection resource in an economic manner.

(2) Identify strains promoting immunotherapy efficacy using combinatorial in vivo animal model screens. Representative strains from the collection will be selected, revived from storage and inoculated into cohorts of germ-free mice. The mice will be subjected to standard cancer models (e.g. metastatic cutaneous squamous cell carcinoma) and given mAb checkpoint immunotherapy (e.g. cemiplimab) and efficacy and response to therapy will be measured. Importantly, the screen will be performed with different combinations of strains rather than individual strains, to enable efficient and higher throughput screens[10]. Strains promoting efficacy of immunotherapy will be identified.

(3) Develop a new microbiome transplantation therapy and formulate strains into stable consortia for delivery. To perform efficient microbiome transplantation, strategies utilizing oral antibiotic therapy to clear to eradicate commensal microbiota and subsequent oral delivery of new microbial strains will be tested in gnotobiotic mouse models with humanized microbiota. Combinations of antibiotics, dosing, and timing of the therapy in addition to physical clearing of the gut and dietary changes will be explored to optimize efficient elimination of endogenous microbiota and colonization of new strains. Next, the identified immunotherapy enhancing strains will be formulated into a complex microbiome consortium recapitulating the ecology and functionality of naturally occurring microbiomes. The stability of the microbiome (i.e. retention of desired strains over time, resistance to invasion by other commensal strains) will be measured in mice models and improved by iterative design.

Some species of gut bacteria may be recalcitrant to in vitro isolation. Recent studies, however, suggest that the majority of the gut microbiome is culturable[12], and the cultivability of species could be further improved by systematic exploration of culture media formulation. The transplantation and resulting microbiome could differ across individuals due to interactions between the strains and the host. However, recent studies suggest that environment dominates host genotype in determining microbiota composition, implying that microbiome transplantation may be reproducible across different host backgrounds[13].

Although there may be variability of microbiomes across individuals, direct therapeutic microbiomes interventions can be used. Alternatively, new microbiomes with desired functionality can be designed and replaced. Cancer immunotherapy offers a salient first application of the concept, but the pipeline could be broadly scaled to other microbiome linked human disorders.

REFERENCES

1. Spanogiannopoulos, P., Bess, E. N., Carmody, R. N. & Turnbaugh, P. J. The microbial pharmacists within us: a metagenomic view of xenobiotic metabolism. Nature Reviews Microbiology 14, 273-287 (2016).

2. Zitvogel, L., Ma, Y., Raoult, D., Kroemer, G. & Gajewski, T. F. The microbiome in cancer immunotherapy: Diagnostic tools and therapeutic strategies. Science 359, 1366-1370 (2018).
3. Sivan, A. et al. Commensal *Bifidobacterium* promotes antitumor immunity and facilitates anti-PD-L1 efficacy. Science 350, 1084-1089 (2015).
4. Matson, V. et al. The commensal microbiome is associated with anti-PD-1 efficacy in metastatic melanoma patients. Science 359, 104-108 (2018).
5. Routy, B. et al. Gut microbiome influences efficacy of PD-1-based immunotherapy against epithelial tumors. Science 359, 91-97 (2018).
6. Gopalakrishnan, V. et al. Gut microbiome modulates response to anti-PD-1 immunotherapy in melanoma patients. Science 359, 97-103 (2018).
7. Vétizou, M. et al. Anticancer immunotherapy by CTLA-4 blockade relies on the gut microbiota. Science 350, 1079-1084 (2015).
8. Sheth, R. U., Cabral, V., Chen, S. P. & Wang, H. H. Manipulating Bacterial Communities by in situ Microbiome Engineering. Trends in Genetics 32, 189-200 (2016).
9. Maldonado-Gómez, M. X. et al. Stable Engraftment of *Bifidobacterium longum* AH1206 in the Human Gut Depends on Individualized Features of the Resident Microbiome. Cell Host & Microbe 20, 515-526 (2016).
10. Faith, J. J., Ahern, P. P., Ridaura, V. K., Cheng, J. & Gordon, J. I. Identifying gut microbe-host phenotype relationships using combinatorial communities in gnotobiotic mice. Science Translational Medicine 6, 220ra11-220ra11 (2014).
11. Sheth, R. U., Yim, S. S., Wu, F. L. & Wang, H. H. Multiplex recording of cellular events over time on CRISPR biological tape. Science 358, 1457-1461 (2017).
12. Browne, H. P. et al. Culturing of 'unculturable' human microbiota reveals novel taxa and extensive sporulation. Nature 533, 543-546 (2016).
13. Rothschild, D. et al. Environment dominates over host genetics in shaping human gut microbiota. Nature 555, 210-215 (2018).

Example 3 Antibiotics I

Figures 15A, 15B:
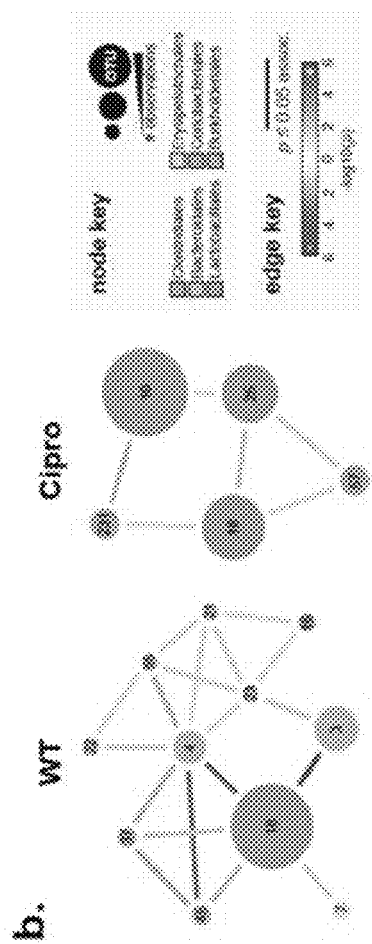
FIGS. 15a-15b: Preliminary results of spatial changes in small intestinal microbiome in wild-type (WT) and ciprofloxacin (Cipro)-treated mice. a) Bulk abundance and composition in the murine small intestine. b) Spatial co-occurrence network of murine microbiome in WT and Cipro conditions. Each node correspond to a significant OTU. Each edge corresponds to co-occurrence of two OTUs with colors denoting increasing likelihood of co-occurrence.

Disruption of the normal homeostatic balance of the gut can lead to profound changes in the gut microbiome. For example, antibiotics are known to cause large-scale alterations to the gut microbiome. In general, antibiotics not only target the intended pathogens, but often cause collateral damage in wiping out native commensal microbiota that have sensitivity to the compound. Clinical administration of antibiotics not only reduces biodiversity in the gut microbiome, but also predisposes individuals to a variety of short- and long-term diseases, including antibiotic-associated *C. difficile* infections, diabetes, and inflammation. While it is generally believed that antibiotic exposure disrupts the state of the microbiome by increasing its fragility and susceptibility to pathogenic infections, specific mechanisms mediating this process is not understood. In large ecological systems, changes in spatial patterning can play an important role in susceptibility to invasion, for example in exotic plant invasion in river and creek ecosystems. Exposure to antibiotics c a n lead to destabilization of the natural commensal microbiota by removing key members in the community that facilitate robust interspecies interactions, which in turn is marked by a profound change in the microbial spatial architecture that reduces the microbiome's natural resistance to colonization by pathogens. We used two wild-type C57BL6/J mice that were both fed on a conventional diet and co-housed prior to normalize their gut microbiota, which was validated by bulk fecal sequencing. We then separated the mice into individual cages and introduced ciprofloxacin (0.625 mg/mL) in drinking water ad-libitum for 2 days in one cage and a sham control in the other cage. We extracted small intestinal tissues from both the control and ciprofloxacin-treated mice and applied bulk 16S sequencing and MIST-seq. As expected, exposure to antibiotics significantly shifted the gut community, leading to an overall loss in microbiome diversity and the domination of particular groups (e.g. Lactobacillales and Clostridiales) compared to the wild-type control (FIG. 15A). More interestingly, we observed a robust small intestinal interaction network (FIG. 15B) that is significantly disrupted by ciprofloxacin, resulting in a few dominant species with drastically altered spatial organization.

Example 4 Antibiotics II

Figures 16A, 16B:
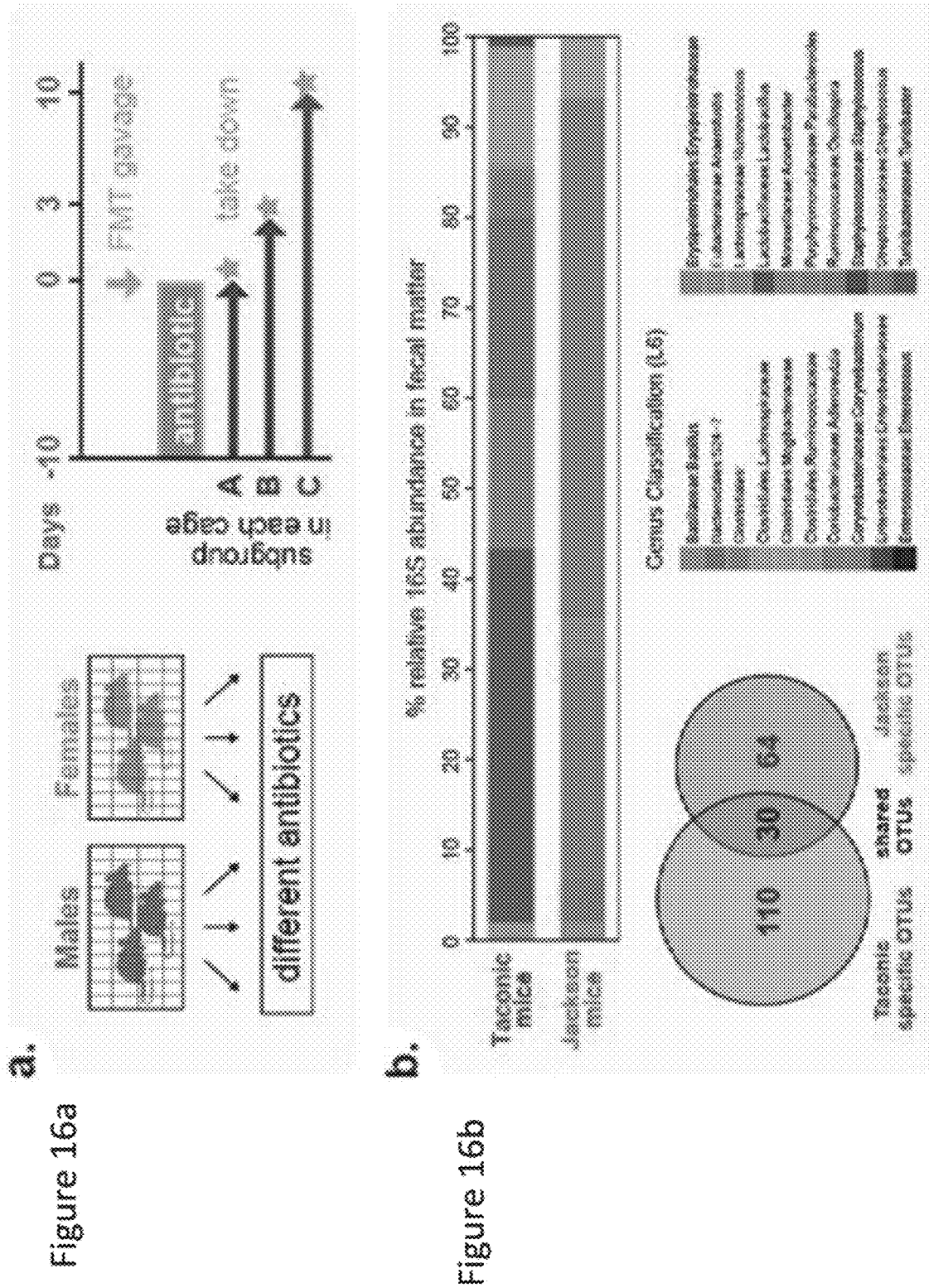
FIGS. 16a-16b: a) Antibiotics-FMT study design. b) Comparison of fecal microbiome of wild-type C57BL6/J mice from two suppliers, Taconic and Jackson Labs.

The prevalent use of antibiotics both in pediatrics and adult populations and its impact on the gut microbiome is hypothesized to be a key contributor in the rise of autoimmune and metabolic disorders. However, the impact of specific antibiotics on the gut microbiome can vary significantly depending on the type (e.g. broad vs narrow spectrum, antibiotic class), therapeutic dosage and duration, resistance profiles of endogenous bacteria, and geographic location along the GI. We will explore how antibiotics can alter the spatial microbiota organization. Altered spatial patterns due to antibiotics exposure may reflect changes in microbiota function beyond simple variations in community composition or abundance. We will use antibiotics with various modes of action and varying levels of host and microbiota impact. Specifically, we will administer Ciprofloxacin (Lincoasimide; single oral gavage 10 mg/kg), Vancomycin (Glycopeptide, 0.625 mg/mL, drinking water ad libitum), Ampicillin ($\beta$-lactam, 0.5 mg/mL, drinking water ad libitum), Streptomycin (Aminoglycoside, 5 mg/mL, drinking water ad libitum) to different cohorts of 5 pre-cohoused wild-type C57BL6/J mice as previously described. Mice from each cohort will be sacrificed at day 0 (before treatment), 3, 7 and 10 (FIG. 16a). Samples from the small intestine, colon and fecal matter will be analyzed by MIST-seq. We collect temporal samples to assess the transition states from an unperturbed microbiota to one that is compromised by antibiotics. Three biological replicate studies will be performed and both male and female mice will be tested separately. As before, should additional replicates be needed for sufficient statistical power, we will increase the number of mice per group accordingly. Based on our preliminary studies, we expect knockdown or abolition of specific species and a loss in biodiversity upon treatment. We anticipate that the spatial ecological role of strains killed by an antibiotic will be a key factor in its degree of GI microbiome disruption. Disrupted networks may lead to more fragile states with reduced inter-microbial interactions and increased vulnerability to infiltration by a pathogen. Importantly, previous work showed that some antibiotics (e.g. Ampicillin, Streptomycin) increased murine gut susceptibility to *C. difficile* infection, whereas others (e.g. Ciprofloxacin, Vancomycin) led to resistance. We will compare spatial mapping results between these two antibiotic "classes" to identify systematic spatial differences and key players. For validation, we will perform bulk sequencing to assess abundance and compositional changes. In addition, we will apply FISH techniques to visualize specific architectural changes using specific probes to identify major microbiota families, pre- and post-antibiotic treatment. We will also perform in vitro culture studies and antibiotic sensitivity assays on isolates to validate MIST-seq findings.

To functionally characterize gut microbiota ecology, we will employ a classical ecology approach to introduce species into novel or perturbed environments, and tracked them longitudinally over space and time. We will introduce "mock" murine fecal transplants into wild-type and antibiotic-perturbed mice and profile the colonization process. Specifically, 5 cohorts of C57BL6/J mice will be obtained commercially (Taconic Biosciences), 4 of which will be orally treated with different antibiotics for 10 days, and the remaining will serve as a control group. We will isolate live fecal microbiota from mice obtained through another vendor (i.e. Jackson Laboratories, Charles River Laboratories) that are known to harbor highly distinct microbiomes, which we will validate by bulk 16S sequencing (FIG. 16b). Freshly collected fecal pellets will be placed in pre-reduced PBS in anaerobic conditions and live microbiota will be isolated by established protocols. Two groups of 3 mice from each of the four cohorts will receive a different fecal microbiota gavage (approximating a human FMT procedure); the control group will receive a gavage of pre-reduced PBS; animals will be sacrificed at days 0, 3 and 10, and tissue from the small intestine and colon will be profiled; the experiment will be performed in triplicate and with gender-controlled cohorts. As before, should additional replicates be necessary for sufficient statistical power, we will increase the number of mice per group accordingly. We will then perform detailed analysis of ecosystem assembly of the two different "donor" fecal transplants in the five "recipient" ecological contexts. Importantly, this will allow us to assess processes shaping FMT efficacy in an in vivo context. For example, given that diet plays an important role in microbiota composition via environmental filtering (i.e. available nutrients), the spatial and compositional structure of microbiota after FMT may be similar to that before perturbation. On the other hand, novel spatial patterns may form due to other ecological processes such as microbial competition[17] or cooperation. Thus, this study will advance our functional knowledge of principles that contribute to microbiota colonization and maintenance, relevant for designing better FMT therapies (e.g. defined communities or personalized FMT).

TABLE 6

Sequences

| Sequence ID Number | Sequence | Species |
|---|---|---|
| SEQ ID NO: 1 | GACTACTCCACGACGCTCTTCCGATCT | Synthetic |
| SEQ ID NO: 2 | ATTAGGTCGACGTGTGCTCTTCCGATCTGGACTACNVGGGTWTCTAAT | Synthetic |
| SEQ ID NO: 3 | TTACCGCGGCKGCTGRCAC | Synthetic |
| SEQ ID NO: 4 | CGCTCAGCAGTGTCTCGCACCTAGTAGATCGGAAGAGCGTCGTG | Synthetic |
| SEQ ID NO: 5 | CGCTCAGCAGTGTCTCGCTAGAGCTAGATCGGAAGAGCGTCGTG | Synthetic |
| SEQ ID NO: 6 | CGCTCAGCAGTGTCTCGCACTCTCTAGATCGGAAGAGCGTCGTG | Synthetic |
| SEQ ID NO: 7 | CGCTCAGCAGTGTCTCGCGGAACACAGATCGGAAGAGCGTCGTG | Synthetic |
| SEQ ID NO: 8 | CGCTCAGCAGTGTCTCGCCAGCTAAAGATCGGAAGAGCGTCGTG | Synthetic |
| SEQ ID NO: 9 | CGCTCAGCAGTGTCTCGCGTATGGTAGATCGGAAGAGCGTCGTG | Synthetic |
| SEQ ID NO: 10 | CGCTCAGCAGTGTCTCGCAACGGTAAGATCGGAAGAGCGTCGTG | Synthetic |
| SEQ ID NO: 11 | CGCTCAGCAGTGTCTCGCAGTTGGCAGATCGGAAGAGCGTCGTG | Synthetic |
| SEQ ID NO: 12 | CGCTCAGCAGTGTCTCGCAGACTTCAGATCGGAAGAGCGTCGTG | Synthetic |
| SEQ ID NO: 13 | CGCTCAGCAGTGTCTCGCGTGCTTAAGATCGGAAGAGCGTCGTG | Synthetic |
| SEQ ID NO: 14 | CGCTCAGCAGTGTCTCGCCCACTAGAGATCGGAAGAGCGTCGTG | Synthetic |
| SEQ ID NO: 15 | CGCTCAGCAGTGTCTCGCGCGCTATAGATCGGAAGAGCGTCGTG | Synthetic |
| SEQ ID NO: 16 | CGCTCAGCAGTGTCTCGCTGACACTAGATCGGAAGAGCGTCGTG | Synthetic |

TABLE 6-continued

Sequences

| Sequence ID Number | Sequence | Species |
|---|---|---|
| SEQ ID NO: 17 | CGCTCAGCAGTGTCTCGCGAGGAACAGATCGGAAGAGCGTCGTG | Synthetic |
| SEQ ID NO: 18 | CGCTCAGCAGTGTCTCGCTTGACCAAGATCGGAAGAGCGTCGTG | Synthetic |
| SEQ ID NO: 19 | CGCTCAGCAGTGTCTCGCGGTAGCAAGATCGGAAGAGCGTCGTG | Synthetic |
| SEQ ID NO: 20 | CGCTCAGCAGTGTCTCGCCGTTGAGAGATCGGAAGAGCGTCGTG | Synthetic |
| SEQ ID NO: 21 | CGCTCAGCAGTGTCTCGCACAACTGAGATCGGAAGAGCGTCGTG | Synthetic |
| SEQ ID NO: 22 | CGCTCAGCAGTGTCTCGCTCAGTCAAGATCGGAAGAGCGTCGTG | Synthetic |
| SEQ ID NO: 23 | CGCTCAGCAGTGTCTCGCCGTACATAGATCGGAAGAGCGTCGTG | Synthetic |
| SEQ ID NO: 24 | CGCTCAGCAGTGTCTCGCTGAGTGCAGATCGGAAGAGCGTCGTG | Synthetic |
| SEQ ID NO: 25 | CGCTCAGCAGTGTCTCGCCCTGTTAAGATCGGAAGAGCGTCGTG | Synthetic |
| SEQ ID NO: 26 | CGCTCAGCAGTGTCTCGCACCTCTAAGATCGGAAGAGCGTCGTG | Synthetic |
| SEQ ID NO: 27 | CGCTCAGCAGTGTCTCGCATTCCACAGATCGGAAGAGCGTCGTG | Synthetic |
| SEQ ID NO: 28 | CGCTCAGCAGTGTCTCGCTCGTATGAGATCGGAAGAGCGTCGTG | Synthetic |
| SEQ ID NO: 29 | CGCTCAGCAGTGTCTCGCAGGTTGTAGATCGGAAGAGCGTCGTG | Synthetic |
| SEQ ID NO: 30 | CGCTCAGCAGTGTCTCGCCGTAGTCAGATCGGAAGAGCGTCGTG | Synthetic |
| SEQ ID NO: 31 | CGCTCAGCAGTGTCTCGCCTTCTCGAGATCGGAAGAGCGTCGTG | Synthetic |
| SEQ ID NO: 32 | CGCTCAGCAGTGTCTCGCAGGTAAGAGATCGGAAGAGCGTCGTG | Synthetic |
| SEQ ID NO: 33 | CGCTCAGCAGTGTCTCGCGATCTCAAGATCGGAAGAGCGTCGTG | Synthetic |
| SEQ ID NO: 34 | CGCTCAGCAGTGTCTCGCATCGAACAGATCGGAAGAGCGTCGTG | Synthetic |
| SEQ ID NO: 35 | CGCTCAGCAGTGTCTCGCCACGCATAGATCGGAAGAGCGTCGTG | Synthetic |
| SEQ ID NO: 36 | CGCTCAGCAGTGTCTCGCAACTCAGGAGATCGGAAGAGCGTCGTG | Synthetic |
| SEQ ID NO: 37 | CGCTCAGCAGTGTCTCGCTGCCACAAAGATCGGAAGAGCGTCGTG | Synthetic |
| SEQ ID NO: 38 | CGCTCAGCAGTGTCTCGCATGGCGATAGATCGGAAGAGCGTCGTG | Synthetic |
| SEQ ID NO: 39 | CGCTCAGCAGTGTCTCGCAATCAGCGAGATCGGAAGAGCGTCGTG | Synthetic |
| SEQ ID NO: 40 | CGCTCAGCAGTGTCTCGCGGTTGTACAGATCGGAAGAGCGTCGTG | Synthetic |
| SEQ ID NO: 41 | CGCTCAGCAGTGTCTCGCCTCGACTTAGATCGGAAGAGCGTCGTG | Synthetic |

TABLE 6-continued

Sequences

| Sequence ID Number | Sequence | Species |
|---|---|---|
| SEQ ID NO: 42 | CGCTCAGCAGTGTCTCGCTAGGAAGCAGATCGGAAGAG CGTCGTG | Synthetic |
| SEQ ID NO: 43 | CGCTCAGCAGTGTCTCGCGTGCATGTAGATCGGAAGAGC GTCGTG | Synthetic |
| SEQ ID NO: 44 | CGCTCAGCAGTGTCTCGCTCAATCGGAGATCGGAAGAGC GTCGTG | Synthetic |
| SEQ ID NO: 45 | CGCTCAGCAGTGTCTCGCTCAAGCTCAGATCGGAAGAGC GTCGTG | Synthetic |
| SEQ ID NO: 46 | CGCTCAGCAGTGTCTCGCAGTGTCACAGATCGGAAGAGC GTCGTG | Synthetic |
| SEQ ID NO: 47 | CGCTCAGCAGTGTCTCGCTGTGTTCCAGATCGGAAGAGC GTCGTG | Synthetic |
| SEQ ID NO: 48 | CGCTCAGCAGTGTCTCGCTCCGAATCAGATCGGAAGAGC GTCGTG | Synthetic |
| SEQ ID NO: 49 | CGCTCAGCAGTGTCTCGCGGAGTACAAGATCGGAAGAG CGTCGTG | Synthetic |
| SEQ ID NO: 50 | CGCTCAGCAGTGTCTCGCAGGACAGAAGATCGGAAGAG CGTCGTG | Synthetic |
| SEQ ID NO: 51 | CGCTCAGCAGTGTCTCGCGCACAGTTAGATCGGAAGAGC GTCGTG | Synthetic |
| SEQ ID NO: 52 | CGCTCAGCAGTGTCTCGCCGACAACAAGATCGGAAGAG CGTCGTG | Synthetic |
| SEQ ID NO: 53 | CGCTCAGCAGTGTCTCGCAGCACGTAAGATCGGAAGAG CGTCGTG | Synthetic |
| SEQ ID NO: 54 | CGCTCAGCAGTGTCTCGCCCAACAGTAGATCGGAAGAGC GTCGTG | Synthetic |
| SEQ ID NO: 55 | CGCTCAGCAGTGTCTCGCTCAGGACAAGATCGGAAGAG CGTCGTG | Synthetic |
| SEQ ID NO: 56 | CGCTCAGCAGTGTCTCGCCTATCCTGAGATCGGAAGAGC GTCGTG | Synthetic |
| SEQ ID NO: 57 | CGCTCAGCAGTGTCTCGCTGTCTGTCAGATCGGAAGAGC GTCGTG | Synthetic |
| SEQ ID NO: 58 | CGCTCAGCAGTGTCTCGCCCTAGTCTAGATCGGAAGAGC GTCGTG | Synthetic |
| SEQ ID NO: 59 | CGCTCAGCAGTGTCTCGCGTAATGGCAGATCGGAAGAGC GTCGTG | Synthetic |
| SEQ ID NO: 60 | CGCTCAGCAGTGTCTCGCTAGTGGCTAGATCGGAAGAGC GTCGTG | Synthetic |
| SEQ ID NO: 61 | CGCTCAGCAGTGTCTCGCGAATCTGCAGATCGGAAGAGC GTCGTG | Synthetic |
| SEQ ID NO: 62 | CGCTCAGCAGTGTCTCGCTTCGATGCAGATCGGAAGAGC GTCGTG | Synthetic |
| SEQ ID NO: 63 | CGCTCAGCAGTGTCTCGCGCTTGGTTAGATCGGAAGAGC GTCGTG | Synthetic |
| SEQ ID NO: 64 | CGCTCAGCAGTGTCTCGCAGCTGATCAGATCGGAAGAGC GTCGTG | Synthetic |
| SEQ ID NO: 65 | CGCTCAGCAGTGTCTCGCATAAGCGGAGATCGGAAGAG CGTCGTG | Synthetic |
| SEQ ID NO: 66 | CGCTCAGCAGTGTCTCGCACTTCGGAAGATCGGAAGAGC GTCGTG | Synthetic |

TABLE 6-continued

Sequences

| Sequence ID Number | Sequence | Species |
|---|---|---|
| SEQ ID NO: 67 | CGCTCAGCAGTGTCTCGCCTAGTCGAAGATCGGAAGAGCGTCGTG | Synthetic |
| SEQ ID NO: 68 | CGCTCAGCAGTGTCTCGCCGTTCTTGCAGATCGGAAGAGCGTCGTG | Synthetic |
| SEQ ID NO: 69 | CGCTCAGCAGTGTCTCGCTGTAGACTCAGATCGGAAGAGCGTCGTG | Synthetic |
| SEQ ID NO: 70 | CGCTCAGCAGTGTCTCGCGAAGGCCTAAGATCGGAAGAGCGTCGTG | Synthetic |
| SEQ ID NO: 71 | CGCTCAGCAGTGTCTCGCTTCGTAAGGAGATCGGAAGAGCGTCGTG | Synthetic |
| SEQ ID NO: 72 | CGCTCAGCAGTGTCTCGCTGATCACCTAGATCGGAAGAGCGTCGTG | Synthetic |
| SEQ ID NO: 73 | CGCTCAGCAGTGTCTCGCTAGCTAACGAGATCGGAAGAGCGTCGTG | Synthetic |
| SEQ ID NO: 74 | CGCTCAGCAGTGTCTCGCCGTAGAAGGAGATCGGAAGAGCGTCGTG | Synthetic |
| SEQ ID NO: 75 | CGCTCAGCAGTGTCTCGCTCTCTCGAAAGATCGGAAGAGCGTCGTG | Synthetic |
| SEQ ID NO: 76 | CGCTCAGCAGTGTCTCGCTCTAGTTCCAGATCGGAAGAGCGTCGTG | Synthetic |
| SEQ ID NO: 77 | CGCTCAGCAGTGTCTCGCCCGAAGAGAAGATCGGAAGAGCGTCGTG | Synthetic |
| SEQ ID NO: 78 | CGCTCAGCAGTGTCTCGCAGGTGACATAGATCGGAAGAGCGTCGTG | Synthetic |
| SEQ ID NO: 79 | CGCTCAGCAGTGTCTCGCCTGAGAACGAGATCGGAAGAGCGTCGTG | Synthetic |
| SEQ ID NO: 80 | CGCTCAGCAGTGTCTCGCCCAGCTGAAAGATCGGAAGAGCGTCGTG | Synthetic |
| SEQ ID NO: 81 | CGCTCAGCAGTGTCTCGCCGTTCGACAAGATCGGAAGAGCGTCGTG | Synthetic |
| SEQ ID NO: 82 | CGCTCAGCAGTGTCTCGCTCTTAGACCAGATCGGAAGAGCGTCGTG | Synthetic |
| SEQ ID NO: 83 | CGCTCAGCAGTGTCTCGCCACGAGCAAAGATCGGAAGAGCGTCGTG | Synthetic |
| SEQ ID NO: 84 | CGCTCAGCAGTGTCTCGCCTGCCGAATAGATCGGAAGAGCGTCGTG | Synthetic |
| SEQ ID NO: 85 | CGCTCAGCAGTGTCTCGCGGGCTCATAAGATCGGAAGAGCGTCGTG | Synthetic |
| SEQ ID NO: 86 | CGCTCAGCAGTGTCTCGCCACCGTACTAGATCGGAAGAGCGTCGTG | Synthetic |
| SEQ ID NO: 87 | CGCTCAGCAGTGTCTCGCGTGTCTCGAAGATCGGAAGAGCGTCGTG | Synthetic |
| SEQ ID NO: 88 | CGCTCAGCAGTGTCTCGCTTACTGCGAAGATCGGAAGAGCGTCGTG | Synthetic |
| SEQ ID NO: 89 | CGCTCAGCAGTGTCTCGCTCCATACGAAGATCGGAAGAGCGTCGTG | Synthetic |
| SEQ ID NO: 90 | CGCTCAGCAGTGTCTCGCGATCCAGGTAGATCGGAAGAGCGTCGTG | Synthetic |
| SEQ ID NO: 91 | CGCTCAGCAGTGTCTCGCAGTTGCGAAAGATCGGAAGAGCGTCGTG | Synthetic |

TABLE 6-continued

Sequences

| Sequence ID Number | Sequence | Species |
|---|---|---|
| SEQ ID NO: 92 | CGCTCAGCAGTGTCTCGCAGGTTGAGAAGATCGGAAGAGCGTCGTG | Synthetic |
| SEQ ID NO: 93 | CGCTCAGCAGTGTCTCGCGTTGCGCTTAGATCGGAAGAGCGTCGTG | Synthetic |
| SEQ ID NO: 94 | CGCTCAGCAGTGTCTCGCCTCGAGAGAAGATCGGAAGAGCGTCGTG | Synthetic |
| SEQ ID NO: 95 | CGCTCAGCAGTGTCTCGCTGTTCCTAGAGATCGGAAGAGCGTCGTG | Synthetic |
| SEQ ID NO: 96 | CGCTCAGCAGTGTCTCGCCTCACACTGAGATCGGAAGAGCGTCGTG | Synthetic |
| SEQ ID NO: 97 | CGCTCAGCAGTGTCTCGCACCACATGTAGATCGGAAGAGCGTCGTG | Synthetic |
| SEQ ID NO: 98 | CGCTCAGCAGTGTCTCGCAGCTTAACCAGATCGGAAGAGCGTCGTG | Synthetic |
| SEQ ID NO: 99 | CGCTCAGCAGTGTCTCGCCACCTATGCAGATCGGAAGAGCGTCGTG | Synthetic |
| SEQ ID NO: 100 | CGACGAGGCTGGAGTGACACTGGTACCGCTCAGCAGTGTCTCGC | Synthetic |
| SEQ ID NO: 101 | CGACGAGGCTGGAGTGACGGTACTGTCGCTCAGCAGTGTCTCGC | Synthetic |
| SEQ ID NO: 102 | CGACGAGGCTGGAGTGACTCTGTGTGCGCTCAGCAGTGTCTCGC | Synthetic |
| SEQ ID NO: 103 | CGACGAGGCTGGAGTGACTATGGCTCCGCTCAGCAGTGTCTCGC | Synthetic |
| SEQ ID NO: 104 | CGACGAGGCTGGAGTGACGTTGTCAGCGCTCAGCAGTGTCTCGC | Synthetic |
| SEQ ID NO: 105 | CGACGAGGCTGGAGTGACATGCCAGTCGCTCAGCAGTGTCTCGC | Synthetic |
| SEQ ID NO: 106 | CGACGAGGCTGGAGTGACCGCTACTACGCTCAGCAGTGTCTCGC | Synthetic |
| SEQ ID NO: 107 | CGACGAGGCTGGAGTGACCATACACGCGCTCAGCAGTGTCTCGC | Synthetic |
| SEQ ID NO: 108 | CGACGAGGCTGGAGTGACTCGAGGATCGCTCAGCAGTGTCTCGC | Synthetic |
| SEQ ID NO: 109 | CGACGAGGCTGGAGTGACGGTTCGATCGCTCAGCAGTGTCTCGC | Synthetic |
| SEQ ID NO: 110 | CGACGAGGCTGGAGTGACACGGAACACGCTCAGCAGTGTCTCGC | Synthetic |
| SEQ ID NO: 111 | CGACGAGGCTGGAGTGACCGTTGCATCGCTCAGCAGTGTCTCGC | Synthetic |
| SEQ ID NO: 112 | CGACGAGGCTGGAGTGACATACGTCCCGCTCAGCAGTGTCTCGC | Synthetic |
| SEQ ID NO: 113 | CGACGAGGCTGGAGTGACGATCTGGACGCTCAGCAGTGTCTCGC | Synthetic |
| SEQ ID NO: 114 | CGACGAGGCTGGAGTGACTCTCGAAGCGCTCAGCAGTGTCTCGC | Synthetic |
| SEQ ID NO: 115 | CGACGAGGCTGGAGTGACCTGTGCTACGCTCAGCAGTGTCTCGC | Synthetic |
| SEQ ID NO: 116 | CGACGAGGCTGGAGTGACAGGTGGAACGCTCAGCAGTGTCTCGC | Synthetic |

TABLE 6-continued

Sequences

| Sequence ID Number | Sequence | Species |
|---|---|---|
| SEQ ID NO: 117 | CGACGAGGCTGGAGTGACTAGCAACGCGCTCAGCAGTGTCTCGC | Synthetic |
| SEQ ID NO: 118 | CGACGAGGCTGGAGTGACGGTCATTCCGCTCAGCAGTGTCTCGC | Synthetic |
| SEQ ID NO: 119 | CGACGAGGCTGGAGTGACAGATACGCCGCTCAGCAGTGTCTCGC | Synthetic |
| SEQ ID NO: 120 | CGACGAGGCTGGAGTGACGAACTGCTCGCTCAGCAGTGTCTCGC | Synthetic |
| SEQ ID NO: 121 | CGACGAGGCTGGAGTGACAGTGCACACGCTCAGCAGTGTCTCGC | Synthetic |
| SEQ ID NO: 122 | CGACGAGGCTGGAGTGACCCGATCATCGCTCAGCAGTGTCTCGC | Synthetic |
| SEQ ID NO: 123 | CGACGAGGCTGGAGTGACACAAGGACCGCTCAGCAGTGTCTCGC | Synthetic |
| SEQ ID NO: 124 | CGACGAGGCTGGAGTGACATTCGGTCCGCTCAGCAGTGTCTCGC | Synthetic |
| SEQ ID NO: 125 | CGACGAGGCTGGAGTGACTTGTGACGCGCTCAGCAGTGTCTCGC | Synthetic |
| SEQ ID NO: 126 | CGACGAGGCTGGAGTGACGAAGTCTGCGCTCAGCAGTGTCTCGC | Synthetic |
| SEQ ID NO: 127 | CGACGAGGCTGGAGTGACTGGACGAACGCTCAGCAGTGTCTCGC | Synthetic |
| SEQ ID NO: 128 | CGACGAGGCTGGAGTGACGAGTTCCTCGCTCAGCAGTGTCTCGC | Synthetic |
| SEQ ID NO: 129 | CGACGAGGCTGGAGTGACGATAGGAGCGCTCAGCAGTGTCTCGC | Synthetic |
| SEQ ID NO: 130 | CGACGAGGCTGGAGTGACAGCTTGGACGCTCAGCAGTGTCTCGC | Synthetic |
| SEQ ID NO: 131 | CGACGAGGCTGGAGTGACCACATCCTCGCTCAGCAGTGTCTCGC | Synthetic |
| SEQ ID NO: 132 | CGACGAGGCTGGAGTGACAGTCCTGACGCTCAGCAGTGTCTCGC | Synthetic |
| SEQ ID NO: 133 | CGACGAGGCTGGAGTGACCTTGTAGCCGCTCAGCAGTGTCTCGC | Synthetic |
| SEQ ID NO: 134 | CGACGAGGCTGGAGTGACCAGGAGTACGCTCAGCAGTGTCTCGC | Synthetic |
| SEQ ID NO: 135 | CGACGAGGCTGGAGTGACCACAAGGACGCTCAGCAGTGTCTCGC | Synthetic |
| SEQ ID NO: 136 | CGACGAGGCTGGAGTGACTTCCTCTGCGCTCAGCAGTGTCTCGC | Synthetic |
| SEQ ID NO: 137 | CGACGAGGCTGGAGTGACCCATTGCTCGCTCAGCAGTGTCTCGC | Synthetic |
| SEQ ID NO: 138 | CGACGAGGCTGGAGTGACGCACATAGCGCTCAGCAGTGTCTCGC | Synthetic |
| SEQ ID NO: 139 | CGACGAGGCTGGAGTGACCACTGTACCGCTCAGCAGTGTCTCGC | Synthetic |
| SEQ ID NO: 140 | CGACGAGGCTGGAGTGACGTGATCTCCGCTCAGCAGTGTCTCGC | Synthetic |
| SEQ ID NO: 141 | CGACGAGGCTGGAGTGACAATGCCGTCGCTCAGCAGTGTCTCGC | Synthetic |

TABLE 6-continued

Sequences

| Sequence ID Number | Sequence | Species |
|---|---|---|
| SEQ ID NO: 142 | CGACGAGGCTGGAGTGACTCCTTGTCCGCTCAGCAGTGTCTCGC | Synthetic |
| SEQ ID NO: 143 | CGACGAGGCTGGAGTGACAGTAGGCACGCTCAGCAGTGTCTCGC | Synthetic |
| SEQ ID NO: 144 | CGACGAGGCTGGAGTGACAGCCTCTTCGCTCAGCAGTGTCTCGC | Synthetic |
| SEQ ID NO: 145 | CGACGAGGCTGGAGTGACCGATTACGCGCTCAGCAGTGTCTCGC | Synthetic |
| SEQ ID NO: 146 | CGACGAGGCTGGAGTGACCCAGGAATCGCTCAGCAGTGTCTCGC | Synthetic |
| SEQ ID NO: 147 | CGACGAGGCTGGAGTGACGAGTCAGTCGCTCAGCAGTGTCTCGC | Synthetic |
| SEQ ID NO: 148 | CGACGAGGCTGGAGTGACTGAGAGGACGCTCAGCAGTGTCTCGC | Synthetic |
| SEQ ID NO: 149 | CGACGAGGCTGGAGTGACACGACTCACGCTCAGCAGTGTCTCGC | Synthetic |
| SEQ ID NO: 150 | CGACGAGGCTGGAGTGACTAGCTCAGCGCTCAGCAGTGTCTCGC | Synthetic |
| SEQ ID NO: 151 | CGACGAGGCTGGAGTGACTAACCGGTCGCTCAGCAGTGTCTCGC | Synthetic |
| SEQ ID NO: 152 | CGACGAGGCTGGAGTGACGTACTGAGCGCTCAGCAGTGTCTCGC | Synthetic |
| SEQ ID NO: 153 | CGACGAGGCTGGAGTGACAACCACTCCGCTCAGCAGTGTCTCGC | Synthetic |
| SEQ ID NO: 154 | CGACGAGGCTGGAGTGACCAGTTACCCGCTCAGCAGTGTCTCGC | Synthetic |
| SEQ ID NO: 155 | CGACGAGGCTGGAGTGACGATGGATGCGCTCAGCAGTGTCTCGC | Synthetic |
| SEQ ID NO: 156 | CGACGAGGCTGGAGTGACCTACCTCTCGCTCAGCAGTGTCTCGC | Synthetic |
| SEQ ID NO: 157 | CGACGAGGCTGGAGTGACGTCAAGAGCGCTCAGCAGTGTCTCGC | Synthetic |
| SEQ ID NO: 158 | CGACGAGGCTGGAGTGACGATCTACGCGCTCAGCAGTGTCTCGC | Synthetic |
| SEQ ID NO: 159 | CGACGAGGCTGGAGTGACACATTCCGCGCTCAGCAGTGTCTCGC | Synthetic |
| SEQ ID NO: 160 | CGACGAGGCTGGAGTGACCTGAATCCCGCTCAGCAGTGTCTCGC | Synthetic |
| SEQ ID NO: 161 | CGACGAGGCTGGAGTGACTGGCCATACGCTCAGCAGTGTCTCGC | Synthetic |
| SEQ ID NO: 162 | CGACGAGGCTGGAGTGACGTCTTGCTCGCTCAGCAGTGTCTCGC | Synthetic |
| SEQ ID NO: 163 | CGACGAGGCTGGAGTGACACGTGTTGCGCTCAGCAGTGTCTCGC | Synthetic |
| SEQ ID NO: 164 | CGACGAGGCTGGAGTGACGAAGCGTTCGCTCAGCAGTGTCTCGC | Synthetic |
| SEQ ID NO: 165 | CGACGAGGCTGGAGTGACTAACGCCACGCTCAGCAGTGTCTCGC | Synthetic |
| SEQ ID NO: 166 | CGACGAGGCTGGAGTGACAGGCTGTACGCTCAGCAGTGTCTCGC | Synthetic |

TABLE 6-continued

Sequences

| Sequence ID Number | Sequence | Species |
|---|---|---|
| SEQ ID NO: 167 | CGACGAGGCTGGAGTGACCTACAGTGCGCTCAGCAGTGTCTCGC | Synthetic |
| SEQ ID NO: 168 | CGACGAGGCTGGAGTGACTTCAGAGCCGCTCAGCAGTGTCTCGC | Synthetic |
| SEQ ID NO: 169 | CGACGAGGCTGGAGTGACTGCCTACACGCTCAGCAGTGTCTCGC | Synthetic |
| SEQ ID NO: 170 | CGACGAGGCTGGAGTGACCGGATTGACGCTCAGCAGTGTCTCGC | Synthetic |
| SEQ ID NO: 171 | CGACGAGGCTGGAGTGACGGAGGATTCGCTCAGCAGTGTCTCGC | Synthetic |
| SEQ ID NO: 172 | CGACGAGGCTGGAGTGACCATTAGCCCGCTCAGCAGTGTCTCGC | Synthetic |
| SEQ ID NO: 173 | CGACGAGGCTGGAGTGACTTGGTCACCGCTCAGCAGTGTCTCGC | Synthetic |
| SEQ ID NO: 174 | CGACGAGGCTGGAGTGACCAAGCAAGCGCTCAGCAGTGTCTCGC | Synthetic |
| SEQ ID NO: 175 | CGACGAGGCTGGAGTGACCAACATCCCGCTCAGCAGTGTCTCGC | Synthetic |
| SEQ ID NO: 176 | CGACGAGGCTGGAGTGACGACGACAACGCTCAGCAGTGTCTCGC | Synthetic |
| SEQ ID NO: 177 | CGACGAGGCTGGAGTGACATCGAGTCCGCTCAGCAGTGTCTCGC | Synthetic |
| SEQ ID NO: 178 | CGACGAGGCTGGAGTGACTATGCGAGCGCTCAGCAGTGTCTCGC | Synthetic |
| SEQ ID NO: 179 | CGACGAGGCTGGAGTGACTAGCTTCCCGCTCAGCAGTGTCTCGC | Synthetic |
| SEQ ID NO: 180 | CGACGAGGCTGGAGTGACACCAACGTCGCTCAGCAGTGTCTCGC | Synthetic |
| SEQ ID NO: 181 | CGACGAGGCTGGAGTGACACGCGATACGCTCAGCAGTGTCTCGC | Synthetic |
| SEQ ID NO: 182 | CGACGAGGCTGGAGTGACGTCAGCTACGCTCAGCAGTGTCTCGC | Synthetic |
| SEQ ID NO: 183 | CGACGAGGCTGGAGTGACCACCAGATCGCTCAGCAGTGTCTCGC | Synthetic |
| SEQ ID NO: 184 | CGACGAGGCTGGAGTGACCAACCTTGCGCTCAGCAGTGTCTCGC | Synthetic |
| SEQ ID NO: 185 | CGACGAGGCTGGAGTGACTTGCCTTGCGCTCAGCAGTGTCTCGC | Synthetic |
| SEQ ID NO: 186 | CGACGAGGCTGGAGTGACAGTCTGCTCGCTCAGCAGTGTCTCGC | Synthetic |
| SEQ ID NO: 187 | CGACGAGGCTGGAGTGACGTCCTTCACGCTCAGCAGTGTCTCGC | Synthetic |
| SEQ ID NO: 188 | CGACGAGGCTGGAGTGACCGGTCTATCGCTCAGCAGTGTCTCGC | Synthetic |
| SEQ ID NO: 189 | CGACGAGGCTGGAGTGACTCTGCCTTCGCTCAGCAGTGTCTCGC | Synthetic |
| SEQ ID NO: 190 | CGACGAGGCTGGAGTGACCAAGTTGGCGCTCAGCAGTGTCTCGC | Synthetic |
| SEQ ID NO: 191 | CGACGAGGCTGGAGTGACATCTACGGCGCTCAGCAGTGTCTCGC | Synthetic |

TABLE 6-continued

Sequences

| Sequence ID Number | Sequence | Species |
|---|---|---|
| SEQ ID NO: 192 | CGACGAGGCTGGAGTGACCACTTCTGCGCTCAGCAGTGT CTCGC | Synthetic |
| SEQ ID NO: 193 | CGACGAGGCTGGAGTGACCACACAACCGCTCAGCAGTG TCTCGC | Synthetic |
| SEQ ID NO: 194 | CGACGAGGCTGGAGTGACGCCTAATGCGCTCAGCAGTGT CTCGC | Synthetic |
| SEQ ID NO: 195 | CGACGAGGCTGGAGTGACGTTCGCATCGCTCAGCAGTGT CTCGC | Synthetic |
| SEQ ID NO: 196 | TTACCGCGGCKGCTGRCACACGAGTCTAGCGACGAGGCT GGAGTGAC | Synthetic |
| SEQ ID NO: 197 | TTACCGCGGCKGCTGRCACACGCCTCTATCGACGAGGCT GGAGTGAC | Synthetic |
| SEQ ID NO: 198 | TTACCGCGGCKGCTGRCACACGCCATTCTCGACGAGGCT GGAGTGAC | Synthetic |
| SEQ ID NO: 199 | TTACCGCGGCKGCTGRCACACTACGGTTGCGACGAGGCT GGAGTGAC | Synthetic |
| SEQ ID NO: 200 | TTACCGCGGCKGCTGRCACACTCTACCCGACGAGGCT GGAGTGAC | Synthetic |
| SEQ ID NO: 201 | TTACCGCGGCKGCTGRCACACTAGGTCCACGACGAGGCT GGAGTGAC | Synthetic |
| SEQ ID NO: 202 | TTACCGCGGCKGCTGRCACACTCCTGAGTCGACGAGGCT GGAGTGAC | Synthetic |
| SEQ ID NO: 203 | TTACCGCGGCKGCTGRCACACGTGGATAGCGACGAGGCT GGAGTGAC | Synthetic |
| SEQ ID NO: 204 | TTACCGCGGCKGCTGRCACACGCGCTATTCGACGAGGCT GGAGTGAC | Synthetic |
| SEQ ID NO: 205 | TTACCGCGGCKGCTGRCACACGGAAGGAACGACGAGGC TGGAGTGAC | Synthetic |
| SEQ ID NO: 206 | TTACCGCGGCKGCTGRCACACGGACTCAACGACGAGGCT GGAGTGAC | Synthetic |
| SEQ ID NO: 207 | TTACCGCGGCKGCTGRCACACAACACTCGCGACGAGGCT GGAGTGAC | Synthetic |
| SEQ ID NO: 208 | TTACCGCGGCKGCTGRCACACCCGGAATTCGACGAGGCT GGAGTGAC | Synthetic |
| SEQ ID NO: 209 | TTACCGCGGCKGCTGRCACACAACTTGCCCGACGAGGCT GGAGTGAC | Synthetic |
| SEQ ID NO: 210 | TTACCGCGGCKGCTGRCACACTTGACAGGCGACGAGGCT GGAGTGAC | Synthetic |
| SEQ ID NO: 211 | TTACCGCGGCKGCTGRCACACTCTTAGCGCGACGAGGCT GGAGTGAC | Synthetic |
| SEQ ID NO: 212 | TTACCGCGGCKGCTGRCACACCTGTTGCACGACGAGGCT GGAGTGAC | Synthetic |
| SEQ ID NO: 213 | TTACCGCGGCKGCTGRCACACAGAACACGCGACGAGGC TGGAGTGAC | Synthetic |
| SEQ ID NO: 214 | TTACCGCGGCKGCTGRCACACCCTTGATGCGACGAGGCT GGAGTGAC | Synthetic |
| SEQ ID NO: 215 | TTACCGCGGCKGCTGRCACACAGCGATCTCGACGAGGCT GGAGTGAC | Synthetic |
| SEQ ID NO: 216 | TTACCGCGGCKGCTGRCACACGCTCAGAACGACGAGGCT GGAGTGAC | Synthetic |

TABLE 6-continued

Sequences

| Sequence ID Number | Sequence | Species |
|---|---|---|
| SEQ ID NO: 217 | TTACCGCGGCKGCTGRCACACATTGCGTGCGACGAGGCTGGAGTGAC | Synthetic |
| SEQ ID NO: 218 | TTACCGCGGCKGCTGRCACACCATCCGTTCGACGAGGCTGGAGTGAC | Synthetic |
| SEQ ID NO: 219 | TTACCGCGGCKGCTGRCACACTCTCTGGTCGACGAGGCTGGAGTGAC | Synthetic |
| SEQ ID NO: 220 | TTACCGCGGCKGCTGRCACACAACGAGCACGACGAGGCTGGAGTGAC | Synthetic |
| SEQ ID NO: 221 | TTACCGCGGCKGCTGRCACACGTTCACCGACGAGGCTGGAGTGAC | Synthetic |
| SEQ ID NO: 222 | TTACCGCGGCKGCTGRCACACATCAGCACCGACGAGGCTGGAGTGAC | Synthetic |
| SEQ ID NO: 223 | TTACCGCGGCKGCTGRCACACGATAGCGACGACGAGGCTGGAGTGAC | Synthetic |
| SEQ ID NO: 224 | TTACCGCGGCKGCTGRCACACAGAGCTTGCGACGAGGCTGGAGTGAC | Synthetic |
| SEQ ID NO: 225 | TTACCGCGGCKGCTGRCACACTGATCGTCCGACGAGGCTGGAGTGAC | Synthetic |
| SEQ ID NO: 226 | TTACCGCGGCKGCTGRCACACACGATACGCGACGAGGCTGGAGTGAC | Synthetic |
| SEQ ID NO: 227 | TTACCGCGGCKGCTGRCACACCTAACTGGCGACGAGGCTGGAGTGAC | Synthetic |
| SEQ ID NO: 228 | TTACCGCGGCKGCTGRCACACTCGCGTAACGACGAGGCTGGAGTGAC | Synthetic |
| SEQ ID NO: 229 | TTACCGCGGCKGCTGRCACACCGGTTCTTCGACGAGGCTGGAGTGAC | Synthetic |
| SEQ ID NO: 230 | TTACCGCGGCKGCTGRCACACTTGGTTCGCGACGAGGCTGGAGTGAC | Synthetic |
| SEQ ID NO: 231 | TTACCGCGGCKGCTGRCACACGAAGTAGCCGACGAGGCTGGAGTGAC | Synthetic |
| SEQ ID NO: 232 | TTACCGCGGCKGCTGRCACACGGCTAGAACGACGAGGCTGGAGTGAC | Synthetic |
| SEQ ID NO: 233 | TTACCGCGGCKGCTGRCACACCATCGTGACGACGAGGCTGGAGTGAC | Synthetic |
| SEQ ID NO: 234 | TTACCGCGGCKGCTGRCACACTCACCAACCGACGAGGCTGGAGTGAC | Synthetic |
| SEQ ID NO: 235 | TTACCGCGGCKGCTGRCACACCTTCAAGGCGACGAGGCTGGAGTGAC | Synthetic |
| SEQ ID NO: 236 | TTACCGCGGCKGCTGRCACACAGTAGCTCCGACGAGGCTGGAGTGAC | Synthetic |
| SEQ ID NO: 237 | TTACCGCGGCKGCTGRCACACGCCACATTCGACGAGGCTGGAGTGAC | Synthetic |
| SEQ ID NO: 238 | TTACCGCGGCKGCTGRCACACTTCACGGACGACGAGGCTGGAGTGAC | Synthetic |
| SEQ ID NO: 239 | TTACCGCGGCKGCTGRCACACTGACGTTGCGACGAGGCTGGAGTGAC | Synthetic |
| SEQ ID NO: 240 | TTACCGCGGCKGCTGRCACACTCATCTGGCGACGAGGCTGGAGTGAC | Synthetic |
| SEQ ID NO: 241 | TTACCGCGGCKGCTGRCACACCGTTCATCCGACGAGGCTGGAGTGAC | Synthetic |

TABLE 6-continued

Sequences

| Sequence ID Number | Sequence | Species |
|---|---|---|
| SEQ ID NO: 242 | TTACCGCGGCKGCTGRCACACAACCGTCACGACGAGGCT GGAGTGAC | Synthetic |
| SEQ ID NO: 243 | TTACCGCGGCKGCTGRCACACTGCTAAGCCGACGAGGCT GGAGTGAC | Synthetic |
| SEQ ID NO: 244 | TTACCGCGGCKGCTGRCACACCAGGTAGACGACGAGGC TGGAGTGAC | Synthetic |
| SEQ ID NO: 245 | TTACCGCGGCKGCTGRCACACAAGAACCGCGACGAGGC TGGAGTGAC | Synthetic |
| SEQ ID NO: 246 | TTACCGCGGCKGCTGRCACACAGGAGACTCGACGAGGC TGGAGTGAC | Synthetic |
| SEQ ID NO: 247 | TTACCGCGGCKGCTGRCACACAGTGAAGGCGACGAGGC TGGAGTGAC | Synthetic |
| SEQ ID NO: 248 | TTACCGCGGCKGCTGRCACACTCTTCAGCCGACGAGGCT GGAGTGAC | Synthetic |
| SEQ ID NO: 249 | TTACCGCGGCKGCTGRCACACAACGGAGTCGACGAGGC TGGAGTGAC | Synthetic |
| SEQ ID NO: 250 | TTACCGCGGCKGCTGRCACACGAAGAGACCGACGAGGC TGGAGTGAC | Synthetic |
| SEQ ID NO: 251 | TTACCGCGGCKGCTGRCACACATTGGTGGCGACGAGGCT GGAGTGAC | Synthetic |
| SEQ ID NO: 252 | TTACCGCGGCKGCTGRCACACCTGTCAAGCGACGAGGCT GGAGTGAC | Synthetic |
| SEQ ID NO: 253 | TTACCGCGGCKGCTGRCACACAGGCATCACGACGAGGCT GGAGTGAC | Synthetic |
| SEQ ID NO: 254 | TTACCGCGGCKGCTGRCACACAAGAGGTCCGACGAGGC TGGAGTGAC | Synthetic |
| SEQ ID NO: 255 | TTACCGCGGCKGCTGRCACACTGCATTCGCGACGAGGCT GGAGTGAC | Synthetic |
| SEQ ID NO: 256 | TTACCGCGGCKGCTGRCACACTTGGACGTCGACGAGGCT GGAGTGAC | Synthetic |
| SEQ ID NO: 257 | TTACCGCGGCKGCTGRCACACTTGCTGGACGACGAGGCT GGAGTGAC | Synthetic |
| SEQ ID NO: 258 | TTACCGCGGCKGCTGRCACACTGGAGATGCGACGAGGCT GGAGTGAC | Synthetic |
| SEQ ID NO: 259 | TTACCGCGGCKGCTGRCACACTACGTACCCGACGAGGCT GGAGTGAC | Synthetic |
| SEQ ID NO: 260 | TTACCGCGGCKGCTGRCACACTGACACCTCGACGAGGCT GGAGTGAC | Synthetic |
| SEQ ID NO: 261 | TTACCGCGGCKGCTGRCACACGTCCATTGCGACGAGGCT GGAGTGAC | Synthetic |
| SEQ ID NO: 262 | TTACCGCGGCKGCTGRCACACCAGAGAAGCGACGAGGC TGGAGTGAC | Synthetic |
| SEQ ID NO: 263 | TTACCGCGGCKGCTGRCACACTGCTTCAGCGACGAGGCT GGAGTGAC | Synthetic |
| SEQ ID NO: 264 | TTACCGCGGCKGCTGRCACACTACACTGCCGACGAGGCT GGAGTGAC | Synthetic |
| SEQ ID NO: 265 | TTACCGCGGCKGCTGRCACACGGACGTATCGACGAGGCT GGAGTGAC | Synthetic |
| SEQ ID NO: 266 | TTACCGCGGCKGCTGRCACACCTCGCATACGACGAGGCT GGAGTGAC | Synthetic |

TABLE 6-continued

Sequences

| Sequence ID Number | Sequence | Species |
|---|---|---|
| SEQ ID NO: 267 | TTACCGCGGCKGCTGRCACACGCATCCTACGACGAGGCTGGAGTGAC | Synthetic |
| SEQ ID NO: 268 | TTACCGCGGCKGCTGRCACACAGGCTTACGACGAGGCTGGAGTGAC | Synthetic |
| SEQ ID NO: 269 | TTACCGCGGCKGCTGRCACACGTAAGTCGCGACGAGGCTGGAGTGAC | Synthetic |
| SEQ ID NO: 270 | TTACCGCGGCKGCTGRCACACTTCTGGAGCGACGAGGCTGGAGTGAC | Synthetic |
| SEQ ID NO: 271 | TTACCGCGGCKGCTGRCACACGACACACACGACGAGGCTGGAGTGAC | Synthetic |
| SEQ ID NO: 272 | TTACCGCGGCKGCTGRCACACACCAGACACGACGAGGCTGGAGTGAC | Synthetic |
| SEQ ID NO: 273 | TTACCGCGGCKGCTGRCACACTGCAGCTTCGACGAGGCTGGAGTGAC | Synthetic |
| SEQ ID NO: 274 | TTACCGCGGCKGCTGRCACACGCAACTTCCGACGAGGCTGGAGTGAC | Synthetic |
| SEQ ID NO: 275 | TTACCGCGGCKGCTGRCACACTCGCTTCGACGAGGCTGGAGTGAC | Synthetic |
| SEQ ID NO: 276 | TTACCGCGGCKGCTGRCACACTGAACTCCCGACGAGGCTGGAGTGAC | Synthetic |
| SEQ ID NO: 277 | TTACCGCGGCKGCTGRCACACGTGTAAGCCGACGAGGCTGGAGTGAC | Synthetic |
| SEQ ID NO: 278 | TTACCGCGGCKGCTGRCACACATGCACCTCGACGAGGCTGGAGTGAC | Synthetic |
| SEQ ID NO: 279 | TTACCGCGGCKGCTGRCACACTCCGTCAACGACGAGGCTGGAGTGAC | Synthetic |
| SEQ ID NO: 280 | TTACCGCGGCKGCTGRCACACGTCGGTATCGACGAGGCTGGAGTGAC | Synthetic |
| SEQ ID NO: 281 | TTACCGCGGCKGCTGRCACACACAGATCCCGACGAGGCTGGAGTGAC | Synthetic |
| SEQ ID NO: 282 | TTACCGCGGCKGCTGRCACACTCGGATCTCGACGAGGCTGGAGTGAC | Synthetic |
| SEQ ID NO: 283 | TTACCGCGGCKGCTGRCACACAGAGTCGTCGACGAGGCTGGAGTGAC | Synthetic |
| SEQ ID NO: 284 | TTACCGCGGCKGCTGRCACACGAATAGCGCGACGAGGCTGGAGTGAC | Synthetic |
| SEQ ID NO: 285 | TTACCGCGGCKGCTGRCACACGGATTGGTCGACGAGGCTGGAGTGAC | Synthetic |
| SEQ ID NO: 286 | TTACCGCGGCKGCTGRCACACGCCATAGACGACGAGGCTGGAGTGAC | Synthetic |
| SEQ ID NO: 287 | TTACCGCGGCKGCTGRCACACTGTCAGAGCGACGAGGCTGGAGTGAC | Synthetic |
| SEQ ID NO: 288 | TTACCGCGGCKGCTGRCACACCCTACGAACGACGAGGCTGGAGTGAC | Synthetic |
| SEQ ID NO: 289 | TTACCGCGGCKGCTGRCACACGTTACGTCCGACGAGGCTGGAGTGAC | Synthetic |
| SEQ ID NO: 290 | TTACCGCGGCKGCTGRCACACCGAGATACCGACGAGGCTGGAGTGAC | Synthetic |
| SEQ ID NO: 291 | TTACCGCGGCKGCTGRCACACGCATTGACCGACGAGGCTGGAGTGAC | Synthetic |

TABLE 6-continued

Sequences

| Sequence ID Number | Sequence | Species |
|---|---|---|
| SEQ ID NO: 292 | ACTAGGT | Synthetic |
| SEQ ID NO: 293 | AGCTCTA | Synthetic |
| SEQ ID NO: 294 | AGAGAGT | Synthetic |
| SEQ ID NO: 295 | GTGTTCC | Synthetic |
| SEQ ID NO: 296 | TTAGCTG | Synthetic |
| SEQ ID NO: 297 | ACCATAC | Synthetic |
| SEQ ID NO: 298 | TACCGTT | Synthetic |
| SEQ ID NO: 299 | GCCAACT | Synthetic |
| SEQ ID NO: 300 | GAAGTCT | Synthetic |
| SEQ ID NO: 301 | TAAGCAC | Synthetic |
| SEQ ID NO: 302 | CTAGTGG | Synthetic |
| SEQ ID NO: 303 | ATAGCGC | Synthetic |
| SEQ ID NO: 304 | AGTGTCA | Synthetic |
| SEQ ID NO: 305 | GTTCCTC | Synthetic |
| SEQ ID NO: 306 | TGGTCAA | Synthetic |
| SEQ ID NO: 307 | TGCTACC | Synthetic |
| SEQ ID NO: 308 | CTCAACG | Synthetic |
| SEQ ID NO: 309 | CAGTTGT | Synthetic |
| SEQ ID NO: 310 | TGACTGA | Synthetic |
| SEQ ID NO: 311 | ATGTACG | Synthetic |
| SEQ ID NO: 312 | GCACTCA | Synthetic |
| SEQ ID NO: 313 | TAACAGG | Synthetic |
| SEQ ID NO: 314 | TAGAGGT | Synthetic |
| SEQ ID NO: 315 | GTGGAAT | Synthetic |
| SEQ ID NO: 316 | CATACGA | Synthetic |
| SEQ ID NO: 317 | ACAACCT | Synthetic |
| SEQ ID NO: 318 | GACTACG | Synthetic |
| SEQ ID NO: 319 | CGAGAAG | Synthetic |
| SEQ ID NO: 320 | CTTACCT | Synthetic |
| SEQ ID NO: 321 | TGAGATC | Synthetic |
| SEQ ID NO: 322 | GTTCGAT | Synthetic |
| SEQ ID NO: 323 | ATGCGTG | Synthetic |
| SEQ ID NO: 324 | CCTGAGTT | Synthetic |
| SEQ ID NO: 325 | TTGTGGCA | Synthetic |
| SEQ ID NO: 326 | ATCGCCAT | Synthetic |
| SEQ ID NO: 327 | CGCTGATT | Synthetic |
| SEQ ID NO: 328 | GTACAACC | Synthetic |

TABLE 6-continued

Sequences

| Sequence ID Number | Sequence | Species |
|---|---|---|
| SEQ ID NO: 329 | AAGTCGAG | Synthetic |
| SEQ ID NO: 330 | GCTTCCTA | Synthetic |
| SEQ ID NO: 331 | ACATGCAC | Synthetic |
| SEQ ID NO: 332 | CCGATTGA | Synthetic |
| SEQ ID NO: 333 | GAGCTTGA | Synthetic |
| SEQ ID NO: 334 | GTGACACT | Synthetic |
| SEQ ID NO: 335 | GGAACACA | Synthetic |
| SEQ ID NO: 336 | GATTCGGA | Synthetic |
| SEQ ID NO: 337 | TGTACTCC | Synthetic |
| SEQ ID NO: 338 | TCTGTCCT | Synthetic |
| SEQ ID NO: 339 | AACTGTGC | Synthetic |
| SEQ ID NO: 340 | TGTTGTCG | Synthetic |
| SEQ ID NO: 341 | TACGTGCT | Synthetic |
| SEQ ID NO: 342 | ACTGTTGG | Synthetic |
| SEQ ID NO: 343 | TGTCCTGA | Synthetic |
| SEQ ID NO: 344 | CAGGATAG | Synthetic |
| SEQ ID NO: 345 | GACAGACA | Synthetic |
| SEQ ID NO: 346 | AGACTAGG | Synthetic |
| SEQ ID NO: 347 | GCCATTAC | Synthetic |
| SEQ ID NO: 348 | AGCCACTA | Synthetic |
| SEQ ID NO: 349 | GCAGATTC | Synthetic |
| SEQ ID NO: 350 | GCATCGAA | Synthetic |
| SEQ ID NO: 351 | AACCAAGC | Synthetic |
| SEQ ID NO: 352 | GATCAGCT | Synthetic |
| SEQ ID NO: 353 | CCGCTTAT | Synthetic |
| SEQ ID NO: 354 | TCCGAAGT | Synthetic |
| SEQ ID NO: 355 | TCGACTAG | Synthetic |
| SEQ ID NO: 356 | GCAAGAACG | Synthetic |
| SEQ ID NO: 357 | GAGTCTACA | Synthetic |
| SEQ ID NO: 358 | TAGGCCTTC | Synthetic |
| SEQ ID NO: 359 | CCTTACGAA | Synthetic |
| SEQ ID NO: 360 | AGGTGATCA | Synthetic |
| SEQ ID NO: 361 | CGTTAGCTA | Synthetic |
| SEQ ID NO: 362 | CCTTCTACG | Synthetic |
| SEQ ID NO: 363 | TTCGAGAGA | Synthetic |
| SEQ ID NO: 364 | GGAACTAGA | Synthetic |
| SEQ ID NO: 365 | TCTCTTCGG | Synthetic |
| SEQ ID NO: 366 | ATGTCACCT | Synthetic |

TABLE 6-continued

Sequences

| Sequence ID Number | Sequence | Species |
|---|---|---|
| SEQ ID NO: 367 | CGTTCTCAG | Synthetic |
| SEQ ID NO: 368 | TTCAGCTGG | Synthetic |
| SEQ ID NO: 369 | TGTCGAACG | Synthetic |
| SEQ ID NO: 370 | GGTCTAAGA | Synthetic |
| SEQ ID NO: 371 | TTGCTCGTG | Synthetic |
| SEQ ID NO: 372 | ATTCGGCAG | Synthetic |
| SEQ ID NO: 373 | TATGAGCCC | Synthetic |
| SEQ ID NO: 374 | AGTACGGTG | Synthetic |
| SEQ ID NO: 375 | TCGAGACAC | Synthetic |
| SEQ ID NO: 376 | TCGCAGTAA | Synthetic |
| SEQ ID NO: 377 | TCGTATGGA | Synthetic |
| SEQ ID NO: 378 | ACCTGGATC | Synthetic |
| SEQ ID NO: 379 | TTCGCAACT | Synthetic |
| SEQ ID NO: 380 | TCTCAACCT | Synthetic |
| SEQ ID NO: 381 | AAGCGCAAC | Synthetic |
| SEQ ID NO: 382 | TCTCTCGAG | Synthetic |
| SEQ ID NO: 383 | CTAGGAACA | Synthetic |
| SEQ ID NO: 384 | CAGTGTGAG | Synthetic |
| SEQ ID NO: 385 | ACATGTGGT | Synthetic |
| SEQ ID NO: 386 | GGTTAAGCT | Synthetic |
| SEQ ID NO: 387 | GCATAGGTG | Synthetic |
| SEQ ID NO: 388 | GTACCAGT | Synthetic |
| SEQ ID NO: 389 | ACAGTACC | Synthetic |
| SEQ ID NO: 390 | CACACAGA | Synthetic |
| SEQ ID NO: 391 | GAGCCATA | Synthetic |
| SEQ ID NO: 392 | CTGACAAC | Synthetic |
| SEQ ID NO: 393 | ACTGGCAT | Synthetic |
| SEQ ID NO: 394 | TAGTAGCG | Synthetic |
| SEQ ID NO: 395 | CGTGTATG | Synthetic |
| SEQ ID NO: 396 | ATCCTCGA | Synthetic |
| SEQ ID NO: 397 | ATCGAACC | Synthetic |
| SEQ ID NO: 398 | TGTTCCGT | Synthetic |
| SEQ ID NO: 399 | ATGCAACG | Synthetic |
| SEQ ID NO: 400 | GGACGTAT | Synthetic |
| SEQ ID NO: 401 | TCCAGATC | Synthetic |
| SEQ ID NO: 402 | CTTCGAGA | Synthetic |
| SEQ ID NO: 403 | TAGCACAG | Synthetic |

TABLE 6-continued

Sequences

| Sequence ID Number | Sequence | Species |
|---|---|---|
| SEQ ID NO: 404 | TTCCACCT | Synthetic |
| SEQ ID NO: 405 | CGTTGCTA | Synthetic |
| SEQ ID NO: 406 | GAATGACC | Synthetic |
| SEQ ID NO: 407 | GCGTATCT | Synthetic |
| SEQ ID NO: 408 | AGCAGTTC | Synthetic |
| SEQ ID NO: 409 | TGTGCACT | Synthetic |
| SEQ ID NO: 410 | ATGATCGG | Synthetic |
| SEQ ID NO: 411 | GTCCTTGT | Synthetic |
| SEQ ID NO: 412 | GACCGAAT | Synthetic |
| SEQ ID NO: 413 | CGTCACAA | Synthetic |
| SEQ ID NO: 414 | CAGACTTC | Synthetic |
| SEQ ID NO: 415 | TTCGTCCA | Synthetic |
| SEQ ID NO: 416 | AGGAACTC | Synthetic |
| SEQ ID NO: 417 | CTCCTATC | Synthetic |
| SEQ ID NO: 418 | TCCAAGCT | Synthetic |
| SEQ ID NO: 419 | AGGATGTG | Synthetic |
| SEQ ID NO: 420 | TCAGGACT | Synthetic |
| SEQ ID NO: 421 | GCTACAAG | Synthetic |
| SEQ ID NO: 422 | TACTCCTG | Synthetic |
| SEQ ID NO: 423 | TCCTTGTG | Synthetic |
| SEQ ID NO: 424 | CAGAGGAA | Synthetic |
| SEQ ID NO: 425 | AGCAATGG | Synthetic |
| SEQ ID NO: 426 | CTATGTGC | Synthetic |
| SEQ ID NO: 427 | GTACAGTG | Synthetic |
| SEQ ID NO: 428 | GAGATCAC | Synthetic |
| SEQ ID NO: 429 | ACGGCATT | Synthetic |
| SEQ ID NO: 430 | GACAAGGA | Synthetic |
| SEQ ID NO: 431 | TGCCTACT | Synthetic |
| SEQ ID NO: 432 | AAGAGGCT | Synthetic |
| SEQ ID NO: 433 | CGTAATCG | Synthetic |
| SEQ ID NO: 434 | ATTCCTGG | Synthetic |
| SEQ ID NO: 435 | ACTGACTC | Synthetic |
| SEQ ID NO: 436 | TCCTCTCA | Synthetic |
| SEQ ID NO: 437 | TGAGTCGT | Synthetic |
| SEQ ID NO: 438 | CTGAGCTA | Synthetic |
| SEQ ID NO: 439 | ACCGGTTA | Synthetic |
| SEQ ID NO: 440 | CTCAGTAC | Synthetic |
| SEQ ID NO: 441 | GAGTGGTT | Synthetic |

TABLE 6-continued

Sequences

| Sequence ID Number | Sequence | Species |
|---|---|---|
| SEQ ID NO: 442 | GGTAACTG | Synthetic |
| SEQ ID NO: 443 | CATCCATC | Synthetic |
| SEQ ID NO: 444 | AGAGGTAG | Synthetic |
| SEQ ID NO: 445 | CTCTTGAC | Synthetic |
| SEQ ID NO: 446 | CGTAGATC | Synthetic |
| SEQ ID NO: 447 | CGGAATGT | Synthetic |
| SEQ ID NO: 448 | GGATTCAG | Synthetic |
| SEQ ID NO: 449 | TATGGCCA | Synthetic |
| SEQ ID NO: 450 | AGCAAGAC | Synthetic |
| SEQ ID NO: 451 | CAACACGT | Synthetic |
| SEQ ID NO: 452 | AACGCTTC | Synthetic |
| SEQ ID NO: 453 | TGGCGTTA | Synthetic |
| SEQ ID NO: 454 | TACAGCCT | Synthetic |
| SEQ ID NO: 455 | CACTGTAG | Synthetic |
| SEQ ID NO: 456 | GCTCTGAA | Synthetic |
| SEQ ID NO: 457 | TGTAGGCA | Synthetic |
| SEQ ID NO: 458 | TCAATCCG | Synthetic |
| SEQ ID NO: 459 | AATCCTCC | Synthetic |
| SEQ ID NO: 460 | GGCTAATG | Synthetic |
| SEQ ID NO: 461 | GTGACCAA | Synthetic |
| SEQ ID NO: 462 | CTTGCTTG | Synthetic |
| SEQ ID NO: 463 | GGATGTTG | Synthetic |
| SEQ ID NO: 464 | TTGTCGTC | Synthetic |
| SEQ ID NO: 465 | GACTCGAT | Synthetic |
| SEQ ID NO: 466 | CTCGCATA | Synthetic |
| SEQ ID NO: 467 | GGAAGCTA | Synthetic |
| SEQ ID NO: 468 | ACGTTGGT | Synthetic |
| SEQ ID NO: 469 | TATCGCGT | Synthetic |
| SEQ ID NO: 470 | TAGCTGAC | Synthetic |
| SEQ ID NO: 471 | ATCTGGTG | Synthetic |
| SEQ ID NO: 472 | CAAGGTTG | Synthetic |
| SEQ ID NO: 473 | CAAGGCAA | Synthetic |
| SEQ ID NO: 474 | AGCAGACT | Synthetic |
| SEQ ID NO: 475 | TGAAGGAC | Synthetic |
| SEQ ID NO: 476 | ATAGACCG | Synthetic |
| SEQ ID NO: 477 | AAGGCAGA | Synthetic |
| SEQ ID NO: 478 | CCAACTTG | Synthetic |

TABLE 6-continued

Sequences

| Sequence ID Number | Sequence | Species |
|---|---|---|
| SEQ ID NO: 479 | CCGTAGAT | Synthetic |
| SEQ ID NO: 480 | CAGAAGTG | Synthetic |
| SEQ ID NO: 481 | GTTGTGTG | Synthetic |
| SEQ ID NO: 482 | CATTAGGC | Synthetic |
| SEQ ID NO: 483 | ATGCGAAC | Synthetic |
| SEQ ID NO: 484 | CTAGACTC | Synthetic |
| SEQ ID NO: 485 | ATAGAGGC | Synthetic |
| SEQ ID NO: 486 | AGAATGGC | Synthetic |
| SEQ ID NO: 487 | CAACCGTA | Synthetic |
| SEQ ID NO: 488 | GGTAGAGT | Synthetic |
| SEQ ID NO: 489 | TGGACCTA | Synthetic |
| SEQ ID NO: 490 | ACTCAGGA | Synthetic |
| SEQ ID NO: 491 | CTATCCAC | Synthetic |
| SEQ ID NO: 492 | AATAGCGC | Synthetic |
| SEQ ID NO: 493 | TTCCTTCC | Synthetic |
| SEQ ID NO: 494 | TTGAGTCC | Synthetic |
| SEQ ID NO: 495 | CGAGTGTT | Synthetic |
| SEQ ID NO: 496 | AATTCCGG | Synthetic |
| SEQ ID NO: 497 | GGCAAGTT | Synthetic |
| SEQ ID NO: 498 | CCTGTCAA | Synthetic |
| SEQ ID NO: 499 | CGCTAAGA | Synthetic |
| SEQ ID NO: 500 | TGCAACAG | Synthetic |
| SEQ ID NO: 501 | CGTGTTCT | Synthetic |
| SEQ ID NO: 502 | CATCAAGG | Synthetic |
| SEQ ID NO: 503 | AGATCGCT | Synthetic |
| SEQ ID NO: 504 | TTCTGAGC | Synthetic |
| SEQ ID NO: 505 | CACGCAAT | Synthetic |
| SEQ ID NO: 506 | AACGGATG | Synthetic |
| SEQ ID NO: 507 | ACCAGAGA | Synthetic |
| SEQ ID NO: 508 | TGCTCGTT | Synthetic |
| SEQ ID NO: 509 | GTGAACGT | Synthetic |
| SEQ ID NO: 510 | GTGCTGAT | Synthetic |
| SEQ ID NO: 511 | TCGCTATC | Synthetic |
| SEQ ID NO: 512 | CAAGCTCT | Synthetic |
| SEQ ID NO: 513 | GACGATCA | Synthetic |
| SEQ ID NO: 514 | CGTATCGT | Synthetic |
| SEQ ID NO: 515 | CCAGTTAG | Synthetic |
| SEQ ID NO: 516 | TTACGCGA | Synthetic |

TABLE 6-continued

Sequences

| Sequence ID Number | Sequence | Species |
|---|---|---|
| SEQ ID NO: 517 | AAGAACCG | Synthetic |
| SEQ ID NO: 518 | CGAACCAA | Synthetic |
| SEQ ID NO: 519 | GCTACTTC | Synthetic |
| SEQ ID NO: 520 | TTCTAGCC | Synthetic |
| SEQ ID NO: 521 | TCACGATG | Synthetic |
| SEQ ID NO: 522 | GTTGGTGA | Synthetic |
| SEQ ID NO: 523 | CCTTGAAG | Synthetic |
| SEQ ID NO: 524 | GAGCTACT | Synthetic |
| SEQ ID NO: 525 | AATGTGGC | Synthetic |
| SEQ ID NO: 526 | TCCGTGAA | Synthetic |
| SEQ ID NO: 527 | CAACGTCA | Synthetic |
| SEQ ID NO: 528 | CCAGATGA | Synthetic |
| SEQ ID NO: 529 | GATGAACG | Synthetic |
| SEQ ID NO: 530 | TGACGGTT | Synthetic |
| SEQ ID NO: 531 | GCTTAGCA | Synthetic |
| SEQ ID NO: 532 | TCTACCTG | Synthetic |
| SEQ ID NO: 533 | CGGTTCTT | Synthetic |
| SEQ ID NO: 534 | AGTCTCCT | Synthetic |
| SEQ ID NO: 535 | CCTTCACT | Synthetic |
| SEQ ID NO: 536 | GCTGAAGA | Synthetic |
| SEQ ID NO: 537 | ACTCCGTT | Synthetic |
| SEQ ID NO: 538 | GTCTCTTC | Synthetic |
| SEQ ID NO: 539 | CCACCAAT | Synthetic |
| SEQ ID NO: 540 | CTTGACAG | Synthetic |
| SEQ ID NO: 541 | TGATGCCT | Synthetic |
| SEQ ID NO: 542 | GACCTCTT | Synthetic |
| SEQ ID NO: 543 | CGAATGCA | Synthetic |
| SEQ ID NO: 544 | ACGTCCAA | Synthetic |
| SEQ ID NO: 545 | TCCAGCAA | Synthetic |
| SEQ ID NO: 546 | CATCTCCA | Synthetic |
| SEQ ID NO: 547 | GGTACGTA | Synthetic |
| SEQ ID NO: 548 | AGGTGTCA | Synthetic |
| SEQ ID NO: 549 | CAATGGAC | Synthetic |
| SEQ ID NO: 550 | CTTCTCTG | Synthetic |
| SEQ ID NO: 551 | CTGAAGCA | Synthetic |
| SEQ ID NO: 552 | GCAGTGTA | Synthetic |
| SEQ ID NO: 553 | ATACGTCC | Synthetic |

TABLE 6-continued

Sequences

| Sequence ID Number | Sequence | Species |
|---|---|---|
| SEQ ID NO: 554 | TATGCGAG | Synthetic |
| SEQ ID NO: 555 | TAGGATGC | Synthetic |
| SEQ ID NO: 556 | GTAAGCCT | Synthetic |
| SEQ ID NO: 557 | CGACTTAC | Synthetic |
| SEQ ID NO: 558 | CTCCAGAA | Synthetic |
| SEQ ID NO: 559 | TGTGTGTC | Synthetic |
| SEQ ID NO: 560 | TGTCTGGT | Synthetic |
| SEQ ID NO: 561 | AAGCTGCA | Synthetic |
| SEQ ID NO: 562 | GAAGTTGC | Synthetic |
| SEQ ID NO: 563 | AAGCGAGT | Synthetic |
| SEQ ID NO: 564 | GGAGTTCA | Synthetic |
| SEQ ID NO: 565 | GCTTACAC | Synthetic |
| SEQ ID NO: 566 | AGGTGCAT | Synthetic |
| SEQ ID NO: 567 | TTGACGGA | Synthetic |
| SEQ ID NO: 568 | ATACCGAC | Synthetic |
| SEQ ID NO: 569 | GGATCTGT | Synthetic |
| SEQ ID NO: 570 | AGATCCGA | Synthetic |
| SEQ ID NO: 571 | ACGACTCT | Synthetic |
| SEQ ID NO: 572 | CGCTATTC | Synthetic |
| SEQ ID NO: 573 | ACCAATCC | Synthetic |
| SEQ ID NO: 574 | TCTATGGC | Synthetic |
| SEQ ID NO: 575 | CTCTGACA | Synthetic |
| SEQ ID NO: 576 | TTCGTAGG | Synthetic |
| SEQ ID NO: 577 | GACGTAAC | Synthetic |
| SEQ ID NO: 578 | GTATCTCG | Synthetic |
| SEQ ID NO: 579 | GTCAATGC | Synthetic |
| SEQ ID NO: 580 | CAAGCAGAAGACGGCATACGAGATTCGATGAGGTGACTGGAGTTCAGACGTGTGCTCTTCCGATCT | Synthetic |
| SEQ ID NO: 581 | CAAGCAGAAGACGGCATACGAGATAACGATCCGTGACTGGAGTTCAGACGTGTGCTCTTCCGATCT | Synthetic |
| SEQ ID NO: 582 | CAAGCAGAAGACGGCATACGAGATTAACGTGGGTGACTGGAGTTCAGACGTGTGCTCTTCCGATCT | Synthetic |
| SEQ ID NO: 583 | CAAGCAGAAGACGGCATACGAGATATGGAGGAGTGACTGGAGTTCAGACGTGTGCTCTTCCGATCT | Synthetic |
| SEQ ID NO: 584 | CAAGCAGAAGACGGCATACGAGATGCGAAGATGTGACTGGAGTTCAGACGTGTGCTCTTCCGATCT | Synthetic |
| SEQ ID NO: 585 | CAAGCAGAAGACGGCATACGAGATACTTCGCTGTGACTGGAGTTCAGACGTGTGCTCTTCCGATCT | Synthetic |
| SEQ ID NO: 586 | CAAGCAGAAGACGGCATACGAGATTGCGTAAGGTGACTGGAGTTCAGACGTGTGCTCTTCCGATCT | Synthetic |
| SEQ ID NO: 587 | CAAGCAGAAGACGGCATACGAGATGGTCAAGTGTGACTGGAGTTCAGACGTGTGCTCTTCCGATCT | Synthetic |

TABLE 6-continued

Sequences

| Sequence ID Number | Sequence | Species |
|---|---|---|
| SEQ ID NO: 588 | CAAGCAGAAGACGGCATACGAGATAGGCTTACGTGACT GGAGTTCAGACGTGTGCTCTTCCGATCT | Synthetic |
| SEQ ID NO: 589 | CAAGCAGAAGACGGCATACGAGATGATTCTCGGTGACT GGAGTTCAGACGTGTGCTCTTCCGATCT | Synthetic |
| SEQ ID NO: 590 | CAAGCAGAAGACGGCATACGAGATGTCTCCTAGTGACT GGAGTTCAGACGTGTGCTCTTCCGATCT | Synthetic |
| SEQ ID NO: 591 | CAAGCAGAAGACGGCATACGAGATGACGGTATGTGACT GGAGTTCAGACGTGTGCTCTTCCGATCT | Synthetic |
| SEQ ID NO: 592 | CAAGCAGAAGACGGCATACGAGATCATGGTGTGTGACT GGAGTTCAGACGTGTGCTCTTCCGATCT | Synthetic |
| SEQ ID NO: 593 | CAAGCAGAAGACGGCATACGAGATTGTCTACCGTGACT GGAGTTCAGACGTGTGCTCTTCCGATCT | Synthetic |
| SEQ ID NO: 594 | CAAGCAGAAGACGGCATACGAGATACCATGCAGTGACT GGAGTTCAGACGTGTGCTCTTCCGATCT | Synthetic |
| SEQ ID NO: 595 | CAAGCAGAAGACGGCATACGAGATCATTCCTGGTGACT GGAGTTCAGACGTGTGCTCTTCCGATCT | Synthetic |
| SEQ ID NO: 596 | CAAGCAGAAGACGGCATACGAGATAGGACTAGGTGACT GGAGTTCAGACGTGTGCTCTTCCGATCT | Synthetic |
| SEQ ID NO: 597 | CAAGCAGAAGACGGCATACGAGATGCTTGTTGGTGACT GGAGTTCAGACGTGTGCTCTTCCGATCT | Synthetic |
| SEQ ID NO: 598 | CAAGCAGAAGACGGCATACGAGATAGTCACACGTGACT GGAGTTCAGACGTGTGCTCTTCCGATCT | Synthetic |
| SEQ ID NO: 599 | CAAGCAGAAGACGGCATACGAGATCCAGTTGTGTGACT GGAGTTCAGACGTGTGCTCTTCCGATCT | Synthetic |
| SEQ ID NO: 600 | CAAGCAGAAGACGGCATACGAGATCTCCATTCGTGACTG GAGTTCAGACGTGTGCTCTTCCGATCT | Synthetic |
| SEQ ID NO: 601 | CAAGCAGAAGACGGCATACGAGATTTGCCAACGTGACT GGAGTTCAGACGTGTGCTCTTCCGATCT | Synthetic |
| SEQ ID NO: 602 | CAAGCAGAAGACGGCATACGAGATGAGCACATGTGACT GGAGTTCAGACGTGTGCTCTTCCGATCT | Synthetic |
| SEQ ID NO: 603 | CAAGCAGAAGACGGCATACGAGATATGTGGTGGTGACT GGAGTTCAGACGTGTGCTCTTCCGATCT | Synthetic |
| SEQ ID NO: 604 | AATGATACGGCGACCACCGAGATCTACACTAGATCGCAC ACTCTTTCCCTACACGACGCTCTTCCGATCT | Synthetic |
| SEQ ID NO: 605 | AATGATACGGCGACCACCGAGATCTACACCTCTCTATAC ACTCTTTCCCTACACGACGCTCTTCCGATCT | Synthetic |
| SEQ ID NO: 606 | AATGATACGGCGACCACCGAGATCTACACTATCCTCTAC ACTCTTTCCCTACACGACGCTCTTCCGATCT | Synthetic |
| SEQ ID NO: 607 | AATGATACGGCGACCACCGAGATCTACACAGAGTAGAA CACTCTTTCCCTACACGACGCTCTTCCGATCT | Synthetic |
| SEQ ID NO: 608 | AATGATACGGCGACCACCGAGATCTACACGTAAGGAGA CACTCTTTCCCTACACGACGCTCTTCCGATCT | Synthetic |
| SEQ ID NO: 609 | AATGATACGGCGACCACCGAGATCTACACACTGCATAAC ACTCTTTCCCTACACGACGCTCTTCCGATCT | Synthetic |
| SEQ ID NO: 610 | AATGATACGGCGACCACCGAGATCTACACAAGGAGTAA CACTCTTTCCCTACACGACGCTCTTCCGATCT | Synthetic |
| SEQ ID NO: 611 | AATGATACGGCGACCACCGAGATCTACACCTAAGCCTAC ACTCTTTCCCTACACGACGCTCTTCCGATCT | Synthetic |

TABLE 6-continued

Sequences

| Sequence ID Number | Sequence | Species |
|---|---|---|
| SEQ ID NO: 612 | CTCATCGA | Synthetic |
| SEQ ID NO: 613 | GGATCGTT | Synthetic |
| SEQ ID NO: 614 | CCACGTTA | Synthetic |
| SEQ ID NO: 615 | TCCTCCAT | Synthetic |
| SEQ ID NO: 616 | ATCTTCGC | Synthetic |
| SEQ ID NO: 617 | AGCGAAGT | Synthetic |
| SEQ ID NO: 618 | CTTACGCA | Synthetic |
| SEQ ID NO: 619 | ACTTGACC | Synthetic |
| SEQ ID NO: 620 | GTAAGCCT | Synthetic |
| SEQ ID NO: 621 | CGAGAATC | Synthetic |
| SEQ ID NO: 622 | TAGGAGAC | Synthetic |
| SEQ ID NO: 623 | ATACCGTC | Synthetic |
| SEQ ID NO: 624 | ACACCATG | Synthetic |
| SEQ ID NO: 625 | GGTAGACA | Synthetic |
| SEQ ID NO: 626 | TGCATGGT | Synthetic |
| SEQ ID NO: 627 | CAGGAATG | Synthetic |
| SEQ ID NO: 628 | CTAGTCCT | Synthetic |
| SEQ ID NO: 629 | CAACAAGC | Synthetic |
| SEQ ID NO: 630 | GTGTGACT | Synthetic |
| SEQ ID NO: 631 | ACAACTGG | Synthetic |
| SEQ ID NO: 632 | GAATGGAG | Synthetic |
| SEQ ID NO: 633 | GTTGGCAA | Synthetic |
| SEQ ID NO: 634 | ATGTGCTC | Synthetic |
| SEQ ID NO: 635 | CACCACAT | Synthetic |
| SEQ ID NO: 636 | TAGATCGC | Synthetic |
| SEQ ID NO: 637 | CTCTCTAT | Synthetic |
| SEQ ID NO: 638 | TATCCTCT | Synthetic |
| SEQ ID NO: 639 | AGAGTAGA | Synthetic |
| SEQ ID NO: 640 | GTAAGGAG | Synthetic |
| SEQ ID NO: 641 | ACTGCATA | Synthetic |
| SEQ ID NO: 642 | AAGGAGTA | Synthetic |
| SEQ ID NO: 643 | CTAAGCCT | Synthetic |
| SEQ ID NO: 644 | AGATCGGAAGAGCGTCGTG | Synthetic |
| SEQ ID NO: 645 | TTACCGCGGCKGCTGRCAC | Synthetic |
| SEQ ID NO: 646 | GCTTCTTAGTCAGGTACCG | Synthetic |
| SEQ ID NO: 647 | GGTATTAGCAYCTGTTTCCA | Synthetic |
| SEQ ID NO: 648 | GGTCGGTCTCTCAACCC | Synthetic |

TABLE 6-continued

Sequences

| Sequence ID Number | Sequence | Species |
| --- | --- | --- |
| SEQ ID NO: 649 | GCTTCTTAGTCAGGTACCG | Synthetic |
| SEQ ID NO: 650 | GCTGCCTCCCGTAGGAGT | Synthetic |
| SEQ ID NO: 651 | ACTCCTACGGGAGGCAGC | Synthetic |

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A method of determining microbial identities and/or abundances in a biological sample, the method comprising:
   (a) immobilizing the biological sample in a matrix;
   (b) fracturing the matrix into clusters; and
   (c) determining identities and/or abundances of microbes in the clusters,
   wherein in step (b) the matrix is fractured through cryo-fracturing.

2. The method of claim 1, wherein the clusters comprise co-localized cells.

3. The method of claim 1, wherein in step (c) identities and/or abundances of microbes are determined by sequencing DNAs and/or RNAs.

4. The method of claim 3, wherein the DNAs are genomic DNAs.

5. The method of claim 1, wherein the in step (c) identities and/or abundances of microbes are determined by analyzing proteins, polypeptides, and/or metabolites.

6. The method of claim 1, wherein in step (a) the biological sample is immobilized via perfusion and polymerization of the matrix.

7. The method of claim 1, wherein the matrix comprises a polymer.

8. The method of claim 1, wherein the matrix comprises an acrylamide polymer.

9. The method of claim 1, wherein the matrix comprises a plurality of 16S ribosomal RNA (16S rRNA) amplification primers.

10. The method of claim 9, wherein the plurality of 16S rRNA amplification primers are covalently linked to the matrix.

11. The method of claim 9, wherein the plurality of 16S rRNA amplification primers are linked to the matrix through photocleavable linkers.

12. The method of claim 11, wherein the photocleavable linkers are acrydite linkers.

13. The method of claim 1, further comprising step (d) processing the matrix by chemical or enzymatic means after step (a) or step (b).

14. The method of claim 13, wherein step (d) comprises lysing cells.

15. The method of claim 1, further comprising passing the clusters through a filter for size selection.

16. The method of claim 15, wherein after passing the clusters through a filter for size selection the clusters have a median diameter ranging from about 1 μm to about 100 μm.

17. The method of claim 15, wherein after passing the clusters through a filter for size selection the clusters have a median diameter ranging from about 10 μm to about 50 μm.

18. The method of claim 15, wherein after passing the clusters through a filter for size selection the clusters have a median diameter ranging from about 1 μm to about 20 μm.

19. The method of claim 1, wherein the clusters are microparticles.

20. The method of claim 1, wherein the cryo-fracturing is cryo-bead beating.

21. The method of claim 1, wherein in step (c) identities and/or abundances of microbes are determined through droplet-based encapsulation.

22. The method of claim 21, wherein the droplet-based encapsulation is through co-encapsulating the clusters with beads in droplets, wherein each droplet comprises a cluster and a bead, each bead comprising a unique molecular barcode.

23. The method of claim 22, wherein the beads comprise a plurality of 16S rRNA amplification primers, and wherein the plurality of 16S rRNA amplification primers linked to each bead comprise a unique molecular barcode.

24. The method of claim 23, wherein the plurality of 16S rRNA amplification primers are covalently linked to the beads.

25. The method of claim 23, wherein the plurality of 16S rRNA amplification primers are linked to the beads through photocleavable linkers.

26. The method of claim 25, wherein the photocleavable linkers are acrydite linkers.

27. The method of claim 22, wherein the beads comprise a polymer.

28. The method of claim 22, wherein the beads comprise an acrylamide polymer.

29. The method of claim 21, wherein the droplet-based encapsulation is through capturing the clusters in emulsion droplets comprising molecular barcodes, each emulsion droplet comprising identical molecular barcodes.

30. The method of claim 29, wherein the emulsion droplets have a diameter ranging from about 35 μm to about 45 μm.

31. The method of claim 1, further comprising cleaving the plurality of 16S rRNA amplification primers from the matrix and/or the beads.

32. The method of claim 1, further comprising degrading the matrix.

33. The method of claim 32, wherein the matrix is degraded through exposure to reducing conditions.

34. The method of claim 1, further comprising polymerase chain reaction (PCR) amplification.

35. The method of claim 3, wherein the sequencing is deep sequencing.

36. The method of claim 1, wherein the biological sample is obtained from a mammal.

37. The method of claim 36, wherein the biological sample is obtained from a nervous system, a pulmonary system, a peripheral vascular system, a cardiovascular system, and/or a gastrointestinal system of a mammal.

38. The method of claim 36, wherein the biological sample is obtained from the brain, a lung, a bronchus, an alveolus, an artery, a vein, a heart, an esophagus, a stomach, a small intestine, a large intestine, or combinations thereof.

39. The method of claim 1, wherein the biological sample is obtained from a tumor or is a tumor sample.

40. The method of claim 1, wherein the biological sample is a soil sample, a gut sample, and/or a biofilm sample.

41. The method of claim 1, wherein the biological sample is an environmental sample.

42. A method of determining microbial identities and/or abundances in a biological sample, the method comprising:
  (a) immobilizing the biological sample in a matrix;
  (b) fracturing the matrix into clusters; and
  (c) determining identities and/or abundances of microbes in the clusters,
wherein the matrix comprises an acrylamide polymer.

\* \* \* \* \*

SEQUENCE LISTING

<160> NUMBER OF SEQ ID NOS: 651

<210> SEQ ID NO 1
<211> LENGTH: 27
<212> TYPE: DNA
<213> ORGANISM: Artificial Sequence
<220> FEATURE:
<223> OTHER INFORMATION: Synthetic

<400> SEQUENCE: 1
gactactcca cgacgctctt ccgatct                                          27

<210> SEQ ID NO 2
<211> LENGTH: 48
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (36)..(36)
<223> OTHER INFORMATION: n is a, c, g, or t

<400> SEQUENCE: 2
attaggtcga cgtgtgctct tccgatctgg actacnvggg twtctaat                   48

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
ttaccgcggc kgctgrcac                                                   19

<210> SEQ ID NO 4
<211> LENGTH: 44
<212> TYPE: DNA
<213> ORGANISM: Artificial Sequence
<220> FEATURE:
<223> OTHER INFORMATION: Synthetic

<400> SEQUENCE: 4
cgctcagcag tgtctcgcac ctagtagatc ggaagagcgt cgtg            44

<210> SEQ ID NO 5
<211> LENGTH: 44
<212> TYPE: DNA
<213> ORGANISM: Artificial Sequence
<220> FEATURE:
<223> OTHER INFORMATION: Synthetic

<400> SEQUENCE: 5
cgctcagcag tgtctcgcta gagctagatc ggaagagcgt cgtg            44

<210> SEQ ID NO 6
<211> LENGTH: 44
<212> TYPE: DNA
<213> ORGANISM: Artificial Sequence
<220> FEATURE:
<223> OTHER INFORMATION: Synthetic

<400> SEQUENCE: 6
cgctcagcag tgtctcgcac tctctagatc ggaagagcgt cgtg            44

<210> SEQ ID NO 7
<211> LENGTH: 44
<212> TYPE: DNA
<213> ORGANISM: Artificial Sequence
<220> FEATURE:
<223> OTHER INFORMATION: Synthetic

<400> SEQUENCE: 7
cgctcagcag tgtctcgcgg aacacagatc ggaagagcgt cgtg            44

<210> SEQ ID NO 8
<211> LENGTH: 44
<212> TYPE: DNA
<213> ORGANISM: Artificial Sequence
<220> FEATURE:
<223> OTHER INFORMATION: Synthetic

<400> SEQUENCE: 8
cgctcagcag tgtctcgcca gctaaagatc ggaagagcgt cgtg            44

<210> SEQ ID NO 9
<211> LENGTH: 44
<212> TYPE: DNA
<213> ORGANISM: Artificial Sequence
<220> FEATURE:
<223> OTHER INFORMATION: Synthetic

<400> SEQUENCE: 9
cgctcagcag tgtctcgcgt atggtagatc ggaagagcgt cgtg            44

<210> SEQ ID NO 10
<211> LENGTH: 44
<212> TYPE: DNA
<213> ORGANISM: Artificial Sequence
<220> FEATURE:
<223> OTHER INFORMATION: Synthetic

<400> SEQUENCE: 10
cgctcagcag tgtctcgcaa cggtaagatc ggaagagcgt cgtg            44

<210> SEQ ID NO 11

<211> LENGTH: 44
<212> TYPE: DNA
<213> ORGANISM: Artificial Sequence
<220> FEATURE:
<223> OTHER INFORMATION: Synthetic

<400> SEQUENCE: 11
cgctcagcag tgtctcgcag ttggcagatc ggaagagcgt cgtg         44

<210> SEQ ID NO 12
<211> LENGTH: 44
<212> TYPE: DNA
<213> ORGANISM: Artificial Sequence
<220> FEATURE:
<223> OTHER INFORMATION: Synthetic

<400> SEQUENCE: 12
cgctcagcag tgtctcgcag acttcagatc ggaagagcgt cgtg         44

<210> SEQ ID NO 13
<211> LENGTH: 44
<212> TYPE: DNA
<213> ORGANISM: Artificial Sequence
<220> FEATURE:
<223> OTHER INFORMATION: Synthetic

<400> SEQUENCE: 13
cgctcagcag tgtctcgcgt gcttaagatc ggaagagcgt cgtg         44

<210> SEQ ID NO 14
<211> LENGTH: 44
<212> TYPE: DNA
<213> ORGANISM: Artificial Sequence
<220> FEATURE:
<223> OTHER INFORMATION: Synthetic

<400> SEQUENCE: 14
cgctcagcag tgtctcgccc actagagatc ggaagagcgt cgtg         44

<210> SEQ ID NO 15
<211> LENGTH: 44
<212> TYPE: DNA
<213> ORGANISM: Artificial Sequence
<220> FEATURE:
<223> OTHER INFORMATION: Synthetic

<400> SEQUENCE: 15
cgctcagcag tgtctcgcgc gctatagatc ggaagagcgt cgtg         44

<210> SEQ ID NO 16
<211> LENGTH: 44
<212> TYPE: DNA
<213> ORGANISM: Artificial Sequence
<220> FEATURE:
<223> OTHER INFORMATION: Synthetic

<400> SEQUENCE: 16
cgctcagcag tgtctcgctg acactagatc ggaagagcgt cgtg         44

<210> SEQ ID NO 17
<211> LENGTH: 44
<212> TYPE: DNA
<213> ORGANISM: Artificial Sequence
<220> FEATURE:
<223> OTHER INFORMATION: Synthetic

<400> SEQUENCE: 17
cgctcagcag tgtctcgcga ggaacagatc ggaagagcgt cgtg    44

<210> SEQ ID NO 18
<211> LENGTH: 44
<212> TYPE: DNA
<213> ORGANISM: Artificial Sequence
<220> FEATURE:
<223> OTHER INFORMATION: Synthetic

<400> SEQUENCE: 18
cgctcagcag tgtctcgctt gaccaagatc ggaagagcgt cgtg    44

<210> SEQ ID NO 19
<211> LENGTH: 44
<212> TYPE: DNA
<213> ORGANISM: Artificial Sequence
<220> FEATURE:
<223> OTHER INFORMATION: Synthetic

<400> SEQUENCE: 19
cgctcagcag tgtctcgcgg tagcaagatc ggaagagcgt cgtg    44

<210> SEQ ID NO 20
<211> LENGTH: 44
<212> TYPE: DNA
<213> ORGANISM: Artificial Sequence
<220> FEATURE:
<223> OTHER INFORMATION: Synthetic

<400> SEQUENCE: 20
cgctcagcag tgtctcgccg ttgagagatc ggaagagcgt cgtg    44

<210> SEQ ID NO 21
<211> LENGTH: 44
<212> TYPE: DNA
<213> ORGANISM: Artificial Sequence
<220> FEATURE:
<223> OTHER INFORMATION: Synthetic

<400> SEQUENCE: 21
cgctcagcag tgtctcgcac aactgagatc ggaagagcgt cgtg    44

<210> SEQ ID NO 22
<211> LENGTH: 44
<212> TYPE: DNA
<213> ORGANISM: Artificial Sequence
<220> FEATURE:
<223> OTHER INFORMATION: Synthetic

<400> SEQUENCE: 22
cgctcagcag tgtctcgctc agtcaagatc ggaagagcgt cgtg    44

<210> SEQ ID NO 23
<211> LENGTH: 44
<212> TYPE: DNA
<213> ORGANISM: Artificial Sequence
<220> FEATURE:
<223> OTHER INFORMATION: Synthetic

<400> SEQUENCE: 23
cgctcagcag tgtctcgccg tacatagatc ggaagagcgt cgtg    44

<210> SEQ ID NO 24
<211> LENGTH: 44
<212> TYPE: DNA

```
<213> ORGANISM: Artificial Sequence
<220> FEATURE:
<223> OTHER INFORMATION: Synthetic

<400> SEQUENCE: 24
cgctcagcag tgtctcgctg agtgcagatc ggaagagcgt cgtg          44

<210> SEQ ID NO 25
<211> LENGTH: 44
<212> TYPE: DNA
<213> ORGANISM: Artificial Sequence
<220> FEATURE:
<223> OTHER INFORMATION: Synthetic

<400> SEQUENCE: 25
cgctcagcag tgtctcgccc tgttaagatc ggaagagcgt cgtg          44

<210> SEQ ID NO 26
<211> LENGTH: 44
<212> TYPE: DNA
<213> ORGANISM: Artificial Sequence
<220> FEATURE:
<223> OTHER INFORMATION: Synthetic

<400> SEQUENCE: 26
cgctcagcag tgtctcgcac ctctaagatc ggaagagcgt cgtg          44

<210> SEQ ID NO 27
<211> LENGTH: 44
<212> TYPE: DNA
<213> ORGANISM: Artificial Sequence
<220> FEATURE:
<223> OTHER INFORMATION: Synthetic

<400> SEQUENCE: 27
cgctcagcag tgtctcgcat tccacagatc ggaagagcgt cgtg          44

<210> SEQ ID NO 28
<211> LENGTH: 44
<212> TYPE: DNA
<213> ORGANISM: Artificial Sequence
<220> FEATURE:
<223> OTHER INFORMATION: Synthetic

<400> SEQUENCE: 28
cgctcagcag tgtctcgctc gtatgagatc ggaagagcgt cgtg          44

<210> SEQ ID NO 29
<211> LENGTH: 44
<212> TYPE: DNA
<213> ORGANISM: Artificial Sequence
<220> FEATURE:
<223> OTHER INFORMATION: Synthetic

<400> SEQUENCE: 29
cgctcagcag tgtctcgcag gttgtagatc ggaagagcgt cgtg          44

<210> SEQ ID NO 30
<211> LENGTH: 44
<212> TYPE: DNA
<213> ORGANISM: Artificial Sequence
<220> FEATURE:
<223> OTHER INFORMATION: Synthetic

<400> SEQUENCE: 30
cgctcagcag tgtctcgccg tagtcagatc ggaagagcgt cgtg          44
```

<210> SEQ ID NO 31
<211> LENGTH: 44
<212> TYPE: DNA
<213> ORGANISM: Artificial Sequence
<220> FEATURE:
<223> OTHER INFORMATION: Synthetic

<400> SEQUENCE: 31
cgctcagcag tgtctcgcct tctcgagatc ggaagagcgt cgtg       44

<210> SEQ ID NO 32
<211> LENGTH: 44
<212> TYPE: DNA
<213> ORGANISM: Artificial Sequence
<220> FEATURE:
<223> OTHER INFORMATION: Synthetic

<400> SEQUENCE: 32
cgctcagcag tgtctcgcag gtaagagatc ggaagagcgt cgtg       44

<210> SEQ ID NO 33
<211> LENGTH: 44
<212> TYPE: DNA
<213> ORGANISM: Artificial Sequence
<220> FEATURE:
<223> OTHER INFORMATION: Synthetic

<400> SEQUENCE: 33
cgctcagcag tgtctcgcga tctcaagatc ggaagagcgt cgtg       44

<210> SEQ ID NO 34
<211> LENGTH: 44
<212> TYPE: DNA
<213> ORGANISM: Artificial Sequence
<220> FEATURE:
<223> OTHER INFORMATION: Synthetic

<400> SEQUENCE: 34
cgctcagcag tgtctcgcat cgaacagatc ggaagagcgt cgtg       44

<210> SEQ ID NO 35
<211> LENGTH: 44
<212> TYPE: DNA
<213> ORGANISM: Artificial Sequence
<220> FEATURE:
<223> OTHER INFORMATION: Synthetic

<400> SEQUENCE: 35
cgctcagcag tgtctcgcca cgcatagatc ggaagagcgt cgtg       44

<210> SEQ ID NO 36
<211> LENGTH: 45
<212> TYPE: DNA
<213> ORGANISM: Artificial Sequence
<220> FEATURE:
<223> OTHER INFORMATION: Synthetic

<400> SEQUENCE: 36
cgctcagcag tgtctcgcaa ctcaggagat cggaagagcg tcgtg      45

<210> SEQ ID NO 37
<211> LENGTH: 45
<212> TYPE: DNA
<213> ORGANISM: Artificial Sequence
<220> FEATURE:

<223> OTHER INFORMATION: Synthetic

<400> SEQUENCE: 37
cgctcagcag tgtctcgctg ccacaaagat cggaagagcg tcgtg        45

<210> SEQ ID NO 38
<211> LENGTH: 45
<212> TYPE: DNA
<213> ORGANISM: Artificial Sequence
<220> FEATURE:
<223> OTHER INFORMATION: Synthetic

<400> SEQUENCE: 38
cgctcagcag tgtctcgcat ggcgatagat cggaagagcg tcgtg        45

<210> SEQ ID NO 39
<211> LENGTH: 45
<212> TYPE: DNA
<213> ORGANISM: Artificial Sequence
<220> FEATURE:
<223> OTHER INFORMATION: Synthetic

<400> SEQUENCE: 39
cgctcagcag tgtctcgcaa tcagcgagat cggaagagcg tcgtg        45

<210> SEQ ID NO 40
<211> LENGTH: 45
<212> TYPE: DNA
<213> ORGANISM: Artificial Sequence
<220> FEATURE:
<223> OTHER INFORMATION: Synthetic

<400> SEQUENCE: 40
cgctcagcag tgtctcgcgg ttgtacagat cggaagagcg tcgtg        45

<210> SEQ ID NO 41
<211> LENGTH: 45
<212> TYPE: DNA
<213> ORGANISM: Artificial Sequence
<220> FEATURE:
<223> OTHER INFORMATION: Synthetic

<400> SEQUENCE: 41
cgctcagcag tgtctcgcct cgacttagat cggaagagcg tcgtg        45

<210> SEQ ID NO 42
<211> LENGTH: 45
<212> TYPE: DNA
<213> ORGANISM: Artificial Sequence
<220> FEATURE:
<223> OTHER INFORMATION: Synthetic

<400> SEQUENCE: 42
cgctcagcag tgtctcgcta ggaagcagat cggaagagcg tcgtg        45

<210> SEQ ID NO 43
<211> LENGTH: 45
<212> TYPE: DNA
<213> ORGANISM: Artificial Sequence
<220> FEATURE:
<223> OTHER INFORMATION: Synthetic

<400> SEQUENCE: 43
cgctcagcag tgtctcgcgt gcatgtagat cggaagagcg tcgtg        45

```
<210> SEQ ID NO 44
<211> LENGTH: 45
<212> TYPE: DNA
<213> ORGANISM: Artificial Sequence
<220> FEATURE:
<223> OTHER INFORMATION: Synthetic

<400> SEQUENCE: 44
cgctcagcag tgtctcgctc aatcggagat cggaagagcg tcgtg         45

<210> SEQ ID NO 45
<211> LENGTH: 45
<212> TYPE: DNA
<213> ORGANISM: Artificial Sequence
<220> FEATURE:
<223> OTHER INFORMATION: Synthetic

<400> SEQUENCE: 45
cgctcagcag tgtctcgctc aagctcagat cggaagagcg tcgtg         45

<210> SEQ ID NO 46
<211> LENGTH: 45
<212> TYPE: DNA
<213> ORGANISM: Artificial Sequence
<220> FEATURE:
<223> OTHER INFORMATION: Synthetic

<400> SEQUENCE: 46
cgctcagcag tgtctcgcag tgtcacagat cggaagagcg tcgtg         45

<210> SEQ ID NO 47
<211> LENGTH: 45
<212> TYPE: DNA
<213> ORGANISM: Artificial Sequence
<220> FEATURE:
<223> OTHER INFORMATION: Synthetic

<400> SEQUENCE: 47
cgctcagcag tgtctcgctg tgttccagat cggaagagcg tcgtg         45

<210> SEQ ID NO 48
<211> LENGTH: 45
<212> TYPE: DNA
<213> ORGANISM: Artificial Sequence
<220> FEATURE:
<223> OTHER INFORMATION: Synthetic

<400> SEQUENCE: 48
cgctcagcag tgtctcgctc cgaatcagat cggaagagcg tcgtg         45

<210> SEQ ID NO 49
<211> LENGTH: 45
<212> TYPE: DNA
<213> ORGANISM: Artificial Sequence
<220> FEATURE:
<223> OTHER INFORMATION: Synthetic

<400> SEQUENCE: 49
cgctcagcag tgtctcgcgg agtacaagat cggaagagcg tcgtg         45

<210> SEQ ID NO 50
<211> LENGTH: 45
<212> TYPE: DNA
<213> ORGANISM: Artificial Sequence
<220> FEATURE:
<223> OTHER INFORMATION: Synthetic
```

```
<400> SEQUENCE: 50
cgctcagcag tgtctcgcag gacagaagat cggaagagcg tcgtg          45

<210> SEQ ID NO 51
<211> LENGTH: 45
<212> TYPE: DNA
<213> ORGANISM: Artificial Sequence
<220> FEATURE:
<223> OTHER INFORMATION: Synthetic

<400> SEQUENCE: 51
cgctcagcag tgtctcgcgc acagttagat cggaagagcg tcgtg          45

<210> SEQ ID NO 52
<211> LENGTH: 45
<212> TYPE: DNA
<213> ORGANISM: Artificial Sequence
<220> FEATURE:
<223> OTHER INFORMATION: Synthetic

<400> SEQUENCE: 52
cgctcagcag tgtctcgccg acaacaagat cggaagagcg tcgtg          45

<210> SEQ ID NO 53
<211> LENGTH: 45
<212> TYPE: DNA
<213> ORGANISM: Artificial Sequence
<220> FEATURE:
<223> OTHER INFORMATION: Synthetic

<400> SEQUENCE: 53
cgctcagcag tgtctcgcag cacgtaagat cggaagagcg tcgtg          45

<210> SEQ ID NO 54
<211> LENGTH: 45
<212> TYPE: DNA
<213> ORGANISM: Artificial Sequence
<220> FEATURE:
<223> OTHER INFORMATION: Synthetic

<400> SEQUENCE: 54
cgctcagcag tgtctcgccc aacagtagat cggaagagcg tcgtg          45

<210> SEQ ID NO 55
<211> LENGTH: 45
<212> TYPE: DNA
<213> ORGANISM: Artificial Sequence
<220> FEATURE:
<223> OTHER INFORMATION: Synthetic

<400> SEQUENCE: 55
cgctcagcag tgtctcgctc aggacaagat cggaagagcg tcgtg          45

<210> SEQ ID NO 56
<211> LENGTH: 45
<212> TYPE: DNA
<213> ORGANISM: Artificial Sequence
<220> FEATURE:
<223> OTHER INFORMATION: Synthetic

<400> SEQUENCE: 56
cgctcagcag tgtctcgcct atcctgagat cggaagagcg tcgtg          45

<210> SEQ ID NO 57
<211> LENGTH: 45
```

```
<212> TYPE: DNA
<213> ORGANISM: Artificial Sequence
<220> FEATURE:
<223> OTHER INFORMATION: Synthetic

<400> SEQUENCE: 57
cgctcagcag tgtctcgctg tctgtcagat cggaagagcg tcgtg            45

<210> SEQ ID NO 58
<211> LENGTH: 45
<212> TYPE: DNA
<213> ORGANISM: Artificial Sequence
<220> FEATURE:
<223> OTHER INFORMATION: Synthetic

<400> SEQUENCE: 58
cgctcagcag tgtctcgccc tagtctagat cggaagagcg tcgtg            45

<210> SEQ ID NO 59
<211> LENGTH: 45
<212> TYPE: DNA
<213> ORGANISM: Artificial Sequence
<220> FEATURE:
<223> OTHER INFORMATION: Synthetic

<400> SEQUENCE: 59
cgctcagcag tgtctcgcgt aatggcagat cggaagagcg tcgtg            45

<210> SEQ ID NO 60
<211> LENGTH: 45
<212> TYPE: DNA
<213> ORGANISM: Artificial Sequence
<220> FEATURE:
<223> OTHER INFORMATION: Synthetic

<400> SEQUENCE: 60
cgctcagcag tgtctcgcta gtggctagat cggaagagcg tcgtg            45

<210> SEQ ID NO 61
<211> LENGTH: 45
<212> TYPE: DNA
<213> ORGANISM: Artificial Sequence
<220> FEATURE:
<223> OTHER INFORMATION: Synthetic

<400> SEQUENCE: 61
cgctcagcag tgtctcgcga atctgcagat cggaagagcg tcgtg            45

<210> SEQ ID NO 62
<211> LENGTH: 45
<212> TYPE: DNA
<213> ORGANISM: Artificial Sequence
<220> FEATURE:
<223> OTHER INFORMATION: Synthetic

<400> SEQUENCE: 62
cgctcagcag tgtctcgctt cgatgcagat cggaagagcg tcgtg            45

<210> SEQ ID NO 63
<211> LENGTH: 45
<212> TYPE: DNA
<213> ORGANISM: Artificial Sequence
<220> FEATURE:
<223> OTHER INFORMATION: Synthetic

<400> SEQUENCE: 63
```
cgctcagcag tgtctcgcgc ttggttagat cggaagagcg tcgtg   45

<210> SEQ ID NO 64
<211> LENGTH: 45
<212> TYPE: DNA
<213> ORGANISM: Artificial Sequence
<220> FEATURE:
<223> OTHER INFORMATION: Synthetic

<400> SEQUENCE: 64
cgctcagcag tgtctcgcag ctgatcagat cggaagagcg tcgtg   45

<210> SEQ ID NO 65
<211> LENGTH: 45
<212> TYPE: DNA
<213> ORGANISM: Artificial Sequence
<220> FEATURE:
<223> OTHER INFORMATION: Synthetic

<400> SEQUENCE: 65
cgctcagcag tgtctcgcat aagcggagat cggaagagcg tcgtg   45

<210> SEQ ID NO 66
<211> LENGTH: 45
<212> TYPE: DNA
<213> ORGANISM: Artificial Sequence
<220> FEATURE:
<223> OTHER INFORMATION: Synthetic

<400> SEQUENCE: 66
cgctcagcag tgtctcgcac ttcggaagat cggaagagcg tcgtg   45

<210> SEQ ID NO 67
<211> LENGTH: 45
<212> TYPE: DNA
<213> ORGANISM: Artificial Sequence
<220> FEATURE:
<223> OTHER INFORMATION: Synthetic

<400> SEQUENCE: 67
cgctcagcag tgtctcgcct agtcgaagat cggaagagcg tcgtg   45

<210> SEQ ID NO 68
<211> LENGTH: 46
<212> TYPE: DNA
<213> ORGANISM: Artificial Sequence
<220> FEATURE:
<223> OTHER INFORMATION: Synthetic

<400> SEQUENCE: 68
cgctcagcag tgtctcgctg tagactcaga tcggaagagc gtcgtg   46

<210> SEQ ID NO 69
<211> LENGTH: 46
<212> TYPE: DNA
<213> ORGANISM: Artificial Sequence
<220> FEATURE:
<223> OTHER INFORMATION: Synthetic

<400> SEQUENCE: 69
cgctcagcag tgtctcgctg tagactcaga tcggaagagc gtcgtg   46

<210> SEQ ID NO 70
<211> LENGTH: 46
<212> TYPE: DNA
<213> ORGANISM: Artificial Sequence
<220> FEATURE:
<223> OTHER INFORMATION: Synthetic

<400> SEQUENCE: 70
cgctcagcag tgtctcgcga aggcctaaga tcggaagagc gtcgtg        46

<210> SEQ ID NO 71
<211> LENGTH: 46
<212> TYPE: DNA
<213> ORGANISM: Artificial Sequence
<220> FEATURE:
<223> OTHER INFORMATION: Synthetic

<400> SEQUENCE: 71
cgctcagcag tgtctcgctt cgtaaggaga tcggaagagc gtcgtg        46

<210> SEQ ID NO 72
<211> LENGTH: 46
<212> TYPE: DNA
<213> ORGANISM: Artificial Sequence
<220> FEATURE:
<223> OTHER INFORMATION: Synthetic

<400> SEQUENCE: 72
cgctcagcag tgtctcgctg atcacctaga tcggaagagc gtcgtg        46

<210> SEQ ID NO 73
<211> LENGTH: 46
<212> TYPE: DNA
<213> ORGANISM: Artificial Sequence
<220> FEATURE:
<223> OTHER INFORMATION: Synthetic

<400> SEQUENCE: 73
cgctcagcag tgtctcgcta gctaacgaga tcggaagagc gtcgtg        46

<210> SEQ ID NO 74
<211> LENGTH: 46
<212> TYPE: DNA
<213> ORGANISM: Artificial Sequence
<220> FEATURE:
<223> OTHER INFORMATION: Synthetic

<400> SEQUENCE: 74
cgctcagcag tgtctcgccg tagaaggaga tcggaagagc gtcgtg        46

<210> SEQ ID NO 75
<211> LENGTH: 46
<212> TYPE: DNA
<213> ORGANISM: Artificial Sequence
<220> FEATURE:
<223> OTHER INFORMATION: Synthetic

<400> SEQUENCE: 75
cgctcagcag tgtctcgctc tctcgaaaga tcggaagagc gtcgtg        46

<210> SEQ ID NO 76
<211> LENGTH: 46
<212> TYPE: DNA
<213> ORGANISM: Artificial Sequence
<220> FEATURE:
<223> OTHER INFORMATION: Synthetic

<400> SEQUENCE: 76
cgctcagcag tgtctcgctc tagttccaga tcggaagagc gtcgtg        46

<210> SEQ ID NO 77
<211> LENGTH: 46
<212> TYPE: DNA
<213> ORGANISM: Artificial Sequence
<220> FEATURE:
<223> OTHER INFORMATION: Synthetic

<400> SEQUENCE: 77
cgctcagcag tgtctcgccc gaagagaaga tcggaagagc gtcgtg            46

<210> SEQ ID NO 78
<211> LENGTH: 46
<212> TYPE: DNA
<213> ORGANISM: Artificial Sequence
<220> FEATURE:
<223> OTHER INFORMATION: Synthetic

<400> SEQUENCE: 78
cgctcagcag tgtctcgcag gtgacataga tcggaagagc gtcgtg            46

<210> SEQ ID NO 79
<211> LENGTH: 46
<212> TYPE: DNA
<213> ORGANISM: Artificial Sequence
<220> FEATURE:
<223> OTHER INFORMATION: Synthetic

<400> SEQUENCE: 79
cgctcagcag tgtctcgcct gagaacgaga tcggaagagc gtcgtg            46

<210> SEQ ID NO 80
<211> LENGTH: 46
<212> TYPE: DNA
<213> ORGANISM: Artificial Sequence
<220> FEATURE:
<223> OTHER INFORMATION: Synthetic

<400> SEQUENCE: 80
cgctcagcag tgtctcgccc agctgaaaga tcggaagagc gtcgtg            46

<210> SEQ ID NO 81
<211> LENGTH: 46
<212> TYPE: DNA
<213> ORGANISM: Artificial Sequence
<220> FEATURE:
<223> OTHER INFORMATION: Synthetic

<400> SEQUENCE: 81
cgctcagcag tgtctcgccg ttcgacaaga tcggaagagc gtcgtg            46

<210> SEQ ID NO 82
<211> LENGTH: 46
<212> TYPE: DNA
<213> ORGANISM: Artificial Sequence
<220> FEATURE:
<223> OTHER INFORMATION: Synthetic

<400> SEQUENCE: 82
cgctcagcag tgtctcgctc ttagaccaga tcggaagagc gtcgtg            46

<210> SEQ ID NO 83
<211> LENGTH: 46
<212> TYPE: DNA
<213> ORGANISM: Artificial Sequence
<220> FEATURE:
<223> OTHER INFORMATION: Synthetic

<400> SEQUENCE: 83
cgctcagcag tgtctcgcca cgagcaaaga tcggaagagc gtcgtg         46

<210> SEQ ID NO 84
<211> LENGTH: 46
<212> TYPE: DNA
<213> ORGANISM: Artificial Sequence
<220> FEATURE:
<223> OTHER INFORMATION: Synthetic

<400> SEQUENCE: 84
cgctcagcag tgtctcgcct gccgaataga tcggaagagc gtcgtg         46

<210> SEQ ID NO 85
<211> LENGTH: 46
<212> TYPE: DNA
<213> ORGANISM: Artificial Sequence
<220> FEATURE:
<223> OTHER INFORMATION: Synthetic

<400> SEQUENCE: 85
cgctcagcag tgtctcgcgg gctcataaga tcggaagagc gtcgtg         46

<210> SEQ ID NO 86
<211> LENGTH: 46
<212> TYPE: DNA
<213> ORGANISM: Artificial Sequence
<220> FEATURE:
<223> OTHER INFORMATION: Synthetic

<400> SEQUENCE: 86
cgctcagcag tgtctcgcca ccgtactaga tcggaagagc gtcgtg         46

<210> SEQ ID NO 87
<211> LENGTH: 46
<212> TYPE: DNA
<213> ORGANISM: Artificial Sequence
<220> FEATURE:
<223> OTHER INFORMATION: Synthetic

<400> SEQUENCE: 87
cgctcagcag tgtctcgcgt gtctcgaaga tcggaagagc gtcgtg         46

<210> SEQ ID NO 88
<211> LENGTH: 46
<212> TYPE: DNA
<213> ORGANISM: Artificial Sequence
<220> FEATURE:
<223> OTHER INFORMATION: Synthetic

<400> SEQUENCE: 88
cgctcagcag tgtctcgctt actgcgaaga tcggaagagc gtcgtg         46

<210> SEQ ID NO 89
<211> LENGTH: 46
<212> TYPE: DNA
<213> ORGANISM: Artificial Sequence
<220> FEATURE:
<223> OTHER INFORMATION: Synthetic

<400> SEQUENCE: 89
cgctcagcag tgtctcgctc catacgaaga tcggaagagc gtcgtg         46

<210> SEQ ID NO 90

```
<211> LENGTH: 46
<212> TYPE: DNA
<213> ORGANISM: Artificial Sequence
<220> FEATURE:
<223> OTHER INFORMATION: Synthetic

<400> SEQUENCE: 90
cgctcagcag tgtctcgcga tccaggtaga tcggaagagc gtcgtg                    46

<210> SEQ ID NO 91
<211> LENGTH: 46
<212> TYPE: DNA
<213> ORGANISM: Artificial Sequence
<220> FEATURE:
<223> OTHER INFORMATION: Synthetic

<400> SEQUENCE: 91
cgctcagcag tgtctcgcag ttgcgaaaga tcggaagagc gtcgtg                    46

<210> SEQ ID NO 92
<211> LENGTH: 46
<212> TYPE: DNA
<213> ORGANISM: Artificial Sequence
<220> FEATURE:
<223> OTHER INFORMATION: Synthetic

<400> SEQUENCE: 92
cgctcagcag tgtctcgcag gttgagaaga tcggaagagc gtcgtg                    46

<210> SEQ ID NO 93
<211> LENGTH: 46
<212> TYPE: DNA
<213> ORGANISM: Artificial Sequence
<220> FEATURE:
<223> OTHER INFORMATION: Synthetic

<400> SEQUENCE: 93
cgctcagcag tgtctcgcgt tgcgcttaga tcggaagagc gtcgtg                    46

<210> SEQ ID NO 94
<211> LENGTH: 46
<212> TYPE: DNA
<213> ORGANISM: Artificial Sequence
<220> FEATURE:
<223> OTHER INFORMATION: Synthetic

<400> SEQUENCE: 94
cgctcagcag tgtctcgcct cgagagaaga tcggaagagc gtcgtg                    46

<210> SEQ ID NO 95
<211> LENGTH: 46
<212> TYPE: DNA
<213> ORGANISM: Artificial Sequence
<220> FEATURE:
<223> OTHER INFORMATION: Synthetic

<400> SEQUENCE: 95
cgctcagcag tgtctcgctg ttcctagaga tcggaagagc gtcgtg                    46

<210> SEQ ID NO 96
<211> LENGTH: 46
<212> TYPE: DNA
<213> ORGANISM: Artificial Sequence
<220> FEATURE:
<223> OTHER INFORMATION: Synthetic

<400> SEQUENCE: 96
```

```
cgctcagcag tgtctcgcct cacactgaga tcggaagagc gtcgtg          46
```

<210> SEQ ID NO 97
<211> LENGTH: 46
<212> TYPE: DNA
<213> ORGANISM: Artificial Sequence
<220> FEATURE:
<223> OTHER INFORMATION: Synthetic

<400> SEQUENCE: 97

```
cgctcagcag tgtctcgcac cacatgtaga tcggaagagc gtcgtg          46
```

<210> SEQ ID NO 98
<211> LENGTH: 46
<212> TYPE: DNA
<213> ORGANISM: Artificial Sequence
<220> FEATURE:
<223> OTHER INFORMATION: Synthetic

<400> SEQUENCE: 98

```
cgctcagcag tgtctcgcag cttaaccaga tcggaagagc gtcgtg          46
```

<210> SEQ ID NO 99
<211> LENGTH: 46
<212> TYPE: DNA
<213> ORGANISM: Artificial Sequence
<220> FEATURE:
<223> OTHER INFORMATION: Synthetic

<400> SEQUENCE: 99

```
cgctcagcag tgtctcgcca cctatgcaga tcggaagagc gtcgtg          46
```

<210> SEQ ID NO 100
<211> LENGTH: 44
<212> TYPE: DNA
<213> ORGANISM: Artificial Sequence
<220> FEATURE:
<223> OTHER INFORMATION: Synthetic

<400> SEQUENCE: 100

```
cgacgaggct ggagtgacac tggtaccgct cagcagtgtc tcgc            44
```

<210> SEQ ID NO 101
<211> LENGTH: 44
<212> TYPE: DNA
<213> ORGANISM: Artificial Sequence
<220> FEATURE:
<223> OTHER INFORMATION: Synthetic

<400> SEQUENCE: 101

```
cgacgaggct ggagtgacgg tactgtcgct cagcagtgtc tcgc            44
```

<210> SEQ ID NO 102
<211> LENGTH: 44
<212> TYPE: DNA
<213> ORGANISM: Artificial Sequence
<220> FEATURE:
<223> OTHER INFORMATION: Synthetic

<400> SEQUENCE: 102

```
cgacgaggct ggagtgactc tgtgtgcgct cagcagtgtc tcgc            44
```

<210> SEQ ID NO 103
<211> LENGTH: 44
<212> TYPE: DNA

<213> ORGANISM: Artificial Sequence
<220> FEATURE:
<223> OTHER INFORMATION: Synthetic

<400> SEQUENCE: 103
cgacgaggct ggagtgacta tggctccgct cagcagtgtc tcgc            44

<210> SEQ ID NO 104
<211> LENGTH: 44
<212> TYPE: DNA
<213> ORGANISM: Artificial Sequence
<220> FEATURE:
<223> OTHER INFORMATION: Synthetic

<400> SEQUENCE: 104
cgacgaggct ggagtgacgt tgtcagcgct cagcagtgtc tcgc            44

<210> SEQ ID NO 105
<211> LENGTH: 44
<212> TYPE: DNA
<213> ORGANISM: Artificial Sequence
<220> FEATURE:
<223> OTHER INFORMATION: Synthetic

<400> SEQUENCE: 105
cgacgaggct ggagtgacat gccagtcgct cagcagtgtc tcgc            44

<210> SEQ ID NO 106
<211> LENGTH: 44
<212> TYPE: DNA
<213> ORGANISM: Artificial Sequence
<220> FEATURE:
<223> OTHER INFORMATION: Synthetic

<400> SEQUENCE: 106
cgacgaggct ggagtgaccg ctactacgct cagcagtgtc tcgc            44

<210> SEQ ID NO 107
<211> LENGTH: 44
<212> TYPE: DNA
<213> ORGANISM: Artificial Sequence
<220> FEATURE:
<223> OTHER INFORMATION: Synthetic

<400> SEQUENCE: 107
cgacgaggct ggagtgacca tacacgcgct cagcagtgtc tcgc            44

<210> SEQ ID NO 108
<211> LENGTH: 44
<212> TYPE: DNA
<213> ORGANISM: Artificial Sequence
<220> FEATURE:
<223> OTHER INFORMATION: Synthetic

<400> SEQUENCE: 108
cgacgaggct ggagtgactc gaggatcgct cagcagtgtc tcgc            44

<210> SEQ ID NO 109
<211> LENGTH: 44
<212> TYPE: DNA
<213> ORGANISM: Artificial Sequence
<220> FEATURE:
<223> OTHER INFORMATION: Synthetic

<400> SEQUENCE: 109
cgacgaggct ggagtgacgg ttcgatcgct cagcagtgtc tcgc            44

<210> SEQ ID NO 110
<211> LENGTH: 44
<212> TYPE: DNA
<213> ORGANISM: Artificial Sequence
<220> FEATURE:
<223> OTHER INFORMATION: Synthetic

<400> SEQUENCE: 110
cgacgaggct ggagtgacac ggaacacgct cagcagtgtc tcgc                     44

<210> SEQ ID NO 111
<211> LENGTH: 44
<212> TYPE: DNA
<213> ORGANISM: Artificial Sequence
<220> FEATURE:
<223> OTHER INFORMATION: Synthetic

<400> SEQUENCE: 111
cgacgaggct ggagtgaccg ttgcatcgct cagcagtgtc tcgc                     44

<210> SEQ ID NO 112
<211> LENGTH: 44
<212> TYPE: DNA
<213> ORGANISM: Artificial Sequence
<220> FEATURE:
<223> OTHER INFORMATION: Synthetic

<400> SEQUENCE: 112
cgacgaggct ggagtgacat acgtcccgct cagcagtgtc tcgc                     44

<210> SEQ ID NO 113
<211> LENGTH: 44
<212> TYPE: DNA
<213> ORGANISM: Artificial Sequence
<220> FEATURE:
<223> OTHER INFORMATION: Synthetic

<400> SEQUENCE: 113
cgacgaggct ggagtgacga tctggacgct cagcagtgtc tcgc                     44

<210> SEQ ID NO 114
<211> LENGTH: 44
<212> TYPE: DNA
<213> ORGANISM: Artificial Sequence
<220> FEATURE:
<223> OTHER INFORMATION: Synthetic

<400> SEQUENCE: 114
cgacgaggct ggagtgactc tcgaagcgct cagcagtgtc tcgc                     44

<210> SEQ ID NO 115
<211> LENGTH: 44
<212> TYPE: DNA
<213> ORGANISM: Artificial Sequence
<220> FEATURE:
<223> OTHER INFORMATION: Synthetic

<400> SEQUENCE: 115
cgacgaggct ggagtgacct gtgctacgct cagcagtgtc tcgc                     44

<210> SEQ ID NO 116
<211> LENGTH: 44
<212> TYPE: DNA
<213> ORGANISM: Artificial Sequence
<220> FEATURE:

<223> OTHER INFORMATION: Synthetic

<400> SEQUENCE: 116
cgacgaggct ggagtgacag gtggaacgct cagcagtgtc tcgc            44

<210> SEQ ID NO 117
<211> LENGTH: 44
<212> TYPE: DNA
<213> ORGANISM: Artificial Sequence
<220> FEATURE:
<223> OTHER INFORMATION: Synthetic

<400> SEQUENCE: 117
cgacgaggct ggagtgacta gcaacgcgct cagcagtgtc tcgc            44

<210> SEQ ID NO 118
<211> LENGTH: 44
<212> TYPE: DNA
<213> ORGANISM: Artificial Sequence
<220> FEATURE:
<223> OTHER INFORMATION: Synthetic

<400> SEQUENCE: 118
cgacgaggct ggagtgacgg tcattccgct cagcagtgtc tcgc            44

<210> SEQ ID NO 119
<211> LENGTH: 44
<212> TYPE: DNA
<213> ORGANISM: Artificial Sequence
<220> FEATURE:
<223> OTHER INFORMATION: Synthetic

<400> SEQUENCE: 119
cgacgaggct ggagtgacag atacgccgct cagcagtgtc tcgc            44

<210> SEQ ID NO 120
<211> LENGTH: 44
<212> TYPE: DNA
<213> ORGANISM: Artificial Sequence
<220> FEATURE:
<223> OTHER INFORMATION: Synthetic

<400> SEQUENCE: 120
cgacgaggct ggagtgacga actgctcgct cagcagtgtc tcgc            44

<210> SEQ ID NO 121
<211> LENGTH: 44
<212> TYPE: DNA
<213> ORGANISM: Artificial Sequence
<220> FEATURE:
<223> OTHER INFORMATION: Synthetic

<400> SEQUENCE: 121
cgacgaggct ggagtgacag tgcacacgct cagcagtgtc tcgc            44

<210> SEQ ID NO 122
<211> LENGTH: 44
<212> TYPE: DNA
<213> ORGANISM: Artificial Sequence
<220> FEATURE:
<223> OTHER INFORMATION: Synthetic

<400> SEQUENCE: 122
cgacgaggct ggagtgaccc gatcatcgct cagcagtgtc tcgc            44

```
<210> SEQ ID NO 123
<211> LENGTH: 44
<212> TYPE: DNA
<213> ORGANISM: Artificial Sequence
<220> FEATURE:
<223> OTHER INFORMATION: Synthetic

<400> SEQUENCE: 123
cgacgaggct ggagtgacac aaggaccgct cagcagtgtc tcgc          44

<210> SEQ ID NO 124
<211> LENGTH: 44
<212> TYPE: DNA
<213> ORGANISM: Artificial Sequence
<220> FEATURE:
<223> OTHER INFORMATION: Synthetic

<400> SEQUENCE: 124
cgacgaggct ggagtgacat cggtccgct cagcagtgtc tcgc           44

<210> SEQ ID NO 125
<211> LENGTH: 44
<212> TYPE: DNA
<213> ORGANISM: Artificial Sequence
<220> FEATURE:
<223> OTHER INFORMATION: Synthetic

<400> SEQUENCE: 125
cgacgaggct ggagtgactt gtgacgcgct cagcagtgtc tcgc          44

<210> SEQ ID NO 126
<211> LENGTH: 44
<212> TYPE: DNA
<213> ORGANISM: Artificial Sequence
<220> FEATURE:
<223> OTHER INFORMATION: Synthetic

<400> SEQUENCE: 126
cgacgaggct ggagtgacga agtctgcgct cagcagtgtc tcgc          44

<210> SEQ ID NO 127
<211> LENGTH: 44
<212> TYPE: DNA
<213> ORGANISM: Artificial Sequence
<220> FEATURE:
<223> OTHER INFORMATION: Synthetic

<400> SEQUENCE: 127
cgacgaggct ggagtgactg gacgaacgct cagcagtgtc tcgc          44

<210> SEQ ID NO 128
<211> LENGTH: 44
<212> TYPE: DNA
<213> ORGANISM: Artificial Sequence
<220> FEATURE:
<223> OTHER INFORMATION: Synthetic

<400> SEQUENCE: 128
cgacgaggct ggagtgacga gttcctcgct cagcagtgtc tcgc          44

<210> SEQ ID NO 129
<211> LENGTH: 44
<212> TYPE: DNA
<213> ORGANISM: Artificial Sequence
<220> FEATURE:
<223> OTHER INFORMATION: Synthetic
```

<400> SEQUENCE: 129
cgacgaggct ggagtgacga taggagcgct cagcagtgtc tcgc         44

<210> SEQ ID NO 130
<211> LENGTH: 44
<212> TYPE: DNA
<213> ORGANISM: Artificial Sequence
<220> FEATURE:
<223> OTHER INFORMATION: Synthetic

<400> SEQUENCE: 130
cgacgaggct ggagtgacag cttggacgct cagcagtgtc tcgc         44

<210> SEQ ID NO 131
<211> LENGTH: 44
<212> TYPE: DNA
<213> ORGANISM: Artificial Sequence
<220> FEATURE:
<223> OTHER INFORMATION: Synthetic

<400> SEQUENCE: 131
cgacgaggct ggagtgacca catcctcgct cagcagtgtc tcgc         44

<210> SEQ ID NO 132
<211> LENGTH: 44
<212> TYPE: DNA
<213> ORGANISM: Artificial Sequence
<220> FEATURE:
<223> OTHER INFORMATION: Synthetic

<400> SEQUENCE: 132
cgacgaggct ggagtgacag tcctgacgct cagcagtgtc tcgc         44

<210> SEQ ID NO 133
<211> LENGTH: 44
<212> TYPE: DNA
<213> ORGANISM: Artificial Sequence
<220> FEATURE:
<223> OTHER INFORMATION: Synthetic

<400> SEQUENCE: 133
cgacgaggct ggagtgacct tgtagccgct cagcagtgtc tcgc         44

<210> SEQ ID NO 134
<211> LENGTH: 44
<212> TYPE: DNA
<213> ORGANISM: Artificial Sequence
<220> FEATURE:
<223> OTHER INFORMATION: Synthetic

<400> SEQUENCE: 134
cgacgaggct ggagtgacca ggagtacgct cagcagtgtc tcgc         44

<210> SEQ ID NO 135
<211> LENGTH: 44
<212> TYPE: DNA
<213> ORGANISM: Artificial Sequence
<220> FEATURE:
<223> OTHER INFORMATION: Synthetic

<400> SEQUENCE: 135
cgacgaggct ggagtgacca caaggacgct cagcagtgtc tcgc         44

<210> SEQ ID NO 136
<211> LENGTH: 44

<212> TYPE: DNA
<213> ORGANISM: Artificial Sequence
<220> FEATURE:
<223> OTHER INFORMATION: Synthetic

<400> SEQUENCE: 136
cgacgaggct ggagtgactt cctctgcgct cagcagtgtc tcgc            44

<210> SEQ ID NO 137
<211> LENGTH: 44
<212> TYPE: DNA
<213> ORGANISM: Artificial Sequence
<220> FEATURE:
<223> OTHER INFORMATION: Synthetic

<400> SEQUENCE: 137
cgacgaggct ggagtgaccc attgctcgct cagcagtgtc tcgc            44

<210> SEQ ID NO 138
<211> LENGTH: 44
<212> TYPE: DNA
<213> ORGANISM: Artificial Sequence
<220> FEATURE:
<223> OTHER INFORMATION: Synthetic

<400> SEQUENCE: 138
cgacgaggct ggagtgacgc acatagcgct cagcagtgtc tcgc            44

<210> SEQ ID NO 139
<211> LENGTH: 44
<212> TYPE: DNA
<213> ORGANISM: Artificial Sequence
<220> FEATURE:
<223> OTHER INFORMATION: Synthetic

<400> SEQUENCE: 139
cgacgaggct ggagtgacca ctgtaccgct cagcagtgtc tcgc            44

<210> SEQ ID NO 140
<211> LENGTH: 44
<212> TYPE: DNA
<213> ORGANISM: Artificial Sequence
<220> FEATURE:
<223> OTHER INFORMATION: Synthetic

<400> SEQUENCE: 140
cgacgaggct ggagtgacgt gatctccgct cagcagtgtc tcgc            44

<210> SEQ ID NO 141
<211> LENGTH: 44
<212> TYPE: DNA
<213> ORGANISM: Artificial Sequence
<220> FEATURE:
<223> OTHER INFORMATION: Synthetic

<400> SEQUENCE: 141
cgacgaggct ggagtgacaa tgccgtcgct cagcagtgtc tcgc            44

<210> SEQ ID NO 142
<211> LENGTH: 44
<212> TYPE: DNA
<213> ORGANISM: Artificial Sequence
<220> FEATURE:
<223> OTHER INFORMATION: Synthetic

<400> SEQUENCE: 142
cgacgaggct ggagtgactc cttgtccgct cagcagtgtc tcgc        44

<210> SEQ ID NO 143
<211> LENGTH: 44
<212> TYPE: DNA
<213> ORGANISM: Artificial Sequence
<220> FEATURE:
<223> OTHER INFORMATION: Synthetic

<400> SEQUENCE: 143
cgacgaggct ggagtgacag taggcacgct cagcagtgtc tcgc        44

<210> SEQ ID NO 144
<211> LENGTH: 44
<212> TYPE: DNA
<213> ORGANISM: Artificial Sequence
<220> FEATURE:
<223> OTHER INFORMATION: Synthetic

<400> SEQUENCE: 144
cgacgaggct ggagtgacag cctcttcgct cagcagtgtc tcgc        44

<210> SEQ ID NO 145
<211> LENGTH: 44
<212> TYPE: DNA
<213> ORGANISM: Artificial Sequence
<220> FEATURE:
<223> OTHER INFORMATION: Synthetic

<400> SEQUENCE: 145
cgacgaggct ggagtgaccg attacgcgct cagcagtgtc tcgc        44

<210> SEQ ID NO 146
<211> LENGTH: 44
<212> TYPE: DNA
<213> ORGANISM: Artificial Sequence
<220> FEATURE:
<223> OTHER INFORMATION: Synthetic

<400> SEQUENCE: 146
cgacgaggct ggagtgaccc aggaatcgct cagcagtgtc tcgc        44

<210> SEQ ID NO 147
<211> LENGTH: 44
<212> TYPE: DNA
<213> ORGANISM: Artificial Sequence
<220> FEATURE:
<223> OTHER INFORMATION: Synthetic

<400> SEQUENCE: 147
cgacgaggct ggagtgacga gtcagtcgct cagcagtgtc tcgc        44

<210> SEQ ID NO 148
<211> LENGTH: 44
<212> TYPE: DNA
<213> ORGANISM: Artificial Sequence
<220> FEATURE:
<223> OTHER INFORMATION: Synthetic

<400> SEQUENCE: 148
cgacgaggct ggagtgactg agaggacgct cagcagtgtc tcgc        44

<210> SEQ ID NO 149
<211> LENGTH: 44
<212> TYPE: DNA
<213> ORGANISM: Artificial Sequence

```
<220> FEATURE:
<223> OTHER INFORMATION: Synthetic

<400> SEQUENCE: 149
cgacgaggct ggagtgacac gactcacgct cagcagtgtc tcgc            44

<210> SEQ ID NO 150
<211> LENGTH: 44
<212> TYPE: DNA
<213> ORGANISM: Artificial Sequence
<220> FEATURE:
<223> OTHER INFORMATION: Synthetic

<400> SEQUENCE: 150
cgacgaggct ggagtgacta gctcagcgct cagcagtgtc tcgc            44

<210> SEQ ID NO 151
<211> LENGTH: 44
<212> TYPE: DNA
<213> ORGANISM: Artificial Sequence
<220> FEATURE:
<223> OTHER INFORMATION: Synthetic

<400> SEQUENCE: 151
cgacgaggct ggagtgacta accggtcgct cagcagtgtc tcgc            44

<210> SEQ ID NO 152
<211> LENGTH: 44
<212> TYPE: DNA
<213> ORGANISM: Artificial Sequence
<220> FEATURE:
<223> OTHER INFORMATION: Synthetic

<400> SEQUENCE: 152
cgacgaggct ggagtgacgt actgagcgct cagcagtgtc tcgc            44

<210> SEQ ID NO 153
<211> LENGTH: 44
<212> TYPE: DNA
<213> ORGANISM: Artificial Sequence
<220> FEATURE:
<223> OTHER INFORMATION: Synthetic

<400> SEQUENCE: 153
cgacgaggct ggagtgacaa ccactccgct cagcagtgtc tcgc            44

<210> SEQ ID NO 154
<211> LENGTH: 44
<212> TYPE: DNA
<213> ORGANISM: Artificial Sequence
<220> FEATURE:
<223> OTHER INFORMATION: Synthetic

<400> SEQUENCE: 154
cgacgaggct ggagtgacca gttacccgct cagcagtgtc tcgc            44

<210> SEQ ID NO 155
<211> LENGTH: 44
<212> TYPE: DNA
<213> ORGANISM: Artificial Sequence
<220> FEATURE:
<223> OTHER INFORMATION: Synthetic

<400> SEQUENCE: 155
cgacgaggct ggagtgacga tggatgcgct cagcagtgtc tcgc            44
```

<210> SEQ ID NO 156
<211> LENGTH: 44
<212> TYPE: DNA
<213> ORGANISM: Artificial Sequence
<220> FEATURE:
<223> OTHER INFORMATION: Synthetic

<400> SEQUENCE: 156
cgacgaggct ggagtgacct acctctcgct cagcagtgtc tcgc            44

<210> SEQ ID NO 157
<211> LENGTH: 44
<212> TYPE: DNA
<213> ORGANISM: Artificial Sequence
<220> FEATURE:
<223> OTHER INFORMATION: Synthetic

<400> SEQUENCE: 157
cgacgaggct ggagtgacgt caagagcgct cagcagtgtc tcgc            44

<210> SEQ ID NO 158
<211> LENGTH: 44
<212> TYPE: DNA
<213> ORGANISM: Artificial Sequence
<220> FEATURE:
<223> OTHER INFORMATION: Synthetic

<400> SEQUENCE: 158
cgacgaggct ggagtgacga tctacgcgct cagcagtgtc tcgc            44

<210> SEQ ID NO 159
<211> LENGTH: 44
<212> TYPE: DNA
<213> ORGANISM: Artificial Sequence
<220> FEATURE:
<223> OTHER INFORMATION: Synthetic

<400> SEQUENCE: 159
cgacgaggct ggagtgacac attccgcgct cagcagtgtc tcgc            44

<210> SEQ ID NO 160
<211> LENGTH: 44
<212> TYPE: DNA
<213> ORGANISM: Artificial Sequence
<220> FEATURE:
<223> OTHER INFORMATION: Synthetic

<400> SEQUENCE: 160
cgacgaggct ggagtgacct gaatcccgct cagcagtgtc tcgc            44

<210> SEQ ID NO 161
<211> LENGTH: 44
<212> TYPE: DNA
<213> ORGANISM: Artificial Sequence
<220> FEATURE:
<223> OTHER INFORMATION: Synthetic

<400> SEQUENCE: 161
cgacgaggct ggagtgactg gccatacgct cagcagtgtc tcgc            44

<210> SEQ ID NO 162
<211> LENGTH: 44
<212> TYPE: DNA
<213> ORGANISM: Artificial Sequence
<220> FEATURE:
<223> OTHER INFORMATION: Synthetic

<400> SEQUENCE: 162
cgacgaggct ggagtgacgt cttgctcgct cagcagtgtc tcgc        44

<210> SEQ ID NO 163
<211> LENGTH: 44
<212> TYPE: DNA
<213> ORGANISM: Artificial Sequence
<220> FEATURE:
<223> OTHER INFORMATION: Synthetic

<400> SEQUENCE: 163
cgacgaggct ggagtgacac gtgttgcgct cagcagtgtc tcgc        44

<210> SEQ ID NO 164
<211> LENGTH: 44
<212> TYPE: DNA
<213> ORGANISM: Artificial Sequence
<220> FEATURE:
<223> OTHER INFORMATION: Synthetic

<400> SEQUENCE: 164
cgacgaggct ggagtgacga agcgttcgct cagcagtgtc tcgc        44

<210> SEQ ID NO 165
<211> LENGTH: 44
<212> TYPE: DNA
<213> ORGANISM: Artificial Sequence
<220> FEATURE:
<223> OTHER INFORMATION: Synthetic

<400> SEQUENCE: 165
cgacgaggct ggagtgacta acgccacgct cagcagtgtc tcgc        44

<210> SEQ ID NO 166
<211> LENGTH: 44
<212> TYPE: DNA
<213> ORGANISM: Artificial Sequence
<220> FEATURE:
<223> OTHER INFORMATION: Synthetic

<400> SEQUENCE: 166
cgacgaggct ggagtgacag gctgtacgct cagcagtgtc tcgc        44

<210> SEQ ID NO 167
<211> LENGTH: 44
<212> TYPE: DNA
<213> ORGANISM: Artificial Sequence
<220> FEATURE:
<223> OTHER INFORMATION: Synthetic

<400> SEQUENCE: 167
cgacgaggct ggagtgacct acagtgcgct cagcagtgtc tcgc        44

<210> SEQ ID NO 168
<211> LENGTH: 44
<212> TYPE: DNA
<213> ORGANISM: Artificial Sequence
<220> FEATURE:
<223> OTHER INFORMATION: Synthetic

<400> SEQUENCE: 168
cgacgaggct ggagtgactt cagagccgct cagcagtgtc tcgc        44

<210> SEQ ID NO 169

```
<211> LENGTH: 44
<212> TYPE: DNA
<213> ORGANISM: Artificial Sequence
<220> FEATURE:
<223> OTHER INFORMATION: Synthetic

<400> SEQUENCE: 169
cgacgaggct ggagtgactg cctacacgct cagcagtgtc tcgc              44

<210> SEQ ID NO 170
<211> LENGTH: 44
<212> TYPE: DNA
<213> ORGANISM: Artificial Sequence
<220> FEATURE:
<223> OTHER INFORMATION: Synthetic

<400> SEQUENCE: 170
cgacgaggct ggagtgaccg gattgacgct cagcagtgtc tcgc              44

<210> SEQ ID NO 171
<211> LENGTH: 44
<212> TYPE: DNA
<213> ORGANISM: Artificial Sequence
<220> FEATURE:
<223> OTHER INFORMATION: Synthetic

<400> SEQUENCE: 171
cgacgaggct ggagtgacgg aggattcgct cagcagtgtc tcgc              44

<210> SEQ ID NO 172
<211> LENGTH: 44
<212> TYPE: DNA
<213> ORGANISM: Artificial Sequence
<220> FEATURE:
<223> OTHER INFORMATION: Synthetic

<400> SEQUENCE: 172
cgacgaggct ggagtgacca ttagcccgct cagcagtgtc tcgc              44

<210> SEQ ID NO 173
<211> LENGTH: 44
<212> TYPE: DNA
<213> ORGANISM: Artificial Sequence
<220> FEATURE:
<223> OTHER INFORMATION: Synthetic

<400> SEQUENCE: 173
cgacgaggct ggagtgactt ggtcaccgct cagcagtgtc tcgc              44

<210> SEQ ID NO 174
<211> LENGTH: 44
<212> TYPE: DNA
<213> ORGANISM: Artificial Sequence
<220> FEATURE:
<223> OTHER INFORMATION: Synthetic

<400> SEQUENCE: 174
cgacgaggct ggagtgacca agcaagcgct cagcagtgtc tcgc              44

<210> SEQ ID NO 175
<211> LENGTH: 44
<212> TYPE: DNA
<213> ORGANISM: Artificial Sequence
<220> FEATURE:
<223> OTHER INFORMATION: Synthetic

<400> SEQUENCE: 175
```

```
cgacgaggct ggagtgacca acatcccgct cagcagtgtc tcgc          44
```

<210> SEQ ID NO 176
<211> LENGTH: 44
<212> TYPE: DNA
<213> ORGANISM: Artificial Sequence
<220> FEATURE:
<223> OTHER INFORMATION: Synthetic

<400> SEQUENCE: 176

```
cgacgaggct ggagtgacga cgacaacgct cagcagtgtc tcgc          44
```

<210> SEQ ID NO 177
<211> LENGTH: 44
<212> TYPE: DNA
<213> ORGANISM: Artificial Sequence
<220> FEATURE:
<223> OTHER INFORMATION: Synthetic

<400> SEQUENCE: 177

```
cgacgaggct ggagtgacat cgagtccgct cagcagtgtc tcgc          44
```

<210> SEQ ID NO 178
<211> LENGTH: 44
<212> TYPE: DNA
<213> ORGANISM: Artificial Sequence
<220> FEATURE:
<223> OTHER INFORMATION: Synthetic

<400> SEQUENCE: 178

```
cgacgaggct ggagtgacta tgcgagcgct cagcagtgtc tcgc          44
```

<210> SEQ ID NO 179
<211> LENGTH: 44
<212> TYPE: DNA
<213> ORGANISM: Artificial Sequence
<220> FEATURE:
<223> OTHER INFORMATION: Synthetic

<400> SEQUENCE: 179

```
cgacgaggct ggagtgacta gcttcccgct cagcagtgtc tcgc          44
```

<210> SEQ ID NO 180
<211> LENGTH: 44
<212> TYPE: DNA
<213> ORGANISM: Artificial Sequence
<220> FEATURE:
<223> OTHER INFORMATION: Synthetic

<400> SEQUENCE: 180

```
cgacgaggct ggagtgacac caacgtcgct cagcagtgtc tcgc          44
```

<210> SEQ ID NO 181
<211> LENGTH: 44
<212> TYPE: DNA
<213> ORGANISM: Artificial Sequence
<220> FEATURE:
<223> OTHER INFORMATION: Synthetic

<400> SEQUENCE: 181

```
cgacgaggct ggagtgacac gcgatacgct cagcagtgtc tcgc          44
```

<210> SEQ ID NO 182
<211> LENGTH: 44
<212> TYPE: DNA

```
<213> ORGANISM: Artificial Sequence
<220> FEATURE:
<223> OTHER INFORMATION: Synthetic

<400> SEQUENCE: 182
cgacgaggct ggagtgacgt cagctacgct cagcagtgtc tcgc                    44

<210> SEQ ID NO 183
<211> LENGTH: 44
<212> TYPE: DNA
<213> ORGANISM: Artificial Sequence
<220> FEATURE:
<223> OTHER INFORMATION: Synthetic

<400> SEQUENCE: 183
cgacgaggct ggagtgacca ccagatcgct cagcagtgtc tcgc                    44

<210> SEQ ID NO 184
<211> LENGTH: 44
<212> TYPE: DNA
<213> ORGANISM: Artificial Sequence
<220> FEATURE:
<223> OTHER INFORMATION: Synthetic

<400> SEQUENCE: 184
cgacgaggct ggagtgacca accttgcgct cagcagtgtc tcgc                    44

<210> SEQ ID NO 185
<211> LENGTH: 44
<212> TYPE: DNA
<213> ORGANISM: Artificial Sequence
<220> FEATURE:
<223> OTHER INFORMATION: Synthetic

<400> SEQUENCE: 185
cgacgaggct ggagtgactt gccttgcgct cagcagtgtc tcgc                    44

<210> SEQ ID NO 186
<211> LENGTH: 44
<212> TYPE: DNA
<213> ORGANISM: Artificial Sequence
<220> FEATURE:
<223> OTHER INFORMATION: Synthetic

<400> SEQUENCE: 186
cgacgaggct ggagtgacag tctgctcgct cagcagtgtc tcgc                    44

<210> SEQ ID NO 187
<211> LENGTH: 44
<212> TYPE: DNA
<213> ORGANISM: Artificial Sequence
<220> FEATURE:
<223> OTHER INFORMATION: Synthetic

<400> SEQUENCE: 187
cgacgaggct ggagtgacgt ccttcacgct cagcagtgtc tcgc                    44

<210> SEQ ID NO 188
<211> LENGTH: 44
<212> TYPE: DNA
<213> ORGANISM: Artificial Sequence
<220> FEATURE:
<223> OTHER INFORMATION: Synthetic

<400> SEQUENCE: 188
cgacgaggct ggagtgaccg gtctatcgct cagcagtgtc tcgc                    44
```

<210> SEQ ID NO 189
<211> LENGTH: 44
<212> TYPE: DNA
<213> ORGANISM: Artificial Sequence
<220> FEATURE:
<223> OTHER INFORMATION: Synthetic

<400> SEQUENCE: 189
cgacgaggct ggagtgactc tgccttcgct cagcagtgtc tcgc                    44

<210> SEQ ID NO 190
<211> LENGTH: 44
<212> TYPE: DNA
<213> ORGANISM: Artificial Sequence
<220> FEATURE:
<223> OTHER INFORMATION: Synthetic

<400> SEQUENCE: 190
cgacgaggct ggagtgacca agttggcgct cagcagtgtc tcgc                    44

<210> SEQ ID NO 191
<211> LENGTH: 44
<212> TYPE: DNA
<213> ORGANISM: Artificial Sequence
<220> FEATURE:
<223> OTHER INFORMATION: Synthetic

<400> SEQUENCE: 191
cgacgaggct ggagtgacat ctacggcgct cagcagtgtc tcgc                    44

<210> SEQ ID NO 192
<211> LENGTH: 44
<212> TYPE: DNA
<213> ORGANISM: Artificial Sequence
<220> FEATURE:
<223> OTHER INFORMATION: Synthetic

<400> SEQUENCE: 192
cgacgaggct ggagtgacca cttctgcgct cagcagtgtc tcgc                    44

<210> SEQ ID NO 193
<211> LENGTH: 44
<212> TYPE: DNA
<213> ORGANISM: Artificial Sequence
<220> FEATURE:
<223> OTHER INFORMATION: Synthetic

<400> SEQUENCE: 193
cgacgaggct ggagtgacca cacaaccgct cagcagtgtc tcgc                    44

<210> SEQ ID NO 194
<211> LENGTH: 44
<212> TYPE: DNA
<213> ORGANISM: Artificial Sequence
<220> FEATURE:
<223> OTHER INFORMATION: Synthetic

<400> SEQUENCE: 194
cgacgaggct ggagtgacgc ctaatgcgct cagcagtgtc tcgc                    44

<210> SEQ ID NO 195
<211> LENGTH: 44
<212> TYPE: DNA
<213> ORGANISM: Artificial Sequence
<220> FEATURE:

```
<223> OTHER INFORMATION: Synthetic

<400> SEQUENCE: 195
cgacgaggct ggagtgacgt tcgcatcgct cagcagtgtc tcgc              44

<210> SEQ ID NO 196
<211> LENGTH: 47
<212> TYPE: DNA
<213> ORGANISM: Artificial Sequence
<220> FEATURE:
<223> OTHER INFORMATION: Synthetic

<400> SEQUENCE: 196
ttaccgcggc kgctgrcaca cgagtctagc gacgaggctg gagtgac           47

<210> SEQ ID NO 197
<211> LENGTH: 47
<212> TYPE: DNA
<213> ORGANISM: Artificial Sequence
<220> FEATURE:
<223> OTHER INFORMATION: Synthetic

<400> SEQUENCE: 197
ttaccgcggc kgctgrcaca cgcctctatc gacgaggctg gagtgac           47

<210> SEQ ID NO 198
<211> LENGTH: 47
<212> TYPE: DNA
<213> ORGANISM: Artificial Sequence
<220> FEATURE:
<223> OTHER INFORMATION: Synthetic

<400> SEQUENCE: 198
ttaccgcggc kgctgrcaca cgccattctc gacgaggctg gagtgac           47

<210> SEQ ID NO 199
<211> LENGTH: 47
<212> TYPE: DNA
<213> ORGANISM: Artificial Sequence
<220> FEATURE:
<223> OTHER INFORMATION: Synthetic

<400> SEQUENCE: 199
ttaccgcggc kgctgrcaca ctacggttgc gacgaggctg gagtgac           47

<210> SEQ ID NO 200
<211> LENGTH: 47
<212> TYPE: DNA
<213> ORGANISM: Artificial Sequence
<220> FEATURE:
<223> OTHER INFORMATION: Synthetic

<400> SEQUENCE: 200
ttaccgcggc kgctgrcaca cactctaccc gacgaggctg gagtgac           47

<210> SEQ ID NO 201
<211> LENGTH: 47
<212> TYPE: DNA
<213> ORGANISM: Artificial Sequence
<220> FEATURE:
<223> OTHER INFORMATION: Synthetic

<400> SEQUENCE: 201
ttaccgcggc kgctgrcaca ctaggtccac gacgaggctg gagtgac           47
```

```
<210> SEQ ID NO 202
<211> LENGTH: 47
<212> TYPE: DNA
<213> ORGANISM: Artificial Sequence
<220> FEATURE:
<223> OTHER INFORMATION: Synthetic

<400> SEQUENCE: 202
ttaccgcggc kgctgrcaca ctcctgagtc gacgaggctg gagtgac         47

<210> SEQ ID NO 203
<211> LENGTH: 47
<212> TYPE: DNA
<213> ORGANISM: Artificial Sequence
<220> FEATURE:
<223> OTHER INFORMATION: Synthetic

<400> SEQUENCE: 203
ttaccgcggc kgctgrcaca cgtggatagc gacgaggctg gagtgac         47

<210> SEQ ID NO 204
<211> LENGTH: 47
<212> TYPE: DNA
<213> ORGANISM: Artificial Sequence
<220> FEATURE:
<223> OTHER INFORMATION: Synthetic

<400> SEQUENCE: 204
ttaccgcggc kgctgrcaca cgcgctattc gacgaggctg gagtgac         47

<210> SEQ ID NO 205
<211> LENGTH: 47
<212> TYPE: DNA
<213> ORGANISM: Artificial Sequence
<220> FEATURE:
<223> OTHER INFORMATION: Synthetic

<400> SEQUENCE: 205
ttaccgcggc kgctgrcaca cggaaggaac gacgaggctg gagtgac         47

<210> SEQ ID NO 206
<211> LENGTH: 47
<212> TYPE: DNA
<213> ORGANISM: Artificial Sequence
<220> FEATURE:
<223> OTHER INFORMATION: Synthetic

<400> SEQUENCE: 206
ttaccgcggc kgctgrcaca cggactcaac gacgaggctg gagtgac         47

<210> SEQ ID NO 207
<211> LENGTH: 47
<212> TYPE: DNA
<213> ORGANISM: Artificial Sequence
<220> FEATURE:
<223> OTHER INFORMATION: Synthetic

<400> SEQUENCE: 207
ttaccgcggc kgctgrcaca caacactcgc gacgaggctg gagtgac         47

<210> SEQ ID NO 208
<211> LENGTH: 47
<212> TYPE: DNA
<213> ORGANISM: Artificial Sequence
<220> FEATURE:
<223> OTHER INFORMATION: Synthetic
```

```
<400> SEQUENCE: 208
ttaccgcggc kgctgrcaca cccggaattc gacgaggctg gagtgac        47

<210> SEQ ID NO 209
<211> LENGTH: 47
<212> TYPE: DNA
<213> ORGANISM: Artificial Sequence
<220> FEATURE:
<223> OTHER INFORMATION: Synthetic

<400> SEQUENCE: 209
ttaccgcggc kgctgrcaca caacttgccc gacgaggctg gagtgac        47

<210> SEQ ID NO 210
<211> LENGTH: 47
<212> TYPE: DNA
<213> ORGANISM: Artificial Sequence
<220> FEATURE:
<223> OTHER INFORMATION: Synthetic

<400> SEQUENCE: 210
ttaccgcggc kgctgrcaca cttgacaggc gacgaggctg gagtgac        47

<210> SEQ ID NO 211
<211> LENGTH: 47
<212> TYPE: DNA
<213> ORGANISM: Artificial Sequence
<220> FEATURE:
<223> OTHER INFORMATION: Synthetic

<400> SEQUENCE: 211
ttaccgcggc kgctgrcaca ctcttagcgc gacgaggctg gagtgac        47

<210> SEQ ID NO 212
<211> LENGTH: 47
<212> TYPE: DNA
<213> ORGANISM: Artificial Sequence
<220> FEATURE:
<223> OTHER INFORMATION: Synthetic

<400> SEQUENCE: 212
ttaccgcggc kgctgrcaca cctgttgcac gacgaggctg gagtgac        47

<210> SEQ ID NO 213
<211> LENGTH: 47
<212> TYPE: DNA
<213> ORGANISM: Artificial Sequence
<220> FEATURE:
<223> OTHER INFORMATION: Synthetic

<400> SEQUENCE: 213
ttaccgcggc kgctgrcaca cagaacacgc gacgaggctg gagtgac        47

<210> SEQ ID NO 214
<211> LENGTH: 47
<212> TYPE: DNA
<213> ORGANISM: Artificial Sequence
<220> FEATURE:
<223> OTHER INFORMATION: Synthetic

<400> SEQUENCE: 214
ttaccgcggc kgctgrcaca cccttgatgc gacgaggctg gagtgac        47

<210> SEQ ID NO 215
<211> LENGTH: 47
```

```
<212> TYPE: DNA
<213> ORGANISM: Artificial Sequence
<220> FEATURE:
<223> OTHER INFORMATION: Synthetic

<400> SEQUENCE: 215
ttaccgcggc kgctgrcaca cagcgatctc gacgaggctg gagtgac        47

<210> SEQ ID NO 216
<211> LENGTH: 47
<212> TYPE: DNA
<213> ORGANISM: Artificial Sequence
<220> FEATURE:
<223> OTHER INFORMATION: Synthetic

<400> SEQUENCE: 216
ttaccgcggc kgctgrcaca cgctcagaac gacgaggctg gagtgac        47

<210> SEQ ID NO 217
<211> LENGTH: 47
<212> TYPE: DNA
<213> ORGANISM: Artificial Sequence
<220> FEATURE:
<223> OTHER INFORMATION: Synthetic

<400> SEQUENCE: 217
ttaccgcggc kgctgrcaca cattgcgtgc gacgaggctg gagtgac        47

<210> SEQ ID NO 218
<211> LENGTH: 47
<212> TYPE: DNA
<213> ORGANISM: Artificial Sequence
<220> FEATURE:
<223> OTHER INFORMATION: Synthetic

<400> SEQUENCE: 218
ttaccgcggc kgctgrcaca ccatccgttc gacgaggctg gagtgac        47

<210> SEQ ID NO 219
<211> LENGTH: 47
<212> TYPE: DNA
<213> ORGANISM: Artificial Sequence
<220> FEATURE:
<223> OTHER INFORMATION: Synthetic

<400> SEQUENCE: 219
ttaccgcggc kgctgrcaca ctctctggtc gacgaggctg gagtgac        47

<210> SEQ ID NO 220
<211> LENGTH: 47
<212> TYPE: DNA
<213> ORGANISM: Artificial Sequence
<220> FEATURE:
<223> OTHER INFORMATION: Synthetic

<400> SEQUENCE: 220
ttaccgcggc kgctgrcaca caacgagcac gacgaggctg gagtgac        47

<210> SEQ ID NO 221
<211> LENGTH: 47
<212> TYPE: DNA
<213> ORGANISM: Artificial Sequence
<220> FEATURE:
<223> OTHER INFORMATION: Synthetic

<400> SEQUENCE: 221
```

```
ttaccgcggc kgctgrcaca cacgttcacc gacgaggctg gagtgac        47
```

<210> SEQ ID NO 222
<211> LENGTH: 47
<212> TYPE: DNA
<213> ORGANISM: Artificial Sequence
<220> FEATURE:
<223> OTHER INFORMATION: Synthetic

<400> SEQUENCE: 222

```
ttaccgcggc kgctgrcaca catcagcacc gacgaggctg gagtgac        47
```

<210> SEQ ID NO 223
<211> LENGTH: 47
<212> TYPE: DNA
<213> ORGANISM: Artificial Sequence
<220> FEATURE:
<223> OTHER INFORMATION: Synthetic

<400> SEQUENCE: 223

```
ttaccgcggc kgctgrcaca cgatagcgac gacgaggctg gagtgac        47
```

<210> SEQ ID NO 224
<211> LENGTH: 47
<212> TYPE: DNA
<213> ORGANISM: Artificial Sequence
<220> FEATURE:
<223> OTHER INFORMATION: Synthetic

<400> SEQUENCE: 224

```
ttaccgcggc kgctgrcaca cagagcttgc gacgaggctg gagtgac        47
```

<210> SEQ ID NO 225
<211> LENGTH: 47
<212> TYPE: DNA
<213> ORGANISM: Artificial Sequence
<220> FEATURE:
<223> OTHER INFORMATION: Synthetic

<400> SEQUENCE: 225

```
ttaccgcggc kgctgrcaca ctgatcgtcc gacgaggctg gagtgac        47
```

<210> SEQ ID NO 226
<211> LENGTH: 47
<212> TYPE: DNA
<213> ORGANISM: Artificial Sequence
<220> FEATURE:
<223> OTHER INFORMATION: Synthetic

<400> SEQUENCE: 226

```
ttaccgcggc kgctgrcaca cacgatacgc gacgaggctg gagtgac        47
```

<210> SEQ ID NO 227
<211> LENGTH: 47
<212> TYPE: DNA
<213> ORGANISM: Artificial Sequence
<220> FEATURE:
<223> OTHER INFORMATION: Synthetic

<400> SEQUENCE: 227

```
ttaccgcggc kgctgrcaca cctaactggc gacgaggctg gagtgac        47
```

<210> SEQ ID NO 228
<211> LENGTH: 47
<212> TYPE: DNA
<213> ORGANISM: Artificial Sequence

```
<220> FEATURE:
<223> OTHER INFORMATION: Synthetic

<400> SEQUENCE: 228
ttaccgcggc kgctgrcaca ctcgcgtaac gacgaggctg gagtgac       47

<210> SEQ ID NO 229
<211> LENGTH: 47
<212> TYPE: DNA
<213> ORGANISM: Artificial Sequence
<220> FEATURE:
<223> OTHER INFORMATION: Synthetic

<400> SEQUENCE: 229
ttaccgcggc kgctgrcaca ccggttcttc gacgaggctg gagtgac       47

<210> SEQ ID NO 230
<211> LENGTH: 47
<212> TYPE: DNA
<213> ORGANISM: Artificial Sequence
<220> FEATURE:
<223> OTHER INFORMATION: Synthetic

<400> SEQUENCE: 230
ttaccgcggc kgctgrcaca cttggttcgc gacgaggctg gagtgac       47

<210> SEQ ID NO 231
<211> LENGTH: 47
<212> TYPE: DNA
<213> ORGANISM: Artificial Sequence
<220> FEATURE:
<223> OTHER INFORMATION: Synthetic

<400> SEQUENCE: 231
ttaccgcggc kgctgrcaca cgaagtagcc gacgaggctg gagtgac       47

<210> SEQ ID NO 232
<211> LENGTH: 47
<212> TYPE: DNA
<213> ORGANISM: Artificial Sequence
<220> FEATURE:
<223> OTHER INFORMATION: Synthetic

<400> SEQUENCE: 232
ttaccgcggc kgctgrcaca cggctagaac gacgaggctg gagtgac       47

<210> SEQ ID NO 233
<211> LENGTH: 47
<212> TYPE: DNA
<213> ORGANISM: Artificial Sequence
<220> FEATURE:
<223> OTHER INFORMATION: Synthetic

<400> SEQUENCE: 233
ttaccgcggc kgctgrcaca ccatcgtgac gacgaggctg gagtgac       47

<210> SEQ ID NO 234
<211> LENGTH: 47
<212> TYPE: DNA
<213> ORGANISM: Artificial Sequence
<220> FEATURE:
<223> OTHER INFORMATION: Synthetic

<400> SEQUENCE: 234
ttaccgcggc kgctgrcaca ctcaccaacc gacgaggctg gagtgac       47
```

<210> SEQ ID NO 235
<211> LENGTH: 47
<212> TYPE: DNA
<213> ORGANISM: Artificial Sequence
<220> FEATURE:
<223> OTHER INFORMATION: Synthetic

<400> SEQUENCE: 235
ttaccgcggc kgctgrcaca ccttcaaggc gacgaggctg gagtgac        47

<210> SEQ ID NO 236
<211> LENGTH: 47
<212> TYPE: DNA
<213> ORGANISM: Artificial Sequence
<220> FEATURE:
<223> OTHER INFORMATION: Synthetic

<400> SEQUENCE: 236
ttaccgcggc kgctgrcaca cagtagctcc gacgaggctg gagtgac        47

<210> SEQ ID NO 237
<211> LENGTH: 47
<212> TYPE: DNA
<213> ORGANISM: Artificial Sequence
<220> FEATURE:
<223> OTHER INFORMATION: Synthetic

<400> SEQUENCE: 237
ttaccgcggc kgctgrcaca cgccacattc gacgaggctg gagtgac        47

<210> SEQ ID NO 238
<211> LENGTH: 47
<212> TYPE: DNA
<213> ORGANISM: Artificial Sequence
<220> FEATURE:
<223> OTHER INFORMATION: Synthetic

<400> SEQUENCE: 238
ttaccgcggc kgctgrcaca cttcacggac gacgaggctg gagtgac        47

<210> SEQ ID NO 239
<211> LENGTH: 47
<212> TYPE: DNA
<213> ORGANISM: Artificial Sequence
<220> FEATURE:
<223> OTHER INFORMATION: Synthetic

<400> SEQUENCE: 239
ttaccgcggc kgctgrcaca ctgacgttgc gacgaggctg gagtgac        47

<210> SEQ ID NO 240
<211> LENGTH: 47
<212> TYPE: DNA
<213> ORGANISM: Artificial Sequence
<220> FEATURE:
<223> OTHER INFORMATION: Synthetic

<400> SEQUENCE: 240
ttaccgcggc kgctgrcaca ctcatctggc gacgaggctg gagtgac        47

<210> SEQ ID NO 241
<211> LENGTH: 47
<212> TYPE: DNA
<213> ORGANISM: Artificial Sequence
<220> FEATURE:
<223> OTHER INFORMATION: Synthetic

```
<400> SEQUENCE: 241
ttaccgcggc kgctgrcaca ccgttcatcc gacgaggctg gagtgac          47

<210> SEQ ID NO 242
<211> LENGTH: 47
<212> TYPE: DNA
<213> ORGANISM: Artificial Sequence
<220> FEATURE:
<223> OTHER INFORMATION: Synthetic

<400> SEQUENCE: 242
ttaccgcggc kgctgrcaca caaccgtcac gacgaggctg gagtgac          47

<210> SEQ ID NO 243
<211> LENGTH: 47
<212> TYPE: DNA
<213> ORGANISM: Artificial Sequence
<220> FEATURE:
<223> OTHER INFORMATION: Synthetic

<400> SEQUENCE: 243
ttaccgcggc kgctgrcaca ctgctaagcc gacgaggctg gagtgac          47

<210> SEQ ID NO 244
<211> LENGTH: 47
<212> TYPE: DNA
<213> ORGANISM: Artificial Sequence
<220> FEATURE:
<223> OTHER INFORMATION: Synthetic

<400> SEQUENCE: 244
ttaccgcggc kgctgrcaca ccaggtagac gacgaggctg gagtgac          47

<210> SEQ ID NO 245
<211> LENGTH: 47
<212> TYPE: DNA
<213> ORGANISM: Artificial Sequence
<220> FEATURE:
<223> OTHER INFORMATION: Synthetic

<400> SEQUENCE: 245
ttaccgcggc kgctgrcaca caagaaccgc gacgaggctg gagtgac          47

<210> SEQ ID NO 246
<211> LENGTH: 47
<212> TYPE: DNA
<213> ORGANISM: Artificial Sequence
<220> FEATURE:
<223> OTHER INFORMATION: Synthetic

<400> SEQUENCE: 246
ttaccgcggc kgctgrcaca caggagactc gacgaggctg gagtgac          47

<210> SEQ ID NO 247
<211> LENGTH: 47
<212> TYPE: DNA
<213> ORGANISM: Artificial Sequence
<220> FEATURE:
<223> OTHER INFORMATION: Synthetic

<400> SEQUENCE: 247
ttaccgcggc kgctgrcaca cagtgaaggc gacgaggctg gagtgac          47

<210> SEQ ID NO 248
```

```
<211> LENGTH: 47
<212> TYPE: DNA
<213> ORGANISM: Artificial Sequence
<220> FEATURE:
<223> OTHER INFORMATION: Synthetic

<400> SEQUENCE: 248
ttaccgcggc kgctgrcaca ctcttcagcc gacgaggctg gagtgac        47

<210> SEQ ID NO 249
<211> LENGTH: 47
<212> TYPE: DNA
<213> ORGANISM: Artificial Sequence
<220> FEATURE:
<223> OTHER INFORMATION: Synthetic

<400> SEQUENCE: 249
ttaccgcggc kgctgrcaca caacggagtc gacgaggctg gagtgac        47

<210> SEQ ID NO 250
<211> LENGTH: 47
<212> TYPE: DNA
<213> ORGANISM: Artificial Sequence
<220> FEATURE:
<223> OTHER INFORMATION: Synthetic

<400> SEQUENCE: 250
ttaccgcggc kgctgrcaca cgaagagacc gacgaggctg gagtgac        47

<210> SEQ ID NO 251
<211> LENGTH: 47
<212> TYPE: DNA
<213> ORGANISM: Artificial Sequence
<220> FEATURE:
<223> OTHER INFORMATION: Synthetic

<400> SEQUENCE: 251
ttaccgcggc kgctgrcaca cattggtggc gacgaggctg gagtgac        47

<210> SEQ ID NO 252
<211> LENGTH: 47
<212> TYPE: DNA
<213> ORGANISM: Artificial Sequence
<220> FEATURE:
<223> OTHER INFORMATION: Synthetic

<400> SEQUENCE: 252
ttaccgcggc kgctgrcaca cctgtcaagc gacgaggctg gagtgac        47

<210> SEQ ID NO 253
<211> LENGTH: 47
<212> TYPE: DNA
<213> ORGANISM: Artificial Sequence
<220> FEATURE:
<223> OTHER INFORMATION: Synthetic

<400> SEQUENCE: 253
ttaccgcggc kgctgrcaca caggcatcac gacgaggctg gagtgac        47

<210> SEQ ID NO 254
<211> LENGTH: 47
<212> TYPE: DNA
<213> ORGANISM: Artificial Sequence
<220> FEATURE:
<223> OTHER INFORMATION: Synthetic

<400> SEQUENCE: 254
```
ttaccgcggc kgctgrcaca caagaggtcc gacgaggctg gagtgac         47

<210> SEQ ID NO 255
<211> LENGTH: 47
<212> TYPE: DNA
<213> ORGANISM: Artificial Sequence
<220> FEATURE:
<223> OTHER INFORMATION: Synthetic

<400> SEQUENCE: 255
ttaccgcggc kgctgrcaca ctgcattcgc gacgaggctg gagtgac         47

<210> SEQ ID NO 256
<211> LENGTH: 47
<212> TYPE: DNA
<213> ORGANISM: Artificial Sequence
<220> FEATURE:
<223> OTHER INFORMATION: Synthetic

<400> SEQUENCE: 256
ttaccgcggc kgctgrcaca cttggacgtc gacgaggctg gagtgac         47

<210> SEQ ID NO 257
<211> LENGTH: 47
<212> TYPE: DNA
<213> ORGANISM: Artificial Sequence
<220> FEATURE:
<223> OTHER INFORMATION: Synthetic

<400> SEQUENCE: 257
ttaccgcggc kgctgrcaca cttgctggac gacgaggctg gagtgac         47

<210> SEQ ID NO 258
<211> LENGTH: 47
<212> TYPE: DNA
<213> ORGANISM: Artificial Sequence
<220> FEATURE:
<223> OTHER INFORMATION: Synthetic

<400> SEQUENCE: 258
ttaccgcggc kgctgrcaca ctggagatgc gacgaggctg gagtgac         47

<210> SEQ ID NO 259
<211> LENGTH: 47
<212> TYPE: DNA
<213> ORGANISM: Artificial Sequence
<220> FEATURE:
<223> OTHER INFORMATION: Synthetic

<400> SEQUENCE: 259
ttaccgcggc kgctgrcaca ctacgtaccc gacgaggctg gagtgac         47

<210> SEQ ID NO 260
<211> LENGTH: 47
<212> TYPE: DNA
<213> ORGANISM: Artificial Sequence
<220> FEATURE:
<223> OTHER INFORMATION: Synthetic

<400> SEQUENCE: 260
ttaccgcggc kgctgrcaca ctgacacctc gacgaggctg gagtgac         47

<210> SEQ ID NO 261
<211> LENGTH: 47
<212> TYPE: DNA

<213> ORGANISM: Artificial Sequence
<220> FEATURE:
<223> OTHER INFORMATION: Synthetic

<400> SEQUENCE: 261
ttaccgcggc kgctgrcaca cgtccattgc gacgaggctg gagtgac        47

<210> SEQ ID NO 262
<211> LENGTH: 47
<212> TYPE: DNA
<213> ORGANISM: Artificial Sequence
<220> FEATURE:
<223> OTHER INFORMATION: Synthetic

<400> SEQUENCE: 262
ttaccgcggc kgctgrcaca ccagagaagc gacgaggctg gagtgac        47

<210> SEQ ID NO 263
<211> LENGTH: 47
<212> TYPE: DNA
<213> ORGANISM: Artificial Sequence
<220> FEATURE:
<223> OTHER INFORMATION: Synthetic

<400> SEQUENCE: 263
ttaccgcggc kgctgrcaca ctgcttcagc gacgaggctg gagtgac        47

<210> SEQ ID NO 264
<211> LENGTH: 47
<212> TYPE: DNA
<213> ORGANISM: Artificial Sequence
<220> FEATURE:
<223> OTHER INFORMATION: Synthetic

<400> SEQUENCE: 264
ttaccgcggc kgctgrcaca ctacactgcc gacgaggctg gagtgac        47

<210> SEQ ID NO 265
<211> LENGTH: 47
<212> TYPE: DNA
<213> ORGANISM: Artificial Sequence
<220> FEATURE:
<223> OTHER INFORMATION: Synthetic

<400> SEQUENCE: 265
ttaccgcggc kgctgrcaca cggacgtatc gacgaggctg gagtgac        47

<210> SEQ ID NO 266
<211> LENGTH: 47
<212> TYPE: DNA
<213> ORGANISM: Artificial Sequence
<220> FEATURE:
<223> OTHER INFORMATION: Synthetic

<400> SEQUENCE: 266
ttaccgcggc kgctgrcaca cctcgcatac gacgaggctg gagtgac        47

<210> SEQ ID NO 267
<211> LENGTH: 47
<212> TYPE: DNA
<213> ORGANISM: Artificial Sequence
<220> FEATURE:
<223> OTHER INFORMATION: Synthetic

<400> SEQUENCE: 267
ttaccgcggc kgctgrcaca cgcatcctac gacgaggctg gagtgac        47

<210> SEQ ID NO 268
<211> LENGTH: 47
<212> TYPE: DNA
<213> ORGANISM: Artificial Sequence
<220> FEATURE:
<223> OTHER INFORMATION: Synthetic

<400> SEQUENCE: 268
ttaccgcggc kgctgrcaca caggcttacc gacgaggctg gagtgac         47

<210> SEQ ID NO 269
<211> LENGTH: 47
<212> TYPE: DNA
<213> ORGANISM: Artificial Sequence
<220> FEATURE:
<223> OTHER INFORMATION: Synthetic

<400> SEQUENCE: 269
ttaccgcggc kgctgrcaca cgtaagtcgc gacgaggctg gagtgac         47

<210> SEQ ID NO 270
<211> LENGTH: 47
<212> TYPE: DNA
<213> ORGANISM: Artificial Sequence
<220> FEATURE:
<223> OTHER INFORMATION: Synthetic

<400> SEQUENCE: 270
ttaccgcggc kgctgrcaca cttctggagc gacgaggctg gagtgac         47

<210> SEQ ID NO 271
<211> LENGTH: 47
<212> TYPE: DNA
<213> ORGANISM: Artificial Sequence
<220> FEATURE:
<223> OTHER INFORMATION: Synthetic

<400> SEQUENCE: 271
ttaccgcggc kgctgrcaca cgacacacac gacgaggctg gagtgac         47

<210> SEQ ID NO 272
<211> LENGTH: 47
<212> TYPE: DNA
<213> ORGANISM: Artificial Sequence
<220> FEATURE:
<223> OTHER INFORMATION: Synthetic

<400> SEQUENCE: 272
ttaccgcggc kgctgrcaca caccagacac gacgaggctg gagtgac         47

<210> SEQ ID NO 273
<211> LENGTH: 47
<212> TYPE: DNA
<213> ORGANISM: Artificial Sequence
<220> FEATURE:
<223> OTHER INFORMATION: Synthetic

<400> SEQUENCE: 273
ttaccgcggc kgctgrcaca ctgcagcttc gacgaggctg gagtgac         47

<210> SEQ ID NO 274
<211> LENGTH: 47
<212> TYPE: DNA
<213> ORGANISM: Artificial Sequence
<220> FEATURE:

```
<223> OTHER INFORMATION: Synthetic

<400> SEQUENCE: 274
ttaccgcggc kgctgrcaca cgcaacttcc gacgaggctg gagtgac        47

<210> SEQ ID NO 275
<211> LENGTH: 47
<212> TYPE: DNA
<213> ORGANISM: Artificial Sequence
<220> FEATURE:
<223> OTHER INFORMATION: Synthetic

<400> SEQUENCE: 275
ttaccgcggc kgctgrcaca cactcgcttc gacgaggctg gagtgac        47

<210> SEQ ID NO 276
<211> LENGTH: 47
<212> TYPE: DNA
<213> ORGANISM: Artificial Sequence
<220> FEATURE:
<223> OTHER INFORMATION: Synthetic

<400> SEQUENCE: 276
ttaccgcggc kgctgrcaca ctgaactccc gacgaggctg gagtgac        47

<210> SEQ ID NO 277
<211> LENGTH: 47
<212> TYPE: DNA
<213> ORGANISM: Artificial Sequence
<220> FEATURE:
<223> OTHER INFORMATION: Synthetic

<400> SEQUENCE: 277
ttaccgcggc kgctgrcaca cgtgtaagcc gacgaggctg gagtgac        47

<210> SEQ ID NO 278
<211> LENGTH: 47
<212> TYPE: DNA
<213> ORGANISM: Artificial Sequence
<220> FEATURE:
<223> OTHER INFORMATION: Synthetic

<400> SEQUENCE: 278
ttaccgcggc kgctgrcaca catgcacctc gacgaggctg gagtgac        47

<210> SEQ ID NO 279
<211> LENGTH: 47
<212> TYPE: DNA
<213> ORGANISM: Artificial Sequence
<220> FEATURE:
<223> OTHER INFORMATION: Synthetic

<400> SEQUENCE: 279
ttaccgcggc kgctgrcaca ctccgtcaac gacgaggctg gagtgac        47

<210> SEQ ID NO 280
<211> LENGTH: 47
<212> TYPE: DNA
<213> ORGANISM: Artificial Sequence
<220> FEATURE:
<223> OTHER INFORMATION: Synthetic

<400> SEQUENCE: 280
ttaccgcggc kgctgrcaca cgtcggtatc gacgaggctg gagtgac        47
```

```
<210> SEQ ID NO 281
<211> LENGTH: 47
<212> TYPE: DNA
<213> ORGANISM: Artificial Sequence
<220> FEATURE:
<223> OTHER INFORMATION: Synthetic

<400> SEQUENCE: 281
ttaccgcggc kgctgrcaca cgtcggtatc gacgaggctg gagtgac          47

<210> SEQ ID NO 282
<211> LENGTH: 47
<212> TYPE: DNA
<213> ORGANISM: Artificial Sequence
<220> FEATURE:
<223> OTHER INFORMATION: Synthetic

<400> SEQUENCE: 282
ttaccgcggc kgctgrcaca ctcggatctc gacgaggctg gagtgac          47

<210> SEQ ID NO 283
<211> LENGTH: 47
<212> TYPE: DNA
<213> ORGANISM: Artificial Sequence
<220> FEATURE:
<223> OTHER INFORMATION: Synthetic

<400> SEQUENCE: 283
ttaccgcggc kgctgrcaca cagagtcgtc gacgaggctg gagtgac          47

<210> SEQ ID NO 284
<211> LENGTH: 47
<212> TYPE: DNA
<213> ORGANISM: Artificial Sequence
<220> FEATURE:
<223> OTHER INFORMATION: Synthetic

<400> SEQUENCE: 284
ttaccgcggc kgctgrcaca cagagtcgtc gacgaggctg gagtgac          47

<210> SEQ ID NO 285
<211> LENGTH: 47
<212> TYPE: DNA
<213> ORGANISM: Artificial Sequence
<220> FEATURE:
<223> OTHER INFORMATION: Synthetic

<400> SEQUENCE: 285
ttaccgcggc kgctgrcaca cggattggtc gacgaggctg gagtgac          47

<210> SEQ ID NO 286
<211> LENGTH: 47
<212> TYPE: DNA
<213> ORGANISM: Artificial Sequence
<220> FEATURE:
<223> OTHER INFORMATION: Synthetic

<400> SEQUENCE: 286
ttaccgcggc kgctgrcaca cgccatagac gacgaggctg gagtgac          47

<210> SEQ ID NO 287
<211> LENGTH: 47
<212> TYPE: DNA
<213> ORGANISM: Artificial Sequence
<220> FEATURE:
<223> OTHER INFORMATION: Synthetic
```

<400> SEQUENCE: 287
ttaccgcggc kgctgrcaca ctgtcagagc gacgaggctg gagtgac        47

<210> SEQ ID NO 288
<211> LENGTH: 47
<212> TYPE: DNA
<213> ORGANISM: Artificial Sequence
<220> FEATURE:
<223> OTHER INFORMATION: Synthetic

<400> SEQUENCE: 288
ttaccgcggc kgctgrcaca ccctacgaac gacgaggctg gagtgac        47

<210> SEQ ID NO 289
<211> LENGTH: 47
<212> TYPE: DNA
<213> ORGANISM: Artificial Sequence
<220> FEATURE:
<223> OTHER INFORMATION: Synthetic

<400> SEQUENCE: 289
ttaccgcggc kgctgrcaca cgttacgtcc gacgaggctg gagtgac        47

<210> SEQ ID NO 290
<211> LENGTH: 47
<212> TYPE: DNA
<213> ORGANISM: Artificial Sequence
<220> FEATURE:
<223> OTHER INFORMATION: Synthetic

<400> SEQUENCE: 290
ttaccgcggc kgctgrcaca ccgagatacc gacgaggctg gagtgac        47

<210> SEQ ID NO 291
<211> LENGTH: 47
<212> TYPE: DNA
<213> ORGANISM: Artificial Sequence
<220> FEATURE:
<223> OTHER INFORMATION: Synthetic

<400> SEQUENCE: 291
ttaccgcggc kgctgrcaca cgcattgacc gacgaggctg gagtgac        47

<210> SEQ ID NO 292
<211> LENGTH: 7
<212> TYPE: DNA
<213> ORGANISM: Artificial Sequence
<220> FEATURE:
<223> OTHER INFORMATION: Synthetic

<400> SEQUENCE: 292 actaggt        7

<210> SEQ ID NO 293
<211> LENGTH: 7
<212> TYPE: DNA
<213> ORGANISM: Artificial Sequence
<220> FEATURE:
<223> OTHER INFORMATION: Synthetic

<400> SEQUENCE: 293 agctcta        7

<210> SEQ ID NO 294
<211> LENGTH: 7

```
<212> TYPE: DNA
<213> ORGANISM: Artificial Sequence
<220> FEATURE:
<223> OTHER INFORMATION: Synthetic

<400> SEQUENCE: 294 agagagt                                                                    7

<210> SEQ ID NO 295
<211> LENGTH: 7
<212> TYPE: DNA
<213> ORGANISM: Artificial Sequence
<220> FEATURE:
<223> OTHER INFORMATION: Synthetic

<400> SEQUENCE: 295 gtgttcc                                                                    7

<210> SEQ ID NO 296
<211> LENGTH: 7
<212> TYPE: DNA
<213> ORGANISM: Artificial Sequence
<220> FEATURE:
<223> OTHER INFORMATION: Synthetic

<400> SEQUENCE: 296 gtgttcc                                                                    7

<210> SEQ ID NO 297
<211> LENGTH: 7
<212> TYPE: DNA
<213> ORGANISM: Artificial Sequence
<220> FEATURE:
<223> OTHER INFORMATION: Synthetic

<400> SEQUENCE: 297 accatac                                                                    7

<210> SEQ ID NO 298
<211> LENGTH: 7
<212> TYPE: DNA
<213> ORGANISM: Artificial Sequence
<220> FEATURE:
<223> OTHER INFORMATION: Synthetic

<400> SEQUENCE: 298 taccgtt                                                                    7

<210> SEQ ID NO 299
<211> LENGTH: 7
<212> TYPE: DNA
<213> ORGANISM: Artificial Sequence
<220> FEATURE:
<223> OTHER INFORMATION: Synthetic

<400> SEQUENCE: 299 gccaact                                                                    7

<210> SEQ ID NO 300
<211> LENGTH: 7
<212> TYPE: DNA
<213> ORGANISM: Artificial Sequence
<220> FEATURE:
<223> OTHER INFORMATION: Synthetic

<400> SEQUENCE: 300
```

```
gaagtct                                                          7

<210> SEQ ID NO 301
<211> LENGTH: 7
<212> TYPE: DNA
<213> ORGANISM: Artificial Sequence
<220> FEATURE:
<223> OTHER INFORMATION: Synthetic

<400> SEQUENCE: 301 taagcac                                                          7

<210> SEQ ID NO 302
<211> LENGTH: 7
<212> TYPE: DNA
<213> ORGANISM: Artificial Sequence
<220> FEATURE:
<223> OTHER INFORMATION: Synthetic

<400> SEQUENCE: 302 ctagtgg                                                          7

<210> SEQ ID NO 303
<211> LENGTH: 7
<212> TYPE: DNA
<213> ORGANISM: Artificial Sequence
<220> FEATURE:
<223> OTHER INFORMATION: Synthetic

<400> SEQUENCE: 303 atagcgc                                                          7

<210> SEQ ID NO 304
<211> LENGTH: 7
<212> TYPE: DNA
<213> ORGANISM: Artificial Sequence
<220> FEATURE:
<223> OTHER INFORMATION: Synthetic

<400> SEQUENCE: 304 agtgtca                                                          7

<210> SEQ ID NO 305
<211> LENGTH: 7
<212> TYPE: DNA
<213> ORGANISM: Artificial Sequence
<220> FEATURE:
<223> OTHER INFORMATION: Synthetic

<400> SEQUENCE: 305 gttcctc                                                          7

<210> SEQ ID NO 306
<211> LENGTH: 7
<212> TYPE: DNA
<213> ORGANISM: Artificial Sequence
<220> FEATURE:
<223> OTHER INFORMATION: Synthetic

<400> SEQUENCE: 306 tggtcaa                                                          7

<210> SEQ ID NO 307
<211> LENGTH: 7
<212> TYPE: DNA
<213> ORGANISM: Artificial Sequence
```

```
<220> FEATURE:
<223> OTHER INFORMATION: Synthetic

<400> SEQUENCE: 307 tgctacc                                                           7

<210> SEQ ID NO 308
<211> LENGTH: 7
<212> TYPE: DNA
<213> ORGANISM: Artificial Sequence
<220> FEATURE:
<223> OTHER INFORMATION: Synthetic

<400> SEQUENCE: 308 ctcaacg                                                           7

<210> SEQ ID NO 309
<211> LENGTH: 7
<212> TYPE: DNA
<213> ORGANISM: Artificial Sequence
<220> FEATURE:
<223> OTHER INFORMATION: Synthetic

<400> SEQUENCE: 309 cagttgt                                                           7

<210> SEQ ID NO 310
<211> LENGTH: 7
<212> TYPE: DNA
<213> ORGANISM: Artificial Sequence
<220> FEATURE:
<223> OTHER INFORMATION: Synthetic

<400> SEQUENCE: 310 tgactga                                                           7

<210> SEQ ID NO 311
<211> LENGTH: 7
<212> TYPE: DNA
<213> ORGANISM: Artificial Sequence
<220> FEATURE:
<223> OTHER INFORMATION: Synthetic

<400> SEQUENCE: 311 atgtacg                                                           7

<210> SEQ ID NO 312
<211> LENGTH: 7
<212> TYPE: DNA
<213> ORGANISM: Artificial Sequence
<220> FEATURE:
<223> OTHER INFORMATION: Synthetic

<400> SEQUENCE: 312 gcactca                                                           7

<210> SEQ ID NO 313
<211> LENGTH: 7
<212> TYPE: DNA
<213> ORGANISM: Artificial Sequence
<220> FEATURE:
<223> OTHER INFORMATION: Synthetic

<400> SEQUENCE: 313 taacagg                                                           7
```

```
<210> SEQ ID NO 314
<211> LENGTH: 7
<212> TYPE: DNA
<213> ORGANISM: Artificial Sequence
<220> FEATURE:
<223> OTHER INFORMATION: Synthetic

<400> SEQUENCE: 314 tagaggt                                                                   7

<210> SEQ ID NO 315
<211> LENGTH: 7
<212> TYPE: DNA
<213> ORGANISM: Artificial Sequence
<220> FEATURE:
<223> OTHER INFORMATION: Synthetic

<400> SEQUENCE: 315 gtggaat                                                                   7

<210> SEQ ID NO 316
<211> LENGTH: 7
<212> TYPE: DNA
<213> ORGANISM: Artificial Sequence
<220> FEATURE:
<223> OTHER INFORMATION: Synthetic

<400> SEQUENCE: 316 catacga                                                                   7

<210> SEQ ID NO 317
<211> LENGTH: 7
<212> TYPE: DNA
<213> ORGANISM: Artificial Sequence
<220> FEATURE:
<223> OTHER INFORMATION: Synthetic

<400> SEQUENCE: 317 acaacct                                                                   7

<210> SEQ ID NO 318
<211> LENGTH: 7
<212> TYPE: DNA
<213> ORGANISM: Artificial Sequence
<220> FEATURE:
<223> OTHER INFORMATION: Synthetic

<400> SEQUENCE: 318 gactacg                                                                   7

<210> SEQ ID NO 319
<211> LENGTH: 7
<212> TYPE: DNA
<213> ORGANISM: Artificial Sequence
<220> FEATURE:
<223> OTHER INFORMATION: Synthetic

<400> SEQUENCE: 319 cgagaag                                                                   7

<210> SEQ ID NO 320
<211> LENGTH: 7
<212> TYPE: DNA
<213> ORGANISM: Artificial Sequence
<220> FEATURE:
<223> OTHER INFORMATION: Synthetic
```

```
<400> SEQUENCE: 320 cttacct                                                              7

<210> SEQ ID NO 321
<211> LENGTH: 7
<212> TYPE: DNA
<213> ORGANISM: Artificial Sequence
<220> FEATURE:
<223> OTHER INFORMATION: Synthetic

<400> SEQUENCE: 321 tgagatc                                                              7

<210> SEQ ID NO 322
<211> LENGTH: 7
<212> TYPE: DNA
<213> ORGANISM: Artificial Sequence
<220> FEATURE:
<223> OTHER INFORMATION: Synthetic

<400> SEQUENCE: 322 gttcgat                                                              7

<210> SEQ ID NO 323
<211> LENGTH: 7
<212> TYPE: DNA
<213> ORGANISM: Artificial Sequence
<220> FEATURE:
<223> OTHER INFORMATION: Synthetic

<400> SEQUENCE: 323 gttcgat                                                              7

<210> SEQ ID NO 324
<211> LENGTH: 8
<212> TYPE: DNA
<213> ORGANISM: Artificial Sequence
<220> FEATURE:
<223> OTHER INFORMATION: Synthetic

<400> SEQUENCE: 324 cctgagtt                                                             8

<210> SEQ ID NO 325
<211> LENGTH: 8
<212> TYPE: DNA
<213> ORGANISM: Artificial Sequence
<220> FEATURE:
<223> OTHER INFORMATION: Synthetic

<400> SEQUENCE: 325 ttgtggca                                                             8

<210> SEQ ID NO 326
<211> LENGTH: 8
<212> TYPE: DNA
<213> ORGANISM: Artificial Sequence
<220> FEATURE:
<223> OTHER INFORMATION: Synthetic

<400> SEQUENCE: 326 atcgccat                                                             8

<210> SEQ ID NO 327
```

```
<211> LENGTH: 8
<212> TYPE: DNA
<213> ORGANISM: Artificial Sequence
<220> FEATURE:
<223> OTHER INFORMATION: Synthetic

<400> SEQUENCE: 327 atcgccat                                                                8

<210> SEQ ID NO 328
<211> LENGTH: 8
<212> TYPE: DNA
<213> ORGANISM: Artificial Sequence
<220> FEATURE:
<223> OTHER INFORMATION: Synthetic

<400> SEQUENCE: 328 gtacaacc                                                                8

<210> SEQ ID NO 329
<211> LENGTH: 8
<212> TYPE: DNA
<213> ORGANISM: Artificial Sequence
<220> FEATURE:
<223> OTHER INFORMATION: Synthetic

<400> SEQUENCE: 329 aagtcgag                                                                8

<210> SEQ ID NO 330
<211> LENGTH: 8
<212> TYPE: DNA
<213> ORGANISM: Artificial Sequence
<220> FEATURE:
<223> OTHER INFORMATION: Synthetic

<400> SEQUENCE: 330 gcttccta                                                                8

<210> SEQ ID NO 331
<211> LENGTH: 8
<212> TYPE: DNA
<213> ORGANISM: Artificial Sequence
<220> FEATURE:
<223> OTHER INFORMATION: Synthetic

<400> SEQUENCE: 331 acatgcac                                                                8

<210> SEQ ID NO 332
<211> LENGTH: 8
<212> TYPE: DNA
<213> ORGANISM: Artificial Sequence
<220> FEATURE:
<223> OTHER INFORMATION: Synthetic

<400> SEQUENCE: 332 ccgattga                                                                8

<210> SEQ ID NO 333
<211> LENGTH: 8
<212> TYPE: DNA
<213> ORGANISM: Artificial Sequence
<220> FEATURE:
<223> OTHER INFORMATION: Synthetic

<400> SEQUENCE: 333
``` gagcttga                                                                    8

<210> SEQ ID NO 334
<211> LENGTH: 8
<212> TYPE: DNA
<213> ORGANISM: Artificial Sequence
<220> FEATURE:
<223> OTHER INFORMATION: Synthetic

<400> SEQUENCE: 334 gtgacact                                                                    8

<210> SEQ ID NO 335
<211> LENGTH: 8
<212> TYPE: DNA
<213> ORGANISM: Artificial Sequence
<220> FEATURE:
<223> OTHER INFORMATION: Synthetic

<400> SEQUENCE: 335 ggaacaca                                                                    8

<210> SEQ ID NO 336
<211> LENGTH: 8
<212> TYPE: DNA
<213> ORGANISM: Artificial Sequence
<220> FEATURE:
<223> OTHER INFORMATION: Synthetic

<400> SEQUENCE: 336 gattcgga                                                                    8

<210> SEQ ID NO 337
<211> LENGTH: 8
<212> TYPE: DNA
<213> ORGANISM: Artificial Sequence
<220> FEATURE:
<223> OTHER INFORMATION: Synthetic

<400> SEQUENCE: 337 tgtactcc                                                                    8

<210> SEQ ID NO 338
<211> LENGTH: 8
<212> TYPE: DNA
<213> ORGANISM: Artificial Sequence
<220> FEATURE:
<223> OTHER INFORMATION: Synthetic

<400> SEQUENCE: 338 tctgtcct                                                                    8

<210> SEQ ID NO 339
<211> LENGTH: 8
<212> TYPE: DNA
<213> ORGANISM: Artificial Sequence
<220> FEATURE:
<223> OTHER INFORMATION: Synthetic

<400> SEQUENCE: 339 aactgtgc                                                                    8

<210> SEQ ID NO 340
<211> LENGTH: 8
<212> TYPE: DNA

```
<213> ORGANISM: Artificial Sequence
<220> FEATURE:
<223> OTHER INFORMATION: Synthetic

<400> SEQUENCE: 340 tgttgtcg                                                                8

<210> SEQ ID NO 341
<211> LENGTH: 8
<212> TYPE: DNA
<213> ORGANISM: Artificial Sequence
<220> FEATURE:
<223> OTHER INFORMATION: Synthetic

<400> SEQUENCE: 341 tacgtgct                                                                8

<210> SEQ ID NO 342
<211> LENGTH: 8
<212> TYPE: DNA
<213> ORGANISM: Artificial Sequence
<220> FEATURE:
<223> OTHER INFORMATION: Synthetic

<400> SEQUENCE: 342 actgttgg                                                                8

<210> SEQ ID NO 343
<211> LENGTH: 8
<212> TYPE: DNA
<213> ORGANISM: Artificial Sequence
<220> FEATURE:
<223> OTHER INFORMATION: Synthetic

<400> SEQUENCE: 343 actgttgg                                                                8

<210> SEQ ID NO 344
<211> LENGTH: 8
<212> TYPE: DNA
<213> ORGANISM: Artificial Sequence
<220> FEATURE:
<223> OTHER INFORMATION: Synthetic

<400> SEQUENCE: 344 caggatag                                                                8

<210> SEQ ID NO 345
<211> LENGTH: 8
<212> TYPE: DNA
<213> ORGANISM: Artificial Sequence
<220> FEATURE:
<223> OTHER INFORMATION: Synthetic

<400> SEQUENCE: 345 gacagaca                                                                8

<210> SEQ ID NO 346
<211> LENGTH: 8
<212> TYPE: DNA
<213> ORGANISM: Artificial Sequence
<220> FEATURE:
<223> OTHER INFORMATION: Synthetic

<400> SEQUENCE: 346 agactagg                                                                8
```

```
<210> SEQ ID NO 347
<211> LENGTH: 8
<212> TYPE: DNA
<213> ORGANISM: Artificial Sequence
<220> FEATURE:
<223> OTHER INFORMATION: Synthetic

<400> SEQUENCE: 347 agactagg                                                                   8

<210> SEQ ID NO 348
<211> LENGTH: 8
<212> TYPE: DNA
<213> ORGANISM: Artificial Sequence
<220> FEATURE:
<223> OTHER INFORMATION: Synthetic

<400> SEQUENCE: 348 agccacta                                                                   8

<210> SEQ ID NO 349
<211> LENGTH: 8
<212> TYPE: DNA
<213> ORGANISM: Artificial Sequence
<220> FEATURE:
<223> OTHER INFORMATION: Synthetic

<400> SEQUENCE: 349 gcagattc                                                                   8

<210> SEQ ID NO 350
<211> LENGTH: 8
<212> TYPE: DNA
<213> ORGANISM: Artificial Sequence
<220> FEATURE:
<223> OTHER INFORMATION: Synthetic

<400> SEQUENCE: 350 gcatcgaa                                                                   8

<210> SEQ ID NO 351
<211> LENGTH: 8
<212> TYPE: DNA
<213> ORGANISM: Artificial Sequence
<220> FEATURE:
<223> OTHER INFORMATION: Synthetic

<400> SEQUENCE: 351 aaccaagc                                                                   8

<210> SEQ ID NO 352
<211> LENGTH: 8
<212> TYPE: DNA
<213> ORGANISM: Artificial Sequence
<220> FEATURE:
<223> OTHER INFORMATION: Synthetic

<400> SEQUENCE: 352 gatcagct                                                                   8

<210> SEQ ID NO 353
<211> LENGTH: 8
<212> TYPE: DNA
<213> ORGANISM: Artificial Sequence
<220> FEATURE:
```

-continued

<223> OTHER INFORMATION: Synthetic

<400> SEQUENCE: 353 ccgcttat                                                                  8

<210> SEQ ID NO 354
<211> LENGTH: 8
<212> TYPE: DNA
<213> ORGANISM: Artificial Sequence
<220> FEATURE:
<223> OTHER INFORMATION: Synthetic

<400> SEQUENCE: 354 tccgaagt                                                                  8

<210> SEQ ID NO 355
<211> LENGTH: 8
<212> TYPE: DNA
<213> ORGANISM: Artificial Sequence
<220> FEATURE:
<223> OTHER INFORMATION: Synthetic

<400> SEQUENCE: 355 tcgactag                                                                  8

<210> SEQ ID NO 356
<211> LENGTH: 9
<212> TYPE: DNA
<213> ORGANISM: Artificial Sequence
<220> FEATURE:
<223> OTHER INFORMATION: Synthetic

<400> SEQUENCE: 356 gcaagaacg                                                                 9

<210> SEQ ID NO 357
<211> LENGTH: 9
<212> TYPE: DNA
<213> ORGANISM: Artificial Sequence
<220> FEATURE:
<223> OTHER INFORMATION: Synthetic

<400> SEQUENCE: 357 gagtctaca                                                                 9

<210> SEQ ID NO 358
<211> LENGTH: 9
<212> TYPE: DNA
<213> ORGANISM: Artificial Sequence
<220> FEATURE:
<223> OTHER INFORMATION: Synthetic

<400> SEQUENCE: 358 taggccttc                                                                 9

<210> SEQ ID NO 359
<211> LENGTH: 9
<212> TYPE: DNA
<213> ORGANISM: Artificial Sequence
<220> FEATURE:
<223> OTHER INFORMATION: Synthetic

<400> SEQUENCE: 359 ccttacgaa                                                                 9

```
<210> SEQ ID NO 360
<211> LENGTH: 9
<212> TYPE: DNA
<213> ORGANISM: Artificial Sequence
<220> FEATURE:
<223> OTHER INFORMATION: Synthetic

<400> SEQUENCE: 360 aggtgatca                                                              9

<210> SEQ ID NO 361
<211> LENGTH: 9
<212> TYPE: DNA
<213> ORGANISM: Artificial Sequence
<220> FEATURE:
<223> OTHER INFORMATION: Artificial Sequence

<400> SEQUENCE: 361 cgttagcta                                                              9

<210> SEQ ID NO 362
<211> LENGTH: 9
<212> TYPE: DNA
<213> ORGANISM: Artificial Sequence
<220> FEATURE:
<223> OTHER INFORMATION: Synthetic

<400> SEQUENCE: 362 ccttctacg                                                              9

<210> SEQ ID NO 363
<211> LENGTH: 9
<212> TYPE: DNA
<213> ORGANISM: Artificial Sequence
<220> FEATURE:
<223> OTHER INFORMATION: Synthetic

<400> SEQUENCE: 363 ttcgagaga                                                              9

<210> SEQ ID NO 364
<211> LENGTH: 9
<212> TYPE: DNA
<213> ORGANISM: Artificial Sequence
<220> FEATURE:
<223> OTHER INFORMATION: Synthetic

<400> SEQUENCE: 364 ggaactaga                                                              9

<210> SEQ ID NO 365
<211> LENGTH: 9
<212> TYPE: DNA
<213> ORGANISM: Artificial Sequence
<220> FEATURE:
<223> OTHER INFORMATION: Synthetic

<400> SEQUENCE: 365 tctcttcgg                                                              9

<210> SEQ ID NO 366
<211> LENGTH: 9
<212> TYPE: DNA
<213> ORGANISM: Artificial Sequence
<220> FEATURE:
<223> OTHER INFORMATION: Synthetic
```

```
<400> SEQUENCE: 366 atgtcacct                                                                9

<210> SEQ ID NO 367
<211> LENGTH: 9
<212> TYPE: DNA
<213> ORGANISM: Artificial Sequence
<220> FEATURE:
<223> OTHER INFORMATION: Synthetic

<400> SEQUENCE: 367 cgttctcag                                                                9

<210> SEQ ID NO 368
<211> LENGTH: 9
<212> TYPE: DNA
<213> ORGANISM: Artificial Sequence
<220> FEATURE:
<223> OTHER INFORMATION: Synthetic

<400> SEQUENCE: 368 ttcagctgg                                                                9

<210> SEQ ID NO 369
<211> LENGTH: 9
<212> TYPE: DNA
<213> ORGANISM: Artificial Sequence
<220> FEATURE:
<223> OTHER INFORMATION: Synthetic

<400> SEQUENCE: 369 tgtcgaacg                                                                9

<210> SEQ ID NO 370
<211> LENGTH: 9
<212> TYPE: DNA
<213> ORGANISM: Artificial Sequence
<220> FEATURE:
<223> OTHER INFORMATION: Synthetic

<400> SEQUENCE: 370 ggtctaaga                                                                9

<210> SEQ ID NO 371
<211> LENGTH: 9
<212> TYPE: DNA
<213> ORGANISM: Artificial Sequence
<220> FEATURE:
<223> OTHER INFORMATION: Synthetic

<400> SEQUENCE: 371 ttgctcgtg                                                                9

<210> SEQ ID NO 372
<211> LENGTH: 9
<212> TYPE: DNA
<213> ORGANISM: Artificial Sequence
<220> FEATURE:
<223> OTHER INFORMATION: Synthetic

<400> SEQUENCE: 372 attcggcag                                                                9

<210> SEQ ID NO 373
<211> LENGTH: 9
```

```
<212> TYPE: DNA
<213> ORGANISM: Artificial Sequence
<220> FEATURE:
<223> OTHER INFORMATION: Synthetic

<400> SEQUENCE: 373 tatgagccc                                                                9

<210> SEQ ID NO 374
<211> LENGTH: 9
<212> TYPE: DNA
<213> ORGANISM: Artificial Sequence
<220> FEATURE:
<223> OTHER INFORMATION: Synthetic

<400> SEQUENCE: 374 agtacggtg                                                                9

<210> SEQ ID NO 375
<211> LENGTH: 9
<212> TYPE: DNA
<213> ORGANISM: Artificial sequence
<220> FEATURE:
<223> OTHER INFORMATION: Synthetic

<400> SEQUENCE: 375 tcgagacac                                                                9

<210> SEQ ID NO 376
<211> LENGTH: 9
<212> TYPE: DNA
<213> ORGANISM: Artificial Sequence
<220> FEATURE:
<223> OTHER INFORMATION: Synthetic

<400> SEQUENCE: 376 tcgcagtaa                                                                9

<210> SEQ ID NO 377
<211> LENGTH: 9
<212> TYPE: DNA
<213> ORGANISM: Artificial Sequence
<220> FEATURE:
<223> OTHER INFORMATION: Synthetic

<400> SEQUENCE: 377 tcgtatgga                                                                9

<210> SEQ ID NO 378
<211> LENGTH: 9
<212> TYPE: DNA
<213> ORGANISM: Artificial Sequence
<220> FEATURE:
<223> OTHER INFORMATION: Synthetic

<400> SEQUENCE: 378 acctggatc                                                                9

<210> SEQ ID NO 379
<211> LENGTH: 9
<212> TYPE: DNA
<213> ORGANISM: Artificial Sequence
<220> FEATURE:
<223> OTHER INFORMATION: Synthetic

<400> SEQUENCE: 379
``` ttcgcaact                                                                        9

<210> SEQ ID NO 380
<211> LENGTH: 9
<212> TYPE: DNA
<213> ORGANISM: Artificial Sequence
<220> FEATURE:
<223> OTHER INFORMATION: Synthetic

<400> SEQUENCE: 380 tctcaacct                                                                        9

<210> SEQ ID NO 381
<211> LENGTH: 9
<212> TYPE: DNA
<213> ORGANISM: Artificial Sequence
<220> FEATURE:
<223> OTHER INFORMATION: Synthetic

<400> SEQUENCE: 381 aagcgcaac                                                                        9

<210> SEQ ID NO 382
<211> LENGTH: 9
<212> TYPE: DNA
<213> ORGANISM: Artificial Sequence
<220> FEATURE:
<223> OTHER INFORMATION: Synthetic

<400> SEQUENCE: 382 tctctcgag                                                                        9

<210> SEQ ID NO 383
<211> LENGTH: 9
<212> TYPE: DNA
<213> ORGANISM: Artificial Sequence
<220> FEATURE:
<223> OTHER INFORMATION: Synthetic

<400> SEQUENCE: 383 ctaggaaca                                                                        9

<210> SEQ ID NO 384
<211> LENGTH: 9
<212> TYPE: DNA
<213> ORGANISM: Artificial Sequence
<220> FEATURE:
<223> OTHER INFORMATION: Synthetic

<400> SEQUENCE: 384 cagtgtgag                                                                        9

<210> SEQ ID NO 385
<211> LENGTH: 9
<212> TYPE: DNA
<213> ORGANISM: Artificial Sequence
<220> FEATURE:
<223> OTHER INFORMATION: Synthetic

<400> SEQUENCE: 385 acatgtggt                                                                        9

<210> SEQ ID NO 386
<211> LENGTH: 9
<212> TYPE: DNA
<213> ORGANISM: Artificial Sequence

```
<220> FEATURE:
<223> OTHER INFORMATION: Synthetic

<400> SEQUENCE: 386 ggttaagct                                                                        9

<210> SEQ ID NO 387
<211> LENGTH: 9
<212> TYPE: DNA
<213> ORGANISM: Artificial Sequence
<220> FEATURE:
<223> OTHER INFORMATION: Synthetic

<400> SEQUENCE: 387 gcataggtg                                                                        9

<210> SEQ ID NO 388
<211> LENGTH: 8
<212> TYPE: DNA
<213> ORGANISM: Artificial Sequence
<220> FEATURE:
<223> OTHER INFORMATION: Synthetic

<400> SEQUENCE: 388 gtaccagt                                                                         8

<210> SEQ ID NO 389
<211> LENGTH: 8
<212> TYPE: DNA
<213> ORGANISM: Artificial Sequence
<220> FEATURE:
<223> OTHER INFORMATION: Synthetic

<400> SEQUENCE: 389 acagtacc                                                                         8

<210> SEQ ID NO 390
<211> LENGTH: 8
<212> TYPE: DNA
<213> ORGANISM: Artificial Sequence
<220> FEATURE:
<223> OTHER INFORMATION: Synthetic

<400> SEQUENCE: 390 cacacaga                                                                         8

<210> SEQ ID NO 391
<211> LENGTH: 8
<212> TYPE: DNA
<213> ORGANISM: Artificial Sequence
<220> FEATURE:
<223> OTHER INFORMATION: Synthetic

<400> SEQUENCE: 391 gagccata                                                                         8

<210> SEQ ID NO 392
<211> LENGTH: 8
<212> TYPE: DNA
<213> ORGANISM: Artificial Sequence
<220> FEATURE:
<223> OTHER INFORMATION: Synthetic

<400> SEQUENCE: 392 ctgacaac                                                                         8
```

```
<210> SEQ ID NO 393
<211> LENGTH: 8
<212> TYPE: DNA
<213> ORGANISM: Artificial Sequence
<220> FEATURE:
<223> OTHER INFORMATION: Synthetic

<400> SEQUENCE: 393 actggcat                                                                8

<210> SEQ ID NO 394
<211> LENGTH: 8
<212> TYPE: DNA
<213> ORGANISM: Artificial Sequence
<220> FEATURE:
<223> OTHER INFORMATION: Synthetic

<400> SEQUENCE: 394 tagtagcg                                                                8

<210> SEQ ID NO 395
<211> LENGTH: 8
<212> TYPE: DNA
<213> ORGANISM: Artificial Sequence
<220> FEATURE:
<223> OTHER INFORMATION: Synthetic

<400> SEQUENCE: 395 cgtgtatg                                                                8

<210> SEQ ID NO 396
<211> LENGTH: 8
<212> TYPE: DNA
<213> ORGANISM: Artificial Sequence
<220> FEATURE:
<223> OTHER INFORMATION: Synthetic

<400> SEQUENCE: 396 atcctcga                                                                8

<210> SEQ ID NO 397
<211> LENGTH: 8
<212> TYPE: DNA
<213> ORGANISM: Artificial Sequence
<220> FEATURE:
<223> OTHER INFORMATION: Synthetic

<400> SEQUENCE: 397 atcgaacc                                                                8

<210> SEQ ID NO 398
<211> LENGTH: 8
<212> TYPE: DNA
<213> ORGANISM: Artificial Sequence
<220> FEATURE:
<223> OTHER INFORMATION: Synthetic

<400> SEQUENCE: 398 tgttccgt                                                                8

<210> SEQ ID NO 399
<211> LENGTH: 8
<212> TYPE: DNA
<213> ORGANISM: Artificial Sequence
<220> FEATURE:
<223> OTHER INFORMATION: Synthetic
```

```
<400> SEQUENCE: 399 atgcaacg                                                                8

<210> SEQ ID NO 400
<211> LENGTH: 8
<212> TYPE: DNA
<213> ORGANISM: Artificial Sequence
<220> FEATURE:
<223> OTHER INFORMATION: Synthetic

<400> SEQUENCE: 400 ggacgtat                                                                8

<210> SEQ ID NO 401
<211> LENGTH: 8
<212> TYPE: DNA
<213> ORGANISM: Artificial Sequence
<220> FEATURE:
<223> OTHER INFORMATION: Synthetic

<400> SEQUENCE: 401 tccagatc                                                                8

<210> SEQ ID NO 402
<211> LENGTH: 8
<212> TYPE: DNA
<213> ORGANISM: Artificial Sequence
<220> FEATURE:
<223> OTHER INFORMATION: Synthetic

<400> SEQUENCE: 402 cttcgaga                                                                8

<210> SEQ ID NO 403
<211> LENGTH: 8
<212> TYPE: DNA
<213> ORGANISM: Artificial Sequence
<220> FEATURE:
<223> OTHER INFORMATION: Synthetic

<400> SEQUENCE: 403 tagcacag                                                                8

<210> SEQ ID NO 404
<211> LENGTH: 8
<212> TYPE: DNA
<213> ORGANISM: Artificial Sequence
<220> FEATURE:
<223> OTHER INFORMATION: Synthetic

<400> SEQUENCE: 404 ttccacct                                                                8

<210> SEQ ID NO 405
<211> LENGTH: 8
<212> TYPE: DNA
<213> ORGANISM: Artificial Sequence
<220> FEATURE:
<223> OTHER INFORMATION: Synthetic

<400> SEQUENCE: 405 cgttgcta                                                                8

<210> SEQ ID NO 406
```

```
<211> LENGTH: 8
<212> TYPE: DNA
<213> ORGANISM: Artificial Sequence
<220> FEATURE:
<223> OTHER INFORMATION: Synthetic

<400> SEQUENCE: 406 gaatgacc                                                                 8

<210> SEQ ID NO 407
<211> LENGTH: 8
<212> TYPE: DNA
<213> ORGANISM: Artificial Sequence
<220> FEATURE:
<223> OTHER INFORMATION: Synthetic

<400> SEQUENCE: 407 gcgtatct                                                                 8

<210> SEQ ID NO 408
<211> LENGTH: 8
<212> TYPE: DNA
<213> ORGANISM: Artificial Sequence
<220> FEATURE:
<223> OTHER INFORMATION: Synthetic

<400> SEQUENCE: 408 agcagttc                                                                 8

<210> SEQ ID NO 409
<211> LENGTH: 8
<212> TYPE: DNA
<213> ORGANISM: Artificial Sequence
<220> FEATURE:
<223> OTHER INFORMATION: Synthetic

<400> SEQUENCE: 409 tgtgcact                                                                 8

<210> SEQ ID NO 410
<211> LENGTH: 8
<212> TYPE: DNA
<213> ORGANISM: Artificial Sequence
<220> FEATURE:
<223> OTHER INFORMATION: Synthetic

<400> SEQUENCE: 410 atgatcgg                                                                 8

<210> SEQ ID NO 411
<211> LENGTH: 8
<212> TYPE: DNA
<213> ORGANISM: Artificial Sequence
<220> FEATURE:
<223> OTHER INFORMATION: Synthetic

<400> SEQUENCE: 411 gtccttgt                                                                 8

<210> SEQ ID NO 412
<211> LENGTH: 8
<212> TYPE: DNA
<213> ORGANISM: Artificial Sequence
<220> FEATURE:
<223> OTHER INFORMATION: Synthetic

<400> SEQUENCE: 412
``` gaccgaat                                                                    8

<210> SEQ ID NO 413
<211> LENGTH: 8
<212> TYPE: DNA
<213> ORGANISM: Artificial Sequence
<220> FEATURE:
<223> OTHER INFORMATION: Synthetic

<400> SEQUENCE: 413 cgtcacaa                                                                    8

<210> SEQ ID NO 414
<211> LENGTH: 8
<212> TYPE: DNA
<213> ORGANISM: Artificial Sequence
<220> FEATURE:
<223> OTHER INFORMATION: Synthetic

<400> SEQUENCE: 414 cagacttc                                                                    8

<210> SEQ ID NO 415
<211> LENGTH: 8
<212> TYPE: DNA
<213> ORGANISM: Artificial Sequence
<220> FEATURE:
<223> OTHER INFORMATION: Synthetic

<400> SEQUENCE: 415 ttcgtcca                                                                    8

<210> SEQ ID NO 416
<211> LENGTH: 8
<212> TYPE: DNA
<213> ORGANISM: Artificial Sequence
<220> FEATURE:
<223> OTHER INFORMATION: Synthetic

<400> SEQUENCE: 416 aggaactc                                                                    8

<210> SEQ ID NO 417
<211> LENGTH: 8
<212> TYPE: DNA
<213> ORGANISM: Artificial Sequence
<220> FEATURE:
<223> OTHER INFORMATION: Synthetic

<400> SEQUENCE: 417 ctcctatc                                                                    8

<210> SEQ ID NO 418
<211> LENGTH: 8
<212> TYPE: DNA
<213> ORGANISM: Artificial Sequence
<220> FEATURE:
<223> OTHER INFORMATION: Synthetic

<400> SEQUENCE: 418 tccaagct                                                                    8

<210> SEQ ID NO 419
<211> LENGTH: 8
<212> TYPE: DNA

```
<213> ORGANISM: Artificial Sequence
<220> FEATURE:
<223> OTHER INFORMATION: Synthetic

<400> SEQUENCE: 419 aggatgtg                                                                8

<210> SEQ ID NO 420
<211> LENGTH: 8
<212> TYPE: DNA
<213> ORGANISM: Artificial Sequence
<220> FEATURE:
<223> OTHER INFORMATION: Synthetic

<400> SEQUENCE: 420 tcaggact                                                                8

<210> SEQ ID NO 421
<211> LENGTH: 8
<212> TYPE: DNA
<213> ORGANISM: Artificial Sequence
<220> FEATURE:
<223> OTHER INFORMATION: Synthetic

<400> SEQUENCE: 421 gctacaag                                                                8

<210> SEQ ID NO 422
<211> LENGTH: 8
<212> TYPE: DNA
<213> ORGANISM: Artificial Sequence
<220> FEATURE:
<223> OTHER INFORMATION: Synthetic

<400> SEQUENCE: 422 tactcctg                                                                8

<210> SEQ ID NO 423
<211> LENGTH: 8
<212> TYPE: DNA
<213> ORGANISM: Artificial Sequence
<220> FEATURE:
<223> OTHER INFORMATION: Synthetic

<400> SEQUENCE: 423 tccttgtg                                                                8

<210> SEQ ID NO 424
<211> LENGTH: 8
<212> TYPE: DNA
<213> ORGANISM: Artificial Sequence
<220> FEATURE:
<223> OTHER INFORMATION: Synthetic

<400> SEQUENCE: 424 cagaggaa                                                                8

<210> SEQ ID NO 425
<211> LENGTH: 8
<212> TYPE: DNA
<213> ORGANISM: Artificial Sequence
<220> FEATURE:
<223> OTHER INFORMATION: Synthetic

<400> SEQUENCE: 425 agcaatgg                                                                8
```

```
<210> SEQ ID NO 426
<211> LENGTH: 8
<212> TYPE: DNA
<213> ORGANISM: Artificial Sequence
<220> FEATURE:
<223> OTHER INFORMATION: Synthetic

<400> SEQUENCE: 426 ctatgtgc                                                                 8

<210> SEQ ID NO 427
<211> LENGTH: 8
<212> TYPE: DNA
<213> ORGANISM: Artificial Sequence
<220> FEATURE:
<223> OTHER INFORMATION: Synthetic

<400> SEQUENCE: 427 gtacagtg                                                                 8

<210> SEQ ID NO 428
<211> LENGTH: 8
<212> TYPE: DNA
<213> ORGANISM: Artificial Sequence
<220> FEATURE:
<223> OTHER INFORMATION: Synthetic

<400> SEQUENCE: 428 gagatcac                                                                 8

<210> SEQ ID NO 429
<211> LENGTH: 8
<212> TYPE: DNA
<213> ORGANISM: Artificial Sequence
<220> FEATURE:
<223> OTHER INFORMATION: Synthetic

<400> SEQUENCE: 429 acggcatt                                                                 8

<210> SEQ ID NO 430
<211> LENGTH: 8
<212> TYPE: DNA
<213> ORGANISM: Artificial Sequence
<220> FEATURE:
<223> OTHER INFORMATION: Synthetic

<400> SEQUENCE: 430 gacaagga                                                                 8

<210> SEQ ID NO 431
<211> LENGTH: 8
<212> TYPE: DNA
<213> ORGANISM: Artificial Sequence
<220> FEATURE:
<223> OTHER INFORMATION: Synthetic

<400> SEQUENCE: 431 tgcctact                                                                 8

<210> SEQ ID NO 432
<211> LENGTH: 8
<212> TYPE: DNA
<213> ORGANISM: Artificial Sequence
<220> FEATURE:
```

<223> OTHER INFORMATION: Synthetic

<400> SEQUENCE: 432 aagaggct                                                                 8

<210> SEQ ID NO 433
<211> LENGTH: 8
<212> TYPE: DNA
<213> ORGANISM: Artificial Sequence
<220> FEATURE:
<223> OTHER INFORMATION: Synthetic

<400> SEQUENCE: 433 cgtaatcg                                                                 8

<210> SEQ ID NO 434
<211> LENGTH: 8
<212> TYPE: DNA
<213> ORGANISM: Artificial Sequence
<220> FEATURE:
<223> OTHER INFORMATION: Synthetic

<400> SEQUENCE: 434 attcctgg                                                                 8

<210> SEQ ID NO 435
<211> LENGTH: 8
<212> TYPE: DNA
<213> ORGANISM: Artificial Sequence
<220> FEATURE:
<223> OTHER INFORMATION: Synthetic

<400> SEQUENCE: 435 actgactc                                                                 8

<210> SEQ ID NO 436
<211> LENGTH: 8
<212> TYPE: DNA
<213> ORGANISM: Artificial Sequence
<220> FEATURE:
<223> OTHER INFORMATION: Synthetic

<400> SEQUENCE: 436 tcctctca                                                                 8

<210> SEQ ID NO 437
<211> LENGTH: 8
<212> TYPE: DNA
<213> ORGANISM: Artificial Sequence
<220> FEATURE:
<223> OTHER INFORMATION: Synthetic

<400> SEQUENCE: 437 tgagtcgt                                                                 8

<210> SEQ ID NO 438
<211> LENGTH: 8
<212> TYPE: DNA
<213> ORGANISM: Artificial Sequence
<220> FEATURE:
<223> OTHER INFORMATION: Synthetic

<400> SEQUENCE: 438 ctgagcta                                                                 8

```
<210> SEQ ID NO 439
<211> LENGTH: 8
<212> TYPE: DNA
<213> ORGANISM: Artificial Sequence
<220> FEATURE:
<223> OTHER INFORMATION: Synthetic

<400> SEQUENCE: 439 accggtta                                                                 8

<210> SEQ ID NO 440
<211> LENGTH: 8
<212> TYPE: DNA
<213> ORGANISM: Artificial Sequence
<220> FEATURE:
<223> OTHER INFORMATION: Synthetic

<400> SEQUENCE: 440 ctcagtac                                                                 8

<210> SEQ ID NO 441
<211> LENGTH: 8
<212> TYPE: DNA
<213> ORGANISM: Artificial Sequence
<220> FEATURE:
<223> OTHER INFORMATION: Synthetic

<400> SEQUENCE: 441 gagtggtt                                                                 8

<210> SEQ ID NO 442
<211> LENGTH: 8
<212> TYPE: DNA
<213> ORGANISM: Artificial Sequence
<220> FEATURE:
<223> OTHER INFORMATION: Synthetic

<400> SEQUENCE: 442 ggtaactg                                                                 8

<210> SEQ ID NO 443
<211> LENGTH: 8
<212> TYPE: DNA
<213> ORGANISM: Artificial Sequence
<220> FEATURE:
<223> OTHER INFORMATION: Synthetic

<400> SEQUENCE: 443 catccatc                                                                 8

<210> SEQ ID NO 444
<211> LENGTH: 8
<212> TYPE: DNA
<213> ORGANISM: Artificial Sequence
<220> FEATURE:
<223> OTHER INFORMATION: Synthetic

<400> SEQUENCE: 444 agaggtag                                                                 8

<210> SEQ ID NO 445
<211> LENGTH: 8
<212> TYPE: DNA
<213> ORGANISM: Artificial Sequence
<220> FEATURE:
<223> OTHER INFORMATION: Synthetic
```

```
<400> SEQUENCE: 445 ctcttgac                                                                        8

<210> SEQ ID NO 446
<211> LENGTH: 8
<212> TYPE: DNA
<213> ORGANISM: Artificial Sequence
<220> FEATURE:
<223> OTHER INFORMATION: Synthetic

<400> SEQUENCE: 446 cgtagatc                                                                        8

<210> SEQ ID NO 447
<211> LENGTH: 8
<212> TYPE: DNA
<213> ORGANISM: Artificial Sequence
<220> FEATURE:
<223> OTHER INFORMATION: Synthetic

<400> SEQUENCE: 447 cggaatgt                                                                        8

<210> SEQ ID NO 448
<211> LENGTH: 8
<212> TYPE: DNA
<213> ORGANISM: Artificial Sequence
<220> FEATURE:
<223> OTHER INFORMATION: Synthetic

<400> SEQUENCE: 448 ggattcag                                                                        8

<210> SEQ ID NO 449
<211> LENGTH: 8
<212> TYPE: DNA
<213> ORGANISM: Artificial Sequence
<220> FEATURE:
<223> OTHER INFORMATION: Synthetic

<400> SEQUENCE: 449 tatggcca                                                                        8

<210> SEQ ID NO 450
<211> LENGTH: 8
<212> TYPE: DNA
<213> ORGANISM: Artificial Sequence
<220> FEATURE:
<223> OTHER INFORMATION: Synthetic

<400> SEQUENCE: 450 tatggcca                                                                        8

<210> SEQ ID NO 451
<211> LENGTH: 8
<212> TYPE: DNA
<213> ORGANISM: Artificial Sequence
<220> FEATURE:
<223> OTHER INFORMATION: Synthetic

<400> SEQUENCE: 451 caacacgt                                                                        8

<210> SEQ ID NO 452
<211> LENGTH: 8
```

```
<212> TYPE: DNA
<213> ORGANISM: Artificial Sequence
<220> FEATURE:
<223> OTHER INFORMATION: Synthetic

<400> SEQUENCE: 452 aacgcttc                                                              8

<210> SEQ ID NO 453
<211> LENGTH: 8
<212> TYPE: DNA
<213> ORGANISM: Artificial Sequence
<220> FEATURE:
<223> OTHER INFORMATION: Synthetic

<400> SEQUENCE: 453 tggcgtta                                                              8

<210> SEQ ID NO 454
<211> LENGTH: 8
<212> TYPE: DNA
<213> ORGANISM: Artificial Sequence
<220> FEATURE:
<223> OTHER INFORMATION: Synthetic

<400> SEQUENCE: 454 tacagcct                                                              8

<210> SEQ ID NO 455
<211> LENGTH: 8
<212> TYPE: DNA
<213> ORGANISM: Artificial Sequence
<220> FEATURE:
<223> OTHER INFORMATION: Synthetic

<400> SEQUENCE: 455 cactgtag                                                              8

<210> SEQ ID NO 456
<211> LENGTH: 8
<212> TYPE: DNA
<213> ORGANISM: Artificial Sequence
<220> FEATURE:
<223> OTHER INFORMATION: Synthetic

<400> SEQUENCE: 456 gctctgaa                                                              8

<210> SEQ ID NO 457
<211> LENGTH: 8
<212> TYPE: DNA
<213> ORGANISM: Artificial Sequence
<220> FEATURE:
<223> OTHER INFORMATION: Synthetic

<400> SEQUENCE: 457 tgtaggca                                                              8

<210> SEQ ID NO 458
<211> LENGTH: 8
<212> TYPE: DNA
<213> ORGANISM: Artificial Sequence
<220> FEATURE:
<223> OTHER INFORMATION: Synthetic

<400> SEQUENCE: 458
``` tcaatccg                                                                  8

<210> SEQ ID NO 459
<211> LENGTH: 8
<212> TYPE: DNA
<213> ORGANISM: Artificial Sequence
<220> FEATURE:
<223> OTHER INFORMATION: Synthetic

<400> SEQUENCE: 459 aatcctcc                                                                  8

<210> SEQ ID NO 460
<211> LENGTH: 8
<212> TYPE: DNA
<213> ORGANISM: Artificial Sequence
<220> FEATURE:
<223> OTHER INFORMATION: Synthetic

<400> SEQUENCE: 460 ggctaatg                                                                  8

<210> SEQ ID NO 461
<211> LENGTH: 8
<212> TYPE: DNA
<213> ORGANISM: Artificial Sequence
<220> FEATURE:
<223> OTHER INFORMATION: Synthetic

<400> SEQUENCE: 461 gtgaccaa                                                                  8

<210> SEQ ID NO 462
<211> LENGTH: 8
<212> TYPE: DNA
<213> ORGANISM: Artificial Sequence
<220> FEATURE:
<223> OTHER INFORMATION: Synthetic

<400> SEQUENCE: 462 cttgcttg                                                                  8

<210> SEQ ID NO 463
<211> LENGTH: 8
<212> TYPE: DNA
<213> ORGANISM: Artificial Sequence
<220> FEATURE:
<223> OTHER INFORMATION: Synthetic

<400> SEQUENCE: 463 ggatgttg                                                                  8

<210> SEQ ID NO 464
<211> LENGTH: 8
<212> TYPE: DNA
<213> ORGANISM: Artificial Sequence
<220> FEATURE:
<223> OTHER INFORMATION: Synthetic

<400> SEQUENCE: 464 ttgtcgtc                                                                  8

<210> SEQ ID NO 465
<211> LENGTH: 8
<212> TYPE: DNA
<213> ORGANISM: Artificial Sequence

```
<220> FEATURE:
<223> OTHER INFORMATION: Synthetic

<400> SEQUENCE: 465 gactcgat                                                                   8

<210> SEQ ID NO 466
<211> LENGTH: 8
<212> TYPE: DNA
<213> ORGANISM: Artificial Sequence
<220> FEATURE:
<223> OTHER INFORMATION: Synthetic

<400> SEQUENCE: 466 ctcgcata                                                                   8

<210> SEQ ID NO 467
<211> LENGTH: 8
<212> TYPE: DNA
<213> ORGANISM: Artificial Sequence
<220> FEATURE:
<223> OTHER INFORMATION: Synthetic

<400> SEQUENCE: 467 ggaagcta                                                                   8

<210> SEQ ID NO 468
<211> LENGTH: 8
<212> TYPE: DNA
<213> ORGANISM: Artificial Sequence
<220> FEATURE:
<223> OTHER INFORMATION: Synthetic

<400> SEQUENCE: 468 acgttggt                                                                   8

<210> SEQ ID NO 469
<211> LENGTH: 8
<212> TYPE: DNA
<213> ORGANISM: Artificial Sequence
<220> FEATURE:
<223> OTHER INFORMATION: Synthetic

<400> SEQUENCE: 469 tatcgcgt                                                                   8

<210> SEQ ID NO 470
<211> LENGTH: 8
<212> TYPE: DNA
<213> ORGANISM: Artificial Sequence
<220> FEATURE:
<223> OTHER INFORMATION: Synthetic

<400> SEQUENCE: 470 tagctgac                                                                   8

<210> SEQ ID NO 471
<211> LENGTH: 8
<212> TYPE: DNA
<213> ORGANISM: Artificial Sequence
<220> FEATURE:
<223> OTHER INFORMATION: Synthetic

<400> SEQUENCE: 471 atctggtg                                                                   8
```

```
<210> SEQ ID NO 472
<211> LENGTH: 8
<212> TYPE: DNA
<213> ORGANISM: Artificial Sequence
<220> FEATURE:
<223> OTHER INFORMATION: Synthetic

<400> SEQUENCE: 472 caaggttg                                                                  8

<210> SEQ ID NO 473
<211> LENGTH: 8
<212> TYPE: DNA
<213> ORGANISM: Artificial Sequence
<220> FEATURE:
<223> OTHER INFORMATION: Synthetic

<400> SEQUENCE: 473 caaggcaa                                                                  8

<210> SEQ ID NO 474
<211> LENGTH: 8
<212> TYPE: DNA
<213> ORGANISM: Artificial Sequence
<220> FEATURE:
<223> OTHER INFORMATION: Synthetic

<400> SEQUENCE: 474 agcagact                                                                  8

<210> SEQ ID NO 475
<211> LENGTH: 8
<212> TYPE: DNA
<213> ORGANISM: Artificial Sequence
<220> FEATURE:
<223> OTHER INFORMATION: Synthetic

<400> SEQUENCE: 475 tgaaggac                                                                  8

<210> SEQ ID NO 476
<211> LENGTH: 8
<212> TYPE: DNA
<213> ORGANISM: Artificial Sequence
<220> FEATURE:
<223> OTHER INFORMATION: Synthetic

<400> SEQUENCE: 476 atagaccg                                                                  8

<210> SEQ ID NO 477
<211> LENGTH: 8
<212> TYPE: DNA
<213> ORGANISM: Artificial Sequence
<220> FEATURE:
<223> OTHER INFORMATION: Synthetic

<400> SEQUENCE: 477 aaggcaga                                                                  8

<210> SEQ ID NO 478
<211> LENGTH: 8
<212> TYPE: DNA
<213> ORGANISM: Artificial Sequence
<220> FEATURE:
<223> OTHER INFORMATION: Synthetic
```

```
<400> SEQUENCE: 478 ccaacttg                                                            8

<210> SEQ ID NO 479
<211> LENGTH: 8
<212> TYPE: DNA
<213> ORGANISM: Artificial Sequence
<220> FEATURE:
<223> OTHER INFORMATION: Synthetic

<400> SEQUENCE: 479 ccgtagat                                                            8

<210> SEQ ID NO 480
<211> LENGTH: 8
<212> TYPE: DNA
<213> ORGANISM: Artificial Sequence
<220> FEATURE:
<223> OTHER INFORMATION: Synthetic

<400> SEQUENCE: 480 cagaagtg                                                            8

<210> SEQ ID NO 481
<211> LENGTH: 8
<212> TYPE: DNA
<213> ORGANISM: Artificial Sequence
<220> FEATURE:
<223> OTHER INFORMATION: Synthetic

<400> SEQUENCE: 481 gttgtgtg                                                            8

<210> SEQ ID NO 482
<211> LENGTH: 8
<212> TYPE: DNA
<213> ORGANISM: Artificial Sequence
<220> FEATURE:
<223> OTHER INFORMATION: Synthetic

<400> SEQUENCE: 482 cattaggc                                                            8

<210> SEQ ID NO 483
<211> LENGTH: 8
<212> TYPE: DNA
<213> ORGANISM: Artificial Sequence
<220> FEATURE:
<223> OTHER INFORMATION: Synthetic

<400> SEQUENCE: 483 atgcgaac                                                            8

<210> SEQ ID NO 484
<211> LENGTH: 8
<212> TYPE: DNA
<213> ORGANISM: Artificial Sequence
<220> FEATURE:
<223> OTHER INFORMATION: Synthetic

<400> SEQUENCE: 484 ctagactc                                                            8

<210> SEQ ID NO 485
```

```
<211> LENGTH: 8
<212> TYPE: DNA
<213> ORGANISM: Artificial Sequence
<220> FEATURE:
<223> OTHER INFORMATION: Synthetic

<400> SEQUENCE: 485 atagaggc                                                                    8

<210> SEQ ID NO 486
<211> LENGTH: 8
<212> TYPE: DNA
<213> ORGANISM: Artificial Sequence
<220> FEATURE:
<223> OTHER INFORMATION: Synthetic

<400> SEQUENCE: 486 agaatggc                                                                    8

<210> SEQ ID NO 487
<211> LENGTH: 8
<212> TYPE: DNA
<213> ORGANISM: Artificial Sequence
<220> FEATURE:
<223> OTHER INFORMATION: Synthetic

<400> SEQUENCE: 487 caaccgta                                                                    8

<210> SEQ ID NO 488
<211> LENGTH: 8
<212> TYPE: DNA
<213> ORGANISM: Artificial Sequence
<220> FEATURE:
<223> OTHER INFORMATION: Synthetic

<400> SEQUENCE: 488 ggtagagt                                                                    8

<210> SEQ ID NO 489
<211> LENGTH: 8
<212> TYPE: DNA
<213> ORGANISM: Artificial Sequence
<220> FEATURE:
<223> OTHER INFORMATION: Synthetic

<400> SEQUENCE: 489 tggaccta                                                                    8

<210> SEQ ID NO 490
<211> LENGTH: 8
<212> TYPE: DNA
<213> ORGANISM: Artificial Sequence
<220> FEATURE:
<223> OTHER INFORMATION: Synthetic

<400> SEQUENCE: 490 actcagga                                                                    8

<210> SEQ ID NO 491
<211> LENGTH: 8
<212> TYPE: DNA
<213> ORGANISM: Artificial Sequence
<220> FEATURE:
<223> OTHER INFORMATION: Synthetic

<400> SEQUENCE: 491
``` ctatccac                                                                  8

<210> SEQ ID NO 492
<211> LENGTH: 8
<212> TYPE: DNA
<213> ORGANISM: Artificial Sequence
<220> FEATURE:
<223> OTHER INFORMATION: Synthetic

<400> SEQUENCE: 492 aatagcgc                                                                  8

<210> SEQ ID NO 493
<211> LENGTH: 8
<212> TYPE: DNA
<213> ORGANISM: Artificial Sequence
<220> FEATURE:
<223> OTHER INFORMATION: Synthetic

<400> SEQUENCE: 493 ttccttcc                                                                  8

<210> SEQ ID NO 494
<211> LENGTH: 8
<212> TYPE: DNA
<213> ORGANISM: Artificial Sequence
<220> FEATURE:
<223> OTHER INFORMATION: Synthetic

<400> SEQUENCE: 494 ttgagtcc                                                                  8

<210> SEQ ID NO 495
<211> LENGTH: 8
<212> TYPE: DNA
<213> ORGANISM: Artificial Sequence
<220> FEATURE:
<223> OTHER INFORMATION: Synthetic

<400> SEQUENCE: 495 cgagtgtt                                                                  8

<210> SEQ ID NO 496
<211> LENGTH: 8
<212> TYPE: DNA
<213> ORGANISM: Artificial Sequence
<220> FEATURE:
<223> OTHER INFORMATION: Synthetic

<400> SEQUENCE: 496 aattccgg                                                                  8

<210> SEQ ID NO 497
<211> LENGTH: 8
<212> TYPE: DNA
<213> ORGANISM: Artificial Sequence
<220> FEATURE:
<223> OTHER INFORMATION: Synthetic

<400> SEQUENCE: 497 ggcaagtt                                                                  8

<210> SEQ ID NO 498
<211> LENGTH: 8
<212> TYPE: DNA

```
<213> ORGANISM: Artificial Sequence
<220> FEATURE:
<223> OTHER INFORMATION: Synthetic

<400> SEQUENCE: 498 cctgtcaa                                                                8

<210> SEQ ID NO 499
<211> LENGTH: 8
<212> TYPE: DNA
<213> ORGANISM: Artificial Sequence
<220> FEATURE:
<223> OTHER INFORMATION: Synthetic

<400> SEQUENCE: 499 cgctaaga                                                                8

<210> SEQ ID NO 500
<211> LENGTH: 8
<212> TYPE: DNA
<213> ORGANISM: Artificial Sequence
<220> FEATURE:
<223> OTHER INFORMATION: Synthetic

<400> SEQUENCE: 500 tgcaacag                                                                8

<210> SEQ ID NO 501
<211> LENGTH: 8
<212> TYPE: DNA
<213> ORGANISM: Artificial Sequence
<220> FEATURE:
<223> OTHER INFORMATION: Synthetic

<400> SEQUENCE: 501 cgtgttct                                                                8

<210> SEQ ID NO 502
<211> LENGTH: 8
<212> TYPE: DNA
<213> ORGANISM: Artificial Sequence
<220> FEATURE:
<223> OTHER INFORMATION: Synthetic

<400> SEQUENCE: 502 catcaagg                                                                8

<210> SEQ ID NO 503
<211> LENGTH: 8
<212> TYPE: DNA
<213> ORGANISM: Artificial Sequence
<220> FEATURE:
<223> OTHER INFORMATION: Synthetic

<400> SEQUENCE: 503 agatcgct                                                                8

<210> SEQ ID NO 504
<211> LENGTH: 8
<212> TYPE: DNA
<213> ORGANISM: Artificial Sequence
<220> FEATURE:
<223> OTHER INFORMATION: Synthetic

<400> SEQUENCE: 504 ttctgagc                                                                8
```

<210> SEQ ID NO 505
<211> LENGTH: 8
<212> TYPE: DNA
<213> ORGANISM: Artificial Sequence
<220> FEATURE:
<223> OTHER INFORMATION: Synthetic

<400> SEQUENCE: 505 cacgcaat                                                                8

<210> SEQ ID NO 506
<211> LENGTH: 8
<212> TYPE: DNA
<213> ORGANISM: Artificial Sequence
<220> FEATURE:
<223> OTHER INFORMATION: Synthetic

<400> SEQUENCE: 506 aacggatg                                                                8

<210> SEQ ID NO 507
<211> LENGTH: 8
<212> TYPE: DNA
<213> ORGANISM: Artificial Sequence
<220> FEATURE:
<223> OTHER INFORMATION: Synthetic

<400> SEQUENCE: 507 accagaga                                                                8

<210> SEQ ID NO 508
<211> LENGTH: 8
<212> TYPE: DNA
<213> ORGANISM: Artificial Sequence
<220> FEATURE:
<223> OTHER INFORMATION: Synthetic

<400> SEQUENCE: 508 tgctcgtt                                                                8

<210> SEQ ID NO 509
<211> LENGTH: 8
<212> TYPE: DNA
<213> ORGANISM: Artificial Sequence
<220> FEATURE:
<223> OTHER INFORMATION: Synthetic

<400> SEQUENCE: 509 gtgaacgt                                                                8

<210> SEQ ID NO 510
<211> LENGTH: 8
<212> TYPE: DNA
<213> ORGANISM: Artificial Sequence
<220> FEATURE:
<223> OTHER INFORMATION: Synthetic

<400> SEQUENCE: 510 gtgctgat                                                                8

<210> SEQ ID NO 511
<211> LENGTH: 8
<212> TYPE: DNA
<213> ORGANISM: Artificial Sequence
<220> FEATURE:

<223> OTHER INFORMATION: Synthetic

<400> SEQUENCE: 511 tcgctatc                                                                8

<210> SEQ ID NO 512
<211> LENGTH: 8
<212> TYPE: DNA
<213> ORGANISM: Artificial Sequence
<220> FEATURE:
<223> OTHER INFORMATION: Synthetic

<400> SEQUENCE: 512 caagctct                                                                8

<210> SEQ ID NO 513
<211> LENGTH: 8
<212> TYPE: DNA
<213> ORGANISM: Artificial Sequence
<220> FEATURE:
<223> OTHER INFORMATION: Synthetic

<400> SEQUENCE: 513 gacgatca                                                                8

<210> SEQ ID NO 514
<211> LENGTH: 8
<212> TYPE: DNA
<213> ORGANISM: Artificial Sequence
<220> FEATURE:
<223> OTHER INFORMATION: Synthetic

<400> SEQUENCE: 514 cgtatcgt                                                                8

<210> SEQ ID NO 515
<211> LENGTH: 8
<212> TYPE: DNA
<213> ORGANISM: Artificial Sequence
<220> FEATURE:
<223> OTHER INFORMATION: Synthetic

<400> SEQUENCE: 515 ccagttag                                                                8

<210> SEQ ID NO 516
<211> LENGTH: 8
<212> TYPE: DNA
<213> ORGANISM: Artificial Sequence
<220> FEATURE:
<223> OTHER INFORMATION: Synthetic

<400> SEQUENCE: 516 ttacgcga                                                                8

<210> SEQ ID NO 517
<211> LENGTH: 8
<212> TYPE: DNA
<213> ORGANISM: Artificial Sequence
<220> FEATURE:
<223> OTHER INFORMATION: Synthetic

<400> SEQUENCE: 517 aagaaccg                                                                8

```
<210> SEQ ID NO 518
<211> LENGTH: 8
<212> TYPE: DNA
<213> ORGANISM: Artificial Sequence
<220> FEATURE:
<223> OTHER INFORMATION: Synthetic

<400> SEQUENCE: 518 cgaaccaa                                                                 8

<210> SEQ ID NO 519
<211> LENGTH: 8
<212> TYPE: DNA
<213> ORGANISM: Artificial Sequence
<220> FEATURE:
<223> OTHER INFORMATION: Synthetic

<400> SEQUENCE: 519 gctacttc                                                                 8

<210> SEQ ID NO 520
<211> LENGTH: 8
<212> TYPE: DNA
<213> ORGANISM: Artificial Sequence
<220> FEATURE:
<223> OTHER INFORMATION: Synthetic

<400> SEQUENCE: 520 ttctagcc                                                                 8

<210> SEQ ID NO 521
<211> LENGTH: 8
<212> TYPE: DNA
<213> ORGANISM: Artificial Sequence
<220> FEATURE:
<223> OTHER INFORMATION: Synthetic

<400> SEQUENCE: 521 tcacgatg                                                                 8

<210> SEQ ID NO 522
<211> LENGTH: 8
<212> TYPE: DNA
<213> ORGANISM: Artificial Sequence
<220> FEATURE:
<223> OTHER INFORMATION: Synthetic

<400> SEQUENCE: 522 gttggtga                                                                 8

<210> SEQ ID NO 523
<211> LENGTH: 8
<212> TYPE: DNA
<213> ORGANISM: Artificial Sequence
<220> FEATURE:
<223> OTHER INFORMATION: Synthetic

<400> SEQUENCE: 523 ccttgaag                                                                 8

<210> SEQ ID NO 524
<211> LENGTH: 8
<212> TYPE: DNA
<213> ORGANISM: Artificial Sequence
<220> FEATURE:
<223> OTHER INFORMATION: Synthetic
```

```
<400> SEQUENCE: 524 gagctact                                                               8

<210> SEQ ID NO 525
<211> LENGTH: 8
<212> TYPE: DNA
<213> ORGANISM: Artificial Sequence
<220> FEATURE:
<223> OTHER INFORMATION: Synthetic

<400> SEQUENCE: 525 aatgtggc                                                               8

<210> SEQ ID NO 526
<211> LENGTH: 8
<212> TYPE: DNA
<213> ORGANISM: Artificial Sequence
<220> FEATURE:
<223> OTHER INFORMATION: Synthetic

<400> SEQUENCE: 526 tccgtgaa                                                               8

<210> SEQ ID NO 527
<211> LENGTH: 8
<212> TYPE: DNA
<213> ORGANISM: Artificial Sequence
<220> FEATURE:
<223> OTHER INFORMATION: Synthetic

<400> SEQUENCE: 527 caacgtca                                                               8

<210> SEQ ID NO 528
<211> LENGTH: 8
<212> TYPE: DNA
<213> ORGANISM: Artificial Sequence
<220> FEATURE:
<223> OTHER INFORMATION: Synthetic

<400> SEQUENCE: 528 ccagatga                                                               8

<210> SEQ ID NO 529
<211> LENGTH: 8
<212> TYPE: DNA
<213> ORGANISM: Artificial Sequence
<220> FEATURE:
<223> OTHER INFORMATION: Synthetic

<400> SEQUENCE: 529 gatgaacg                                                               8

<210> SEQ ID NO 530
<211> LENGTH: 8
<212> TYPE: DNA
<213> ORGANISM: Artificial Sequence
<220> FEATURE:
<223> OTHER INFORMATION: Synthetic

<400> SEQUENCE: 530 tgacggtt                                                               8

<210> SEQ ID NO 531
<211> LENGTH: 8
```

```
<212> TYPE: DNA
<213> ORGANISM: Artificial Sequence
<220> FEATURE:
<223> OTHER INFORMATION: Synthetic

<400> SEQUENCE: 531 gcttagca                                                                 8

<210> SEQ ID NO 532
<211> LENGTH: 8
<212> TYPE: DNA
<213> ORGANISM: Artificial Sequence
<220> FEATURE:
<223> OTHER INFORMATION: Synthetic

<400> SEQUENCE: 532 tctacctg                                                                 8

<210> SEQ ID NO 533
<211> LENGTH: 8
<212> TYPE: DNA
<213> ORGANISM: Artificial Sequence
<220> FEATURE:
<223> OTHER INFORMATION: Synthetic

<400> SEQUENCE: 533 cggttctt                                                                 8

<210> SEQ ID NO 534
<211> LENGTH: 8
<212> TYPE: DNA
<213> ORGANISM: Artificial Sequence
<220> FEATURE:
<223> OTHER INFORMATION: Synthetic

<400> SEQUENCE: 534 agtctcct                                                                 8

<210> SEQ ID NO 535
<211> LENGTH: 8
<212> TYPE: DNA
<213> ORGANISM: Artificial Sequence
<220> FEATURE:
<223> OTHER INFORMATION: Synthetic

<400> SEQUENCE: 535 ccttcact                                                                 8

<210> SEQ ID NO 536
<211> LENGTH: 8
<212> TYPE: DNA
<213> ORGANISM: Artificial Sequence
<220> FEATURE:
<223> OTHER INFORMATION: Synthetic

<400> SEQUENCE: 536 gctgaaga                                                                 8

<210> SEQ ID NO 537
<211> LENGTH: 8
<212> TYPE: DNA
<213> ORGANISM: Artificial Sequence
<220> FEATURE:
<223> OTHER INFORMATION: Synthetic

<400> SEQUENCE: 537
``` actccgtt 8

<210> SEQ ID NO 538
<211> LENGTH: 8
<212> TYPE: DNA
<213> ORGANISM: Artificial Sequence
<220> FEATURE:
<223> OTHER INFORMATION: Synthetic

<400> SEQUENCE: 538 gtctcttc 8

<210> SEQ ID NO 539
<211> LENGTH: 8
<212> TYPE: DNA
<213> ORGANISM: Artificial Sequence
<220> FEATURE:
<223> OTHER INFORMATION: Synthetic

<400> SEQUENCE: 539 ccaccaat 8

<210> SEQ ID NO 540
<211> LENGTH: 8
<212> TYPE: DNA
<213> ORGANISM: Artificial Sequence
<220> FEATURE:
<223> OTHER INFORMATION: Synthetic

<400> SEQUENCE: 540 cttgacag 8

<210> SEQ ID NO 541
<211> LENGTH: 8
<212> TYPE: DNA
<213> ORGANISM: Artificial Sequence
<220> FEATURE:
<223> OTHER INFORMATION: Synthetic

<400> SEQUENCE: 541 tgatgcct 8

<210> SEQ ID NO 542
<211> LENGTH: 8
<212> TYPE: DNA
<213> ORGANISM: Artificial Sequence
<220> FEATURE:
<223> OTHER INFORMATION: Artificial Sequence

<400> SEQUENCE: 542 gacctctt 8

<210> SEQ ID NO 543
<211> LENGTH: 8
<212> TYPE: DNA
<213> ORGANISM: Artificial Sequence
<220> FEATURE:
<223> OTHER INFORMATION: Synthetic

<400> SEQUENCE: 543 cgaatgca 8

<210> SEQ ID NO 544
<211> LENGTH: 8
<212> TYPE: DNA
<213> ORGANISM: Artificial Sequence

```
<220> FEATURE:
<223> OTHER INFORMATION: Synthetic

<400> SEQUENCE: 544 acgtccaa                                                                    8

<210> SEQ ID NO 545
<211> LENGTH: 8
<212> TYPE: DNA
<213> ORGANISM: Artificial Sequence
<220> FEATURE:
<223> OTHER INFORMATION: Synthetic

<400> SEQUENCE: 545 tccagcaa                                                                    8

<210> SEQ ID NO 546
<211> LENGTH: 8
<212> TYPE: DNA
<213> ORGANISM: Artificial Sequence
<220> FEATURE:
<223> OTHER INFORMATION: Synthetic

<400> SEQUENCE: 546 catctcca                                                                    8

<210> SEQ ID NO 547
<211> LENGTH: 8
<212> TYPE: DNA
<213> ORGANISM: Artificial Sequence
<220> FEATURE:
<223> OTHER INFORMATION: Synthetic

<400> SEQUENCE: 547 ggtacgta                                                                    8

<210> SEQ ID NO 548
<211> LENGTH: 8
<212> TYPE: DNA
<213> ORGANISM: Artificial Sequence
<220> FEATURE:
<223> OTHER INFORMATION: Artificial Sequence

<400> SEQUENCE: 548 aggtgtca                                                                    8

<210> SEQ ID NO 549
<211> LENGTH: 8
<212> TYPE: DNA
<213> ORGANISM: Artificial Sequence
<220> FEATURE:
<223> OTHER INFORMATION: Synthetic

<400> SEQUENCE: 549 aggtgtca                                                                    8

<210> SEQ ID NO 550
<211> LENGTH: 8
<212> TYPE: DNA
<213> ORGANISM: Artificial Sequence
<220> FEATURE:
<223> OTHER INFORMATION: Synthetic

<400> SEQUENCE: 550 cttctctg                                                                    8
```

```
<210> SEQ ID NO 551
<211> LENGTH: 8
<212> TYPE: DNA
<213> ORGANISM: Artificial Sequence
<220> FEATURE:
<223> OTHER INFORMATION: Synthetic

<400> SEQUENCE: 551 ctgaagca                                                                  8

<210> SEQ ID NO 552
<211> LENGTH: 8
<212> TYPE: DNA
<213> ORGANISM: Artificial Sequence
<220> FEATURE:
<223> OTHER INFORMATION: Synthetic

<400> SEQUENCE: 552 gcagtgta                                                                  8

<210> SEQ ID NO 553
<211> LENGTH: 8
<212> TYPE: DNA
<213> ORGANISM: Artificial Sequence
<220> FEATURE:
<223> OTHER INFORMATION: Synthetic

<400> SEQUENCE: 553 atacgtcc                                                                  8

<210> SEQ ID NO 554
<211> LENGTH: 8
<212> TYPE: DNA
<213> ORGANISM: Artificial Sequence
<220> FEATURE:
<223> OTHER INFORMATION: Synthetic

<400> SEQUENCE: 554 tatgcgag                                                                  8

<210> SEQ ID NO 555
<211> LENGTH: 8
<212> TYPE: DNA
<213> ORGANISM: Artificial Sequence
<220> FEATURE:
<223> OTHER INFORMATION: Synthetic

<400> SEQUENCE: 555 taggatgc                                                                  8

<210> SEQ ID NO 556
<211> LENGTH: 8
<212> TYPE: DNA
<213> ORGANISM: Artificial Sequence
<220> FEATURE:
<223> OTHER INFORMATION: Synthetic

<400> SEQUENCE: 556 gtaagcct                                                                  8

<210> SEQ ID NO 557
<211> LENGTH: 8
<212> TYPE: DNA
<213> ORGANISM: Artificial Sequence
<220> FEATURE:
<223> OTHER INFORMATION: Synthetic
```

```
<400> SEQUENCE: 557 cgacttac                                                              8

<210> SEQ ID NO 558
<211> LENGTH: 8
<212> TYPE: DNA
<213> ORGANISM: Artificial Sequence
<220> FEATURE:
<223> OTHER INFORMATION: Synthetic

<400> SEQUENCE: 558 ctccagaa                                                              8

<210> SEQ ID NO 559
<211> LENGTH: 8
<212> TYPE: DNA
<213> ORGANISM: Artificial Sequence
<220> FEATURE:
<223> OTHER INFORMATION: Synthetic

<400> SEQUENCE: 559 tgtgtgtc                                                              8

<210> SEQ ID NO 560
<211> LENGTH: 8
<212> TYPE: DNA
<213> ORGANISM: Artificial Sequence
<220> FEATURE:
<223> OTHER INFORMATION: Synthetic

<400> SEQUENCE: 560 tgtctggt                                                              8

<210> SEQ ID NO 561
<211> LENGTH: 8
<212> TYPE: DNA
<213> ORGANISM: Artificial Sequence
<220> FEATURE:
<223> OTHER INFORMATION: Synthetic

<400> SEQUENCE: 561 aagctgca                                                              8

<210> SEQ ID NO 562
<211> LENGTH: 8
<212> TYPE: DNA
<213> ORGANISM: Artificial Sequence
<220> FEATURE:
<223> OTHER INFORMATION: Synthetic

<400> SEQUENCE: 562 gaagttgc                                                              8

<210> SEQ ID NO 563
<211> LENGTH: 8
<212> TYPE: DNA
<213> ORGANISM: Artificial Sequence
<220> FEATURE:
<223> OTHER INFORMATION: Synthetic

<400> SEQUENCE: 563 aagcgagt                                                              8

<210> SEQ ID NO 564
```

```
<211> LENGTH: 8
<212> TYPE: DNA
<213> ORGANISM: Artificial Sequence
<220> FEATURE:
<223> OTHER INFORMATION: Synthetic

<400> SEQUENCE: 564 ggagttca                                                                  8

<210> SEQ ID NO 565
<211> LENGTH: 8
<212> TYPE: DNA
<213> ORGANISM: Artificial Sequence
<220> FEATURE:
<223> OTHER INFORMATION: Synthetic

<400> SEQUENCE: 565 gcttacac                                                                  8

<210> SEQ ID NO 566
<211> LENGTH: 8
<212> TYPE: DNA
<213> ORGANISM: Artificial Sequence
<220> FEATURE:
<223> OTHER INFORMATION: Synthetic

<400> SEQUENCE: 566 aggtgcat                                                                  8

<210> SEQ ID NO 567
<211> LENGTH: 8
<212> TYPE: DNA
<213> ORGANISM: Artificial Sequence
<220> FEATURE:
<223> OTHER INFORMATION: Synthetic

<400> SEQUENCE: 567 ttgacgga                                                                  8

<210> SEQ ID NO 568
<211> LENGTH: 8
<212> TYPE: DNA
<213> ORGANISM: Artificial Sequence
<220> FEATURE:
<223> OTHER INFORMATION: Synthetic

<400> SEQUENCE: 568 ataccgac                                                                  8

<210> SEQ ID NO 569
<211> LENGTH: 8
<212> TYPE: DNA
<213> ORGANISM: Artificial Sequence
<220> FEATURE:
<223> OTHER INFORMATION: Synthetic

<400> SEQUENCE: 569 ggatctgt                                                                  8

<210> SEQ ID NO 570
<211> LENGTH: 8
<212> TYPE: DNA
<213> ORGANISM: Artificial Sequence
<220> FEATURE:
<223> OTHER INFORMATION: Synthetic

<400> SEQUENCE: 570
``` agatccga                                                      8

<210> SEQ ID NO 571
<211> LENGTH: 8
<212> TYPE: DNA
<213> ORGANISM: Artificial Sequence
<220> FEATURE:
<223> OTHER INFORMATION: Synthetic

<400> SEQUENCE: 571 acgactct                                                      8

<210> SEQ ID NO 572
<211> LENGTH: 8
<212> TYPE: DNA
<213> ORGANISM: Artificial Sequence
<220> FEATURE:
<223> OTHER INFORMATION: Synthetic

<400> SEQUENCE: 572 cgctattc                                                      8

<210> SEQ ID NO 573
<211> LENGTH: 8
<212> TYPE: DNA
<213> ORGANISM: Artificial Sequence
<220> FEATURE:
<223> OTHER INFORMATION: Synthetic

<400> SEQUENCE: 573 accaatcc                                                      8

<210> SEQ ID NO 574
<211> LENGTH: 8
<212> TYPE: DNA
<213> ORGANISM: Artificial Sequence
<220> FEATURE:
<223> OTHER INFORMATION: Synthetic

<400> SEQUENCE: 574 tctatggc                                                      8

<210> SEQ ID NO 575
<211> LENGTH: 8
<212> TYPE: DNA
<213> ORGANISM: Artificial Sequence
<220> FEATURE:
<223> OTHER INFORMATION: Synthetic

<400> SEQUENCE: 575 ctctgaca                                                      8

<210> SEQ ID NO 576
<211> LENGTH: 8
<212> TYPE: DNA
<213> ORGANISM: Artificial Sequence
<220> FEATURE:
<223> OTHER INFORMATION: Synthetic

<400> SEQUENCE: 576 ttcgtagg                                                      8

<210> SEQ ID NO 577
<211> LENGTH: 8
<212> TYPE: DNA

<213> ORGANISM: Artificial Sequence
<220> FEATURE:
<223> OTHER INFORMATION: Synthetic

<400> SEQUENCE: 577 gacgtaac                                                                  8

<210> SEQ ID NO 578
<211> LENGTH: 8
<212> TYPE: DNA
<213> ORGANISM: Artificial Sequence
<220> FEATURE:
<223> OTHER INFORMATION: Synthetic

<400> SEQUENCE: 578 gtatctcg                                                                  8

<210> SEQ ID NO 579
<211> LENGTH: 8
<212> TYPE: DNA
<213> ORGANISM: Artificial Sequence
<220> FEATURE:
<223> OTHER INFORMATION: Synthetic

<400> SEQUENCE: 579 gtcaatgc                                                                  8

<210> SEQ ID NO 580
<211> LENGTH: 66
<212> TYPE: DNA
<213> ORGANISM: Artificial Sequence
<220> FEATURE:
<223> OTHER INFORMATION: Synthetic

<400> SEQUENCE: 580
caagcagaag acggcatacg agattcgatg aggtgactgg agttcagacg tgtgctcttc        60
cgatct                                                                   66

<210> SEQ ID NO 581
<211> LENGTH: 66
<212> TYPE: DNA
<213> ORGANISM: Artificial Sequence
<220> FEATURE:
<223> OTHER INFORMATION: Synthetic

<400> SEQUENCE: 581
caagcagaag acggcatacg agataacgat ccgtgactgg agttcagacg tgtgctcttc        60
cgatct                                                                   66

<210> SEQ ID NO 582
<211> LENGTH: 66
<212> TYPE: DNA
<213> ORGANISM: Artificial Sequence
<220> FEATURE:
<223> OTHER INFORMATION: Synthetic

<400> SEQUENCE: 582
caagcagaag acggcatacg agattaacgt gggtgactgg agttcagacg tgtgctcttc        60
cgatct                                                                   66

<210> SEQ ID NO 583
<211> LENGTH: 66
<212> TYPE: DNA
<213> ORGANISM: Artificial Sequence

```
<220> FEATURE:
<223> OTHER INFORMATION: Synthetic

<400> SEQUENCE: 583
caagcagaag acggcatacg agatatggag gagtgactgg agttcagacg tgtgctcttc      60
cgatct                                                                66

<210> SEQ ID NO 584
<211> LENGTH: 66
<212> TYPE: DNA
<213> ORGANISM: Artificial Sequence
<220> FEATURE:
<223> OTHER INFORMATION: Synthetic

<400> SEQUENCE: 584
caagcagaag acggcatacg agatgcgaag atgtgactgg agttcagacg tgtgctcttc      60
cgatct                                                                66

<210> SEQ ID NO 585
<211> LENGTH: 66
<212> TYPE: DNA
<213> ORGANISM: Artificial Sequence
<220> FEATURE:
<223> OTHER INFORMATION: Synthetic

<400> SEQUENCE: 585
caagcagaag acggcatacg agatacttcg ctgtgactgg agttcagacg tgtgctcttc      60
cgatct                                                                66

<210> SEQ ID NO 586
<211> LENGTH: 66
<212> TYPE: DNA
<213> ORGANISM: Artificial Sequence
<220> FEATURE:
<223> OTHER INFORMATION: Synthetic

<400> SEQUENCE: 586
caagcagaag acggcatacg agattgcgta aggtgactgg agttcagacg tgtgctcttc      60
cgatct                                                                66

<210> SEQ ID NO 587
<211> LENGTH: 66
<212> TYPE: DNA
<213> ORGANISM: Artificial Sequence
<220> FEATURE:
<223> OTHER INFORMATION: Synthetic

<400> SEQUENCE: 587
caagcagaag acggcatacg agatggtcaa gtgtgactgg agttcagacg tgtgctcttc      60
cgatct                                                                66

<210> SEQ ID NO 588
<211> LENGTH: 66
<212> TYPE: DNA
<213> ORGANISM: Artificial Sequence
<220> FEATURE:
<223> OTHER INFORMATION: Synthetic

<400> SEQUENCE: 588
caagcagaag acggcatacg agataggctt acgtgactgg agttcagacg tgtgctcttc      60
cgatct                                                                66
```

```
<210> SEQ ID NO 589
<211> LENGTH: 66
<212> TYPE: DNA
<213> ORGANISM: Artificial Sequence
<220> FEATURE:
<223> OTHER INFORMATION: Synthetic

<400> SEQUENCE: 589
caagcagaag acggcatacg agatgattct cggtgactgg agttcagacg tgtgctcttc    60
cgatct                                                                66

<210> SEQ ID NO 590
<211> LENGTH: 66
<212> TYPE: DNA
<213> ORGANISM: Artificial Sequence
<220> FEATURE:
<223> OTHER INFORMATION: Synthetic

<400> SEQUENCE: 590
caagcagaag acggcatacg agatgtctcc tagtgactgg agttcagacg tgtgctcttc    60
cgatct                                                                66

<210> SEQ ID NO 591
<211> LENGTH: 66
<212> TYPE: DNA
<213> ORGANISM: Artificial Sequence
<220> FEATURE:
<223> OTHER INFORMATION: Synthetic

<400> SEQUENCE: 591
caagcagaag acggcatacg agatgacggt atgtgactgg agttcagacg tgtgctcttc    60
cgatct                                                                66

<210> SEQ ID NO 592
<211> LENGTH: 66
<212> TYPE: DNA
<213> ORGANISM: Artificial Sequence
<220> FEATURE:
<223> OTHER INFORMATION: Synthetic

<400> SEQUENCE: 592
caagcagaag acggcatacg agatcatggt gtgtgactgg agttcagacg tgtgctcttc    60
cgatct                                                                66

<210> SEQ ID NO 593
<211> LENGTH: 66
<212> TYPE: DNA
<213> ORGANISM: Artificial Sequence
<220> FEATURE:
<223> OTHER INFORMATION: Synthetic

<400> SEQUENCE: 593
caagcagaag acggcatacg agattgtcta ccgtgactgg agttcagacg tgtgctcttc    60
cgatct                                                                66

<210> SEQ ID NO 594
<211> LENGTH: 66
<212> TYPE: DNA
<213> ORGANISM: Artificial Sequence
<220> FEATURE:
<223> OTHER INFORMATION: Synthetic

<400> SEQUENCE: 594
```

```
caagcagaag acggcatacg agataccatg cagtgactgg agttcagacg tgtgctcttc    60
cgatct                                                               66

<210> SEQ ID NO 595
<211> LENGTH: 66
<212> TYPE: DNA
<213> ORGANISM: Artificial Sequence
<220> FEATURE:
<223> OTHER INFORMATION: Synthetic

<400> SEQUENCE: 595
caagcagaag acggcatacg agatcattcc tggtgactgg agttcagacg tgtgctcttc    60
cgatct                                                               66

<210> SEQ ID NO 596
<211> LENGTH: 66
<212> TYPE: DNA
<213> ORGANISM: Artificial Sequence
<220> FEATURE:
<223> OTHER INFORMATION: Synthetic

<400> SEQUENCE: 596
caagcagaag acggcatacg agataggact aggtgactgg agttcagacg tgtgctcttc    60
cgatct                                                               66

<210> SEQ ID NO 597
<211> LENGTH: 66
<212> TYPE: DNA
<213> ORGANISM: Artificial Sequence
<220> FEATURE:
<223> OTHER INFORMATION: Synthetic

<400> SEQUENCE: 597
caagcagaag acggcatacg agatgcttgt tggtgactgg agttcagacg tgtgctcttc    60
cgatct                                                               66

<210> SEQ ID NO 598
<211> LENGTH: 66
<212> TYPE: DNA
<213> ORGANISM: Artificial Sequence
<220> FEATURE:
<223> OTHER INFORMATION: Synthetic

<400> SEQUENCE: 598
caagcagaag acggcatacg agatagtcac acgtgactgg agttcagacg tgtgctcttc    60
cgatct                                                               66

<210> SEQ ID NO 599
<211> LENGTH: 66
<212> TYPE: DNA
<213> ORGANISM: Artificial Sequence
<220> FEATURE:
<223> OTHER INFORMATION: Synthetic

<400> SEQUENCE: 599
caagcagaag acggcatacg agatccagtt gtgtgactgg agttcagacg tgtgctcttc    60
cgatct                                                               66

<210> SEQ ID NO 600
<211> LENGTH: 66
<212> TYPE: DNA
```

```
<213> ORGANISM: Artificial Sequence
<220> FEATURE:
<223> OTHER INFORMATION: Synthetic

<400> SEQUENCE: 600
caagcagaag acggcatacg agatctccat tcgtgactgg agttcagacg tgtgctcttc    60
cgatct                                                               66

<210> SEQ ID NO 601
<211> LENGTH: 66
<212> TYPE: DNA
<213> ORGANISM: Artificial Sequence
<220> FEATURE:
<223> OTHER INFORMATION: Synthetic

<400> SEQUENCE: 601
caagcagaag acggcatacg agatttgcca acgtgactgg agttcagacg tgtgctcttc    60
cgatct                                                               66

<210> SEQ ID NO 602
<211> LENGTH: 66
<212> TYPE: DNA
<213> ORGANISM: Artificial Sequence
<220> FEATURE:
<223> OTHER INFORMATION: Synthetic

<400> SEQUENCE: 602
caagcagaag acggcatacg agatgagcac atgtgactgg agttcagacg tgtgctcttc    60
cgatct                                                               66

<210> SEQ ID NO 603
<211> LENGTH: 66
<212> TYPE: DNA
<213> ORGANISM: Artificial Sequence
<220> FEATURE:
<223> OTHER INFORMATION: Synthetic

<400> SEQUENCE: 603
caagcagaag acggcatacg agatatgtgg tggtgactgg agttcagacg tgtgctcttc    60
cgatct                                                               66

<210> SEQ ID NO 604
<211> LENGTH: 70
<212> TYPE: DNA
<213> ORGANISM: Artificial Sequence
<220> FEATURE:
<223> OTHER INFORMATION: Synthetic

<400> SEQUENCE: 604
aatgatacgg cgaccaccga gatctacact agatcgcaca ctctttccct acacgacgct    60
cttccgatct                                                           70

<210> SEQ ID NO 605
<211> LENGTH: 70
<212> TYPE: DNA
<213> ORGANISM: Artificial Sequence
<220> FEATURE:
<223> OTHER INFORMATION: Synthetic

<400> SEQUENCE: 605
aatgatacgg cgaccaccga gatctacacc tctctataca ctctttccct acacgacgct    60
cttccgatct                                                           70
```

<210> SEQ ID NO 606
<211> LENGTH: 70
<212> TYPE: DNA
<213> ORGANISM: Artificial Sequence
<220> FEATURE:
<223> OTHER INFORMATION: Synthetic

<400> SEQUENCE: 606
aatgatacgg cgaccaccga gatctacact atcctctaca ctctttccct acacgacgct    60
cttccgatct                                                          70

<210> SEQ ID NO 607
<211> LENGTH: 70
<212> TYPE: DNA
<213> ORGANISM: Artificial Sequence
<220> FEATURE:
<223> OTHER INFORMATION: Synthetic

<400> SEQUENCE: 607
aatgatacgg cgaccaccga gatctacaca gagtagaaca ctctttccct acacgacgct    60
cttccgatct                                                          70

<210> SEQ ID NO 608
<211> LENGTH: 70
<212> TYPE: DNA
<213> ORGANISM: Artificial Sequence
<220> FEATURE:
<223> OTHER INFORMATION: Synthetic

<400> SEQUENCE: 608
aatgatacgg cgaccaccga gatctacacg taaggagaca ctctttccct acacgacgct    60
cttccgatct                                                          70

<210> SEQ ID NO 609
<211> LENGTH: 70
<212> TYPE: DNA
<213> ORGANISM: Artificial Sequence
<220> FEATURE:
<223> OTHER INFORMATION: Synthetic

<400> SEQUENCE: 609
aatgatacgg cgaccaccga gatctacaca ctgcataaca ctctttccct acacgacgct    60
cttccgatct                                                          70

<210> SEQ ID NO 610
<211> LENGTH: 70
<212> TYPE: DNA
<213> ORGANISM: Artificial Sequence
<220> FEATURE:
<223> OTHER INFORMATION: Synthetic

<400> SEQUENCE: 610
aatgatacgg cgaccaccga gatctacaca aggagtaaca ctctttccct acacgacgct    60
cttccgatct                                                          70

<210> SEQ ID NO 611
<211> LENGTH: 70
<212> TYPE: DNA
<213> ORGANISM: Artificial Sequence
<220> FEATURE:
<223> OTHER INFORMATION: Synthetic

<400> SEQUENCE: 611
aatgatacgg cgaccaccga gatctacacc taagcctaca ctctttccct acacgacgct    60
cttccgatct                                                           70

<210> SEQ ID NO 612
<211> LENGTH: 8
<212> TYPE: DNA
<213> ORGANISM: Artificial Sequence
<220> FEATURE:
<223> OTHER INFORMATION: Synthetic

<400> SEQUENCE: 612 ctcatcga                                                              8

<210> SEQ ID NO 613
<211> LENGTH: 8
<212> TYPE: DNA
<213> ORGANISM: Artificial Sequence
<220> FEATURE:
<223> OTHER INFORMATION: Synthetic

<400> SEQUENCE: 613 ggatcgtt                                                              8

<210> SEQ ID NO 614
<211> LENGTH: 8
<212> TYPE: DNA
<213> ORGANISM: Artificial Sequence
<220> FEATURE:
<223> OTHER INFORMATION: Synthetic

<400> SEQUENCE: 614 ccacgtta                                                              8

<210> SEQ ID NO 615
<211> LENGTH: 8
<212> TYPE: DNA
<213> ORGANISM: Artificial Sequence
<220> FEATURE:
<223> OTHER INFORMATION: Synthetic

<400> SEQUENCE: 615 tcctccat                                                              8

<210> SEQ ID NO 616
<211> LENGTH: 8
<212> TYPE: DNA
<213> ORGANISM: Artificial Sequence
<220> FEATURE:
<223> OTHER INFORMATION: Synthetic

<400> SEQUENCE: 616 atcttcgc                                                              8

<210> SEQ ID NO 617
<211> LENGTH: 8
<212> TYPE: DNA
<213> ORGANISM: Artificial Sequence
<220> FEATURE:
<223> OTHER INFORMATION: Synthetic

<400> SEQUENCE: 617 agcgaagt                                                              8

```
<210> SEQ ID NO 618
<211> LENGTH: 8
<212> TYPE: DNA
<213> ORGANISM: Artificial Sequence
<220> FEATURE:
<223> OTHER INFORMATION: Synthetic

<400> SEQUENCE: 618 cttacgca                                                                 8

<210> SEQ ID NO 619
<211> LENGTH: 8
<212> TYPE: DNA
<213> ORGANISM: Artificial Sequence
<220> FEATURE:
<223> OTHER INFORMATION: Synthetic

<400> SEQUENCE: 619 acttgacc                                                                 8

<210> SEQ ID NO 620
<211> LENGTH: 8
<212> TYPE: DNA
<213> ORGANISM: Artificial Sequence
<220> FEATURE:
<223> OTHER INFORMATION: Synthetic

<400> SEQUENCE: 620 gtaagcct                                                                 8

<210> SEQ ID NO 621
<211> LENGTH: 8
<212> TYPE: DNA
<213> ORGANISM: Artificial Sequence
<220> FEATURE:
<223> OTHER INFORMATION: Synthetic

<400> SEQUENCE: 621 cgagaatc                                                                 8

<210> SEQ ID NO 622
<211> LENGTH: 8
<212> TYPE: DNA
<213> ORGANISM: Artificial Sequence
<220> FEATURE:
<223> OTHER INFORMATION: Synthetic

<400> SEQUENCE: 622 taggagac                                                                 8

<210> SEQ ID NO 623
<211> LENGTH: 8
<212> TYPE: DNA
<213> ORGANISM: Artificial Sequence
<220> FEATURE:
<223> OTHER INFORMATION: Synthetic

<400> SEQUENCE: 623 ataccgtc                                                                 8

<210> SEQ ID NO 624
<211> LENGTH: 8
<212> TYPE: DNA
<213> ORGANISM: Artificial Sequence
<220> FEATURE:
<223> OTHER INFORMATION: Synthetic
```

```
<400> SEQUENCE: 624 acaccatg                                                                    8

<210> SEQ ID NO 625
<211> LENGTH: 8
<212> TYPE: DNA
<213> ORGANISM: Artificial Sequence
<220> FEATURE:
<223> OTHER INFORMATION: Synthetic

<400> SEQUENCE: 625 ggtagaca                                                                    8

<210> SEQ ID NO 626
<211> LENGTH: 8
<212> TYPE: DNA
<213> ORGANISM: Artificial Sequence
<220> FEATURE:
<223> OTHER INFORMATION: Synthetic

<400> SEQUENCE: 626 tgcatggt                                                                    8

<210> SEQ ID NO 627
<211> LENGTH: 8
<212> TYPE: DNA
<213> ORGANISM: Artificial Sequence
<220> FEATURE:
<223> OTHER INFORMATION: Synthetic

<400> SEQUENCE: 627 caggaatg                                                                    8

<210> SEQ ID NO 628
<211> LENGTH: 8
<212> TYPE: DNA
<213> ORGANISM: Artificial Sequence
<220> FEATURE:
<223> OTHER INFORMATION: Synthetic

<400> SEQUENCE: 628 ctagtcct                                                                    8

<210> SEQ ID NO 629
<211> LENGTH: 8
<212> TYPE: DNA
<213> ORGANISM: Artificial Sequence
<220> FEATURE:
<223> OTHER INFORMATION: Synthetic

<400> SEQUENCE: 629 caacaagc                                                                    8

<210> SEQ ID NO 630
<211> LENGTH: 8
<212> TYPE: DNA
<213> ORGANISM: Artificial Sequence
<220> FEATURE:
<223> OTHER INFORMATION: Synthetic

<400> SEQUENCE: 630 gtgtgact                                                                    8

<210> SEQ ID NO 631
<211> LENGTH: 8
```

```
<212> TYPE: DNA
<213> ORGANISM: Artificial Sequence
<220> FEATURE:
<223> OTHER INFORMATION: Synthetic

<400> SEQUENCE: 631 acaactgg                                                                8

<210> SEQ ID NO 632
<211> LENGTH: 8
<212> TYPE: DNA
<213> ORGANISM: Artificial Sequence
<220> FEATURE:
<223> OTHER INFORMATION: Synthetic

<400> SEQUENCE: 632 gaatggag                                                                8

<210> SEQ ID NO 633
<211> LENGTH: 8
<212> TYPE: DNA
<213> ORGANISM: Artificial Sequence
<220> FEATURE:
<223> OTHER INFORMATION: Synthetic

<400> SEQUENCE: 633 gttggcaa                                                                8

<210> SEQ ID NO 634
<211> LENGTH: 8
<212> TYPE: DNA
<213> ORGANISM: Artificial Sequence
<220> FEATURE:
<223> OTHER INFORMATION: Synthetic

<400> SEQUENCE: 634 atgtgctc                                                                8

<210> SEQ ID NO 635
<211> LENGTH: 8
<212> TYPE: DNA
<213> ORGANISM: Artificial Sequence
<220> FEATURE:
<223> OTHER INFORMATION: Synthetic

<400> SEQUENCE: 635 caccacat                                                                8

<210> SEQ ID NO 636
<211> LENGTH: 8
<212> TYPE: DNA
<213> ORGANISM: Artificial Sequence
<220> FEATURE:
<223> OTHER INFORMATION: Synthetic

<400> SEQUENCE: 636 tagatcgc                                                                8

<210> SEQ ID NO 637
<211> LENGTH: 8
<212> TYPE: DNA
<213> ORGANISM: Artificial Sequence
<220> FEATURE:
<223> OTHER INFORMATION: Synthetic

<400> SEQUENCE: 637
``` ctctctat 8

<210> SEQ ID NO 638
<211> LENGTH: 8
<212> TYPE: DNA
<213> ORGANISM: Artificial Sequence
<220> FEATURE:
<223> OTHER INFORMATION: Synthetic

<400> SEQUENCE: 638 tatcctct 8

<210> SEQ ID NO 639
<211> LENGTH: 8
<212> TYPE: DNA
<213> ORGANISM: Artificial Sequence
<220> FEATURE:
<223> OTHER INFORMATION: Synthetic

<400> SEQUENCE: 639 agagtaga 8

<210> SEQ ID NO 640
<211> LENGTH: 8
<212> TYPE: DNA
<213> ORGANISM: Artificial Sequence
<220> FEATURE:
<223> OTHER INFORMATION: Synthetic

<400> SEQUENCE: 640 gtaaggag 8

<210> SEQ ID NO 641
<211> LENGTH: 8
<212> TYPE: DNA
<213> ORGANISM: Artificial Sequence
<220> FEATURE:
<223> OTHER INFORMATION: Synthetic

<400> SEQUENCE: 641 actgcata 8

<210> SEQ ID NO 642
<211> LENGTH: 8
<212> TYPE: DNA
<213> ORGANISM: Artificial Sequence
<220> FEATURE:
<223> OTHER INFORMATION: Synthetic

<400> SEQUENCE: 642 aaggagta 8

<210> SEQ ID NO 643
<211> LENGTH: 8
<212> TYPE: DNA
<213> ORGANISM: Artificial Sequence
<220> FEATURE:
<223> OTHER INFORMATION: Synthetic

<400> SEQUENCE: 643 ctaagcct 8

<210> SEQ ID NO 644
<211> LENGTH: 19
<212> TYPE: DNA
<213> ORGANISM: Artificial Sequence

```
<220> FEATURE:
<223> OTHER INFORMATION: Synthetic

<400> SEQUENCE: 644
agatcggaag agcgtcgtg                                              19

<210> SEQ ID NO 645
<211> LENGTH: 19
<212> TYPE: DNA
<213> ORGANISM: Artificial Sequence
<220> FEATURE:
<223> OTHER INFORMATION: Synthetic

<400> SEQUENCE: 645
ttaccgcggc kgctgrcac                                              19

<210> SEQ ID NO 646
<211> LENGTH: 19
<212> TYPE: DNA
<213> ORGANISM: Artificial Sequence
<220> FEATURE:
<223> OTHER INFORMATION: Synthetic

<400> SEQUENCE: 646
gcttcttagt caggtaccg                                              19

<210> SEQ ID NO 647
<211> LENGTH: 20
<212> TYPE: DNA
<213> ORGANISM: Artificial Sequence
<220> FEATURE:
<223> OTHER INFORMATION: Synthetic

<400> SEQUENCE: 647
ggtattagca yctgtttcca                                             20

<210> SEQ ID NO 648
<211> LENGTH: 17
<212> TYPE: DNA
<213> ORGANISM: Artificial Sequence
<220> FEATURE:
<223> OTHER INFORMATION: Synthetic

<400> SEQUENCE: 648
ggtcggtctc tcaaccc                                                17

<210> SEQ ID NO 649
<211> LENGTH: 19
<212> TYPE: DNA
<213> ORGANISM: Artificial Sequence
<220> FEATURE:
<223> OTHER INFORMATION: Synthetic

<400> SEQUENCE: 649
gcttcttagt caggtaccg                                              19

<210> SEQ ID NO 650
<211> LENGTH: 18
<212> TYPE: DNA
<213> ORGANISM: Artificial Sequence
<220> FEATURE:
<223> OTHER INFORMATION: Synthetic

<400> SEQUENCE: 650
gctgcctccc gtaggagt                                               18
```

```
<210> SEQ ID NO 651
<211> LENGTH: 18
<212> TYPE: DNA
<213> ORGANISM: Artificial Sequence
<220> FEATURE:
<223> OTHER INFORMATION: Synthetic

<400> SEQUENCE: 651
actcctacgg gaggcagc                                                 18
```